United States Patent
Sun et al.

(10) Patent No.: US 10,001,489 B2
(45) Date of Patent: Jun. 19, 2018

(54) METHOD FOR CONSTRUCTING A NOVEL AFFINITY PEPTIDE LIBRARY FOR BINDING IMMUNOGLOBULIN G BASED ON A PROTEIN AFFINITY MODEL OF PROTEIN A

(71) Applicant: TIANJIN UNIVERSITY, Tianjin (CN)

(72) Inventors: Yan Sun, Tianjin (CN); Weiwei Zhao, Tianjin (CN); Fufeng Liu, Tianjin (CN); Qinghong Shi, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 200 days.

(21) Appl. No.: 14/654,731

(22) PCT Filed: Aug. 19, 2013

(86) PCT No.: PCT/CN2013/081761
§ 371 (c)(1),
(2) Date: Jun. 22, 2015

(87) PCT Pub. No.: WO2014/094444
PCT Pub. Date: Jun. 26, 2014

(65) Prior Publication Data
US 2015/0355192 A1    Dec. 10, 2015

(30) Foreign Application Priority Data
Dec. 20, 2012  (CN) .......................... 2012 1 0561815

(51) Int. Cl.
| | | |
|---|---|---|
| *C12N 15/10* | (2006.01) | |
| *G01N 33/68* | (2006.01) | |
| *G06F 19/18* | (2011.01) | |
| *C07K 7/06* | (2006.01) | |
| *C40B 30/02* | (2006.01) | |
| *C40B 50/02* | (2006.01) | |

(52) U.S. Cl.
CPC ........... *G01N 33/6854* (2013.01); *C07K 7/06* (2013.01); *C40B 30/02* (2013.01); *C40B 50/02* (2013.01); *G06F 19/18* (2013.01)

(58) Field of Classification Search
None
See application file for complete search history.

(56) References Cited

U.S. PATENT DOCUMENTS 7,408,030 B2    8/2008  Carbonell et al.

FOREIGN PATENT DOCUMENTS

| CN | 1634990 A | 7/2005 |
|---|---|---|
| CN | 101704879 A | 5/2010 |
| CN | 103014880 A | 4/2013 |
| EP | 2 495 253 A1 | 9/2012 |
| EP | 2 495 254 A1 | 9/2012 |
| JP | 2005-147610 A | 6/2005 |
| JP | 2008-141923 A | 5/2008 |
| JP | 2009-041860 A | 2/2009 |

OTHER PUBLICATIONS

Ehrlich et al., "Identification of Model Peptides as Affinity Ligands for the Purification of Humanized Monoclonal Antibodies by Means of Phage Display", Journal of Biochemical and Biophysical Methods, vol. 49, 2001, pp. 443-454.
Huang, "Rational Design of Affinity Peptide Ligands for Antibody and Chromatographic Characterizations" 2012.
Dec. 22, 2014 Office Action issued in Chinese Patent Application No. 201210561815.8.
Li et al., "Design, Synthesis, and Application of a Protein A Mimetic, Nature Biotechnology", vol. 16, 1998, pp. 190-195.
Jun. 20, 2014 Office Action issued in Chinese Patent Application No. 201210561815.8.
Huang et al., "Molecular Mechanism of the Affinity Interactions between Proten A and Human Immunoglobulin G1 Revealed by Molecular Simulations, The Journal of Physical Chemistry" vol. 115, 2011,4168-4176.
Oct. 21, 2013 Office Action issued in Chinese Patent Application No. 201210561815.8.
Dec. 5, 2013 International Search Report issued in International Patent Application No. PCT/CN2013/081761.
Dec. 5, 2013 International Preliminary Report on Patentability issued in International Patent No. PCT/CN2013/081761.
Fassina et al., "Protein A Mimetic Peptide Ligand for Affinity Purification of Antibodies, Journal of Molecular Recognition", vol. 9, 1996, pp. 564-569.

*Primary Examiner* — Christopher M Gross
(74) *Attorney, Agent, or Firm* — Oliff PLC

(57) ABSTRACT

An affinity ligand peptide library of IgG constructed on the basis of Protein A affinity model and the application of a design method thereof. According to the Molecular Mechanics—Poisson-Boltzmann surface area (MM/PBSA) method and on the basis of the known human IgG-Protein A complex structure, the hot spots of Protein A that have high affinity for human IgG are obtained analytically, and a Protein A simplified affinity model is built thereof. An affinity peptide library of IgG is constructed including heptapeptide and octapeptide structural modes. On the basis of the peptide structural modes, the types of inserted amino acids that 'X' residues represent are further identified using amino acid location method. Then, molecular docking and molecular dynamics simulation methods are used to screen the candidate peptides successively. Finally, the affinity peptide ligands that can effectively purify IgG are identified using affinity chromatography.

8 Claims, 5 Drawing Sheets

SEQUENCE LISTING

<160> NUMBER OF SEQ ID NOS: 2173

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Phe Tyr Cys His Ala Ala Ala Glu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

```
Phe Tyr Cys His Ala Ala Arg Glu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Phe Tyr Cys His Ala Ala Asp Glu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Phe Tyr Cys His Ala Ala Gln Glu
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Phe Tyr Cys His Ala Ala Glu Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Phe Tyr Cys His Ala Ala Leu Glu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Phe Tyr Cys His Ala Ala Lys Glu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8
```

```
Phe Tyr Cys His Ala Ala Met Glu
1               5
```

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

```
Phe Tyr Cys His Ala Ala Pro Glu
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

```
Phe Tyr Cys His Ala Ala Ser Glu
1               5
```

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

```
Phe Tyr Cys His Ala Ala Thr Glu
1               5
```

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

```
Phe Tyr Cys His Ala Gln Ala Glu
1               5
```

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

```
Phe Tyr Cys His Ala Gln Arg Glu
1               5
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

```
Phe Tyr Cys His Ala Gln Asp Glu
```

```
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Phe Tyr Cys His Ala Gln Gln Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Phe Tyr Cys His Ala Gln Glu Glu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Phe Tyr Cys His Ala Gln Leu Glu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Phe Tyr Cys His Ala Gln Lys Glu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Phe Tyr Cys His Ala Gln Met Glu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Phe Tyr Cys His Ala Gln Pro Glu
1               5
```

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Phe Tyr Cys His Ala Gln Ser Glu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Phe Tyr Cys His Ala Gln Thr Glu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Phe Tyr Cys His Ala Glu Ala Glu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Phe Tyr Cys His Ala Glu Arg Glu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Phe Tyr Cys His Ala Glu Asp Glu
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

Phe Tyr Cys His Ala Glu Gln Glu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Phe Tyr Cys His Ala Glu Glu Glu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Phe Tyr Cys His Ala Glu Leu Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Phe Tyr Cys His Ala Glu Lys Glu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Phe Tyr Cys His Ala Glu Met Glu
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Phe Tyr Cys His Ala Glu Pro Glu
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Phe Tyr Cys His Ala Glu Ser Glu
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Phe Tyr Cys His Ala Glu Thr Glu
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Phe Tyr Cys His Ala Ile Ala Glu
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Phe Tyr Cys His Ala Ile Arg Glu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Phe Tyr Cys His Ala Ile Asp Glu
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Phe Tyr Cys His Ala Ile Gln Glu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Phe Tyr Cys His Ala Ile Glu Glu
1               5

<210> SEQ ID NO 39

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 39

Phe Tyr Cys His Ala Ile Leu Glu
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Phe Tyr Cys His Ala Ile Lys Glu
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Phe Tyr Cys His Ala Ile Met Glu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Phe Tyr Cys His Ala Ile Pro Glu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Phe Tyr Cys His Ala Ile Ser Glu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Phe Tyr Cys His Ala Ile Thr Glu
1               5

<210> SEQ ID NO 45
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 45

Phe Tyr Cys His Ala Leu Ala Glu
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Phe Tyr Cys His Ala Leu Arg Glu
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Phe Tyr Cys His Ala Leu Asp Glu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Phe Tyr Cys His Ala Leu Gln Glu
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Phe Tyr Cys His Ala Leu Glu Glu
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Phe Tyr Cys His Ala Leu Leu Glu
1               5

<210> SEQ ID NO 51
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 51

Phe Tyr Cys His Ala Leu Lys Glu
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Phe Tyr Cys His Ala Leu Met Glu
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Phe Tyr Cys His Ala Leu Pro Glu
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Phe Tyr Cys His Ala Leu Ser Glu
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Phe Tyr Cys His Ala Leu Thr Glu
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Phe Tyr Cys His Ala Lys Ala Glu
1               5

<210> SEQ ID NO 57
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 57

Phe Tyr Cys His Ala Lys Arg Glu
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Phe Tyr Cys His Ala Lys Asp Glu
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Phe Tyr Cys His Ala Lys Gln Glu
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Phe Tyr Cys His Ala Lys Glu Glu
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Phe Tyr Cys His Ala Lys Leu Glu
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Phe Tyr Cys His Ala Lys Lys Glu
1               5

<210> SEQ ID NO 63
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 63

Phe Tyr Cys His Ala Lys Met Glu
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct

<400> SEQUENCE: 64

Phe Tyr Cys His Ala Lys Pro Glu
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Construct

<400> SEQUENCE: 65

Phe Tyr Cys His Ala Lys Ser Glu
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic Construct

<400> SEQUENCE: 66

Phe Tyr Cys His Ala Lys Thr Glu
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Construct

<400> SEQUENCE: 67

Phe Tyr Cys His Arg Ala Ala Glu
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Construct

<400> SEQUENCE: 68

Phe Tyr Cys His Arg Ala Arg Glu
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 69

Phe Tyr Cys His Arg Ala Asp Glu
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Construct

<400> SEQUENCE: 70

Phe Tyr Cys His Arg Ala Gln Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Phe Tyr Cys His Arg Ala Glu Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Phe Tyr Cys His Arg Ala Leu Glu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Phe Tyr Cys His Arg Ala Lys Glu
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Phe Tyr Cys His Arg Ala Met Glu
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 75

Phe Tyr Cys His Arg Ala Pro Glu
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Phe Tyr Cys His Arg Ala Ser Glu
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Phe Tyr Cys His Arg Ala Thr Glu
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Construct

<400> SEQUENCE: 78

Phe Tyr Cys His Arg Gln Ala Glu
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Phe Tyr Cys His Arg Gln Arg Glu
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic Construct

<400> SEQUENCE: 80

Phe Tyr Cys His Arg Gln Asp Glu
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81
```

Phe Tyr Cys His Arg Gln Gln Glu
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Phe Tyr Cys His Arg Gln Glu Glu
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct

<400> SEQUENCE: 83

Phe Tyr Cys His Arg Gln Leu Glu
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct

<400> SEQUENCE: 84

Phe Tyr Cys His Arg Gln Lys Glu
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct

<400> SEQUENCE: 85

Phe Tyr Cys His Arg Gln Met Glu
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

Phe Tyr Cys His Arg Gln Pro Glu
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

```
Phe Tyr Cys His Arg Gln Ser Glu
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Phe Tyr Cys His Arg Gln Thr Glu
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Phe Tyr Cys His Arg Glu Ala Glu
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Phe Tyr Cys His Arg Glu Arg Glu
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic Construct

<400> SEQUENCE: 91

Phe Tyr Cys His Arg Glu Asp Glu
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Phe Tyr Cys His Arg Glu Gln Glu
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Phe Tyr Cys His Arg Glu Glu Glu
```

```
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Phe Tyr Cys His Arg Glu Leu Glu
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95

Phe Tyr Cys His Arg Glu Lys Glu
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic Construct

<400> SEQUENCE: 96

Phe Tyr Cys His Arg Glu Met Glu
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

Phe Tyr Cys His Arg Glu Pro Glu
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic Construct

<400> SEQUENCE: 98

Phe Tyr Cys His Arg Glu Ser Glu
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Phe Tyr Cys His Arg Glu Thr Glu
1               5
```

```
<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Phe Tyr Cys His Arg Ile Ala Glu
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Phe Tyr Cys His Arg Ile Arg Glu
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct

<400> SEQUENCE: 102

Phe Tyr Cys His Arg Ile Asp Glu
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 103

Phe Tyr Cys His Arg Ile Gln Glu
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Construct

<400> SEQUENCE: 104

Phe Tyr Cys His Arg Ile Glu Glu
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Phe Tyr Cys His Arg Ile Leu Glu
1               5
```

```
<210> SEQ ID NO 106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 106

Phe Tyr Cys His Arg Ile Lys Glu
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 107

Phe Tyr Cys His Arg Ile Met Glu
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic Construct

<400> SEQUENCE: 108

Phe Tyr Cys His Arg Ile Pro Glu
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Phe Tyr Cys His Arg Ile Ser Glu
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic Construct

<400> SEQUENCE: 110

Phe Tyr Cys His Arg Ile Thr Glu
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic Construct

<400> SEQUENCE: 111

Phe Tyr Cys His Arg Leu Ala Glu
1               5
```

<210> SEQ ID NO 112
<211> LENGTH: 8
<212> TYPE: PRT
<213> ORGANISM: Artificial Sequence
<220> FEATURE:
<223> OTHER INFORMATION: Synthetic Construct

<400> SEQUENCE: 112

Phe Tyr Cys His Arg Leu Arg Glu
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

Phe Tyr Cys His Arg Leu Asp Glu
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 114

Phe Tyr Cys His Arg Leu Gln Glu
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct

<400> SEQUENCE: 115

Phe Tyr Cys His Arg Leu Glu Glu
1               5

<210> SEQ ID NO 116
<211> LENGTH: 8
<212> TYPE: PRT
<213> ORGANISM: Artificial Sequence
<220> FEATURE:
<223> OTHER INFORMATION: Synthetic Construct

<400> SEQUENCE: 116

Phe Tyr Cys His Arg Leu Leu Glu
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic Construct

<400> SEQUENCE: 117

Phe Tyr Cys His Arg Leu Lys Glu
1               5

<210> SEQ ID NO 118

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 118

Phe Tyr Cys His Arg Leu Met Glu
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic Construct

<400> SEQUENCE: 119

Phe Tyr Cys His Arg Leu Pro Glu
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 120

Phe Tyr Cys His Arg Leu Ser Glu
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 121

Phe Tyr Cys His Arg Leu Thr Glu
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic Construct

<400> SEQUENCE: 122

Phe Tyr Cys His Arg Lys Ala Glu
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic Construct

<400> SEQUENCE: 123

Phe Tyr Cys His Arg Lys Arg Glu
1               5

<210> SEQ ID NO 124
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 124

Phe Tyr Cys His Arg Lys Asp Glu
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Phe Tyr Cys His Arg Lys Gln Glu
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Phe Tyr Cys His Arg Lys Glu Glu
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 127

Phe Tyr Cys His Arg Lys Leu Glu
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Phe Tyr Cys His Arg Lys Lys Glu
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic Construct

<400> SEQUENCE: 129

Phe Tyr Cys His Arg Lys Met Glu
1               5

<210> SEQ ID NO 130
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 130

Phe Tyr Cys His Arg Lys Pro Glu
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic Construct

<400> SEQUENCE: 131

Phe Tyr Cys His Arg Lys Ser Glu
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic Construct

<400> SEQUENCE: 132

Phe Tyr Cys His Arg Lys Thr Glu
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic Construct

<400> SEQUENCE: 133

Phe Tyr Cys His Asn Lys Thr Glu
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic Construct

<400> SEQUENCE: 134

Phe Tyr Cys His Asn Ala Ala Glu
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic Construct

<400> SEQUENCE: 135

Phe Tyr Cys His Asn Ala Arg Glu
1               5

<210> SEQ ID NO 136
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 136

Phe Tyr Cys His Asn Ala Asp Glu
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic Construct

<400> SEQUENCE: 137

Phe Tyr Cys His Asn Ala Gln Glu
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic Construct

<400> SEQUENCE: 138

Phe Tyr Cys His Asn Ala Glu Glu
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic Construct

<400> SEQUENCE: 139

Phe Tyr Cys His Asn Ala Leu Glu
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 140

Phe Tyr Cys His Asn Ala Lys Glu
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 141

Phe Tyr Cys His Asn Ala Met Glu
1               5

<210> SEQ ID NO 142
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 142

Phe Tyr Cys His Asn Ala Pro Glu
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct

<400> SEQUENCE: 143

Phe Tyr Cys His Asn Ala Ser Glu
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic Construct

<400> SEQUENCE: 144

Phe Tyr Cys His Asn Ala Thr Glu
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic Construct

<400> SEQUENCE: 145

Phe Tyr Cys His Asn Gln Ala Glu
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic Construct

<400> SEQUENCE: 146

Phe Tyr Cys His Asn Gln Arg Glu
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic Construct

<400> SEQUENCE: 147

Phe Tyr Cys His Asn Gln Asp Glu
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic Construct

<400> SEQUENCE: 148

Phe Tyr Cys His Asn Gln Gln Glu
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149

Phe Tyr Cys His Asn Gln Glu Glu
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Phe Tyr Cys His Asn Gln Leu Glu
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic Construct

<400> SEQUENCE: 151

Phe Tyr Cys His Asn Gln Lys Glu
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic Construct

<400> SEQUENCE: 152

Phe Tyr Cys His Asn Gln Met Glu
1               5

<210> SEQ ID NO 153
<211> LENGTH: 8
<212> TYPE: PRT
<213> ORGANISM: Artificial Sequence
<220> FEATURE:
<223> OTHER INFORMATION: Synthetic Construct

<400> SEQUENCE: 153

Phe Tyr Cys His Asn Gln Pro Glu
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic Construct

<400> SEQUENCE: 154

Phe Tyr Cys His Asn Gln Ser Glu
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic Construct

<400> SEQUENCE: 155

Phe Tyr Cys His Asn Gln Thr Glu
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic Construct

<400> SEQUENCE: 156

Phe Tyr Cys His Asn Glu Ala Glu
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic Construct

<400> SEQUENCE: 157

Phe Tyr Cys His Asn Glu Arg Glu
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic Construct

<400> SEQUENCE: 158

Phe Tyr Cys His Asn Glu Asp Glu
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic Construct

<400> SEQUENCE: 159

Phe Tyr Cys His Asn Glu Gln Glu
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic Construct

<400> SEQUENCE: 160

```
Phe Tyr Cys His Asn Glu Glu Glu
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Phe Tyr Cys His Asn Glu Leu Glu
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic Construct

<400> SEQUENCE: 162

Phe Tyr Cys His Asn Glu Lys Glu
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic Construct

<400> SEQUENCE: 163

Phe Tyr Cys His Asn Glu Met Glu
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic Construct

<400> SEQUENCE: 164

Phe Tyr Cys His Asn Glu Pro Glu
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic Construct

<400> SEQUENCE: 165

Phe Tyr Cys His Asn Glu Ser Glu
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic Construct

<400> SEQUENCE: 166
```

```
Phe Tyr Cys His Asn Glu Thr Glu
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 167

Phe Tyr Cys His Asn Ile Ala Glu
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Phe Tyr Cys His Asn Ile Arg Glu
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct

<400> SEQUENCE: 169

Phe Tyr Cys His Asn Ile Asp Glu
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic Construct

<400> SEQUENCE: 170

Phe Tyr Cys His Asn Ile Gln Glu
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic Construct

<400> SEQUENCE: 171

Phe Tyr Cys His Asn Ile Glu Glu
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic Construct

<400> SEQUENCE: 172

Phe Tyr Cys His Asn Ile Leu Glu
```

1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 173

Phe Tyr Cys His Asn Ile Lys Glu
1               5

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct

<400> SEQUENCE: 174

Phe Tyr Cys His Asn Ile Met Glu
1               5

<210> SEQ ID NO 175
<211> LENGTH: 8
<212> TYPE: PRT
<213> ORGANISM: Artificial Sequence
<220> FEATURE:
<223> OTHER INFORMATION: Synthetic Construct

<400> SEQUENCE: 175

Phe Tyr Cys His Asn Ile Pro Glu
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic Construct

<400> SEQUENCE: 176

Phe Tyr Cys His Asn Ile Ser Glu
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic Construct

<400> SEQUENCE: 177

Phe Tyr Cys His Asn Ile Thr Glu
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic Construct

<400> SEQUENCE: 178

Phe Tyr Cys His Asn Leu Ala Glu
1               5

```
<210> SEQ ID NO 179
<211> LENGTH: 8
<212> TYPE: PRT
<213> ORGANISM: Artificial Sequence
<220> FEATURE:
<223> OTHER INFORMATION: Synthetic Construct

<400> SEQUENCE: 179

Phe Tyr Cys His Asn Leu Arg Glu
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic Construct

<400> SEQUENCE: 180

Phe Tyr Cys His Asn Leu Asp Glu
1               5

<210> SEQ ID NO 181
<211> LENGTH: 8
<212> TYPE: PRT
<213> ORGANISM: Artificial Sequence
<220> FEATURE:
<223> OTHER INFORMATION: Synthetic Construct

<400> SEQUENCE: 181

Phe Tyr Cys His Asn Leu Gln Glu
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic Construct

<400> SEQUENCE: 182

Phe Tyr Cys His Asn Leu Glu Glu
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic Construct

<400> SEQUENCE: 183

Phe Tyr Cys His Asn Leu Leu Glu
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic Construct

<400> SEQUENCE: 184

Phe Tyr Cys His Asn Leu Lys Glu
1               5
```

```
<210> SEQ ID NO 185
<211> LENGTH: 8
<212> TYPE: PRT
<213> ORGANISM: Artificial Sequence
<220> FEATURE:
<223> OTHER INFORMATION: Synthetic Construct

<400> SEQUENCE: 185

Phe Tyr Cys His Asn Leu Met Glu
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic Construct

<400> SEQUENCE: 186

Phe Tyr Cys His Asn Leu Pro Glu
1               5

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Phe Tyr Cys His Asn Leu Ser Glu
1               5

<210> SEQ ID NO 188
<211> LENGTH: 8
<212> TYPE: PRT
<213> ORGANISM: Artificial Sequence
<220> FEATURE:
<223> OTHER INFORMATION: Synthetic Construct

<400> SEQUENCE: 188

Phe Tyr Cys His Asn Leu Thr Glu
1               5

<210> SEQ ID NO 189
<211> LENGTH: 8
<212> TYPE: PRT
<213> ORGANISM: Artificial Sequence
<220> FEATURE:
<223> OTHER INFORMATION: Synthetic Construct

<400> SEQUENCE: 189

Phe Tyr Cys His Asn Lys Ala Glu
1               5

<210> SEQ ID NO 190
<211> LENGTH: 8
<212> TYPE: PRT
<213> ORGANISM: Artificial Sequence
<220> FEATURE:
<223> OTHER INFORMATION: Synthetic Construct

<400> SEQUENCE: 190

Phe Tyr Cys His Asn Lys Arg Glu
1               5
```

```
<210> SEQ ID NO 191
<211> LENGTH: 8
<212> TYPE: PRT
<213> ORGANISM: Artificial Sequence
<220> FEATURE:
<223> OTHER INFORMATION: Synthetic Construct

<400> SEQUENCE: 191

Phe Tyr Cys His Asn Lys Asp Glu
1               5

<210> SEQ ID NO 192
<211> LENGTH: 8
<212> TYPE: PRT
<213> ORGANISM: Artificial Sequence
<220> FEATURE:
<223> OTHER INFORMATION: Synthetic Construct

<400> SEQUENCE: 192

Phe Tyr Cys His Asn Lys Gln Glu
1               5

<210> SEQ ID NO 193
<211> LENGTH: 8
<212> TYPE: PRT
<213> ORGANISM: Artificial Sequence
<220> FEATURE:
<223> OTHER INFORMATION: Synthetic Construct

<400> SEQUENCE: 193

Phe Tyr Cys His Asn Lys Glu Glu
1               5

<210> SEQ ID NO 194
<211> LENGTH: 8
<212> TYPE: PRT
<213> ORGANISM: Artificial Sequence
<220> FEATURE:
<223> OTHER INFORMATION: Synthetic Construct

<400> SEQUENCE: 194

Phe Tyr Cys His Asn Lys Leu Glu
1               5

<210> SEQ ID NO 195
<211> LENGTH: 8
<212> TYPE: PRT
<213> ORGANISM: Artificial Sequence
<220> FEATURE:
<223> OTHER INFORMATION: Synthetic Construct

<400> SEQUENCE: 195

Phe Tyr Cys His Asn Lys Lys Glu
1               5

<210> SEQ ID NO 196
<211> LENGTH: 8
<212> TYPE: PRT
<213> ORGANISM: Artificial Sequence
<220> FEATURE:
<223> OTHER INFORMATION: Synthetic Construct

<400> SEQUENCE: 196

Phe Tyr Cys His Asn Lys Met Glu
1               5

<210> SEQ ID NO 197
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 197

Phe Tyr Cys His Asn Lys Pro Glu
1               5

<210> SEQ ID NO 198
<211> LENGTH: 8
<212> TYPE: PRT
<213> ORGANISM: Artificial Sequence
<220> FEATURE:
<223> OTHER INFORMATION: Synthetic Construct

<400> SEQUENCE: 198

Phe Tyr Cys His Asn Lys Ser Glu
1               5

<210> SEQ ID NO 199
<211> LENGTH: 8
<212> TYPE: PRT
<213> ORGANISM: Artificial Sequence
<220> FEATURE:
<223> OTHER INFORMATION: Synthetic Construct

<400> SEQUENCE: 199

Phe Tyr Cys His Asp Lys Thr Glu
1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic Construct

<400> SEQUENCE: 200

Phe Tyr Cys His Asp Lys Pro Glu
1               5

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 201

Phe Tyr Cys His Asp Lys Ser Glu
1               5

<210> SEQ ID NO 202
<211> LENGTH: 8
<212> TYPE: PRT
<213> ORGANISM: Artificial Sequence
<220> FEATURE:
<223> OTHER INFORMATION: Synthetic Construct

<400> SEQUENCE: 202

Phe Tyr Cys His Asp Lys Arg Glu
1               5

<210> SEQ ID NO 203
<211> LENGTH: 8
```

<212> TYPE: PRT
<213> ORGANISM: Artificial Sequence
<220> FEATURE:
<223> OTHER INFORMATION: Synthetic Construct

<400> SEQUENCE: 203

Phe Tyr Cys His Asp Lys Asp Glu
1               5

<210> SEQ ID NO 204
<211> LENGTH: 8
<212> TYPE: PRT
<213> ORGANISM: Artificial Sequence
<220> FEATURE:
<223> OTHER INFORMATION: Synthetic Construct

<400> SEQUENCE: 204

Phe Tyr Cys His Asp Ala Ala Glu
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic Construct

<400> SEQUENCE: 205

Phe Tyr Cys His Asp Ala Arg Glu
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic Construct

<400> SEQUENCE: 206

Phe Tyr Cys His Asp Ala Asp Glu
1               5

<210> SEQ ID NO 207
<211> LENGTH: 8
<212> TYPE: PRT
<213> ORGANISM: Artificial Sequence
<220> FEATURE:
<223> OTHER INFORMATION: Synthetic Construct

<400> SEQUENCE: 207

Phe Tyr Cys His Asp Ala Gln Glu
1               5

<210> SEQ ID NO 208
<211> LENGTH: 8
<212> TYPE: PRT
<213> ORGANISM: Artificial Sequence
<220> FEATURE:
<223> OTHER INFORMATION: Synthetic Construct

<400> SEQUENCE: 208

Phe Tyr Cys His Asp Ala Glu Glu
1               5

<210> SEQ ID NO 209
<211> LENGTH: 8
<212> TYPE: PRT

<213> ORGANISM: Artificial Sequence
<220> FEATURE:
<223> OTHER INFORMATION: Synthetic Construct

<400> SEQUENCE: 209

Phe Tyr Cys His Asp Ala Leu Glu
1               5

<210> SEQ ID NO 210
<211> LENGTH: 8
<212> TYPE: PRT
<213> ORGANISM: Artificial Sequence
<220> FEATURE:
<223> OTHER INFORMATION: Synthetic Construct

<400> SEQUENCE: 210

Phe Tyr Cys His Asp Ala Lys Glu
1               5

<210> SEQ ID NO 211
<211> LENGTH: 8
<212> TYPE: PRT
<213> ORGANISM: Artificial Sequence
<220> FEATURE:
<223> OTHER INFORMATION: Synthetic Construct

<400> SEQUENCE: 211

Phe Tyr Cys His Asp Ala Met Glu
1               5

<210> SEQ ID NO 212
<211> LENGTH: 8
<212> TYPE: PRT
<213> ORGANISM: Artificial Sequence
<220> FEATURE:
<223> OTHER INFORMATION: Synthetic Construct

<400> SEQUENCE: 212

Phe Tyr Cys His Asp Ala Pro Glu
1               5

<210> SEQ ID NO 213
<211> LENGTH: 8
<212> TYPE: PRT
<213> ORGANISM: Artificial Sequence
<220> FEATURE:
<223> OTHER INFORMATION: Synthetic Construct

<400> SEQUENCE: 213

Phe Tyr Cys His Asp Ala Ser Glu
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic Construct

<400> SEQUENCE: 214

Phe Tyr Cys His Asp Ala Thr Glu
1               5

<210> SEQ ID NO 215
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 215

Phe Tyr Cys His Asp Gln Ala Glu
1               5

<210> SEQ ID NO 216
<211> LENGTH: 8
<212> TYPE: PRT
<213> ORGANISM: Artificial Sequence
<220> FEATURE:
<223> OTHER INFORMATION: Synthetic Construct

<400> SEQUENCE: 216

Phe Tyr Cys His Asp Gln Arg Glu
1               5

<210> SEQ ID NO 217
<211> LENGTH: 8
<212> TYPE: PRT
<213> ORGANISM: Artificial Sequence
<220> FEATURE:
<223> OTHER INFORMATION: Synthetic Construct

<400> SEQUENCE: 217

Phe Tyr Cys His Asp Gln Asp Glu
1               5

<210> SEQ ID NO 218
<211> LENGTH: 8
<212> TYPE: PRT
<213> ORGANISM: Artificial Sequence
<220> FEATURE:
<223> OTHER INFORMATION: Synthetic Construct

<400> SEQUENCE: 218

Phe Tyr Cys His Asp Gln Gln Glu
1               5

<210> SEQ ID NO 219
<211> LENGTH: 8
<212> TYPE: PRT
<213> ORGANISM: Artificial Sequence
<220> FEATURE:
<223> OTHER INFORMATION: Synthetic Construct

<400> SEQUENCE: 219

Phe Tyr Cys His Asp Gln Glu Glu
1               5

<210> SEQ ID NO 220
<211> LENGTH: 8
<212> TYPE: PRT
<213> ORGANISM: Artificial Sequence
<220> FEATURE:
<223> OTHER INFORMATION: Synthetic Construct

<400> SEQUENCE: 220

Phe Tyr Cys His Asp Gln Leu Glu
1               5

<210> SEQ ID NO 221
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 221

Phe Tyr Cys His Asp Gln Lys Glu
1               5

<210> SEQ ID NO 222
<211> LENGTH: 8
<212> TYPE: PRT
<213> ORGANISM: Artificial Sequence
<220> FEATURE:
<223> OTHER INFORMATION: Synthetic Construct

<400> SEQUENCE: 222

Phe Tyr Cys His Asp Gln Met Glu
1               5

<210> SEQ ID NO 223
<211> LENGTH: 8
<212> TYPE: PRT
<213> ORGANISM: Artificial Sequence
<220> FEATURE:
<223> OTHER INFORMATION: Synthetic Construct

<400> SEQUENCE: 223

Phe Tyr Cys His Asp Gln Pro Glu
1               5

<210> SEQ ID NO 224
<211> LENGTH: 8
<212> TYPE: PRT
<213> ORGANISM: Artificial Sequence
<220> FEATURE:
<223> OTHER INFORMATION: Synthetic Construct

<400> SEQUENCE: 224

Phe Tyr Cys His Asp Gln Ser Glu
1               5

<210> SEQ ID NO 225
<211> LENGTH: 8
<212> TYPE: PRT
<213> ORGANISM: Artificial Sequence
<220> FEATURE:
<223> OTHER INFORMATION: Synthetic Construct

<400> SEQUENCE: 225

Phe Tyr Cys His Asp Gln Thr Glu
1               5

<210> SEQ ID NO 226
<211> LENGTH: 8
<212> TYPE: PRT
<213> ORGANISM: Artificial Sequence
<220> FEATURE:
<223> OTHER INFORMATION: Synthetic Construct

<400> SEQUENCE: 226

Phe Tyr Cys His Asp Glu Ala Glu
1               5

<210> SEQ ID NO 227
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 227

Phe Tyr Cys His Asp Glu Arg Glu
1               5

<210> SEQ ID NO 228
<211> LENGTH: 8
<212> TYPE: PRT
<213> ORGANISM: Artificial Sequence
<220> FEATURE:
<223> OTHER INFORMATION: Synthetic Construct

<400> SEQUENCE: 228

Phe Tyr Cys His Asp Glu Asp Glu
1               5

<210> SEQ ID NO 229
<211> LENGTH: 8
<212> TYPE: PRT
<213> ORGANISM: Artificial Sequence
<220> FEATURE:
<223> OTHER INFORMATION: Synthetic Construct

<400> SEQUENCE: 229

Phe Tyr Cys His Asp Glu Gln Glu
1               5

<210> SEQ ID NO 230
<211> LENGTH: 8
<212> TYPE: PRT
<213> ORGANISM: Artificial Sequence
<220> FEATURE:
<223> OTHER INFORMATION: Synthetic Construct

<400> SEQUENCE: 230

Phe Tyr Cys His Asp Glu Glu Glu
1               5

<210> SEQ ID NO 231
<211> LENGTH: 8
<212> TYPE: PRT
<213> ORGANISM: Artificial Sequence
<220> FEATURE:
<223> OTHER INFORMATION: Synthetic Construct

<400> SEQUENCE: 231

Phe Tyr Cys His Asp Glu Leu Glu
1               5

<210> SEQ ID NO 232
<211> LENGTH: 8
<212> TYPE: PRT
<213> ORGANISM: Artificial Sequence
<220> FEATURE:
<223> OTHER INFORMATION: Synthetic Construct

<400> SEQUENCE: 232

Phe Tyr Cys His Asp Glu Lys Glu
1               5

<210> SEQ ID NO 233
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 233

Phe Tyr Cys His Asp Glu Met Glu
1               5

<210> SEQ ID NO 234
<211> LENGTH: 8
<212> TYPE: PRT
<213> ORGANISM: Artificial Sequence
<220> FEATURE:
<223> OTHER INFORMATION: Synthetic Construct

<400> SEQUENCE: 234

Phe Tyr Cys His Asp Glu Pro Glu
1               5

<210> SEQ ID NO 235
<211> LENGTH: 8
<212> TYPE: PRT
<213> ORGANISM: Artificial Sequence
<220> FEATURE:
<223> OTHER INFORMATION: Synthetic Construct

<400> SEQUENCE: 235

Phe Tyr Cys His Asp Glu Ser Glu
1               5

<210> SEQ ID NO 236
<211> LENGTH: 8
<212> TYPE: PRT
<213> ORGANISM: Artificial Sequence
<220> FEATURE:
<223> OTHER INFORMATION: Synthetic Construct

<400> SEQUENCE: 236

Phe Tyr Cys His Asp Glu Thr Glu
1               5

<210> SEQ ID NO 237
<211> LENGTH: 8
<212> TYPE: PRT
<213> ORGANISM: Artificial Sequence
<220> FEATURE:
<223> OTHER INFORMATION: Synthetic Construct

<400> SEQUENCE: 237

Phe Tyr Cys His Asp Ile Ala Glu
1               5

<210> SEQ ID NO 238
<211> LENGTH: 8
<212> TYPE: PRT
<213> ORGANISM: Artificial Sequence
<220> FEATURE:
<223> OTHER INFORMATION: Synthetic Construct

<400> SEQUENCE: 238

Phe Tyr Cys His Asp Ile Arg Glu
1               5

<210> SEQ ID NO 239
<211> LENGTH: 8
<212> TYPE: PRT
<213> ORGANISM: Artificial Sequence
<220> FEATURE:
<223> OTHER INFORMATION: Synthetic Construct

<400> SEQUENCE: 239
```

Phe Tyr Cys His Asp Ile Asp Glu
1               5

<210> SEQ ID NO 240
<211> LENGTH: 8
<212> TYPE: PRT
<213> ORGANISM: Artificial Sequence
<220> FEATURE:
<223> OTHER INFORMATION: Synthetic Construct

<400> SEQUENCE: 240

Phe Tyr Cys His Asp Ile Gln Glu
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic Construct

<400> SEQUENCE: 241

Phe Tyr Cys His Asp Ile Glu Glu
1               5

<210> SEQ ID NO 242
<211> LENGTH: 8
<212> TYPE: PRT
<213> ORGANISM: Artificial Sequence
<220> FEATURE:
<223> OTHER INFORMATION: Synthetic Construct

<400> SEQUENCE: 242

Phe Tyr Cys His Asp Ile Leu Glu
1               5

<210> SEQ ID NO 243
<211> LENGTH: 8
<212> TYPE: PRT
<213> ORGANISM: Artificial Sequence
<220> FEATURE:
<223> OTHER INFORMATION: Synthetic Construct

<400> SEQUENCE: 243

Phe Tyr Cys His Asp Ile Lys Glu
1               5

<210> SEQ ID NO 244
<211> LENGTH: 8
<212> TYPE: PRT
<213> ORGANISM: Artificial Sequence
<220> FEATURE:
<223> OTHER INFORMATION: Synthetic Construct

<400> SEQUENCE: 244

Phe Tyr Cys His Asp Ile Met Glu
1               5

<210> SEQ ID NO 245
<211> LENGTH: 8
<212> TYPE: PRT
<213> ORGANISM: Artificial Sequence
<220> FEATURE:
<223> OTHER INFORMATION: Synthetic Construct

<400> SEQUENCE: 245

Phe Tyr Cys His Asp Ile Pro Glu
1               5

<210> SEQ ID NO 246
<211> LENGTH: 8
<212> TYPE: PRT
<213> ORGANISM: Artificial Sequence
<220> FEATURE:
<223> OTHER INFORMATION: Synthetic Construct

<400> SEQUENCE: 246

Phe Tyr Cys His Asp Ile Ser Glu
1               5

<210> SEQ ID NO 247
<211> LENGTH: 8
<212> TYPE: PRT
<213> ORGANISM: Artificial Sequence
<220> FEATURE:
<223> OTHER INFORMATION: Synthetic Construct

<400> SEQUENCE: 247

Phe Tyr Cys His Asp Ile Thr Glu
1               5

<210> SEQ ID NO 248
<211> LENGTH: 8
<212> TYPE: PRT
<213> ORGANISM: Artificial Sequence
<220> FEATURE:
<223> OTHER INFORMATION: Synthetic Construct

<400> SEQUENCE: 248

Phe Tyr Cys His Asp Leu Ala Glu
1               5

<210> SEQ ID NO 249
<211> LENGTH: 8
<212> TYPE: PRT
<213> ORGANISM: Artificial Sequence
<220> FEATURE:
<223> OTHER INFORMATION: Synthetic Construct

<400> SEQUENCE: 249

Phe Tyr Cys His Asp Leu Arg Glu
1               5

<210> SEQ ID NO 250
<211> LENGTH: 8
<212> TYPE: PRT
<213> ORGANISM: Artificial Sequence
<220> FEATURE:
<223> OTHER INFORMATION: Synthetic Construct

<400> SEQUENCE: 250

Phe Tyr Cys His Asp Leu Asp Glu
1               5

<210> SEQ ID NO 251
<211> LENGTH: 8
<212> TYPE: PRT
<213> ORGANISM: Artificial Sequence
<220> FEATURE:
<223> OTHER INFORMATION: Synthetic Construct

<400> SEQUENCE: 251

Phe Tyr Cys His Asp Leu Gln Glu

```
1               5

<210> SEQ ID NO 252
<211> LENGTH: 8
<212> TYPE: PRT
<213> ORGANISM: Artificial Sequence
<220> FEATURE:
<223> OTHER INFORMATION: Synthetic Construct

<400> SEQUENCE: 252

Phe Tyr Cys His Asp Leu Glu Glu
1               5

<210> SEQ ID NO 253
<211> LENGTH: 8
<212> TYPE: PRT
<213> ORGANISM: Artificial Sequence
<220> FEATURE:
<223> OTHER INFORMATION: Synthetic Construct

<400> SEQUENCE: 253

Phe Tyr Cys His Asp Leu Leu Glu
1               5

<210> SEQ ID NO 254
<211> LENGTH: 8
<212> TYPE: PRT
<213> ORGANISM: Artificial Sequence
<220> FEATURE:
<223> OTHER INFORMATION: Synthetic Construct

<400> SEQUENCE: 254

Phe Tyr Cys His Asp Leu Lys Glu
1               5

<210> SEQ ID NO 255
<211> LENGTH: 8
<212> TYPE: PRT
<213> ORGANISM: Artificial Sequence
<220> FEATURE:
<223> OTHER INFORMATION: Synthetic Construct

<400> SEQUENCE: 255

Phe Tyr Cys His Asp Leu Met Glu
1               5

<210> SEQ ID NO 256
<211> LENGTH: 8
<212> TYPE: PRT
<213> ORGANISM: Artificial Sequence
<220> FEATURE:
<223> OTHER INFORMATION: Synthetic Construct

<400> SEQUENCE: 256

Phe Tyr Cys His Asp Leu Pro Glu
1               5

<210> SEQ ID NO 257
<211> LENGTH: 8
<212> TYPE: PRT
<213> ORGANISM: Artificial Sequence
<220> FEATURE:
<223> OTHER INFORMATION: Synthetic Construct

<400> SEQUENCE: 257

Phe Tyr Cys His Asp Leu Ser Glu
1               5
```

```
<210> SEQ ID NO 258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 258

Phe Tyr Cys His Asp Leu Thr Glu
1               5

<210> SEQ ID NO 259
<211> LENGTH: 8
<212> TYPE: PRT
<213> ORGANISM: Artificial Sequence
<220> FEATURE:
<223> OTHER INFORMATION: Synthetic Construct

<400> SEQUENCE: 259

Phe Tyr Cys His Asp Lys Ala Glu
1               5

<210> SEQ ID NO 260
<211> LENGTH: 8
<212> TYPE: PRT
<213> ORGANISM: Artificial Sequence
<220> FEATURE:
<223> OTHER INFORMATION: Synthetic Construct

<400> SEQUENCE: 260

Phe Tyr Cys His Asp Lys Gln Glu
1               5

<210> SEQ ID NO 261
<211> LENGTH: 8
<212> TYPE: PRT
<213> ORGANISM: Artificial Sequence
<220> FEATURE:
<223> OTHER INFORMATION: Synthetic Construct

<400> SEQUENCE: 261

Phe Tyr Cys His Asp Lys Glu Glu
1               5

<210> SEQ ID NO 262
<211> LENGTH: 8
<212> TYPE: PRT
<213> ORGANISM: Artificial Sequence
<220> FEATURE:
<223> OTHER INFORMATION: Synthetic Construct

<400> SEQUENCE: 262

Phe Tyr Cys His Asp Lys Leu Glu
1               5

<210> SEQ ID NO 263
<211> LENGTH: 8
<212> TYPE: PRT
<213> ORGANISM: Artificial Sequence
<220> FEATURE:
<223> OTHER INFORMATION: Synthetic Construct

<400> SEQUENCE: 263

Phe Tyr Cys His Asp Lys Lys Glu
1               5
```

<210> SEQ ID NO 264
<211> LENGTH: 8
<212> TYPE: PRT
<213> ORGANISM: Artificial Sequence
<220> FEATURE:
<223> OTHER INFORMATION: Synthetic Construct

<400> SEQUENCE: 264

Phe Tyr Cys His Asp Lys Met Glu
1               5

<210> SEQ ID NO 265
<211> LENGTH: 8
<212> TYPE: PRT
<213> ORGANISM: Artificial Sequence
<220> FEATURE:
<223> OTHER INFORMATION: Synthetic Construct

<400> SEQUENCE: 265

Phe Tyr Cys His Gln Lys Thr Glu
1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic Construct

<400> SEQUENCE: 266

Phe Tyr Cys His Gln Lys Pro Glu
1               5

<210> SEQ ID NO 267
<211> LENGTH: 8
<212> TYPE: PRT
<213> ORGANISM: Artificial Sequence
<220> FEATURE:
<223> OTHER INFORMATION: Synthetic Construct

<400> SEQUENCE: 267

Phe Tyr Cys His Gln Ala Ala Glu
1               5

<210> SEQ ID NO 268
<211> LENGTH: 8
<212> TYPE: PRT
<213> ORGANISM: Artificial Sequence
<220> FEATURE:
<223> OTHER INFORMATION: Synthetic Construct

<400> SEQUENCE: 268

Phe Tyr Cys His Gln Ala Arg Glu
1               5

<210> SEQ ID NO 269
<211> LENGTH: 8
<212> TYPE: PRT
<213> ORGANISM: Artificial Sequence
<220> FEATURE:
<223> OTHER INFORMATION: Synthetic Construct

<400> SEQUENCE: 269

Phe Tyr Cys His Gln Ala Asp Glu
1               5

```
<210> SEQ ID NO 270
<211> LENGTH: 8
<212> TYPE: PRT
<213> ORGANISM: Artificial Sequence
<220> FEATURE:
<223> OTHER INFORMATION: Synthetic Construct

<400> SEQUENCE: 270

Phe Tyr Cys His Gln Ala Gln Glu
1               5

<210> SEQ ID NO 271
<211> LENGTH: 8
<212> TYPE: PRT
<213> ORGANISM: Artificial Sequence
<220> FEATURE:
<223> OTHER INFORMATION: Synthetic Construct

<400> SEQUENCE: 271

Phe Tyr Cys His Gln Ala Glu Glu
1               5

<210> SEQ ID NO 272
<211> LENGTH: 8
<212> TYPE: PRT
<213> ORGANISM: Artificial Sequence
<220> FEATURE:
<223> OTHER INFORMATION: Synthetic Construct

<400> SEQUENCE: 272

Phe Tyr Cys His Gln Ala Leu Glu
1               5

<210> SEQ ID NO 273
<211> LENGTH: 8
<212> TYPE: PRT
<213> ORGANISM: Artificial Sequence
<220> FEATURE:
<223> OTHER INFORMATION: Synthetic Construct

<400> SEQUENCE: 273

Phe Tyr Cys His Gln Ala Lys Glu
1               5

<210> SEQ ID NO 274
<211> LENGTH: 8
<212> TYPE: PRT
<213> ORGANISM: Artificial Sequence
<220> FEATURE:
<223> OTHER INFORMATION: Synthetic Construct

<400> SEQUENCE: 274

Phe Tyr Cys His Gln Ala Met Glu
1               5

<210> SEQ ID NO 275
<211> LENGTH: 8
<212> TYPE: PRT
<213> ORGANISM: Artificial Sequence
<220> FEATURE:
<223> OTHER INFORMATION: Synthetic Construct

<400> SEQUENCE: 275

Phe Tyr Cys His Gln Ala Pro Glu
1               5

<210> SEQ ID NO 276
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 276

Phe Tyr Cys His Gln Ala Ser Glu
1               5

<210> SEQ ID NO 277
<211> LENGTH: 8
<212> TYPE: PRT
<213> ORGANISM: Artificial Sequence
<220> FEATURE:
<223> OTHER INFORMATION: Synthetic Construct

<400> SEQUENCE: 277

Phe Tyr Cys His Gln Ala Thr Glu
1               5

<210> SEQ ID NO 278
<211> LENGTH: 8
<212> TYPE: PRT
<213> ORGANISM: Artificial Sequence
<220> FEATURE:
<223> OTHER INFORMATION: Synthetic Construct

<400> SEQUENCE: 278

Phe Tyr Cys His Gln Gln Ala Glu
1               5

<210> SEQ ID NO 279
<211> LENGTH: 8
<212> TYPE: PRT
<213> ORGANISM: Artificial Sequence
<220> FEATURE:
<223> OTHER INFORMATION: Synthetic Construct

<400> SEQUENCE: 279

Phe Tyr Cys His Gln Gln Arg Glu
1               5

<210> SEQ ID NO 280
<211> LENGTH: 8
<212> TYPE: PRT
<213> ORGANISM: Artificial Sequence
<220> FEATURE:
<223> OTHER INFORMATION: Synthetic Construct

<400> SEQUENCE: 280

Phe Tyr Cys His Gln Gln Asp Glu
1               5

<210> SEQ ID NO 281
<211> LENGTH: 8
<212> TYPE: PRT
<213> ORGANISM: Artificial Sequence
<220> FEATURE:
<223> OTHER INFORMATION: Synthetic Construct

<400> SEQUENCE: 281

Phe Tyr Cys His Gln Gln Gln Glu
1               5

<210> SEQ ID NO 282
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 282

Phe Tyr Cys His Gln Gln Glu Glu
1               5

<210> SEQ ID NO 283
<211> LENGTH: 8
<212> TYPE: PRT
<213> ORGANISM: Artificial Sequence
<220> FEATURE:
<223> OTHER INFORMATION: Synthetic Construct

<400> SEQUENCE: 283

Phe Tyr Cys His Gln Gln Leu Glu
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic Construct

<400> SEQUENCE: 284

Phe Tyr Cys His Gln Gln Lys Glu
1               5

<210> SEQ ID NO 285
<211> LENGTH: 8
<212> TYPE: PRT
<213> ORGANISM: Artificial Sequence
<220> FEATURE:
<223> OTHER INFORMATION: Synthetic Construct

<400> SEQUENCE: 285

Phe Tyr Cys His Gln Gln Met Glu
1               5

<210> SEQ ID NO 286
<211> LENGTH: 8
<212> TYPE: PRT
<213> ORGANISM: Artificial Sequence
<220> FEATURE:
<223> OTHER INFORMATION: Synthetic Construct

<400> SEQUENCE: 286

Phe Tyr Cys His Gln Gln Pro Glu
1               5

<210> SEQ ID NO 287
<211> LENGTH: 8
<212> TYPE: PRT
<213> ORGANISM: Artificial Sequence
<220> FEATURE:
<223> OTHER INFORMATION: Synthetic Construct

<400> SEQUENCE: 287

Phe Tyr Cys His Gln Gln Ser Glu
1               5

<210> SEQ ID NO 288
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 288

Phe Tyr Cys His Gln Gln Thr Glu
1               5

<210> SEQ ID NO 289
<211> LENGTH: 8
<212> TYPE: PRT
<213> ORGANISM: Artificial Sequence
<220> FEATURE:
<223> OTHER INFORMATION: Synthetic Construct

<400> SEQUENCE: 289

Phe Tyr Cys His Gln Glu Ala Glu
1               5

<210> SEQ ID NO 290
<211> LENGTH: 8
<212> TYPE: PRT
<213> ORGANISM: Artificial Sequence
<220> FEATURE:
<223> OTHER INFORMATION: Synthetic Construct

<400> SEQUENCE: 290

Phe Tyr Cys His Gln Glu Arg Glu
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic Construct

<400> SEQUENCE: 291

Phe Tyr Cys His Gln Glu Asp Glu
1               5

<210> SEQ ID NO 292
<211> LENGTH: 8
<212> TYPE: PRT
<213> ORGANISM: Artificial Sequence
<220> FEATURE:
<223> OTHER INFORMATION: Synthetic Construct

<400> SEQUENCE: 292

Phe Tyr Cys His Gln Glu Gln Glu
1               5

<210> SEQ ID NO 293
<211> LENGTH: 8
<212> TYPE: PRT
<213> ORGANISM: Artificial Sequence
<220> FEATURE:
<223> OTHER INFORMATION: Synthetic Construct

<400> SEQUENCE: 293

Phe Tyr Cys His Gln Glu Glu Glu
1               5

<210> SEQ ID NO 294
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 294

Phe Tyr Cys His Gln Glu Leu Glu
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic Construct

<400> SEQUENCE: 295

Phe Tyr Cys His Gln Glu Lys Glu
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic Construct

<400> SEQUENCE: 296

Phe Tyr Cys His Gln Glu Met Glu
1               5

<210> SEQ ID NO 297
<211> LENGTH: 8
<212> TYPE: PRT
<213> ORGANISM: Artificial Sequence
<220> FEATURE:
<223> OTHER INFORMATION: Synthetic Construct

<400> SEQUENCE: 297

Phe Tyr Cys His Gln Glu Pro Glu
1               5

<210> SEQ ID NO 298
<211> LENGTH: 8
<212> TYPE: PRT
<213> ORGANISM: Artificial Sequence
<220> FEATURE:
<223> OTHER INFORMATION: Synthetic Construct

<400> SEQUENCE: 298

Phe Tyr Cys His Gln Glu Ser Glu
1               5

<210> SEQ ID NO 299
<211> LENGTH: 8
<212> TYPE: PRT
<213> ORGANISM: Artificial Sequence
<220> FEATURE:
<223> OTHER INFORMATION: Synthetic Construct

<400> SEQUENCE: 299

Phe Tyr Cys His Gln Glu Thr Glu
1               5

<210> SEQ ID NO 300
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 300

Phe Tyr Cys His Gln Ile Ala Glu
1               5

<210> SEQ ID NO 301
<211> LENGTH: 8
<212> TYPE: PRT
<213> ORGANISM: Artificial Sequence
<220> FEATURE:
<223> OTHER INFORMATION: Synthetic Construct

<400> SEQUENCE: 301

Phe Tyr Cys His Gln Ile Arg Glu
1               5

<210> SEQ ID NO 302
<211> LENGTH: 8
<212> TYPE: PRT
<213> ORGANISM: Artificial Sequence
<220> FEATURE:
<223> OTHER INFORMATION: Synthetic Construct

<400> SEQUENCE: 302

Phe Tyr Cys His Gln Ile Asp Glu
1               5

<210> SEQ ID NO 303
<211> LENGTH: 8
<212> TYPE: PRT
<213> ORGANISM: Artificial Sequence
<220> FEATURE:
<223> OTHER INFORMATION: Synthetic Construct

<400> SEQUENCE: 303

Phe Tyr Cys His Gln Ile Gln Glu
1               5

<210> SEQ ID NO 304
<211> LENGTH: 8
<212> TYPE: PRT
<213> ORGANISM: Artificial Sequence
<220> FEATURE:
<223> OTHER INFORMATION: Synthetic Construct

<400> SEQUENCE: 304

Phe Tyr Cys His Gln Ile Glu Glu
1               5

<210> SEQ ID NO 305
<211> LENGTH: 8
<212> TYPE: PRT
<213> ORGANISM: Artificial Sequence
<220> FEATURE:
<223> OTHER INFORMATION: Synthetic Construct

<400> SEQUENCE: 305

Phe Tyr Cys His Gln Ile Leu Glu
1               5

<210> SEQ ID NO 306
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 306

Phe Tyr Cys His Gln Ile Lys Glu
1               5

<210> SEQ ID NO 307
<211> LENGTH: 8
<212> TYPE: PRT
<213> ORGANISM: Artificial Sequence
<220> FEATURE:
<223> OTHER INFORMATION: Synthetic Construct

<400> SEQUENCE: 307

Phe Tyr Cys His Gln Ile Met Glu
1               5

<210> SEQ ID NO 308
<211> LENGTH: 8
<212> TYPE: PRT
<213> ORGANISM: Artificial Sequence
<220> FEATURE:
<223> OTHER INFORMATION: Synthetic Construct

<400> SEQUENCE: 308

Phe Tyr Cys His Gln Ile Pro Glu
1               5

<210> SEQ ID NO 309
<211> LENGTH: 8
<212> TYPE: PRT
<213> ORGANISM: Artificial Sequence
<220> FEATURE:
<223> OTHER INFORMATION: Synthetic Construct

<400> SEQUENCE: 309

Phe Tyr Cys His Gln Ile Ser Glu
1               5

<210> SEQ ID NO 310
<211> LENGTH: 8
<212> TYPE: PRT
<213> ORGANISM: Artificial Sequence
<220> FEATURE:
<223> OTHER INFORMATION: Synthetic Construct

<400> SEQUENCE: 310

Phe Tyr Cys His Gln Ile Thr Glu
1               5

<210> SEQ ID NO 311
<211> LENGTH: 8
<212> TYPE: PRT
<213> ORGANISM: Artificial Sequence
<220> FEATURE:
<223> OTHER INFORMATION: Synthetic Construct

<400> SEQUENCE: 311

Phe Tyr Cys His Gln Leu Ala Glu
1               5

<210> SEQ ID NO 312
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 312

Phe Tyr Cys His Gln Leu Arg Glu
1               5

<210> SEQ ID NO 313
<211> LENGTH: 8
<212> TYPE: PRT
<213> ORGANISM: Artificial Sequence
<220> FEATURE:
<223> OTHER INFORMATION: Synthetic Construct

<400> SEQUENCE: 313

Phe Tyr Cys His Gln Leu Asp Glu
1               5

<210> SEQ ID NO 314
<211> LENGTH: 8
<212> TYPE: PRT
<213> ORGANISM: Artificial Sequence
<220> FEATURE:
<223> OTHER INFORMATION: Synthetic Construct

<400> SEQUENCE: 314

Phe Tyr Cys His Gln Leu Gln Glu
1               5

<210> SEQ ID NO 315
<211> LENGTH: 8
<212> TYPE: PRT
<213> ORGANISM: Artificial Sequence
<220> FEATURE:
<223> OTHER INFORMATION: Synthetic Construct

<400> SEQUENCE: 315

Phe Tyr Cys His Gln Leu Glu Glu
1               5

<210> SEQ ID NO 316
<211> LENGTH: 8
<212> TYPE: PRT
<213> ORGANISM: Artificial Sequence
<220> FEATURE:
<223> OTHER INFORMATION: Synthetic Construct

<400> SEQUENCE: 316

Phe Tyr Cys His Gln Leu Leu Glu
1               5

<210> SEQ ID NO 317
<211> LENGTH: 8
<212> TYPE: PRT
<213> ORGANISM: Artificial Sequence
<220> FEATURE:
<223> OTHER INFORMATION: Synthetic Construct

<400> SEQUENCE: 317

Phe Tyr Cys His Gln Leu Lys Glu
1               5

<210> SEQ ID NO 318
<211> LENGTH: 8
<212> TYPE: PRT
<213> ORGANISM: Artificial Sequence
<220> FEATURE:
<223> OTHER INFORMATION: Synthetic Construct

<400> SEQUENCE: 318
```

```
Phe Tyr Cys His Gln Leu Met Glu
1               5
```

<210> SEQ ID NO 319
<211> LENGTH: 8
<212> TYPE: PRT
<213> ORGANISM: Artificial Sequence
<220> FEATURE:
<223> OTHER INFORMATION: Synthetic Construct

<400> SEQUENCE: 319

```
Phe Tyr Cys His Gln Leu Pro Glu
1               5
```

<210> SEQ ID NO 320
<211> LENGTH: 8
<212> TYPE: PRT
<213> ORGANISM: Artificial Sequence
<220> FEATURE:
<223> OTHER INFORMATION: Synthetic Construct

<400> SEQUENCE: 320

```
Phe Tyr Cys His Gln Leu Ser Glu
1               5
```

<210> SEQ ID NO 321
<211> LENGTH: 8
<212> TYPE: PRT
<213> ORGANISM: Artificial Sequence
<220> FEATURE:
<223> OTHER INFORMATION: Synthetic Construct

<400> SEQUENCE: 321

```
Phe Tyr Cys His Gln Leu Thr Glu
1               5
```

<210> SEQ ID NO 322
<211> LENGTH: 8
<212> TYPE: PRT
<213> ORGANISM: Artificial Sequence
<220> FEATURE:
<223> OTHER INFORMATION: Synthetic Construct

<400> SEQUENCE: 322

```
Phe Tyr Cys His Gln Lys Ala Glu
1               5
```

<210> SEQ ID NO 323
<211> LENGTH: 8
<212> TYPE: PRT
<213> ORGANISM: Artificial Sequence
<220> FEATURE:
<223> OTHER INFORMATION: Synthetic Construct

<400> SEQUENCE: 323

```
Phe Tyr Cys His Gln Lys Gln Glu
1               5
```

<210> SEQ ID NO 324
<211> LENGTH: 8
<212> TYPE: PRT
<213> ORGANISM: Artificial Sequence
<220> FEATURE:
<223> OTHER INFORMATION: Synthetic Construct

<400> SEQUENCE: 324

Phe Tyr Cys His Gln Lys Glu Glu
1               5

<210> SEQ ID NO 325
<211> LENGTH: 8
<212> TYPE: PRT
<213> ORGANISM: Artificial Sequence
<220> FEATURE:
<223> OTHER INFORMATION: Synthetic Construct

<400> SEQUENCE: 325

Phe Tyr Cys His Gln Lys Leu Glu
1               5

<210> SEQ ID NO 326
<211> LENGTH: 8
<212> TYPE: PRT
<213> ORGANISM: Artificial Sequence
<220> FEATURE:
<223> OTHER INFORMATION: Synthetic Construct

<400> SEQUENCE: 326

Phe Tyr Cys His Gln Lys Lys Glu
1               5

<210> SEQ ID NO 327
<211> LENGTH: 8
<212> TYPE: PRT
<213> ORGANISM: Artificial Sequence
<220> FEATURE:
<223> OTHER INFORMATION: Synthetic Construct

<400> SEQUENCE: 327

Phe Tyr Cys His Gln Lys Met Glu
1               5

<210> SEQ ID NO 328
<211> LENGTH: 8
<212> TYPE: PRT
<213> ORGANISM: Artificial Sequence
<220> FEATURE:
<223> OTHER INFORMATION: Synthetic Construct

<400> SEQUENCE: 328

Phe Tyr Cys His Gln Lys Ser Glu
1               5

<210> SEQ ID NO 329
<211> LENGTH: 8
<212> TYPE: PRT
<213> ORGANISM: Artificial Sequence
<220> FEATURE:
<223> OTHER INFORMATION: Synthetic Construct

<400> SEQUENCE: 329

Phe Tyr Cys His Gln Lys Arg Glu
1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic Construct

<400> SEQUENCE: 330

Phe Tyr Cys His Gln Lys Asp Glu 1               5

<210> SEQ ID NO 331
<211> LENGTH: 8
<212> TYPE: PRT
<213> ORGANISM: Artificial Sequence
<220> FEATURE:
<223> OTHER INFORMATION: Synthetic Construct

<400> SEQUENCE: 331

Phe Tyr Cys His Glu Lys Thr Glu
1               5

<210> SEQ ID NO 332
<211> LENGTH: 8
<212> TYPE: PRT
<213> ORGANISM: Artificial Sequence
<220> FEATURE:
<223> OTHER INFORMATION: Synthetic Construct

<400> SEQUENCE: 332

Phe Tyr Cys His Glu Lys Pro Glu
1               5

<210> SEQ ID NO 333
<211> LENGTH: 8
<212> TYPE: PRT
<213> ORGANISM: Artificial Sequence
<220> FEATURE:
<223> OTHER INFORMATION: Synthetic Construct

<400> SEQUENCE: 333

Phe Tyr Cys His Glu Lys Asp Glu
1               5

<210> SEQ ID NO 334
<211> LENGTH: 8
<212> TYPE: PRT
<213> ORGANISM: Artificial Sequence
<220> FEATURE:
<223> OTHER INFORMATION: Synthetic Construct

<400> SEQUENCE: 334

Phe Tyr Cys His Glu Lys Met Glu
1               5

<210> SEQ ID NO 335
<211> LENGTH: 8
<212> TYPE: PRT
<213> ORGANISM: Artificial Sequence
<220> FEATURE:
<223> OTHER INFORMATION: Synthetic Construct

<400> SEQUENCE: 335

Phe Tyr Cys His Glu Lys Ser Glu
1               5

<210> SEQ ID NO 336
<211> LENGTH: 8
<212> TYPE: PRT
<213> ORGANISM: Artificial Sequence
<220> FEATURE:
<223> OTHER INFORMATION: Synthetic Construct

<400> SEQUENCE: 336

Phe Tyr Cys His Glu Lys Arg Glu
1               5

```
<210> SEQ ID NO 337
<211> LENGTH: 8
<212> TYPE: PRT
<213> ORGANISM: Artificial Sequence
<220> FEATURE:
<223> OTHER INFORMATION: Synthetic Construct

<400> SEQUENCE: 337

Phe Tyr Cys His Glu Ala Ala Glu
1               5

<210> SEQ ID NO 338
<211> LENGTH: 8
<212> TYPE: PRT
<213> ORGANISM: Artificial Sequence
<220> FEATURE:
<223> OTHER INFORMATION: Synthetic Construct

<400> SEQUENCE: 338

Phe Tyr Cys His Glu Ala Arg Glu
1               5

<210> SEQ ID NO 339
<211> LENGTH: 8
<212> TYPE: PRT
<213> ORGANISM: Artificial Sequence
<220> FEATURE:
<223> OTHER INFORMATION: Synthetic Construct

<400> SEQUENCE: 339

Phe Tyr Cys His Glu Ala Asp Glu
1               5

<210> SEQ ID NO 340
<211> LENGTH: 8
<212> TYPE: PRT
<213> ORGANISM: Artificial Sequence
<220> FEATURE:
<223> OTHER INFORMATION: Synthetic Construct

<400> SEQUENCE: 340

Phe Tyr Cys His Glu Ala Gln Glu
1               5

<210> SEQ ID NO 341
<211> LENGTH: 8
<212> TYPE: PRT
<213> ORGANISM: Artificial Sequence
<220> FEATURE:
<223> OTHER INFORMATION: Synthetic Construct

<400> SEQUENCE: 341

Phe Tyr Cys His Glu Ala Glu Glu
1               5

<210> SEQ ID NO 342
<211> LENGTH: 8
<212> TYPE: PRT
<213> ORGANISM: Artificial Sequence
<220> FEATURE:
<223> OTHER INFORMATION: Synthetic Construct

<400> SEQUENCE: 342

Phe Tyr Cys His Glu Ala Leu Glu
1               5
```

<210> SEQ ID NO 343
<211> LENGTH: 8
<212> TYPE: PRT
<213> ORGANISM: Artificial Sequence
<220> FEATURE:
<223> OTHER INFORMATION: Synthetic Construct

<400> SEQUENCE: 343

Phe Tyr Cys His Glu Ala Lys Glu
1               5

<210> SEQ ID NO 344
<211> LENGTH: 8
<212> TYPE: PRT
<213> ORGANISM: Artificial Sequence
<220> FEATURE:
<223> OTHER INFORMATION: Synthetic Construct

<400> SEQUENCE: 344

Phe Tyr Cys His Glu Ala Met Glu
1               5

<210> SEQ ID NO 345
<211> LENGTH: 8
<212> TYPE: PRT
<213> ORGANISM: Artificial Sequence
<220> FEATURE:
<223> OTHER INFORMATION: Synthetic Construct

<400> SEQUENCE: 345

Phe Tyr Cys His Glu Ala Pro Glu
1               5

<210> SEQ ID NO 346
<211> LENGTH: 8
<212> TYPE: PRT
<213> ORGANISM: Artificial Sequence
<220> FEATURE:
<223> OTHER INFORMATION: Synthetic Construct

<400> SEQUENCE: 346

Phe Tyr Cys His Glu Ala Ser Glu
1               5

<210> SEQ ID NO 347
<211> LENGTH: 8
<212> TYPE: PRT
<213> ORGANISM: Artificial Sequence
<220> FEATURE:
<223> OTHER INFORMATION: Synthetic Construct

<400> SEQUENCE: 347

Phe Tyr Cys His Glu Ala Thr Glu
1               5

<210> SEQ ID NO 348
<211> LENGTH: 8
<212> TYPE: PRT
<213> ORGANISM: Artificial Sequence
<220> FEATURE:
<223> OTHER INFORMATION: Synthetic Construct

<400> SEQUENCE: 348

Phe Tyr Cys His Glu Gln Ala Glu
1               5

```
<210> SEQ ID NO 349
<211> LENGTH: 8
<212> TYPE: PRT
<213> ORGANISM: Artificial Sequence
<220> FEATURE:
<223> OTHER INFORMATION: Synthetic Construct

<400> SEQUENCE: 349

Phe Tyr Cys His Glu Gln Arg Glu
1               5

<210> SEQ ID NO 350
<211> LENGTH: 8
<212> TYPE: PRT
<213> ORGANISM: Artificial Sequence
<220> FEATURE:
<223> OTHER INFORMATION: Synthetic Construct

<400> SEQUENCE: 350

Phe Tyr Cys His Glu Gln Asp Glu
1               5

<210> SEQ ID NO 351
<211> LENGTH: 8
<212> TYPE: PRT
<213> ORGANISM: Artificial Sequence
<220> FEATURE:
<223> OTHER INFORMATION: Synthetic Construct

<400> SEQUENCE: 351

Phe Tyr Cys His Glu Gln Gln Glu
1               5

<210> SEQ ID NO 352
<211> LENGTH: 8
<212> TYPE: PRT
<213> ORGANISM: Artificial Sequence
<220> FEATURE:
<223> OTHER INFORMATION: Synthetic Construct

<400> SEQUENCE: 352

Phe Tyr Cys His Glu Gln Glu Glu
1               5

<210> SEQ ID NO 353
<211> LENGTH: 8
<212> TYPE: PRT
<213> ORGANISM: Artificial Sequence
<220> FEATURE:
<223> OTHER INFORMATION: Synthetic Construct

<400> SEQUENCE: 353

Phe Tyr Cys His Glu Gln Leu Glu
1               5

<210> SEQ ID NO 354
<211> LENGTH: 8
<212> TYPE: PRT
<213> ORGANISM: Artificial Sequence
<220> FEATURE:
<223> OTHER INFORMATION: Synthetic Construct

<400> SEQUENCE: 354

Phe Tyr Cys His Glu Gln Lys Glu
1               5

<210> SEQ ID NO 355
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 355

Phe Tyr Cys His Glu Gln Met Glu
1               5

<210> SEQ ID NO 356
<211> LENGTH: 8
<212> TYPE: PRT
<213> ORGANISM: Artificial Sequence
<220> FEATURE:
<223> OTHER INFORMATION: Synthetic Construct

<400> SEQUENCE: 356

Phe Tyr Cys His Glu Gln Pro Glu
1               5

<210> SEQ ID NO 357
<211> LENGTH: 8
<212> TYPE: PRT
<213> ORGANISM: Artificial Sequence
<220> FEATURE:
<223> OTHER INFORMATION: Synthetic Construct

<400> SEQUENCE: 357

Phe Tyr Cys His Glu Gln Ser Glu
1               5

<210> SEQ ID NO 358
<211> LENGTH: 8
<212> TYPE: PRT
<213> ORGANISM: Artificial Sequence
<220> FEATURE:
<223> OTHER INFORMATION: Synthetic Construct

<400> SEQUENCE: 358

Phe Tyr Cys His Glu Gln Thr Glu
1               5

<210> SEQ ID NO 359
<211> LENGTH: 8
<212> TYPE: PRT
<213> ORGANISM: Artificial Sequence
<220> FEATURE:
<223> OTHER INFORMATION: Synthetic Construct

<400> SEQUENCE: 359

Phe Tyr Cys His Glu Glu Ala Glu
1               5

<210> SEQ ID NO 360
<211> LENGTH: 8
<212> TYPE: PRT
<213> ORGANISM: Artificial Sequence
<220> FEATURE:
<223> OTHER INFORMATION: Synthetic Construct

<400> SEQUENCE: 360

Phe Tyr Cys His Glu Glu Arg Glu
1               5

<210> SEQ ID NO 361
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 361

Phe Tyr Cys His Glu Glu Asp Glu
1               5

<210> SEQ ID NO 362
<211> LENGTH: 8
<212> TYPE: PRT
<213> ORGANISM: Artificial Sequence
<220> FEATURE:
<223> OTHER INFORMATION: Synthetic Construct

<400> SEQUENCE: 362

Phe Tyr Cys His Glu Glu Gln Glu
1               5

<210> SEQ ID NO 363
<211> LENGTH: 8
<212> TYPE: PRT
<213> ORGANISM: Artificial Sequence
<220> FEATURE:
<223> OTHER INFORMATION: Synthetic Construct

<400> SEQUENCE: 363

Phe Tyr Cys His Glu Glu Glu Glu
1               5

<210> SEQ ID NO 364
<211> LENGTH: 8
<212> TYPE: PRT
<213> ORGANISM: Artificial Sequence
<220> FEATURE:
<223> OTHER INFORMATION: Synthetic Construct

<400> SEQUENCE: 364

Phe Tyr Cys His Glu Glu Leu Glu
1               5

<210> SEQ ID NO 365
<211> LENGTH: 8
<212> TYPE: PRT
<213> ORGANISM: Artificial Sequence
<220> FEATURE:
<223> OTHER INFORMATION: Synthetic Construct

<400> SEQUENCE: 365

Phe Tyr Cys His Glu Glu Lys Glu
1               5

<210> SEQ ID NO 366
<211> LENGTH: 8
<212> TYPE: PRT
<213> ORGANISM: Artificial Sequence
<220> FEATURE:
<223> OTHER INFORMATION: Synthetic Construct

<400> SEQUENCE: 366

Phe Tyr Cys His Glu Glu Met Glu
1               5

<210> SEQ ID NO 367
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 367

Phe Tyr Cys His Glu Glu Pro Glu
1               5

<210> SEQ ID NO 368
<211> LENGTH: 8
<212> TYPE: PRT
<213> ORGANISM: Artificial Sequence
<220> FEATURE:
<223> OTHER INFORMATION: Synthetic Construct

<400> SEQUENCE: 368

Phe Tyr Cys His Glu Glu Ser Glu
1               5

<210> SEQ ID NO 369
<211> LENGTH: 8
<212> TYPE: PRT
<213> ORGANISM: Artificial Sequence
<220> FEATURE:
<223> OTHER INFORMATION: Synthetic Construct

<400> SEQUENCE: 369

Phe Tyr Cys His Glu Glu Thr Glu
1               5

<210> SEQ ID NO 370
<211> LENGTH: 8
<212> TYPE: PRT
<213> ORGANISM: Artificial Sequence
<220> FEATURE:
<223> OTHER INFORMATION: Synthetic Construct

<400> SEQUENCE: 370

Phe Tyr Cys His Glu Ile Ala Glu
1               5

<210> SEQ ID NO 371
<211> LENGTH: 8
<212> TYPE: PRT
<213> ORGANISM: Artificial Sequence
<220> FEATURE:
<223> OTHER INFORMATION: Synthetic Construct

<400> SEQUENCE: 371

Phe Tyr Cys His Glu Ile Arg Glu
1               5

<210> SEQ ID NO 372
<211> LENGTH: 8
<212> TYPE: PRT
<213> ORGANISM: Artificial Sequence
<220> FEATURE:
<223> OTHER INFORMATION: Synthetic Construct

<400> SEQUENCE: 372

Phe Tyr Cys His Glu Ile Asp Glu
1               5

<210> SEQ ID NO 373
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 373

Phe Tyr Cys His Glu Ile Gln Glu
1               5

<210> SEQ ID NO 374
<211> LENGTH: 8
<212> TYPE: PRT
<213> ORGANISM: Artificial Sequence
<220> FEATURE:
<223> OTHER INFORMATION: Synthetic Construct

<400> SEQUENCE: 374

Phe Tyr Cys His Glu Ile Glu Glu
1               5

<210> SEQ ID NO 375
<211> LENGTH: 8
<212> TYPE: PRT
<213> ORGANISM: Artificial Sequence
<220> FEATURE:
<223> OTHER INFORMATION: Synthetic Construct

<400> SEQUENCE: 375

Phe Tyr Cys His Glu Ile Leu Glu
1               5

<210> SEQ ID NO 376
<211> LENGTH: 8
<212> TYPE: PRT
<213> ORGANISM: Artificial Sequence
<220> FEATURE:
<223> OTHER INFORMATION: Synthetic Construct

<400> SEQUENCE: 376

Phe Tyr Cys His Glu Ile Lys Glu
1               5

<210> SEQ ID NO 377
<211> LENGTH: 8
<212> TYPE: PRT
<213> ORGANISM: Artificial Sequence
<220> FEATURE:
<223> OTHER INFORMATION: Synthetic Construct

<400> SEQUENCE: 377

Phe Tyr Cys His Glu Ile Met Glu
1               5

<210> SEQ ID NO 378
<211> LENGTH: 8
<212> TYPE: PRT
<213> ORGANISM: Artificial Sequence
<220> FEATURE:
<223> OTHER INFORMATION: Synthetic Construct

<400> SEQUENCE: 378

Phe Tyr Cys His Glu Ile Pro Glu
1               5

<210> SEQ ID NO 379
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 379

Phe Tyr Cys His Glu Ile Ser Glu
1               5

<210> SEQ ID NO 380
<211> LENGTH: 8
<212> TYPE: PRT
<213> ORGANISM: Artificial Sequence
<220> FEATURE:
<223> OTHER INFORMATION: Synthetic Construct

<400> SEQUENCE: 380

Phe Tyr Cys His Glu Ile Thr Glu
1               5

<210> SEQ ID NO 381
<211> LENGTH: 8
<212> TYPE: PRT
<213> ORGANISM: Artificial Sequence
<220> FEATURE:
<223> OTHER INFORMATION: Synthetic Construct

<400> SEQUENCE: 381

Phe Tyr Cys His Glu Leu Ala Glu
1               5

<210> SEQ ID NO 382
<211> LENGTH: 8
<212> TYPE: PRT
<213> ORGANISM: Artificial Sequence
<220> FEATURE:
<223> OTHER INFORMATION: Synthetic Construct

<400> SEQUENCE: 382

Phe Tyr Cys His Glu Leu Arg Glu
1               5

<210> SEQ ID NO 383
<211> LENGTH: 8
<212> TYPE: PRT
<213> ORGANISM: Artificial Sequence
<220> FEATURE:
<223> OTHER INFORMATION: Synthetic Construct

<400> SEQUENCE: 383

Phe Tyr Cys His Glu Leu Asp Glu
1               5

<210> SEQ ID NO 384
<211> LENGTH: 8
<212> TYPE: PRT
<213> ORGANISM: Artificial Sequence
<220> FEATURE:
<223> OTHER INFORMATION: Synthetic Construct

<400> SEQUENCE: 384

Phe Tyr Cys His Glu Leu Gln Glu
1               5

<210> SEQ ID NO 385
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 385

Phe Tyr Cys His Glu Leu Glu Glu
1               5

<210> SEQ ID NO 386
<211> LENGTH: 8
<212> TYPE: PRT
<213> ORGANISM: Artificial Sequence
<220> FEATURE:
<223> OTHER INFORMATION: Synthetic Construct

<400> SEQUENCE: 386

Phe Tyr Cys His Glu Leu Leu Glu
1               5

<210> SEQ ID NO 387
<211> LENGTH: 8
<212> TYPE: PRT
<213> ORGANISM: Artificial Sequence
<220> FEATURE:
<223> OTHER INFORMATION: Synthetic Construct

<400> SEQUENCE: 387

Phe Tyr Cys His Glu Leu Lys Glu
1               5

<210> SEQ ID NO 388
<211> LENGTH: 8
<212> TYPE: PRT
<213> ORGANISM: Artificial Sequence
<220> FEATURE:
<223> OTHER INFORMATION: Synthetic Construct

<400> SEQUENCE: 388

Phe Tyr Cys His Glu Leu Met Glu
1               5

<210> SEQ ID NO 389
<211> LENGTH: 8
<212> TYPE: PRT
<213> ORGANISM: Artificial Sequence
<220> FEATURE:
<223> OTHER INFORMATION: Synthetic Construct

<400> SEQUENCE: 389

Phe Tyr Cys His Glu Leu Pro Glu
1               5

<210> SEQ ID NO 390
<211> LENGTH: 8
<212> TYPE: PRT
<213> ORGANISM: Artificial Sequence
<220> FEATURE:
<223> OTHER INFORMATION: Synthetic Construct

<400> SEQUENCE: 390

Phe Tyr Cys His Glu Leu Ser Glu
1               5

<210> SEQ ID NO 391
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 391

Phe Tyr Cys His Glu Leu Thr Glu
1               5

<210> SEQ ID NO 392
<211> LENGTH: 8
<212> TYPE: PRT
<213> ORGANISM: Artificial Sequence
<220> FEATURE:
<223> OTHER INFORMATION: Synthetic Construct

<400> SEQUENCE: 392

Phe Tyr Cys His Glu Lys Ala Glu
1               5

<210> SEQ ID NO 393
<211> LENGTH: 8
<212> TYPE: PRT
<213> ORGANISM: Artificial Sequence
<220> FEATURE:
<223> OTHER INFORMATION: Synthetic Construct

<400> SEQUENCE: 393

Phe Tyr Cys His Glu Lys Gln Glu
1               5

<210> SEQ ID NO 394
<211> LENGTH: 8
<212> TYPE: PRT
<213> ORGANISM: Artificial Sequence
<220> FEATURE:
<223> OTHER INFORMATION: Synthetic Construct

<400> SEQUENCE: 394

Phe Tyr Cys His Glu Lys Glu Glu
1               5

<210> SEQ ID NO 395
<211> LENGTH: 8
<212> TYPE: PRT
<213> ORGANISM: Artificial Sequence
<220> FEATURE:
<223> OTHER INFORMATION: Synthetic Construct

<400> SEQUENCE: 395

Phe Tyr Cys His Glu Lys Leu Glu
1               5

<210> SEQ ID NO 396
<211> LENGTH: 8
<212> TYPE: PRT
<213> ORGANISM: Artificial Sequence
<220> FEATURE:
<223> OTHER INFORMATION: Synthetic Construct

<400> SEQUENCE: 396

Phe Tyr Cys His Glu Lys Lys Glu
1               5

<210> SEQ ID NO 397
<211> LENGTH: 8
<212> TYPE: PRT
<213> ORGANISM: Artificial Sequence
<220> FEATURE:
<223> OTHER INFORMATION: Synthetic Construct

<400> SEQUENCE: 397
```

Phe Tyr Cys His His Lys Thr Glu
1               5

<210> SEQ ID NO 398
<211> LENGTH: 8
<212> TYPE: PRT
<213> ORGANISM: Artificial Sequence
<220> FEATURE:
<223> OTHER INFORMATION: Synthetic Construct

<400> SEQUENCE: 398

Phe Tyr Cys His His Lys Pro Glu
1               5

<210> SEQ ID NO 399
<211> LENGTH: 8
<212> TYPE: PRT
<213> ORGANISM: Artificial Sequence
<220> FEATURE:
<223> OTHER INFORMATION: Synthetic Construct

<400> SEQUENCE: 399

Phe Tyr Cys His His Lys Asp Glu
1               5

<210> SEQ ID NO 400
<211> LENGTH: 8
<212> TYPE: PRT
<213> ORGANISM: Artificial Sequence
<220> FEATURE:
<223> OTHER INFORMATION: Synthetic Construct

<400> SEQUENCE: 400

Phe Tyr Cys His His Ala Ala Glu
1               5

<210> SEQ ID NO 401
<211> LENGTH: 8
<212> TYPE: PRT
<213> ORGANISM: Artificial Sequence
<220> FEATURE:
<223> OTHER INFORMATION: Synthetic Construct

<400> SEQUENCE: 401

Phe Tyr Cys His His Ala Arg Glu
1               5

<210> SEQ ID NO 402
<211> LENGTH: 8
<212> TYPE: PRT
<213> ORGANISM: Artificial Sequence
<220> FEATURE:
<223> OTHER INFORMATION: Synthetic Construct

<400> SEQUENCE: 402

Phe Tyr Cys His His Ala Asp Glu
1               5

<210> SEQ ID NO 403
<211> LENGTH: 8
<212> TYPE: PRT
<213> ORGANISM: Artificial Sequence
<220> FEATURE:
<223> OTHER INFORMATION: Synthetic Construct

<400> SEQUENCE: 403

Phe Tyr Cys His His Ala Gln Glu
1               5

<210> SEQ ID NO 404
<211> LENGTH: 8
<212> TYPE: PRT
<213> ORGANISM: Artificial Sequence
<220> FEATURE:
<223> OTHER INFORMATION: Synthetic Construct

<400> SEQUENCE: 404

Phe Tyr Cys His His Ala Glu Glu
1               5

<210> SEQ ID NO 405
<211> LENGTH: 8
<212> TYPE: PRT
<213> ORGANISM: Artificial Sequence
<220> FEATURE:
<223> OTHER INFORMATION: Synthetic Construct

<400> SEQUENCE: 405

Phe Tyr Cys His His Ala Leu Glu
1               5

<210> SEQ ID NO 406
<211> LENGTH: 8
<212> TYPE: PRT
<213> ORGANISM: Artificial Sequence
<220> FEATURE:
<223> OTHER INFORMATION: Synthetic Construct

<400> SEQUENCE: 406

Phe Tyr Cys His His Ala Lys Glu
1               5

<210> SEQ ID NO 407
<211> LENGTH: 8
<212> TYPE: PRT
<213> ORGANISM: Artificial Sequence
<220> FEATURE:
<223> OTHER INFORMATION: Synthetic Construct

<400> SEQUENCE: 407

Phe Tyr Cys His His Ala Met Glu
1               5

<210> SEQ ID NO 408
<211> LENGTH: 8
<212> TYPE: PRT
<213> ORGANISM: Artificial Sequence
<220> FEATURE:
<223> OTHER INFORMATION: Synthetic Construct

<400> SEQUENCE: 408

Phe Tyr Cys His His Ala Pro Glu
1               5

<210> SEQ ID NO 409
<211> LENGTH: 8
<212> TYPE: PRT
<213> ORGANISM: Artificial Sequence
<220> FEATURE:
<223> OTHER INFORMATION: Synthetic Construct

<400> SEQUENCE: 409

Phe Tyr Cys His His Ala Ser Glu

```
1               5

<210> SEQ ID NO 410
<211> LENGTH: 8
<212> TYPE: PRT
<213> ORGANISM: Artificial Sequence
<220> FEATURE:
<223> OTHER INFORMATION: Synthetic Construct

<400> SEQUENCE: 410

Phe Tyr Cys His His Ala Thr Glu
1               5

<210> SEQ ID NO 411
<211> LENGTH: 8
<212> TYPE: PRT
<213> ORGANISM: Artificial Sequence
<220> FEATURE:
<223> OTHER INFORMATION: Synthetic Construct

<400> SEQUENCE: 411

Phe Tyr Cys His His Gln Ala Glu
1               5

<210> SEQ ID NO 412
<211> LENGTH: 8
<212> TYPE: PRT
<213> ORGANISM: Artificial Sequence
<220> FEATURE:
<223> OTHER INFORMATION: Synthetic Construct

<400> SEQUENCE: 412

Phe Tyr Cys His His Gln Arg Glu
1               5

<210> SEQ ID NO 413
<211> LENGTH: 8
<212> TYPE: PRT
<213> ORGANISM: Artificial Sequence
<220> FEATURE:
<223> OTHER INFORMATION: Synthetic Construct

<400> SEQUENCE: 413

Phe Tyr Cys His His Gln Asp Glu
1               5

<210> SEQ ID NO 414
<211> LENGTH: 8
<212> TYPE: PRT
<213> ORGANISM: Artificial Sequence
<220> FEATURE:
<223> OTHER INFORMATION: Synthetic Construct

<400> SEQUENCE: 414

Phe Tyr Cys His His Gln Gln Glu
1               5

<210> SEQ ID NO 415
<211> LENGTH: 8
<212> TYPE: PRT
<213> ORGANISM: Artificial Sequence
<220> FEATURE:
<223> OTHER INFORMATION: Synthetic Construct

<400> SEQUENCE: 415

Phe Tyr Cys His His Gln Glu Glu
1               5
```

```
<210> SEQ ID NO 416
<211> LENGTH: 8
<212> TYPE: PRT
<213> ORGANISM: Artificial Sequence
<220> FEATURE:
<223> OTHER INFORMATION: Synthetic Construct

<400> SEQUENCE: 416

Phe Tyr Cys His His Gln Leu Glu
1               5

<210> SEQ ID NO 417
<211> LENGTH: 8
<212> TYPE: PRT
<213> ORGANISM: Artificial Sequence
<220> FEATURE:
<223> OTHER INFORMATION: Synthetic Construct

<400> SEQUENCE: 417

Phe Tyr Cys His His Gln Lys Glu
1               5

<210> SEQ ID NO 418
<211> LENGTH: 8
<212> TYPE: PRT
<213> ORGANISM: Artificial Sequence
<220> FEATURE:
<223> OTHER INFORMATION: Synthetic Construct

<400> SEQUENCE: 418

Phe Tyr Cys His His Gln Met Glu
1               5

<210> SEQ ID NO 419
<211> LENGTH: 8
<212> TYPE: PRT
<213> ORGANISM: Artificial Sequence
<220> FEATURE:
<223> OTHER INFORMATION: Synthetic Construct

<400> SEQUENCE: 419

Phe Tyr Cys His His Gln Pro Glu
1               5

<210> SEQ ID NO 420
<211> LENGTH: 8
<212> TYPE: PRT
<213> ORGANISM: Artificial Sequence
<220> FEATURE:
<223> OTHER INFORMATION: Synthetic Construct

<400> SEQUENCE: 420

Phe Tyr Cys His His Gln Ser Glu
1               5

<210> SEQ ID NO 421
<211> LENGTH: 8
<212> TYPE: PRT
<213> ORGANISM: Artificial Sequence
<220> FEATURE:
<223> OTHER INFORMATION: Synthetic Construct

<400> SEQUENCE: 421

Phe Tyr Cys His His Gln Thr Glu
1               5
```

```
<210> SEQ ID NO 422
<211> LENGTH: 8
<212> TYPE: PRT
<213> ORGANISM: Artificial Sequence
<220> FEATURE:
<223> OTHER INFORMATION: Synthetic Construct

<400> SEQUENCE: 422

Phe Tyr Cys His His Glu Ala Glu
1               5

<210> SEQ ID NO 423
<211> LENGTH: 8
<212> TYPE: PRT
<213> ORGANISM: Artificial Sequence
<220> FEATURE:
<223> OTHER INFORMATION: Synthetic Construct

<400> SEQUENCE: 423

Phe Tyr Cys His His Glu Arg Glu
1               5

<210> SEQ ID NO 424
<211> LENGTH: 8
<212> TYPE: PRT
<213> ORGANISM: Artificial Sequence
<220> FEATURE:
<223> OTHER INFORMATION: Synthetic Construct

<400> SEQUENCE: 424

Phe Tyr Cys His His Glu Asp Glu
1               5

<210> SEQ ID NO 425
<211> LENGTH: 8
<212> TYPE: PRT
<213> ORGANISM: Artificial Sequence
<220> FEATURE:
<223> OTHER INFORMATION: Synthetic Construct

<400> SEQUENCE: 425

Phe Tyr Cys His His Glu Gln Glu
1               5

<210> SEQ ID NO 426
<211> LENGTH: 8
<212> TYPE: PRT
<213> ORGANISM: Artificial Sequence
<220> FEATURE:
<223> OTHER INFORMATION: Synthetic Construct

<400> SEQUENCE: 426

Phe Tyr Cys His His Glu Glu Glu
1               5

<210> SEQ ID NO 427
<211> LENGTH: 8
<212> TYPE: PRT
<213> ORGANISM: Artificial Sequence
<220> FEATURE:
<223> OTHER INFORMATION: Synthetic Construct

<400> SEQUENCE: 427

Phe Tyr Cys His His Glu Leu Glu
1               5
```

-continued

<210> SEQ ID NO 428
<211> LENGTH: 8
<212> TYPE: PRT
<213> ORGANISM: Artificial Sequence
<220> FEATURE:
<223> OTHER INFORMATION: Synthetic Construct

<400> SEQUENCE: 428

Phe Tyr Cys His His Glu Lys Glu
1               5

<210> SEQ ID NO 429
<211> LENGTH: 8
<212> TYPE: PRT
<213> ORGANISM: Artificial Sequence
<220> FEATURE:
<223> OTHER INFORMATION: Synthetic Construct

<400> SEQUENCE: 429

Phe Tyr Cys His His Glu Met Glu
1               5

<210> SEQ ID NO 430
<211> LENGTH: 8
<212> TYPE: PRT
<213> ORGANISM: Artificial Sequence
<220> FEATURE:
<223> OTHER INFORMATION: Synthetic Construct

<400> SEQUENCE: 430

Phe Tyr Cys His His Glu Pro Glu
1               5

<210> SEQ ID NO 431
<211> LENGTH: 8
<212> TYPE: PRT
<213> ORGANISM: Artificial Sequence
<220> FEATURE:
<223> OTHER INFORMATION: Synthetic Construct

<400> SEQUENCE: 431

Phe Tyr Cys His His Glu Ser Glu
1               5

<210> SEQ ID NO 432
<211> LENGTH: 8
<212> TYPE: PRT
<213> ORGANISM: Artificial Sequence
<220> FEATURE:
<223> OTHER INFORMATION: Synthetic Construct

<400> SEQUENCE: 432

Phe Tyr Cys His His Glu Thr Glu
1               5

<210> SEQ ID NO 433
<211> LENGTH: 8
<212> TYPE: PRT
<213> ORGANISM: Artificial Sequence
<220> FEATURE:
<223> OTHER INFORMATION: Synthetic Construct

<400> SEQUENCE: 433

Phe Tyr Cys His His Ile Ala Glu
1               5

<210> SEQ ID NO 434

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 434

Phe Tyr Cys His His Ile Arg Glu
1               5

<210> SEQ ID NO 435
<211> LENGTH: 8
<212> TYPE: PRT
<213> ORGANISM: Artificial Sequence
<220> FEATURE:
<223> OTHER INFORMATION: Synthetic Construct

<400> SEQUENCE: 435

Phe Tyr Cys His His Ile Asp Glu
1               5

<210> SEQ ID NO 436
<211> LENGTH: 8
<212> TYPE: PRT
<213> ORGANISM: Artificial Sequence
<220> FEATURE:
<223> OTHER INFORMATION: Synthetic Construct

<400> SEQUENCE: 436

Phe Tyr Cys His His Ile Gln Glu
1               5

<210> SEQ ID NO 437
<211> LENGTH: 8
<212> TYPE: PRT
<213> ORGANISM: Artificial Sequence
<220> FEATURE:
<223> OTHER INFORMATION: Synthetic Construct

<400> SEQUENCE: 437

Phe Tyr Cys His His Ile Glu Glu
1               5

<210> SEQ ID NO 438
<211> LENGTH: 8
<212> TYPE: PRT
<213> ORGANISM: Artificial Sequence
<220> FEATURE:
<223> OTHER INFORMATION: Synthetic Construct

<400> SEQUENCE: 438

Phe Tyr Cys His His Ile Leu Glu
1               5

<210> SEQ ID NO 439
<211> LENGTH: 8
<212> TYPE: PRT
<213> ORGANISM: Artificial Sequence
<220> FEATURE:
<223> OTHER INFORMATION: Synthetic Construct

<400> SEQUENCE: 439

Phe Tyr Cys His His Ile Lys Glu
1               5

<210> SEQ ID NO 440
<211> LENGTH: 8
```

-continued

```
<212> TYPE: PRT
<213> ORGANISM: Artificial Sequence
<220> FEATURE:
<223> OTHER INFORMATION: Synthetic Construct

<400> SEQUENCE: 440

Phe Tyr Cys His His Ile Met Glu
1               5

<210> SEQ ID NO 441
<211> LENGTH: 8
<212> TYPE: PRT
<213> ORGANISM: Artificial Sequence
<220> FEATURE:
<223> OTHER INFORMATION: Synthetic Construct

<400> SEQUENCE: 441

Phe Tyr Cys His His Ile Pro Glu
1               5

<210> SEQ ID NO 442
<211> LENGTH: 8
<212> TYPE: PRT
<213> ORGANISM: Artificial Sequence
<220> FEATURE:
<223> OTHER INFORMATION: Synthetic Construct

<400> SEQUENCE: 442

Phe Tyr Cys His His Ile Ser Glu
1               5

<210> SEQ ID NO 443
<211> LENGTH: 8
<212> TYPE: PRT
<213> ORGANISM: Artificial Sequence
<220> FEATURE:
<223> OTHER INFORMATION: Synthetic Construct

<400> SEQUENCE: 443

Phe Tyr Cys His His Ile Thr Glu
1               5

<210> SEQ ID NO 444
<211> LENGTH: 8
<212> TYPE: PRT
<213> ORGANISM: Artificial Sequence
<220> FEATURE:
<223> OTHER INFORMATION: Synthetic Construct

<400> SEQUENCE: 444

Phe Tyr Cys His His Leu Ala Glu
1               5

<210> SEQ ID NO 445
<211> LENGTH: 8
<212> TYPE: PRT
<213> ORGANISM: Artificial Sequence
<220> FEATURE:
<223> OTHER INFORMATION: Synthetic Construct

<400> SEQUENCE: 445

Phe Tyr Cys His His Leu Arg Glu
1               5

<210> SEQ ID NO 446
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 446

Phe Tyr Cys His His Leu Asp Glu
1               5

<210> SEQ ID NO 447
<211> LENGTH: 8
<212> TYPE: PRT
<213> ORGANISM: Artificial Sequence
<220> FEATURE:
<223> OTHER INFORMATION: Synthetic Construct

<400> SEQUENCE: 447

Phe Tyr Cys His His Leu Gln Glu
1               5

<210> SEQ ID NO 448
<211> LENGTH: 8
<212> TYPE: PRT
<213> ORGANISM: Artificial Sequence
<220> FEATURE:
<223> OTHER INFORMATION: Synthetic Construct

<400> SEQUENCE: 448

Phe Tyr Cys His His Leu Glu Glu
1               5

<210> SEQ ID NO 449
<211> LENGTH: 8
<212> TYPE: PRT
<213> ORGANISM: Artificial Sequence
<220> FEATURE:
<223> OTHER INFORMATION: Synthetic Construct

<400> SEQUENCE: 449

Phe Tyr Cys His His Leu Leu Glu
1               5

<210> SEQ ID NO 450
<211> LENGTH: 8
<212> TYPE: PRT
<213> ORGANISM: Artificial Sequence
<220> FEATURE:
<223> OTHER INFORMATION: Synthetic Construct

<400> SEQUENCE: 450

Phe Tyr Cys His His Leu Lys Glu
1               5

<210> SEQ ID NO 451
<211> LENGTH: 8
<212> TYPE: PRT
<213> ORGANISM: Artificial Sequence
<220> FEATURE:
<223> OTHER INFORMATION: Synthetic Construct

<400> SEQUENCE: 451

Phe Tyr Cys His His Leu Met Glu
1               5

<210> SEQ ID NO 452
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 452

Phe Tyr Cys His His Leu Pro Glu
1               5

<210> SEQ ID NO 453
<211> LENGTH: 8
<212> TYPE: PRT
<213> ORGANISM: Artificial Sequence
<220> FEATURE:
<223> OTHER INFORMATION: Synthetic Construct

<400> SEQUENCE: 453

Phe Tyr Cys His His Leu Ser Glu
1               5

<210> SEQ ID NO 454
<211> LENGTH: 8
<212> TYPE: PRT
<213> ORGANISM: Artificial Sequence
<220> FEATURE:
<223> OTHER INFORMATION: Synthetic Construct

<400> SEQUENCE: 454

Phe Tyr Cys His His Leu Thr Glu
1               5

<210> SEQ ID NO 455
<211> LENGTH: 8
<212> TYPE: PRT
<213> ORGANISM: Artificial Sequence
<220> FEATURE:
<223> OTHER INFORMATION: Synthetic Construct

<400> SEQUENCE: 455

Phe Tyr Cys His His Lys Ala Glu
1               5

<210> SEQ ID NO 456
<211> LENGTH: 8
<212> TYPE: PRT
<213> ORGANISM: Artificial Sequence
<220> FEATURE:
<223> OTHER INFORMATION: Synthetic Construct

<400> SEQUENCE: 456

Phe Tyr Cys His His Lys Gln Glu
1               5

<210> SEQ ID NO 457
<211> LENGTH: 8
<212> TYPE: PRT
<213> ORGANISM: Artificial Sequence
<220> FEATURE:
<223> OTHER INFORMATION: Synthetic Construct

<400> SEQUENCE: 457

Phe Tyr Cys His His Lys Glu Glu
1               5

<210> SEQ ID NO 458
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 458

Phe Tyr Cys His His Lys Leu Glu
1               5

<210> SEQ ID NO 459
<211> LENGTH: 8
<212> TYPE: PRT
<213> ORGANISM: Artificial Sequence
<220> FEATURE:
<223> OTHER INFORMATION: Synthetic Construct

<400> SEQUENCE: 459

Phe Tyr Cys His His Lys Lys Glu
1               5

<210> SEQ ID NO 460
<211> LENGTH: 8
<212> TYPE: PRT
<213> ORGANISM: Artificial Sequence
<220> FEATURE:
<223> OTHER INFORMATION: Synthetic Construct

<400> SEQUENCE: 460

Phe Tyr Cys His His Lys Met Glu
1               5

<210> SEQ ID NO 461
<211> LENGTH: 8
<212> TYPE: PRT
<213> ORGANISM: Artificial Sequence
<220> FEATURE:
<223> OTHER INFORMATION: Synthetic Construct

<400> SEQUENCE: 461

Phe Tyr Cys His His Lys Ser Glu
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic Construct

<400> SEQUENCE: 462

Phe Tyr Cys His His Lys Arg Glu
1               5

<210> SEQ ID NO 463
<211> LENGTH: 8
<212> TYPE: PRT
<213> ORGANISM: Artificial Sequence
<220> FEATURE:
<223> OTHER INFORMATION: Synthetic Construct

<400> SEQUENCE: 463

Phe Tyr Cys His Ile Ala Ala Glu
1               5

<210> SEQ ID NO 464
<211> LENGTH: 8
<212> TYPE: PRT
<213> ORGANISM: Artificial Sequence
<220> FEATURE:
<223> OTHER INFORMATION: Synthetic Construct

<400> SEQUENCE: 464

Phe Tyr Cys His Ile Ala Arg Glu
1               5

<210> SEQ ID NO 465
<211> LENGTH: 8
<212> TYPE: PRT
<213> ORGANISM: Artificial Sequence
<220> FEATURE:
<223> OTHER INFORMATION: Synthetic Construct

<400> SEQUENCE: 465

Phe Tyr Cys His Ile Ala Asp Glu
1               5

<210> SEQ ID NO 466
<211> LENGTH: 8
<212> TYPE: PRT
<213> ORGANISM: Artificial Sequence
<220> FEATURE:
<223> OTHER INFORMATION: Synthetic Construct

<400> SEQUENCE: 466

Phe Tyr Cys His Ile Ala Gln Glu
1               5

<210> SEQ ID NO 467
<211> LENGTH: 8
<212> TYPE: PRT
<213> ORGANISM: Artificial Sequence
<220> FEATURE:
<223> OTHER INFORMATION: Synthetic Construct

<400> SEQUENCE: 467

Phe Tyr Cys His Ile Ala Glu Glu
1               5

<210> SEQ ID NO 468
<211> LENGTH: 8
<212> TYPE: PRT
<213> ORGANISM: Artificial Sequence
<220> FEATURE:
<223> OTHER INFORMATION: Synthetic Construct

<400> SEQUENCE: 468

Phe Tyr Cys His Ile Ala Leu Glu
1               5

<210> SEQ ID NO 469
<211> LENGTH: 8
<212> TYPE: PRT
<213> ORGANISM: Artificial Sequence
<220> FEATURE:
<223> OTHER INFORMATION: Synthetic Construct

<400> SEQUENCE: 469

Phe Tyr Cys His Ile Ala Lys Glu
1               5

<210> SEQ ID NO 470
<211> LENGTH: 8
<212> TYPE: PRT
<213> ORGANISM: Artificial Sequence
<220> FEATURE:
<223> OTHER INFORMATION: Synthetic Construct

<400> SEQUENCE: 470

Phe Tyr Cys His Ile Ala Met Glu
1               5

<210> SEQ ID NO 471
<211> LENGTH: 8
<212> TYPE: PRT
<213> ORGANISM: Artificial Sequence
<220> FEATURE:
<223> OTHER INFORMATION: Synthetic Construct

<400> SEQUENCE: 471

Phe Tyr Cys His Ile Ala Pro Glu
1               5

<210> SEQ ID NO 472
<211> LENGTH: 8
<212> TYPE: PRT
<213> ORGANISM: Artificial Sequence
<220> FEATURE:
<223> OTHER INFORMATION: Synthetic Construct

<400> SEQUENCE: 472

Phe Tyr Cys His Ile Ala Ser Glu
1               5

<210> SEQ ID NO 473
<211> LENGTH: 8
<212> TYPE: PRT
<213> ORGANISM: Artificial Sequence
<220> FEATURE:
<223> OTHER INFORMATION: Synthetic Construct

<400> SEQUENCE: 473

Phe Tyr Cys His Ile Ala Thr Glu
1               5

<210> SEQ ID NO 474
<211> LENGTH: 8
<212> TYPE: PRT
<213> ORGANISM: Artificial Sequence
<220> FEATURE:
<223> OTHER INFORMATION: Synthetic Construct

<400> SEQUENCE: 474

Phe Tyr Cys His Ile Gln Ala Glu
1               5

<210> SEQ ID NO 475
<211> LENGTH: 8
<212> TYPE: PRT
<213> ORGANISM: Artificial Sequence
<220> FEATURE:
<223> OTHER INFORMATION: Synthetic Construct

<400> SEQUENCE: 475

Phe Tyr Cys His Ile Gln Arg Glu
1               5

<210> SEQ ID NO 476
<211> LENGTH: 8
<212> TYPE: PRT
<213> ORGANISM: Artificial Sequence
<220> FEATURE:
<223> OTHER INFORMATION: Synthetic Construct

<400> SEQUENCE: 476

```
Phe Tyr Cys His Ile Gln Asp Glu
1               5

<210> SEQ ID NO 477
<211> LENGTH: 8
<212> TYPE: PRT
<213> ORGANISM: Artificial Sequence
<220> FEATURE:
<223> OTHER INFORMATION: Synthetic Construct

<400> SEQUENCE: 477

Phe Tyr Cys His Ile Gln Gln Glu
1               5

<210> SEQ ID NO 478
<211> LENGTH: 8
<212> TYPE: PRT
<213> ORGANISM: Artificial Sequence
<220> FEATURE:
<223> OTHER INFORMATION: Synthetic Construct

<400> SEQUENCE: 478

Phe Tyr Cys His Ile Gln Glu Glu
1               5

<210> SEQ ID NO 479
<211> LENGTH: 8
<212> TYPE: PRT
<213> ORGANISM: Artificial Sequence
<220> FEATURE:
<223> OTHER INFORMATION: Synthetic Construct

<400> SEQUENCE: 479

Phe Tyr Cys His Ile Gln Leu Glu
1               5

<210> SEQ ID NO 480
<211> LENGTH: 8
<212> TYPE: PRT
<213> ORGANISM: Artificial Sequence
<220> FEATURE:
<223> OTHER INFORMATION: Synthetic Construct

<400> SEQUENCE: 480

Phe Tyr Cys His Ile Gln Lys Glu
1               5

<210> SEQ ID NO 481
<211> LENGTH: 8
<212> TYPE: PRT
<213> ORGANISM: Artificial Sequence
<220> FEATURE:
<223> OTHER INFORMATION: Synthetic Construct

<400> SEQUENCE: 481

Phe Tyr Cys His Ile Gln Met Glu
1               5

<210> SEQ ID NO 482
<211> LENGTH: 8
<212> TYPE: PRT
<213> ORGANISM: Artificial Sequence
<220> FEATURE:
<223> OTHER INFORMATION: Synthetic Construct

<400> SEQUENCE: 482
```

```
Phe Tyr Cys His Ile Gln Pro Glu
1               5

<210> SEQ ID NO 483
<211> LENGTH: 8
<212> TYPE: PRT
<213> ORGANISM: Artificial Sequence
<220> FEATURE:
<223> OTHER INFORMATION: Synthetic Construct

<400> SEQUENCE: 483

Phe Tyr Cys His Ile Gln Ser Glu
1               5

<210> SEQ ID NO 484
<211> LENGTH: 8
<212> TYPE: PRT
<213> ORGANISM: Artificial Sequence
<220> FEATURE:
<223> OTHER INFORMATION: Synthetic Construct

<400> SEQUENCE: 484

Phe Tyr Cys His Ile Gln Thr Glu
1               5

<210> SEQ ID NO 485
<211> LENGTH: 8
<212> TYPE: PRT
<213> ORGANISM: Artificial Sequence
<220> FEATURE:
<223> OTHER INFORMATION: Synthetic Construct

<400> SEQUENCE: 485

Phe Tyr Cys His Ile Glu Ala Glu
1               5

<210> SEQ ID NO 486
<211> LENGTH: 8
<212> TYPE: PRT
<213> ORGANISM: Artificial Sequence
<220> FEATURE:
<223> OTHER INFORMATION: Synthetic Construct

<400> SEQUENCE: 486

Phe Tyr Cys His Ile Glu Arg Glu
1               5

<210> SEQ ID NO 487
<211> LENGTH: 8
<212> TYPE: PRT
<213> ORGANISM: Artificial Sequence
<220> FEATURE:
<223> OTHER INFORMATION: Synthetic Construct

<400> SEQUENCE: 487

Phe Tyr Cys His Ile Glu Asp Glu
1               5

<210> SEQ ID NO 488
<211> LENGTH: 8
<212> TYPE: PRT
<213> ORGANISM: Artificial Sequence
<220> FEATURE:
<223> OTHER INFORMATION: Synthetic Construct

<400> SEQUENCE: 488

Phe Tyr Cys His Ile Glu Gln Glu
```

```
1               5
```

<210> SEQ ID NO 489
<211> LENGTH: 8
<212> TYPE: PRT
<213> ORGANISM: Artificial Sequence
<220> FEATURE:
<223> OTHER INFORMATION: Synthetic Construct

<400> SEQUENCE: 489

```
Phe Tyr Cys His Ile Glu Glu Glu
1               5
```

<210> SEQ ID NO 490
<211> LENGTH: 8
<212> TYPE: PRT
<213> ORGANISM: Artificial Sequence
<220> FEATURE:
<223> OTHER INFORMATION: Synthetic Construct

<400> SEQUENCE: 490

```
Phe Tyr Cys His Ile Glu Leu Glu
1               5
```

<210> SEQ ID NO 491
<211> LENGTH: 8
<212> TYPE: PRT
<213> ORGANISM: Artificial Sequence
<220> FEATURE:
<223> OTHER INFORMATION: Synthetic Construct

<400> SEQUENCE: 491

```
Phe Tyr Cys His Ile Glu Lys Glu
1               5
```

<210> SEQ ID NO 492
<211> LENGTH: 8
<212> TYPE: PRT
<213> ORGANISM: Artificial Sequence
<220> FEATURE:
<223> OTHER INFORMATION: Synthetic Construct

<400> SEQUENCE: 492

```
Phe Tyr Cys His Ile Glu Met Glu
1               5
```

<210> SEQ ID NO 493
<211> LENGTH: 8
<212> TYPE: PRT
<213> ORGANISM: Artificial Sequence
<220> FEATURE:
<223> OTHER INFORMATION: Synthetic Construct

<400> SEQUENCE: 493

```
Phe Tyr Cys His Ile Glu Pro Glu
1               5
```

<210> SEQ ID NO 494
<211> LENGTH: 8
<212> TYPE: PRT
<213> ORGANISM: Artificial Sequence
<220> FEATURE:
<223> OTHER INFORMATION: Synthetic Construct

<400> SEQUENCE: 494

```
Phe Tyr Cys His Ile Glu Ser Glu
1               5
```

<210> SEQ ID NO 495
<211> LENGTH: 8
<212> TYPE: PRT
<213> ORGANISM: Artificial Sequence
<220> FEATURE:
<223> OTHER INFORMATION: Synthetic Construct

<400> SEQUENCE: 495

Phe Tyr Cys His Ile Glu Thr Glu
1               5

<210> SEQ ID NO 496
<211> LENGTH: 8
<212> TYPE: PRT
<213> ORGANISM: Artificial Sequence
<220> FEATURE:
<223> OTHER INFORMATION: Synthetic Construct

<400> SEQUENCE: 496

Phe Tyr Cys His Ile Glu Ala Glu
1               5

<210> SEQ ID NO 497
<211> LENGTH: 8
<212> TYPE: PRT
<213> ORGANISM: Artificial Sequence
<220> FEATURE:
<223> OTHER INFORMATION: Synthetic Construct

<400> SEQUENCE: 497

Phe Tyr Cys His Ile Ile Arg Glu
1               5

<210> SEQ ID NO 498
<211> LENGTH: 8
<212> TYPE: PRT
<213> ORGANISM: Artificial Sequence
<220> FEATURE:
<223> OTHER INFORMATION: Synthetic Construct

<400> SEQUENCE: 498

Phe Tyr Cys His Ile Ile Asp Glu
1               5

<210> SEQ ID NO 499
<211> LENGTH: 8
<212> TYPE: PRT
<213> ORGANISM: Artificial Sequence
<220> FEATURE:
<223> OTHER INFORMATION: Synthetic Construct

<400> SEQUENCE: 499

Phe Tyr Cys His Ile Ile Gln Glu
1               5

<210> SEQ ID NO 500
<211> LENGTH: 8
<212> TYPE: PRT
<213> ORGANISM: Artificial Sequence
<220> FEATURE:
<223> OTHER INFORMATION: Synthetic Construct

<400> SEQUENCE: 500

Phe Tyr Cys His Ile Ile Glu Glu
1               5

```
<210> SEQ ID NO 501
<211> LENGTH: 8
<212> TYPE: PRT
<213> ORGANISM: Artificial Sequence
<220> FEATURE:
<223> OTHER INFORMATION: Synthetic Construct

<400> SEQUENCE: 501

Phe Tyr Cys His Ile Ile Leu Glu
1               5

<210> SEQ ID NO 502
<211> LENGTH: 8
<212> TYPE: PRT
<213> ORGANISM: Artificial Sequence
<220> FEATURE:
<223> OTHER INFORMATION: Synthetic Construct

<400> SEQUENCE: 502

Phe Tyr Cys His Ile Ile Lys Glu
1               5

<210> SEQ ID NO 503
<211> LENGTH: 8
<212> TYPE: PRT
<213> ORGANISM: Artificial Sequence
<220> FEATURE:
<223> OTHER INFORMATION: Synthetic Construct

<400> SEQUENCE: 503

Phe Tyr Cys His Ile Ile Met Glu
1               5

<210> SEQ ID NO 504
<211> LENGTH: 8
<212> TYPE: PRT
<213> ORGANISM: Artificial Sequence
<220> FEATURE:
<223> OTHER INFORMATION: Synthetic Construct

<400> SEQUENCE: 504

Phe Tyr Cys His Ile Ile Pro Glu
1               5

<210> SEQ ID NO 505
<211> LENGTH: 8
<212> TYPE: PRT
<213> ORGANISM: Artificial Sequence
<220> FEATURE:
<223> OTHER INFORMATION: Synthetic Construct

<400> SEQUENCE: 505

Phe Tyr Cys His Ile Ile Ser Glu
1               5

<210> SEQ ID NO 506
<211> LENGTH: 8
<212> TYPE: PRT
<213> ORGANISM: Artificial Sequence
<220> FEATURE:
<223> OTHER INFORMATION: Synthetic Construct

<400> SEQUENCE: 506

Phe Tyr Cys His Ile Ile Thr Glu
1               5
```

```
<210> SEQ ID NO 507
<211> LENGTH: 8
<212> TYPE: PRT
<213> ORGANISM: Artificial Sequence
<220> FEATURE:
<223> OTHER INFORMATION: Synthetic Construct

<400> SEQUENCE: 507

Phe Tyr Cys His Ile Leu Ala Glu
1               5

<210> SEQ ID NO 508
<211> LENGTH: 8
<212> TYPE: PRT
<213> ORGANISM: Artificial Sequence
<220> FEATURE:
<223> OTHER INFORMATION: Synthetic Construct

<400> SEQUENCE: 508

Phe Tyr Cys His Ile Leu Arg Glu
1               5

<210> SEQ ID NO 509
<211> LENGTH: 8
<212> TYPE: PRT
<213> ORGANISM: Artificial Sequence
<220> FEATURE:
<223> OTHER INFORMATION: Synthetic Construct

<400> SEQUENCE: 509

Phe Tyr Cys His Ile Leu Asp Glu
1               5

<210> SEQ ID NO 510
<211> LENGTH: 8
<212> TYPE: PRT
<213> ORGANISM: Artificial Sequence
<220> FEATURE:
<223> OTHER INFORMATION: Synthetic Construct

<400> SEQUENCE: 510

Phe Tyr Cys His Ile Leu Gln Glu
1               5

<210> SEQ ID NO 511
<211> LENGTH: 8
<212> TYPE: PRT
<213> ORGANISM: Artificial Sequence
<220> FEATURE:
<223> OTHER INFORMATION: Synthetic Construct

<400> SEQUENCE: 511

Phe Tyr Cys His Ile Leu Glu Glu
1               5

<210> SEQ ID NO 512
<211> LENGTH: 8
<212> TYPE: PRT
<213> ORGANISM: Artificial Sequence
<220> FEATURE:
<223> OTHER INFORMATION: Synthetic Construct

<400> SEQUENCE: 512

Phe Tyr Cys His Ile Leu Leu Glu
1               5

<210> SEQ ID NO 513
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 513

Phe Tyr Cys His Ile Leu Lys Glu
1               5

<210> SEQ ID NO 514
<211> LENGTH: 8
<212> TYPE: PRT
<213> ORGANISM: Artificial Sequence
<220> FEATURE:
<223> OTHER INFORMATION: Synthetic Construct

<400> SEQUENCE: 514

Phe Tyr Cys His Ile Leu Met Glu
1               5

<210> SEQ ID NO 515
<211> LENGTH: 8
<212> TYPE: PRT
<213> ORGANISM: Artificial Sequence
<220> FEATURE:
<223> OTHER INFORMATION: Synthetic Construct

<400> SEQUENCE: 515

Phe Tyr Cys His Ile Leu Pro Glu
1               5

<210> SEQ ID NO 516
<211> LENGTH: 8
<212> TYPE: PRT
<213> ORGANISM: Artificial Sequence
<220> FEATURE:
<223> OTHER INFORMATION: Synthetic Construct

<400> SEQUENCE: 516

Phe Tyr Cys His Ile Leu Ser Glu
1               5

<210> SEQ ID NO 517
<211> LENGTH: 8
<212> TYPE: PRT
<213> ORGANISM: Artificial Sequence
<220> FEATURE:
<223> OTHER INFORMATION: Synthetic Construct

<400> SEQUENCE: 517

Phe Tyr Cys His Ile Leu Thr Glu
1               5

<210> SEQ ID NO 518
<211> LENGTH: 8
<212> TYPE: PRT
<213> ORGANISM: Artificial Sequence
<220> FEATURE:
<223> OTHER INFORMATION: Synthetic Construct

<400> SEQUENCE: 518

Phe Tyr Cys His Ile Lys Ala Glu
1               5

<210> SEQ ID NO 519
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 519

Phe Tyr Cys His Ile Lys Gln Glu
1               5

<210> SEQ ID NO 520
<211> LENGTH: 8
<212> TYPE: PRT
<213> ORGANISM: Artificial Sequence
<220> FEATURE:
<223> OTHER INFORMATION: Synthetic Construct

<400> SEQUENCE: 520

Phe Tyr Cys His Ile Lys Glu Glu
1               5

<210> SEQ ID NO 521
<211> LENGTH: 8
<212> TYPE: PRT
<213> ORGANISM: Artificial Sequence
<220> FEATURE:
<223> OTHER INFORMATION: Synthetic Construct

<400> SEQUENCE: 521

Phe Tyr Cys His Ile Lys Leu Glu
1               5

<210> SEQ ID NO 522
<211> LENGTH: 8
<212> TYPE: PRT
<213> ORGANISM: Artificial Sequence
<220> FEATURE:
<223> OTHER INFORMATION: Synthetic Construct

<400> SEQUENCE: 522

Phe Tyr Cys His Ile Lys Lys Glu
1               5

<210> SEQ ID NO 523
<211> LENGTH: 8
<212> TYPE: PRT
<213> ORGANISM: Artificial Sequence
<220> FEATURE:
<223> OTHER INFORMATION: Synthetic Construct

<400> SEQUENCE: 523

Phe Tyr Cys His Ile Lys Met Glu
1               5

<210> SEQ ID NO 524
<211> LENGTH: 8
<212> TYPE: PRT
<213> ORGANISM: Artificial Sequence
<220> FEATURE:
<223> OTHER INFORMATION: Synthetic Construct

<400> SEQUENCE: 524

Phe Tyr Cys His Ile Lys Ser Glu
1               5

<210> SEQ ID NO 525
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 525

Phe Tyr Cys His Ile Lys Arg Glu
1               5

<210> SEQ ID NO 526
<211> LENGTH: 8
<212> TYPE: PRT
<213> ORGANISM: Artificial Sequence
<220> FEATURE:
<223> OTHER INFORMATION: Synthetic Construct

<400> SEQUENCE: 526

Phe Tyr Cys His Ile Lys Thr Glu
1               5

<210> SEQ ID NO 527
<211> LENGTH: 8
<212> TYPE: PRT
<213> ORGANISM: Artificial Sequence
<220> FEATURE:
<223> OTHER INFORMATION: Synthetic Construct

<400> SEQUENCE: 527

Phe Tyr Cys His Ile Lys Pro Glu
1               5

<210> SEQ ID NO 528
<211> LENGTH: 8
<212> TYPE: PRT
<213> ORGANISM: Artificial Sequence
<220> FEATURE:
<223> OTHER INFORMATION: Synthetic Construct

<400> SEQUENCE: 528

Phe Tyr Cys His Ile Lys Asp Glu
1               5

<210> SEQ ID NO 529
<211> LENGTH: 8
<212> TYPE: PRT
<213> ORGANISM: Artificial Sequence
<220> FEATURE:
<223> OTHER INFORMATION: Synthetic Construct

<400> SEQUENCE: 529

Phe Tyr Cys His Leu Ala Ala Glu
1               5

<210> SEQ ID NO 530
<211> LENGTH: 8
<212> TYPE: PRT
<213> ORGANISM: Artificial Sequence
<220> FEATURE:
<223> OTHER INFORMATION: Synthetic Construct

<400> SEQUENCE: 530

Phe Tyr Cys His Leu Ala Arg Glu
1               5

<210> SEQ ID NO 531
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 531

Phe Tyr Cys His Leu Ala Asp Glu
1               5

<210> SEQ ID NO 532
<211> LENGTH: 8
<212> TYPE: PRT
<213> ORGANISM: Artificial Sequence
<220> FEATURE:
<223> OTHER INFORMATION: Synthetic Construct

<400> SEQUENCE: 532

Phe Tyr Cys His Leu Ala Gln Glu
1               5

<210> SEQ ID NO 533
<211> LENGTH: 8
<212> TYPE: PRT
<213> ORGANISM: Artificial Sequence
<220> FEATURE:
<223> OTHER INFORMATION: Synthetic Construct

<400> SEQUENCE: 533

Phe Tyr Cys His Leu Ala Met Glu
1               5

<210> SEQ ID NO 534
<211> LENGTH: 8
<212> TYPE: PRT
<213> ORGANISM: Artificial Sequence
<220> FEATURE:
<223> OTHER INFORMATION: Synthetic Construct

<400> SEQUENCE: 534

Phe Tyr Cys His Leu Ala Pro Glu
1               5

<210> SEQ ID NO 535
<211> LENGTH: 8
<212> TYPE: PRT
<213> ORGANISM: Artificial Sequence
<220> FEATURE:
<223> OTHER INFORMATION: Synthetic Construct

<400> SEQUENCE: 535

Phe Tyr Cys His Leu Ala Ser Glu
1               5

<210> SEQ ID NO 536
<211> LENGTH: 8
<212> TYPE: PRT
<213> ORGANISM: Artificial Sequence
<220> FEATURE:
<223> OTHER INFORMATION: Synthetic Construct

<400> SEQUENCE: 536

Phe Tyr Cys His Leu Ala Thr Glu
1               5

<210> SEQ ID NO 537
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 537

Phe Tyr Cys His Leu Gln Ala Glu
1               5

<210> SEQ ID NO 538
<211> LENGTH: 8
<212> TYPE: PRT
<213> ORGANISM: Artificial Sequence
<220> FEATURE:
<223> OTHER INFORMATION: Synthetic Construct

<400> SEQUENCE: 538

Phe Tyr Cys His Leu Gln Arg Glu
1               5

<210> SEQ ID NO 539
<211> LENGTH: 8
<212> TYPE: PRT
<213> ORGANISM: Artificial Sequence
<220> FEATURE:
<223> OTHER INFORMATION: Synthetic Construct

<400> SEQUENCE: 539

Phe Tyr Cys His Leu Gln Asp Glu
1               5

<210> SEQ ID NO 540
<211> LENGTH: 8
<212> TYPE: PRT
<213> ORGANISM: Artificial Sequence
<220> FEATURE:
<223> OTHER INFORMATION: Synthetic Construct

<400> SEQUENCE: 540

Phe Tyr Cys His Leu Gln Gln Glu
1               5

<210> SEQ ID NO 541
<211> LENGTH: 8
<212> TYPE: PRT
<213> ORGANISM: Artificial Sequence
<220> FEATURE:
<223> OTHER INFORMATION: Synthetic Construct

<400> SEQUENCE: 541

Phe Tyr Cys His Leu Gln Glu Glu
1               5

<210> SEQ ID NO 542
<211> LENGTH: 8
<212> TYPE: PRT
<213> ORGANISM: Artificial Sequence
<220> FEATURE:
<223> OTHER INFORMATION: Synthetic Construct

<400> SEQUENCE: 542

Phe Tyr Cys His Leu Gln Leu Glu
1               5

<210> SEQ ID NO 543
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 543

Phe Tyr Cys His Leu Gln Lys Glu
1               5

<210> SEQ ID NO 544
<211> LENGTH: 8
<212> TYPE: PRT
<213> ORGANISM: Artificial Sequence
<220> FEATURE:
<223> OTHER INFORMATION: Synthetic Construct

<400> SEQUENCE: 544

Phe Tyr Cys His Leu Gln Met Glu
1               5

<210> SEQ ID NO 545
<211> LENGTH: 8
<212> TYPE: PRT
<213> ORGANISM: Artificial Sequence
<220> FEATURE:
<223> OTHER INFORMATION: Synthetic Construct

<400> SEQUENCE: 545

Phe Tyr Cys His Leu Gln Pro Glu
1               5

<210> SEQ ID NO 546
<211> LENGTH: 8
<212> TYPE: PRT
<213> ORGANISM: Artificial Sequence
<220> FEATURE:
<223> OTHER INFORMATION: Synthetic Construct

<400> SEQUENCE: 546

Phe Tyr Cys His Leu Gln Ser Glu
1               5

<210> SEQ ID NO 547
<211> LENGTH: 8
<212> TYPE: PRT
<213> ORGANISM: Artificial Sequence
<220> FEATURE:
<223> OTHER INFORMATION: Synthetic Construct

<400> SEQUENCE: 547

Phe Tyr Cys His Leu Gln Thr Glu
1               5

<210> SEQ ID NO 548
<211> LENGTH: 8
<212> TYPE: PRT
<213> ORGANISM: Artificial Sequence
<220> FEATURE:
<223> OTHER INFORMATION: Synthetic Construct

<400> SEQUENCE: 548

Phe Tyr Cys His Leu Glu Ala Glu
1               5

<210> SEQ ID NO 549
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 549

Phe Tyr Cys His Leu Glu Arg Glu
1               5

<210> SEQ ID NO 550
<211> LENGTH: 8
<212> TYPE: PRT
<213> ORGANISM: Artificial Sequence
<220> FEATURE:
<223> OTHER INFORMATION: Synthetic Construct

<400> SEQUENCE: 550

Phe Tyr Cys His Leu Glu Asp Glu
1               5

<210> SEQ ID NO 551
<211> LENGTH: 8
<212> TYPE: PRT
<213> ORGANISM: Artificial Sequence
<220> FEATURE:
<223> OTHER INFORMATION: Synthetic Construct

<400> SEQUENCE: 551

Phe Tyr Cys His Leu Glu Gln Glu
1               5

<210> SEQ ID NO 552
<211> LENGTH: 8
<212> TYPE: PRT
<213> ORGANISM: Artificial Sequence
<220> FEATURE:
<223> OTHER INFORMATION: Synthetic Construct

<400> SEQUENCE: 552

Phe Tyr Cys His Leu Glu Glu Glu
1               5

<210> SEQ ID NO 553
<211> LENGTH: 8
<212> TYPE: PRT
<213> ORGANISM: Artificial Sequence
<220> FEATURE:
<223> OTHER INFORMATION: Synthetic Construct

<400> SEQUENCE: 553

Phe Tyr Cys His Leu Glu Leu Glu
1               5

<210> SEQ ID NO 554
<211> LENGTH: 8
<212> TYPE: PRT
<213> ORGANISM: Artificial Sequence
<220> FEATURE:
<223> OTHER INFORMATION: Synthetic Construct

<400> SEQUENCE: 554

Phe Tyr Cys His Leu Glu Lys Glu
1               5

<210> SEQ ID NO 555
<211> LENGTH: 8
<212> TYPE: PRT
<213> ORGANISM: Artificial Sequence
<220> FEATURE:
<223> OTHER INFORMATION: Synthetic Construct

<400> SEQUENCE: 555
```

Phe Tyr Cys His Leu Glu Met Glu
1               5

<210> SEQ ID NO 556
<211> LENGTH: 8
<212> TYPE: PRT
<213> ORGANISM: Artificial Sequence
<220> FEATURE:
<223> OTHER INFORMATION: Synthetic Construct

<400> SEQUENCE: 556

Phe Tyr Cys His Leu Glu Pro Glu
1               5

<210> SEQ ID NO 557
<211> LENGTH: 8
<212> TYPE: PRT
<213> ORGANISM: Artificial Sequence
<220> FEATURE:
<223> OTHER INFORMATION: Synthetic Construct

<400> SEQUENCE: 557

Phe Tyr Cys His Leu Glu Ser Glu
1               5

<210> SEQ ID NO 558
<211> LENGTH: 8
<212> TYPE: PRT
<213> ORGANISM: Artificial Sequence
<220> FEATURE:
<223> OTHER INFORMATION: Synthetic Construct

<400> SEQUENCE: 558

Phe Tyr Cys His Leu Glu Thr Glu
1               5

<210> SEQ ID NO 559
<211> LENGTH: 8
<212> TYPE: PRT
<213> ORGANISM: Artificial Sequence
<220> FEATURE:
<223> OTHER INFORMATION: Synthetic Construct

<400> SEQUENCE: 559

Phe Tyr Cys His Leu Ile Ala Glu
1               5

<210> SEQ ID NO 560
<211> LENGTH: 8
<212> TYPE: PRT
<213> ORGANISM: Artificial Sequence
<220> FEATURE:
<223> OTHER INFORMATION: Synthetic Construct

<400> SEQUENCE: 560

Phe Tyr Cys His Leu Ile Arg Glu
1               5

<210> SEQ ID NO 561
<211> LENGTH: 8
<212> TYPE: PRT
<213> ORGANISM: Artificial Sequence
<220> FEATURE:
<223> OTHER INFORMATION: Synthetic Construct

<400> SEQUENCE: 561

Phe Tyr Cys His Leu Ile Asp Glu
1               5

<210> SEQ ID NO 562
<211> LENGTH: 8
<212> TYPE: PRT
<213> ORGANISM: Artificial Sequence
<220> FEATURE:
<223> OTHER INFORMATION: Synthetic Construct

<400> SEQUENCE: 562

Phe Tyr Cys His Leu Ile Gln Glu
1               5

<210> SEQ ID NO 563
<211> LENGTH: 8
<212> TYPE: PRT
<213> ORGANISM: Artificial Sequence
<220> FEATURE:
<223> OTHER INFORMATION: Synthetic Construct

<400> SEQUENCE: 563

Phe Tyr Cys His Leu Ile Glu Glu
1               5

<210> SEQ ID NO 564
<211> LENGTH: 8
<212> TYPE: PRT
<213> ORGANISM: Artificial Sequence
<220> FEATURE:
<223> OTHER INFORMATION: Synthetic Construct

<400> SEQUENCE: 564

Phe Tyr Cys His Leu Ile Leu Glu
1               5

<210> SEQ ID NO 565
<211> LENGTH: 8
<212> TYPE: PRT
<213> ORGANISM: Artificial Sequence
<220> FEATURE:
<223> OTHER INFORMATION: Synthetic Construct

<400> SEQUENCE: 565

Phe Tyr Cys His Leu Ile Lys Glu
1               5

<210> SEQ ID NO 566
<211> LENGTH: 8
<212> TYPE: PRT
<213> ORGANISM: Artificial Sequence
<220> FEATURE:
<223> OTHER INFORMATION: Synthetic Construct

<400> SEQUENCE: 566

Phe Tyr Cys His Leu Ile Met Glu
1               5

<210> SEQ ID NO 567
<211> LENGTH: 8
<212> TYPE: PRT
<213> ORGANISM: Artificial Sequence
<220> FEATURE:
<223> OTHER INFORMATION: Synthetic Construct

<400> SEQUENCE: 567

Phe Tyr Cys His Leu Ile Pro Glu

```
<210> SEQ ID NO 568
<211> LENGTH: 8
<212> TYPE: PRT
<213> ORGANISM: Artificial Sequence
<220> FEATURE:
<223> OTHER INFORMATION: Synthetic Construct

<400> SEQUENCE: 568

Phe Tyr Cys His Leu Ile Ser Glu
1               5

<210> SEQ ID NO 569
<211> LENGTH: 8
<212> TYPE: PRT
<213> ORGANISM: Artificial Sequence
<220> FEATURE:
<223> OTHER INFORMATION: Synthetic Construct

<400> SEQUENCE: 569

Phe Tyr Cys His Leu Ile Thr Glu
1               5

<210> SEQ ID NO 570
<211> LENGTH: 8
<212> TYPE: PRT
<213> ORGANISM: Artificial Sequence
<220> FEATURE:
<223> OTHER INFORMATION: Synthetic Construct

<400> SEQUENCE: 570

Phe Tyr Cys His Leu Leu Ala Glu
1               5

<210> SEQ ID NO 571
<211> LENGTH: 8
<212> TYPE: PRT
<213> ORGANISM: Artificial Sequence
<220> FEATURE:
<223> OTHER INFORMATION: Synthetic Construct

<400> SEQUENCE: 571

Phe Tyr Cys His Leu Leu Arg Glu
1               5

<210> SEQ ID NO 572
<211> LENGTH: 8
<212> TYPE: PRT
<213> ORGANISM: Artificial Sequence
<220> FEATURE:
<223> OTHER INFORMATION: Synthetic Construct

<400> SEQUENCE: 572

Phe Tyr Cys His Leu Leu Asp Glu
1               5

<210> SEQ ID NO 573
<211> LENGTH: 8
<212> TYPE: PRT
<213> ORGANISM: Artificial Sequence
<220> FEATURE:
<223> OTHER INFORMATION: Synthetic Construct

<400> SEQUENCE: 573

Phe Tyr Cys His Leu Leu Gln Glu
1               5
```

<210> SEQ ID NO 574
<211> LENGTH: 8
<212> TYPE: PRT
<213> ORGANISM: Artificial Sequence
<220> FEATURE:
<223> OTHER INFORMATION: Synthetic Construct

<400> SEQUENCE: 574

Phe Tyr Cys His Leu Leu Glu Glu
1               5

<210> SEQ ID NO 575
<211> LENGTH: 8
<212> TYPE: PRT
<213> ORGANISM: Artificial Sequence
<220> FEATURE:
<223> OTHER INFORMATION: Synthetic Construct

<400> SEQUENCE: 575

Phe Tyr Cys His Leu Leu Leu Glu
1               5

<210> SEQ ID NO 576
<211> LENGTH: 8
<212> TYPE: PRT
<213> ORGANISM: Artificial Sequence
<220> FEATURE:
<223> OTHER INFORMATION: Synthetic Construct

<400> SEQUENCE: 576

Phe Tyr Cys His Leu Leu Lys Glu
1               5

<210> SEQ ID NO 577
<211> LENGTH: 8
<212> TYPE: PRT
<213> ORGANISM: Artificial Sequence
<220> FEATURE:
<223> OTHER INFORMATION: Synthetic Construct

<400> SEQUENCE: 577

Phe Tyr Cys His Leu Leu Met Glu
1               5

<210> SEQ ID NO 578
<211> LENGTH: 8
<212> TYPE: PRT
<213> ORGANISM: Artificial Sequence
<220> FEATURE:
<223> OTHER INFORMATION: Synthetic Construct

<400> SEQUENCE: 578

Phe Tyr Cys His Leu Leu Pro Glu
1               5

<210> SEQ ID NO 579
<211> LENGTH: 8
<212> TYPE: PRT
<213> ORGANISM: Artificial Sequence
<220> FEATURE:
<223> OTHER INFORMATION: Synthetic Construct

<400> SEQUENCE: 579

Phe Tyr Cys His Leu Leu Ser Glu
1               5

```
<210> SEQ ID NO 580
<211> LENGTH: 8
<212> TYPE: PRT
<213> ORGANISM: Artificial Sequence
<220> FEATURE:
<223> OTHER INFORMATION: Synthetic Construct

<400> SEQUENCE: 580

Phe Tyr Cys His Leu Leu Thr Glu
1               5

<210> SEQ ID NO 581
<211> LENGTH: 8
<212> TYPE: PRT
<213> ORGANISM: Artificial Sequence
<220> FEATURE:
<223> OTHER INFORMATION: Synthetic Construct

<400> SEQUENCE: 581

Phe Tyr Cys His Leu Lys Ala Glu
1               5

<210> SEQ ID NO 582
<211> LENGTH: 8
<212> TYPE: PRT
<213> ORGANISM: Artificial Sequence
<220> FEATURE:
<223> OTHER INFORMATION: Synthetic Construct

<400> SEQUENCE: 582

Phe Tyr Cys His Leu Lys Gln Glu
1               5

<210> SEQ ID NO 583
<211> LENGTH: 8
<212> TYPE: PRT
<213> ORGANISM: Artificial Sequence
<220> FEATURE:
<223> OTHER INFORMATION: Synthetic Construct

<400> SEQUENCE: 583

Phe Tyr Cys His Leu Lys Glu Glu
1               5

<210> SEQ ID NO 584
<211> LENGTH: 8
<212> TYPE: PRT
<213> ORGANISM: Artificial Sequence
<220> FEATURE:
<223> OTHER INFORMATION: Synthetic Construct

<400> SEQUENCE: 584

Phe Tyr Cys His Leu Lys Leu Glu
1               5

<210> SEQ ID NO 585
<211> LENGTH: 8
<212> TYPE: PRT
<213> ORGANISM: Artificial Sequence
<220> FEATURE:
<223> OTHER INFORMATION: Synthetic Construct

<400> SEQUENCE: 585

Phe Tyr Cys His Leu Lys Lys Glu
1               5
```

-continued

```
<210> SEQ ID NO 586
<211> LENGTH: 8
<212> TYPE: PRT
<213> ORGANISM: Artificial Sequence
<220> FEATURE:
<223> OTHER INFORMATION: Synthetic Construct

<400> SEQUENCE: 586

Phe Tyr Cys His Leu Lys Met Glu
1               5

<210> SEQ ID NO 587
<211> LENGTH: 8
<212> TYPE: PRT
<213> ORGANISM: Artificial Sequence
<220> FEATURE:
<223> OTHER INFORMATION: Synthetic Construct

<400> SEQUENCE: 587

Phe Tyr Cys His Leu Lys Ser Glu
1               5

<210> SEQ ID NO 588
<211> LENGTH: 8
<212> TYPE: PRT
<213> ORGANISM: Artificial Sequence
<220> FEATURE:
<223> OTHER INFORMATION: Synthetic Construct

<400> SEQUENCE: 588

Phe Tyr Cys His Leu Lys Arg Glu
1               5

<210> SEQ ID NO 589
<211> LENGTH: 8
<212> TYPE: PRT
<213> ORGANISM: Artificial Sequence
<220> FEATURE:
<223> OTHER INFORMATION: Synthetic Construct

<400> SEQUENCE: 589

Phe Tyr Cys His Leu Ala Glu Glu
1               5

<210> SEQ ID NO 590
<211> LENGTH: 8
<212> TYPE: PRT
<213> ORGANISM: Artificial Sequence
<220> FEATURE:
<223> OTHER INFORMATION: Synthetic Construct

<400> SEQUENCE: 590

Phe Tyr Cys His Leu Ala Leu Glu
1               5

<210> SEQ ID NO 591
<211> LENGTH: 8
<212> TYPE: PRT
<213> ORGANISM: Artificial Sequence
<220> FEATURE:
<223> OTHER INFORMATION: Synthetic Construct

<400> SEQUENCE: 591

Phe Tyr Cys His Leu Ala Lys Glu
1               5

<210> SEQ ID NO 592
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 592

Phe Tyr Cys His Leu Lys Thr Glu
1               5

<210> SEQ ID NO 593
<211> LENGTH: 8
<212> TYPE: PRT
<213> ORGANISM: Artificial Sequence
<220> FEATURE:
<223> OTHER INFORMATION: Synthetic Construct

<400> SEQUENCE: 593

Phe Tyr Cys His Leu Lys Pro Glu
1               5

<210> SEQ ID NO 594
<211> LENGTH: 8
<212> TYPE: PRT
<213> ORGANISM: Artificial Sequence
<220> FEATURE:
<223> OTHER INFORMATION: Synthetic Construct

<400> SEQUENCE: 594

Phe Tyr Cys His Leu Lys Asp Glu
1               5

<210> SEQ ID NO 595
<211> LENGTH: 8
<212> TYPE: PRT
<213> ORGANISM: Artificial Sequence
<220> FEATURE:
<223> OTHER INFORMATION: Synthetic Construct

<400> SEQUENCE: 595

Phe Tyr Cys His Lys Ala Ala Glu
1               5

<210> SEQ ID NO 596
<211> LENGTH: 8
<212> TYPE: PRT
<213> ORGANISM: Artificial Sequence
<220> FEATURE:
<223> OTHER INFORMATION: Synthetic Construct

<400> SEQUENCE: 596

Phe Tyr Cys His Lys Ala Met Glu
1               5

<210> SEQ ID NO 597
<211> LENGTH: 8
<212> TYPE: PRT
<213> ORGANISM: Artificial Sequence
<220> FEATURE:
<223> OTHER INFORMATION: Synthetic Construct

<400> SEQUENCE: 597

Phe Tyr Cys His Lys Ala Pro Glu
1               5

<210> SEQ ID NO 598
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 598

Phe Tyr Cys His Lys Ala Ser Glu
1               5

<210> SEQ ID NO 599
<211> LENGTH: 8
<212> TYPE: PRT
<213> ORGANISM: Artificial Sequence
<220> FEATURE:
<223> OTHER INFORMATION: Synthetic Construct

<400> SEQUENCE: 599

Phe Tyr Cys His Lys Ala Thr Glu
1               5

<210> SEQ ID NO 600
<211> LENGTH: 8
<212> TYPE: PRT
<213> ORGANISM: Artificial Sequence
<220> FEATURE:
<223> OTHER INFORMATION: Synthetic Construct

<400> SEQUENCE: 600

Phe Tyr Cys His Lys Gln Ala Glu
1               5

<210> SEQ ID NO 601
<211> LENGTH: 8
<212> TYPE: PRT
<213> ORGANISM: Artificial Sequence
<220> FEATURE:
<223> OTHER INFORMATION: Synthetic Construct

<400> SEQUENCE: 601

Phe Tyr Cys His Lys Gln Arg Glu
1               5

<210> SEQ ID NO 602
<211> LENGTH: 8
<212> TYPE: PRT
<213> ORGANISM: Artificial Sequence
<220> FEATURE:
<223> OTHER INFORMATION: Synthetic Construct

<400> SEQUENCE: 602

Phe Tyr Cys His Lys Gln Asp Glu
1               5

<210> SEQ ID NO 603
<211> LENGTH: 8
<212> TYPE: PRT
<213> ORGANISM: Artificial Sequence
<220> FEATURE:
<223> OTHER INFORMATION: Synthetic Construct

<400> SEQUENCE: 603

Phe Tyr Cys His Lys Gln Gln Glu
1               5

<210> SEQ ID NO 604
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 604

Phe Tyr Cys His Lys Gln Glu Glu
1               5

<210> SEQ ID NO 605
<211> LENGTH: 8
<212> TYPE: PRT
<213> ORGANISM: Artificial Sequence
<220> FEATURE:
<223> OTHER INFORMATION: Synthetic Construct

<400> SEQUENCE: 605

Phe Tyr Cys His Lys Gln Leu Glu
1               5

<210> SEQ ID NO 606
<211> LENGTH: 8
<212> TYPE: PRT
<213> ORGANISM: Artificial Sequence
<220> FEATURE:
<223> OTHER INFORMATION: Synthetic Construct

<400> SEQUENCE: 606

Phe Tyr Cys His Lys Gln Lys Glu
1               5

<210> SEQ ID NO 607
<211> LENGTH: 8
<212> TYPE: PRT
<213> ORGANISM: Artificial Sequence
<220> FEATURE:
<223> OTHER INFORMATION: Synthetic Construct

<400> SEQUENCE: 607

Phe Tyr Cys His Lys Gln Met Glu
1               5

<210> SEQ ID NO 608
<211> LENGTH: 8
<212> TYPE: PRT
<213> ORGANISM: Artificial Sequence
<220> FEATURE:
<223> OTHER INFORMATION: Synthetic Construct

<400> SEQUENCE: 608

Phe Tyr Cys His Lys Gln Pro Glu
1               5

<210> SEQ ID NO 609
<211> LENGTH: 8
<212> TYPE: PRT
<213> ORGANISM: Artificial Sequence
<220> FEATURE:
<223> OTHER INFORMATION: Synthetic Construct

<400> SEQUENCE: 609

Phe Tyr Cys His Lys Gln Ser Glu
1               5

<210> SEQ ID NO 610
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 610

Phe Tyr Cys His Lys Gln Thr Glu
1               5

<210> SEQ ID NO 611
<211> LENGTH: 8
<212> TYPE: PRT
<213> ORGANISM: Artificial Sequence
<220> FEATURE:
<223> OTHER INFORMATION: Synthetic Construct

<400> SEQUENCE: 611

Phe Tyr Cys His Lys Glu Ala Glu
1               5

<210> SEQ ID NO 612
<211> LENGTH: 8
<212> TYPE: PRT
<213> ORGANISM: Artificial Sequence
<220> FEATURE:
<223> OTHER INFORMATION: Synthetic Construct

<400> SEQUENCE: 612

Phe Tyr Cys His Lys Glu Arg Glu
1               5

<210> SEQ ID NO 613
<211> LENGTH: 8
<212> TYPE: PRT
<213> ORGANISM: Artificial Sequence
<220> FEATURE:
<223> OTHER INFORMATION: Synthetic Construct

<400> SEQUENCE: 613

Phe Tyr Cys His Lys Glu Asp Glu
1               5

<210> SEQ ID NO 614
<211> LENGTH: 8
<212> TYPE: PRT
<213> ORGANISM: Artificial Sequence
<220> FEATURE:
<223> OTHER INFORMATION: Synthetic Construct

<400> SEQUENCE: 614

Phe Tyr Cys His Lys Glu Gln Glu
1               5

<210> SEQ ID NO 615
<211> LENGTH: 8
<212> TYPE: PRT
<213> ORGANISM: Artificial Sequence
<220> FEATURE:
<223> OTHER INFORMATION: Synthetic Construct

<400> SEQUENCE: 615

Phe Tyr Cys His Lys Glu Glu Glu
1               5

<210> SEQ ID NO 616
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 616

Phe Tyr Cys His Lys Glu Leu Glu
1               5

<210> SEQ ID NO 617
<211> LENGTH: 8
<212> TYPE: PRT
<213> ORGANISM: Artificial Sequence
<220> FEATURE:
<223> OTHER INFORMATION: Synthetic Construct

<400> SEQUENCE: 617

Phe Tyr Cys His Lys Glu Lys Glu
1               5

<210> SEQ ID NO 618
<211> LENGTH: 8
<212> TYPE: PRT
<213> ORGANISM: Artificial Sequence
<220> FEATURE:
<223> OTHER INFORMATION: Synthetic Construct

<400> SEQUENCE: 618

Phe Tyr Cys His Lys Glu Met Glu
1               5

<210> SEQ ID NO 619
<211> LENGTH: 8
<212> TYPE: PRT
<213> ORGANISM: Artificial Sequence
<220> FEATURE:
<223> OTHER INFORMATION: Synthetic Construct

<400> SEQUENCE: 619

Phe Tyr Cys His Lys Glu Pro Glu
1               5

<210> SEQ ID NO 620
<211> LENGTH: 8
<212> TYPE: PRT
<213> ORGANISM: Artificial Sequence
<220> FEATURE:
<223> OTHER INFORMATION: Synthetic Construct

<400> SEQUENCE: 620

Phe Tyr Cys His Lys Glu Ser Glu
1               5

<210> SEQ ID NO 621
<211> LENGTH: 8
<212> TYPE: PRT
<213> ORGANISM: Artificial Sequence
<220> FEATURE:
<223> OTHER INFORMATION: Synthetic Construct

<400> SEQUENCE: 621

Phe Tyr Cys His Lys Glu Thr Glu
1               5

<210> SEQ ID NO 622
<211> LENGTH: 8
<212> TYPE: PRT
<213> ORGANISM: Artificial Sequence
<220> FEATURE:
<223> OTHER INFORMATION: Synthetic Construct

<400> SEQUENCE: 622

Phe Tyr Cys His Lys Ile Ala Glu
1               5

<210> SEQ ID NO 623
<211> LENGTH: 8
<212> TYPE: PRT
<213> ORGANISM: Artificial Sequence
<220> FEATURE:
<223> OTHER INFORMATION: Synthetic Construct

<400> SEQUENCE: 623

Phe Tyr Cys His Lys Ile Arg Glu
1               5

<210> SEQ ID NO 624
<211> LENGTH: 8
<212> TYPE: PRT
<213> ORGANISM: Artificial Sequence
<220> FEATURE:
<223> OTHER INFORMATION: Synthetic Construct

<400> SEQUENCE: 624

Phe Tyr Cys His Lys Ile Asp Glu
1               5

<210> SEQ ID NO 625
<211> LENGTH: 8
<212> TYPE: PRT
<213> ORGANISM: Artificial Sequence
<220> FEATURE:
<223> OTHER INFORMATION: Synthetic Construct

<400> SEQUENCE: 625

Phe Tyr Cys His Lys Ile Gln Glu
1               5

<210> SEQ ID NO 626
<211> LENGTH: 8
<212> TYPE: PRT
<213> ORGANISM: Artificial Sequence
<220> FEATURE:
<223> OTHER INFORMATION: Synthetic Construct

<400> SEQUENCE: 626

Phe Tyr Cys His Lys Ile Glu Glu
1               5

<210> SEQ ID NO 627
<211> LENGTH: 8
<212> TYPE: PRT
<213> ORGANISM: Artificial Sequence
<220> FEATURE:
<223> OTHER INFORMATION: Synthetic Construct

<400> SEQUENCE: 627

Phe Tyr Cys His Lys Ile Leu Glu
1               5

<210> SEQ ID NO 628
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 628

Phe Tyr Cys His Lys Ile Lys Glu
1               5

<210> SEQ ID NO 629
<211> LENGTH: 8
<212> TYPE: PRT
<213> ORGANISM: Artificial Sequence
<220> FEATURE:
<223> OTHER INFORMATION: Synthetic Construct

<400> SEQUENCE: 629

Phe Tyr Cys His Lys Ile Met Glu
1               5

<210> SEQ ID NO 630
<211> LENGTH: 8
<212> TYPE: PRT
<213> ORGANISM: Artificial Sequence
<220> FEATURE:
<223> OTHER INFORMATION: Synthetic Construct

<400> SEQUENCE: 630

Phe Tyr Cys His Lys Ile Pro Glu
1               5

<210> SEQ ID NO 631
<211> LENGTH: 8
<212> TYPE: PRT
<213> ORGANISM: Artificial Sequence
<220> FEATURE:
<223> OTHER INFORMATION: Synthetic Construct

<400> SEQUENCE: 631

Phe Tyr Cys His Lys Ile Ser Glu
1               5

<210> SEQ ID NO 632
<211> LENGTH: 8
<212> TYPE: PRT
<213> ORGANISM: Artificial Sequence
<220> FEATURE:
<223> OTHER INFORMATION: Synthetic Construct

<400> SEQUENCE: 632

Phe Tyr Cys His Lys Ile Thr Glu
1               5

<210> SEQ ID NO 633
<211> LENGTH: 8
<212> TYPE: PRT
<213> ORGANISM: Artificial Sequence
<220> FEATURE:
<223> OTHER INFORMATION: Synthetic Construct

<400> SEQUENCE: 633

Phe Tyr Cys His Lys Leu Ala Glu
1               5

<210> SEQ ID NO 634
<211> LENGTH: 8
<212> TYPE: PRT
<213> ORGANISM: Artificial Sequence
<220> FEATURE:
<223> OTHER INFORMATION: Synthetic Construct

<400> SEQUENCE: 634
```

```
Phe Tyr Cys His Lys Leu Arg Glu
1               5
```

<210> SEQ ID NO 635
<211> LENGTH: 8
<212> TYPE: PRT
<213> ORGANISM: Artificial Sequence
<220> FEATURE:
<223> OTHER INFORMATION: Synthetic Construct

<400> SEQUENCE: 635

```
Phe Tyr Cys His Lys Leu Asp Glu
1               5
```

<210> SEQ ID NO 636
<211> LENGTH: 8
<212> TYPE: PRT
<213> ORGANISM: Artificial Sequence
<220> FEATURE:
<223> OTHER INFORMATION: Synthetic Construct

<400> SEQUENCE: 636

```
Phe Tyr Cys His Lys Leu Gln Glu
1               5
```

<210> SEQ ID NO 637
<211> LENGTH: 8
<212> TYPE: PRT
<213> ORGANISM: Artificial Sequence
<220> FEATURE:
<223> OTHER INFORMATION: Synthetic Construct

<400> SEQUENCE: 637

```
Phe Tyr Cys His Lys Leu Glu Glu
1               5
```

<210> SEQ ID NO 638
<211> LENGTH: 8
<212> TYPE: PRT
<213> ORGANISM: Artificial Sequence
<220> FEATURE:
<223> OTHER INFORMATION: Synthetic Construct

<400> SEQUENCE: 638

```
Phe Tyr Cys His Lys Leu Leu Glu
1               5
```

<210> SEQ ID NO 639
<211> LENGTH: 8
<212> TYPE: PRT
<213> ORGANISM: Artificial Sequence
<220> FEATURE:
<223> OTHER INFORMATION: Synthetic Construct

<400> SEQUENCE: 639

```
Phe Tyr Cys His Lys Leu Lys Glu
1               5
```

<210> SEQ ID NO 640
<211> LENGTH: 8
<212> TYPE: PRT
<213> ORGANISM: Artificial Sequence
<220> FEATURE:
<223> OTHER INFORMATION: Synthetic Construct

<400> SEQUENCE: 640

Phe Tyr Cys His Lys Leu Met Glu
1               5

<210> SEQ ID NO 641
<211> LENGTH: 8
<212> TYPE: PRT
<213> ORGANISM: Artificial Sequence
<220> FEATURE:
<223> OTHER INFORMATION: Synthetic Construct

<400> SEQUENCE: 641

Phe Tyr Cys His Lys Leu Pro Glu
1               5

<210> SEQ ID NO 642
<211> LENGTH: 8
<212> TYPE: PRT
<213> ORGANISM: Artificial Sequence
<220> FEATURE:
<223> OTHER INFORMATION: Synthetic Construct

<400> SEQUENCE: 642

Phe Tyr Cys His Lys Leu Ser Glu
1               5

<210> SEQ ID NO 643
<211> LENGTH: 8
<212> TYPE: PRT
<213> ORGANISM: Artificial Sequence
<220> FEATURE:
<223> OTHER INFORMATION: Synthetic Construct

<400> SEQUENCE: 643

Phe Tyr Cys His Lys Leu Thr Glu
1               5

<210> SEQ ID NO 644
<211> LENGTH: 8
<212> TYPE: PRT
<213> ORGANISM: Artificial Sequence
<220> FEATURE:
<223> OTHER INFORMATION: Synthetic Construct

<400> SEQUENCE: 644

Phe Tyr Cys His Lys Lys Ala Glu
1               5

<210> SEQ ID NO 645
<211> LENGTH: 8
<212> TYPE: PRT
<213> ORGANISM: Artificial Sequence
<220> FEATURE:
<223> OTHER INFORMATION: Synthetic Construct

<400> SEQUENCE: 645

Phe Tyr Cys His Lys Lys Gln Glu
1               5

<210> SEQ ID NO 646
<211> LENGTH: 8
<212> TYPE: PRT
<213> ORGANISM: Artificial Sequence
<220> FEATURE:
<223> OTHER INFORMATION: Synthetic Construct

<400> SEQUENCE: 646

Phe Tyr Cys His Lys Lys Glu Glu 1               5

<210> SEQ ID NO 647
<211> LENGTH: 8
<212> TYPE: PRT
<213> ORGANISM: Artificial Sequence
<220> FEATURE:
<223> OTHER INFORMATION: Synthetic Construct

<400> SEQUENCE: 647

Phe Tyr Cys His Lys Lys Leu Glu
1               5

<210> SEQ ID NO 648
<211> LENGTH: 8
<212> TYPE: PRT
<213> ORGANISM: Artificial Sequence
<220> FEATURE:
<223> OTHER INFORMATION: Synthetic Construct

<400> SEQUENCE: 648

Phe Tyr Cys His Lys Lys Lys Glu
1               5

<210> SEQ ID NO 649
<211> LENGTH: 8
<212> TYPE: PRT
<213> ORGANISM: Artificial Sequence
<220> FEATURE:
<223> OTHER INFORMATION: Synthetic Construct

<400> SEQUENCE: 649

Phe Tyr Cys His Lys Lys Met Glu
1               5

<210> SEQ ID NO 650
<211> LENGTH: 8
<212> TYPE: PRT
<213> ORGANISM: Artificial Sequence
<220> FEATURE:
<223> OTHER INFORMATION: Synthetic Construct

<400> SEQUENCE: 650

Phe Tyr Cys His Lys Lys Ser Glu
1               5

<210> SEQ ID NO 651
<211> LENGTH: 8
<212> TYPE: PRT
<213> ORGANISM: Artificial Sequence
<220> FEATURE:
<223> OTHER INFORMATION: Synthetic Construct

<400> SEQUENCE: 651

Phe Tyr Cys His Lys Lys Arg Glu
1               5

<210> SEQ ID NO 652
<211> LENGTH: 8
<212> TYPE: PRT
<213> ORGANISM: Artificial Sequence
<220> FEATURE:
<223> OTHER INFORMATION: Synthetic Construct

<400> SEQUENCE: 652

Phe Tyr Cys His Lys Ala Arg Glu
1               5

```
<210> SEQ ID NO 653
<211> LENGTH: 8
<212> TYPE: PRT
<213> ORGANISM: Artificial Sequence
<220> FEATURE:
<223> OTHER INFORMATION: Synthetic Construct

<400> SEQUENCE: 653

Phe Tyr Cys His Lys Ala Asp Glu
1               5

<210> SEQ ID NO 654
<211> LENGTH: 8
<212> TYPE: PRT
<213> ORGANISM: Artificial Sequence
<220> FEATURE:
<223> OTHER INFORMATION: Synthetic Construct

<400> SEQUENCE: 654

Phe Tyr Cys His Lys Ala Gln Glu
1               5

<210> SEQ ID NO 655
<211> LENGTH: 8
<212> TYPE: PRT
<213> ORGANISM: Artificial Sequence
<220> FEATURE:
<223> OTHER INFORMATION: Synthetic Construct

<400> SEQUENCE: 655

Phe Tyr Cys His Lys Ala Glu Glu
1               5

<210> SEQ ID NO 656
<211> LENGTH: 8
<212> TYPE: PRT
<213> ORGANISM: Artificial Sequence
<220> FEATURE:
<223> OTHER INFORMATION: Synthetic Construct

<400> SEQUENCE: 656

Phe Tyr Cys His Lys Ala Leu Glu
1               5

<210> SEQ ID NO 657
<211> LENGTH: 8
<212> TYPE: PRT
<213> ORGANISM: Artificial Sequence
<220> FEATURE:
<223> OTHER INFORMATION: Synthetic Construct

<400> SEQUENCE: 657

Phe Tyr Cys His Lys Ala Lys Glu
1               5

<210> SEQ ID NO 658
<211> LENGTH: 8
<212> TYPE: PRT
<213> ORGANISM: Artificial Sequence
<220> FEATURE:
<223> OTHER INFORMATION: Synthetic Construct

<400> SEQUENCE: 658

Phe Tyr Cys His Lys Lys Thr Glu
1               5
```

<210> SEQ ID NO 659
<211> LENGTH: 8
<212> TYPE: PRT
<213> ORGANISM: Artificial Sequence
<220> FEATURE:
<223> OTHER INFORMATION: Synthetic Construct

<400> SEQUENCE: 659

Phe Tyr Cys His Lys Lys Pro Glu
1               5

<210> SEQ ID NO 660
<211> LENGTH: 8
<212> TYPE: PRT
<213> ORGANISM: Artificial Sequence
<220> FEATURE:
<223> OTHER INFORMATION: Synthetic Construct

<400> SEQUENCE: 660

Phe Tyr Cys His Lys Lys Asp Glu
1               5

<210> SEQ ID NO 661
<211> LENGTH: 8
<212> TYPE: PRT
<213> ORGANISM: Artificial Sequence
<220> FEATURE:
<223> OTHER INFORMATION: Synthetic Construct

<400> SEQUENCE: 661

Phe Tyr Cys His Met Ala Ala Glu
1               5

<210> SEQ ID NO 662
<211> LENGTH: 8
<212> TYPE: PRT
<213> ORGANISM: Artificial Sequence
<220> FEATURE:
<223> OTHER INFORMATION: Synthetic Construct

<400> SEQUENCE: 662

Phe Tyr Cys His Met Lys Pro Glu
1               5

<210> SEQ ID NO 663
<211> LENGTH: 8
<212> TYPE: PRT
<213> ORGANISM: Artificial Sequence
<220> FEATURE:
<223> OTHER INFORMATION: Synthetic Construct

<400> SEQUENCE: 663

Phe Tyr Cys His Met Lys Asp Glu
1               5

<210> SEQ ID NO 664
<211> LENGTH: 8
<212> TYPE: PRT
<213> ORGANISM: Artificial Sequence
<220> FEATURE:
<223> OTHER INFORMATION: Synthetic Construct

<400> SEQUENCE: 664

Phe Tyr Cys His Met Ala Arg Glu
1               5

<210> SEQ ID NO 665
<211> LENGTH: 8
<212> TYPE: PRT
<213> ORGANISM: Artificial Sequence
<220> FEATURE:
<223> OTHER INFORMATION: Synthetic Construct

<400> SEQUENCE: 665

Phe Tyr Cys His Met Ala Asp Glu
1               5

<210> SEQ ID NO 666
<211> LENGTH: 8
<212> TYPE: PRT
<213> ORGANISM: Artificial Sequence
<220> FEATURE:
<223> OTHER INFORMATION: Synthetic Construct

<400> SEQUENCE: 666

Phe Tyr Cys His Met Ala Met Glu
1               5

<210> SEQ ID NO 667
<211> LENGTH: 8
<212> TYPE: PRT
<213> ORGANISM: Artificial Sequence
<220> FEATURE:
<223> OTHER INFORMATION: Synthetic Construct

<400> SEQUENCE: 667

Phe Tyr Cys His Met Ala Pro Glu
1               5

<210> SEQ ID NO 668
<211> LENGTH: 8
<212> TYPE: PRT
<213> ORGANISM: Artificial Sequence
<220> FEATURE:
<223> OTHER INFORMATION: Synthetic Construct

<400> SEQUENCE: 668

Phe Tyr Cys His Met Ala Ser Glu
1               5

<210> SEQ ID NO 669
<211> LENGTH: 8
<212> TYPE: PRT
<213> ORGANISM: Artificial Sequence
<220> FEATURE:
<223> OTHER INFORMATION: Synthetic Construct

<400> SEQUENCE: 669

Phe Tyr Cys His Met Ala Thr Glu
1               5

<210> SEQ ID NO 670
<211> LENGTH: 8
<212> TYPE: PRT
<213> ORGANISM: Artificial Sequence
<220> FEATURE:
<223> OTHER INFORMATION: Synthetic Construct

<400> SEQUENCE: 670

Phe Tyr Cys His Met Gln Ala Glu
1               5

<210> SEQ ID NO 671

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 671

Phe Tyr Cys His Met Gln Arg Glu
1               5

<210> SEQ ID NO 672
<211> LENGTH: 8
<212> TYPE: PRT
<213> ORGANISM: Artificial Sequence
<220> FEATURE:
<223> OTHER INFORMATION: Synthetic Construct

<400> SEQUENCE: 672

Phe Tyr Cys His Met Gln Asp Glu
1               5

<210> SEQ ID NO 673
<211> LENGTH: 8
<212> TYPE: PRT
<213> ORGANISM: Artificial Sequence
<220> FEATURE:
<223> OTHER INFORMATION: Synthetic Construct

<400> SEQUENCE: 673

Phe Tyr Cys His Met Gln Gln Glu
1               5

<210> SEQ ID NO 674
<211> LENGTH: 8
<212> TYPE: PRT
<213> ORGANISM: Artificial Sequence
<220> FEATURE:
<223> OTHER INFORMATION: Synthetic Construct

<400> SEQUENCE: 674

Phe Tyr Cys His Met Gln Glu Glu
1               5

<210> SEQ ID NO 675
<211> LENGTH: 8
<212> TYPE: PRT
<213> ORGANISM: Artificial Sequence
<220> FEATURE:
<223> OTHER INFORMATION: Synthetic Construct

<400> SEQUENCE: 675

Phe Tyr Cys His Met Gln Leu Glu
1               5

<210> SEQ ID NO 676
<211> LENGTH: 8
<212> TYPE: PRT
<213> ORGANISM: Artificial Sequence
<220> FEATURE:
<223> OTHER INFORMATION: Synthetic Construct

<400> SEQUENCE: 676

Phe Tyr Cys His Met Gln Lys Glu
1               5

<210> SEQ ID NO 677
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 677

Phe Tyr Cys His Met Gln Met Glu
1               5

<210> SEQ ID NO 678
<211> LENGTH: 8
<212> TYPE: PRT
<213> ORGANISM: Artificial Sequence
<220> FEATURE:
<223> OTHER INFORMATION: Synthetic Construct

<400> SEQUENCE: 678

Phe Tyr Cys His Met Gln Pro Glu
1               5

<210> SEQ ID NO 679
<211> LENGTH: 8
<212> TYPE: PRT
<213> ORGANISM: Artificial Sequence
<220> FEATURE:
<223> OTHER INFORMATION: Synthetic Construct

<400> SEQUENCE: 679

Phe Tyr Cys His Met Gln Ser Glu
1               5

<210> SEQ ID NO 680
<211> LENGTH: 8
<212> TYPE: PRT
<213> ORGANISM: Artificial Sequence
<220> FEATURE:
<223> OTHER INFORMATION: Synthetic Construct

<400> SEQUENCE: 680

Phe Tyr Cys His Met Gln Thr Glu
1               5

<210> SEQ ID NO 681
<211> LENGTH: 8
<212> TYPE: PRT
<213> ORGANISM: Artificial Sequence
<220> FEATURE:
<223> OTHER INFORMATION: Synthetic Construct

<400> SEQUENCE: 681

Phe Tyr Cys His Met Glu Ala Glu
1               5

<210> SEQ ID NO 682
<211> LENGTH: 8
<212> TYPE: PRT
<213> ORGANISM: Artificial Sequence
<220> FEATURE:
<223> OTHER INFORMATION: Synthetic Construct

<400> SEQUENCE: 682

Phe Tyr Cys His Met Glu Arg Glu
1               5

<210> SEQ ID NO 683
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 683

Phe Tyr Cys His Met Glu Asp Glu
1               5

<210> SEQ ID NO 684
<211> LENGTH: 8
<212> TYPE: PRT
<213> ORGANISM: Artificial Sequence
<220> FEATURE:
<223> OTHER INFORMATION: Synthetic Construct

<400> SEQUENCE: 684

Phe Tyr Cys His Met Glu Gln Glu
1               5

<210> SEQ ID NO 685
<211> LENGTH: 8
<212> TYPE: PRT
<213> ORGANISM: Artificial Sequence
<220> FEATURE:
<223> OTHER INFORMATION: Synthetic Construct

<400> SEQUENCE: 685

Phe Tyr Cys His Met Glu Glu Glu
1               5

<210> SEQ ID NO 686
<211> LENGTH: 8
<212> TYPE: PRT
<213> ORGANISM: Artificial Sequence
<220> FEATURE:
<223> OTHER INFORMATION: Synthetic Construct

<400> SEQUENCE: 686

Phe Tyr Cys His Met Glu Leu Glu
1               5

<210> SEQ ID NO 687
<211> LENGTH: 8
<212> TYPE: PRT
<213> ORGANISM: Artificial Sequence
<220> FEATURE:
<223> OTHER INFORMATION: Synthetic Construct

<400> SEQUENCE: 687

Phe Tyr Cys His Met Glu Lys Glu
1               5

<210> SEQ ID NO 688
<211> LENGTH: 8
<212> TYPE: PRT
<213> ORGANISM: Artificial Sequence
<220> FEATURE:
<223> OTHER INFORMATION: Synthetic Construct

<400> SEQUENCE: 688

Phe Tyr Cys His Met Glu Met Glu
1               5

<210> SEQ ID NO 689
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 689

Phe Tyr Cys His Met Glu Pro Glu
1               5

<210> SEQ ID NO 690
<211> LENGTH: 8
<212> TYPE: PRT
<213> ORGANISM: Artificial Sequence
<220> FEATURE:
<223> OTHER INFORMATION: Synthetic Construct

<400> SEQUENCE: 690

Phe Tyr Cys His Met Glu Ser Glu
1               5

<210> SEQ ID NO 691
<211> LENGTH: 8
<212> TYPE: PRT
<213> ORGANISM: Artificial Sequence
<220> FEATURE:
<223> OTHER INFORMATION: Synthetic Construct

<400> SEQUENCE: 691

Phe Tyr Cys His Met Glu Thr Glu
1               5

<210> SEQ ID NO 692
<211> LENGTH: 8
<212> TYPE: PRT
<213> ORGANISM: Artificial Sequence
<220> FEATURE:
<223> OTHER INFORMATION: Synthetic Construct

<400> SEQUENCE: 692

Phe Tyr Cys His Met Ile Ala Glu
1               5

<210> SEQ ID NO 693
<211> LENGTH: 8
<212> TYPE: PRT
<213> ORGANISM: Artificial Sequence
<220> FEATURE:
<223> OTHER INFORMATION: Synthetic Construct

<400> SEQUENCE: 693

Phe Tyr Cys His Met Ile Arg Glu
1               5

<210> SEQ ID NO 694
<211> LENGTH: 8
<212> TYPE: PRT
<213> ORGANISM: Artificial Sequence
<220> FEATURE:
<223> OTHER INFORMATION: Synthetic Construct

<400> SEQUENCE: 694

Phe Tyr Cys His Met Ile Asp Glu
1               5

<210> SEQ ID NO 695
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 695

Phe Tyr Cys His Met Ile Gln Glu
1               5

<210> SEQ ID NO 696
<211> LENGTH: 8
<212> TYPE: PRT
<213> ORGANISM: Artificial Sequence
<220> FEATURE:
<223> OTHER INFORMATION: Synthetic Construct

<400> SEQUENCE: 696

Phe Tyr Cys His Met Ile Glu Glu
1               5

<210> SEQ ID NO 697
<211> LENGTH: 8
<212> TYPE: PRT
<213> ORGANISM: Artificial Sequence
<220> FEATURE:
<223> OTHER INFORMATION: Synthetic Construct

<400> SEQUENCE: 697

Phe Tyr Cys His Met Ile Leu Glu
1               5

<210> SEQ ID NO 698
<211> LENGTH: 8
<212> TYPE: PRT
<213> ORGANISM: Artificial Sequence
<220> FEATURE:
<223> OTHER INFORMATION: Synthetic Construct

<400> SEQUENCE: 698

Phe Tyr Cys His Met Ile Lys Glu
1               5

<210> SEQ ID NO 699
<211> LENGTH: 8
<212> TYPE: PRT
<213> ORGANISM: Artificial Sequence
<220> FEATURE:
<223> OTHER INFORMATION: Synthetic Construct

<400> SEQUENCE: 699

Phe Tyr Cys His Met Ile Met Glu
1               5

<210> SEQ ID NO 700
<211> LENGTH: 8
<212> TYPE: PRT
<213> ORGANISM: Artificial Sequence
<220> FEATURE:
<223> OTHER INFORMATION: Synthetic Construct

<400> SEQUENCE: 700

Phe Tyr Cys His Met Ile Pro Glu
1               5

<210> SEQ ID NO 701
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 701

Phe Tyr Cys His Met Ile Ser Glu
1               5

<210> SEQ ID NO 702
<211> LENGTH: 8
<212> TYPE: PRT
<213> ORGANISM: Artificial Sequence
<220> FEATURE:
<223> OTHER INFORMATION: Synthetic Construct

<400> SEQUENCE: 702

Phe Tyr Cys His Met Ile Thr Glu
1               5

<210> SEQ ID NO 703
<211> LENGTH: 8
<212> TYPE: PRT
<213> ORGANISM: Artificial Sequence
<220> FEATURE:
<223> OTHER INFORMATION: Synthetic Construct

<400> SEQUENCE: 703

Phe Tyr Cys His Met Leu Ala Glu
1               5

<210> SEQ ID NO 704
<211> LENGTH: 8
<212> TYPE: PRT
<213> ORGANISM: Artificial Sequence
<220> FEATURE:
<223> OTHER INFORMATION: Synthetic Construct

<400> SEQUENCE: 704

Phe Tyr Cys His Met Leu Arg Glu
1               5

<210> SEQ ID NO 705
<211> LENGTH: 8
<212> TYPE: PRT
<213> ORGANISM: Artificial Sequence
<220> FEATURE:
<223> OTHER INFORMATION: Synthetic Construct

<400> SEQUENCE: 705

Phe Tyr Cys His Met Leu Asp Glu
1               5

<210> SEQ ID NO 706
<211> LENGTH: 8
<212> TYPE: PRT
<213> ORGANISM: Artificial Sequence
<220> FEATURE:
<223> OTHER INFORMATION: Synthetic Construct

<400> SEQUENCE: 706

Phe Tyr Cys His Met Leu Gln Glu
1               5

<210> SEQ ID NO 707
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 707

Phe Tyr Cys His Met Leu Glu Glu
1               5

<210> SEQ ID NO 708
<211> LENGTH: 8
<212> TYPE: PRT
<213> ORGANISM: Artificial Sequence
<220> FEATURE:
<223> OTHER INFORMATION: Synthetic Construct

<400> SEQUENCE: 708

Phe Tyr Cys His Met Leu Leu Glu
1               5

<210> SEQ ID NO 709
<211> LENGTH: 8
<212> TYPE: PRT
<213> ORGANISM: Artificial Sequence
<220> FEATURE:
<223> OTHER INFORMATION: Synthetic Construct

<400> SEQUENCE: 709

Phe Tyr Cys His Met Leu Lys Glu
1               5

<210> SEQ ID NO 710
<211> LENGTH: 8
<212> TYPE: PRT
<213> ORGANISM: Artificial Sequence
<220> FEATURE:
<223> OTHER INFORMATION: Synthetic Construct

<400> SEQUENCE: 710

Phe Tyr Cys His Met Leu Met Glu
1               5

<210> SEQ ID NO 711
<211> LENGTH: 8
<212> TYPE: PRT
<213> ORGANISM: Artificial Sequence
<220> FEATURE:
<223> OTHER INFORMATION: Synthetic Construct

<400> SEQUENCE: 711

Phe Tyr Cys His Met Leu Pro Glu
1               5

<210> SEQ ID NO 712
<211> LENGTH: 8
<212> TYPE: PRT
<213> ORGANISM: Artificial Sequence
<220> FEATURE:
<223> OTHER INFORMATION: Synthetic Construct

<400> SEQUENCE: 712

Phe Tyr Cys His Met Leu Ser Glu
1               5

<210> SEQ ID NO 713
<211> LENGTH: 8
<212> TYPE: PRT
<213> ORGANISM: Artificial Sequence
<220> FEATURE:
<223> OTHER INFORMATION: Synthetic Construct

<400> SEQUENCE: 713
```

```
Phe Tyr Cys His Met Leu Thr Glu
1               5

<210> SEQ ID NO 714
<211> LENGTH: 8
<212> TYPE: PRT
<213> ORGANISM: Artificial Sequence
<220> FEATURE:
<223> OTHER INFORMATION: Synthetic Construct

<400> SEQUENCE: 714

Phe Tyr Cys His Met Lys Ala Glu
1               5

<210> SEQ ID NO 715
<211> LENGTH: 8
<212> TYPE: PRT
<213> ORGANISM: Artificial Sequence
<220> FEATURE:
<223> OTHER INFORMATION: Synthetic Construct

<400> SEQUENCE: 715

Phe Tyr Cys His Met Lys Gln Glu
1               5

<210> SEQ ID NO 716
<211> LENGTH: 8
<212> TYPE: PRT
<213> ORGANISM: Artificial Sequence
<220> FEATURE:
<223> OTHER INFORMATION: Synthetic Construct

<400> SEQUENCE: 716

Phe Tyr Cys His Met Lys Glu Glu
1               5

<210> SEQ ID NO 717
<211> LENGTH: 8
<212> TYPE: PRT
<213> ORGANISM: Artificial Sequence
<220> FEATURE:
<223> OTHER INFORMATION: Synthetic Construct

<400> SEQUENCE: 717

Phe Tyr Cys His Met Lys Leu Glu
1               5

<210> SEQ ID NO 718
<211> LENGTH: 8
<212> TYPE: PRT
<213> ORGANISM: Artificial Sequence
<220> FEATURE:
<223> OTHER INFORMATION: Synthetic Construct

<400> SEQUENCE: 718

Phe Tyr Cys His Met Lys Lys Glu
1               5

<210> SEQ ID NO 719
<211> LENGTH: 8
<212> TYPE: PRT
<213> ORGANISM: Artificial Sequence
<220> FEATURE:
<223> OTHER INFORMATION: Synthetic Construct

<400> SEQUENCE: 719
```

```
Phe Tyr Cys His Met Lys Met Glu
1               5

<210> SEQ ID NO 720
<211> LENGTH: 8
<212> TYPE: PRT
<213> ORGANISM: Artificial Sequence
<220> FEATURE:
<223> OTHER INFORMATION: Synthetic Construct

<400> SEQUENCE: 720

Phe Tyr Cys His Met Lys Ser Glu
1               5

<210> SEQ ID NO 721
<211> LENGTH: 8
<212> TYPE: PRT
<213> ORGANISM: Artificial Sequence
<220> FEATURE:
<223> OTHER INFORMATION: Synthetic Construct

<400> SEQUENCE: 721

Phe Tyr Cys His Met Lys Arg Glu
1               5

<210> SEQ ID NO 722
<211> LENGTH: 8
<212> TYPE: PRT
<213> ORGANISM: Artificial Sequence
<220> FEATURE:
<223> OTHER INFORMATION: Synthetic Construct

<400> SEQUENCE: 722

Phe Tyr Cys His Met Ala Gln Glu
1               5

<210> SEQ ID NO 723
<211> LENGTH: 8
<212> TYPE: PRT
<213> ORGANISM: Artificial Sequence
<220> FEATURE:
<223> OTHER INFORMATION: Synthetic Construct

<400> SEQUENCE: 723

Phe Tyr Cys His Met Ala Glu Glu
1               5

<210> SEQ ID NO 724
<211> LENGTH: 8
<212> TYPE: PRT
<213> ORGANISM: Artificial Sequence
<220> FEATURE:
<223> OTHER INFORMATION: Synthetic Construct

<400> SEQUENCE: 724

Phe Tyr Cys His Met Ala Leu Glu
1               5

<210> SEQ ID NO 725
<211> LENGTH: 8
<212> TYPE: PRT
<213> ORGANISM: Artificial Sequence
<220> FEATURE:
<223> OTHER INFORMATION: Synthetic Construct

<400> SEQUENCE: 725

Phe Tyr Cys His Met Ala Lys Glu
```

```
<210> SEQ ID NO 726
<211> LENGTH: 8
<212> TYPE: PRT
<213> ORGANISM: Artificial Sequence
<220> FEATURE:
<223> OTHER INFORMATION: Synthetic Construct

<400> SEQUENCE: 726

Phe Tyr Cys His Met Ala Thr Glu
1               5

<210> SEQ ID NO 727
<211> LENGTH: 8
<212> TYPE: PRT
<213> ORGANISM: Artificial Sequence
<220> FEATURE:
<223> OTHER INFORMATION: Synthetic Construct

<400> SEQUENCE: 727

Phe Tyr Cys His Thr Ala Asp Glu
1               5

<210> SEQ ID NO 728
<211> LENGTH: 8
<212> TYPE: PRT
<213> ORGANISM: Artificial Sequence
<220> FEATURE:
<223> OTHER INFORMATION: Synthetic Construct

<400> SEQUENCE: 728

Phe Tyr Cys His Thr Ala Gln Glu
1               5

<210> SEQ ID NO 729
<211> LENGTH: 8
<212> TYPE: PRT
<213> ORGANISM: Artificial Sequence
<220> FEATURE:
<223> OTHER INFORMATION: Synthetic Construct

<400> SEQUENCE: 729

Phe Tyr Cys His Thr Ala Met Glu
1               5

<210> SEQ ID NO 730
<211> LENGTH: 8
<212> TYPE: PRT
<213> ORGANISM: Artificial Sequence
<220> FEATURE:
<223> OTHER INFORMATION: Synthetic Construct

<400> SEQUENCE: 730

Phe Tyr Cys His Thr Ala Ala Glu
1               5

<210> SEQ ID NO 731
<211> LENGTH: 8
<212> TYPE: PRT
<213> ORGANISM: Artificial Sequence
<220> FEATURE:
<223> OTHER INFORMATION: Synthetic Construct

<400> SEQUENCE: 731

Phe Tyr Cys His Thr Lys Pro Glu
1               5
```

```
<210> SEQ ID NO 732
<211> LENGTH: 8
<212> TYPE: PRT
<213> ORGANISM: Artificial Sequence
<220> FEATURE:
<223> OTHER INFORMATION: Synthetic Construct

<400> SEQUENCE: 732

Phe Tyr Cys His Thr Lys Asp Glu
1               5

<210> SEQ ID NO 733
<211> LENGTH: 8
<212> TYPE: PRT
<213> ORGANISM: Artificial Sequence
<220> FEATURE:
<223> OTHER INFORMATION: Synthetic Construct

<400> SEQUENCE: 733

Phe Tyr Cys His Thr Ala Arg Glu
1               5

<210> SEQ ID NO 734
<211> LENGTH: 8
<212> TYPE: PRT
<213> ORGANISM: Artificial Sequence
<220> FEATURE:
<223> OTHER INFORMATION: Synthetic Construct

<400> SEQUENCE: 734

Phe Tyr Cys His Thr Gln Arg Glu
1               5

<210> SEQ ID NO 735
<211> LENGTH: 8
<212> TYPE: PRT
<213> ORGANISM: Artificial Sequence
<220> FEATURE:
<223> OTHER INFORMATION: Synthetic Construct

<400> SEQUENCE: 735

Phe Tyr Cys His Thr Gln Asp Glu
1               5

<210> SEQ ID NO 736
<211> LENGTH: 8
<212> TYPE: PRT
<213> ORGANISM: Artificial Sequence
<220> FEATURE:
<223> OTHER INFORMATION: Synthetic Construct

<400> SEQUENCE: 736

Phe Tyr Cys His Thr Gln Gln Glu
1               5

<210> SEQ ID NO 737
<211> LENGTH: 8
<212> TYPE: PRT
<213> ORGANISM: Artificial Sequence
<220> FEATURE:
<223> OTHER INFORMATION: Synthetic Construct

<400> SEQUENCE: 737

Phe Tyr Cys His Thr Ala Pro Glu
1               5
```

<210> SEQ ID NO 738
<211> LENGTH: 8
<212> TYPE: PRT
<213> ORGANISM: Artificial Sequence
<220> FEATURE:
<223> OTHER INFORMATION: Synthetic Construct

<400> SEQUENCE: 738

Phe Tyr Cys His Thr Ala Ser Glu
1               5

<210> SEQ ID NO 739
<211> LENGTH: 8
<212> TYPE: PRT
<213> ORGANISM: Artificial Sequence
<220> FEATURE:
<223> OTHER INFORMATION: Synthetic Construct

<400> SEQUENCE: 739

Phe Tyr Cys His Thr Ala Thr Glu
1               5

<210> SEQ ID NO 740
<211> LENGTH: 8
<212> TYPE: PRT
<213> ORGANISM: Artificial Sequence
<220> FEATURE:
<223> OTHER INFORMATION: Synthetic Construct

<400> SEQUENCE: 740

Phe Tyr Cys His Thr Gln Ala Glu
1               5

<210> SEQ ID NO 741
<211> LENGTH: 8
<212> TYPE: PRT
<213> ORGANISM: Artificial Sequence
<220> FEATURE:
<223> OTHER INFORMATION: Synthetic Construct

<400> SEQUENCE: 741

Phe Tyr Cys His Thr Gln Pro Glu
1               5

<210> SEQ ID NO 742
<211> LENGTH: 8
<212> TYPE: PRT
<213> ORGANISM: Artificial Sequence
<220> FEATURE:
<223> OTHER INFORMATION: Synthetic Construct

<400> SEQUENCE: 742

Phe Tyr Cys His Thr Gln Ser Glu
1               5

<210> SEQ ID NO 743
<211> LENGTH: 8
<212> TYPE: PRT
<213> ORGANISM: Artificial Sequence
<220> FEATURE:
<223> OTHER INFORMATION: Synthetic Construct

<400> SEQUENCE: 743

Phe Tyr Cys His Thr Gln Thr Glu
1               5

```
<210> SEQ ID NO 744
<211> LENGTH: 8
<212> TYPE: PRT
<213> ORGANISM: Artificial Sequence
<220> FEATURE:
<223> OTHER INFORMATION: Synthetic Construct

<400> SEQUENCE: 744

Phe Tyr Cys His Thr Gln Glu Glu
1               5

<210> SEQ ID NO 745
<211> LENGTH: 8
<212> TYPE: PRT
<213> ORGANISM: Artificial Sequence
<220> FEATURE:
<223> OTHER INFORMATION: Synthetic Construct

<400> SEQUENCE: 745

Phe Tyr Cys His Thr Gln Leu Glu
1               5

<210> SEQ ID NO 746
<211> LENGTH: 8
<212> TYPE: PRT
<213> ORGANISM: Artificial Sequence
<220> FEATURE:
<223> OTHER INFORMATION: Synthetic Construct

<400> SEQUENCE: 746

Phe Tyr Cys His Thr Gln Lys Glu
1               5

<210> SEQ ID NO 747
<211> LENGTH: 8
<212> TYPE: PRT
<213> ORGANISM: Artificial Sequence
<220> FEATURE:
<223> OTHER INFORMATION: Synthetic Construct

<400> SEQUENCE: 747

Phe Tyr Cys His Thr Gln Met Glu
1               5

<210> SEQ ID NO 748
<211> LENGTH: 8
<212> TYPE: PRT
<213> ORGANISM: Artificial Sequence
<220> FEATURE:
<223> OTHER INFORMATION: Synthetic Construct

<400> SEQUENCE: 748

Phe Tyr Cys His Thr Glu Glu Glu
1               5

<210> SEQ ID NO 749
<211> LENGTH: 8
<212> TYPE: PRT
<213> ORGANISM: Artificial Sequence
<220> FEATURE:
<223> OTHER INFORMATION: Synthetic Construct

<400> SEQUENCE: 749

Phe Tyr Cys His Thr Glu Leu Glu
1               5

<210> SEQ ID NO 750
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 750

Phe Tyr Cys His Thr Glu Lys Glu
1               5

<210> SEQ ID NO 751
<211> LENGTH: 8
<212> TYPE: PRT
<213> ORGANISM: Artificial Sequence
<220> FEATURE:
<223> OTHER INFORMATION: Synthetic Construct

<400> SEQUENCE: 751

Phe Tyr Cys His Thr Glu Ala Glu
1               5

<210> SEQ ID NO 752
<211> LENGTH: 8
<212> TYPE: PRT
<213> ORGANISM: Artificial Sequence
<220> FEATURE:
<223> OTHER INFORMATION: Synthetic Construct

<400> SEQUENCE: 752

Phe Tyr Cys His Thr Glu Arg Glu
1               5

<210> SEQ ID NO 753
<211> LENGTH: 8
<212> TYPE: PRT
<213> ORGANISM: Artificial Sequence
<220> FEATURE:
<223> OTHER INFORMATION: Synthetic Construct

<400> SEQUENCE: 753

Phe Tyr Cys His Thr Glu Asp Glu
1               5

<210> SEQ ID NO 754
<211> LENGTH: 8
<212> TYPE: PRT
<213> ORGANISM: Artificial Sequence
<220> FEATURE:
<223> OTHER INFORMATION: Synthetic Construct

<400> SEQUENCE: 754

Phe Tyr Cys His Thr Glu Gln Glu
1               5

<210> SEQ ID NO 755
<211> LENGTH: 8
<212> TYPE: PRT
<213> ORGANISM: Artificial Sequence
<220> FEATURE:
<223> OTHER INFORMATION: Synthetic Construct

<400> SEQUENCE: 755

Phe Tyr Cys His Thr Ile Ala Glu
1               5

<210> SEQ ID NO 756
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 756

Phe Tyr Cys His Thr Ile Arg Glu
1               5

<210> SEQ ID NO 757
<211> LENGTH: 8
<212> TYPE: PRT
<213> ORGANISM: Artificial Sequence
<220> FEATURE:
<223> OTHER INFORMATION: Synthetic Construct

<400> SEQUENCE: 757

Phe Tyr Cys His Thr Ile Asp Glu
1               5

<210> SEQ ID NO 758
<211> LENGTH: 8
<212> TYPE: PRT
<213> ORGANISM: Artificial Sequence
<220> FEATURE:
<223> OTHER INFORMATION: Synthetic Construct

<400> SEQUENCE: 758

Phe Tyr Cys His Thr Glu Met Glu
1               5

<210> SEQ ID NO 759
<211> LENGTH: 8
<212> TYPE: PRT
<213> ORGANISM: Artificial Sequence
<220> FEATURE:
<223> OTHER INFORMATION: Synthetic Construct

<400> SEQUENCE: 759

Phe Tyr Cys His Thr Glu Pro Glu
1               5

<210> SEQ ID NO 760
<211> LENGTH: 8
<212> TYPE: PRT
<213> ORGANISM: Artificial Sequence
<220> FEATURE:
<223> OTHER INFORMATION: Synthetic Construct

<400> SEQUENCE: 760

Phe Tyr Cys His Thr Glu Ser Glu
1               5

<210> SEQ ID NO 761
<211> LENGTH: 8
<212> TYPE: PRT
<213> ORGANISM: Artificial Sequence
<220> FEATURE:
<223> OTHER INFORMATION: Synthetic Construct

<400> SEQUENCE: 761

Phe Tyr Cys His Thr Glu Thr Glu
1               5

<210> SEQ ID NO 762
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 762

Phe Tyr Cys His Thr Ile Met Glu
1               5

<210> SEQ ID NO 763
<211> LENGTH: 8
<212> TYPE: PRT
<213> ORGANISM: Artificial Sequence
<220> FEATURE:
<223> OTHER INFORMATION: Synthetic Construct

<400> SEQUENCE: 763

Phe Tyr Cys His Thr Ile Pro Glu
1               5

<210> SEQ ID NO 764
<211> LENGTH: 8
<212> TYPE: PRT
<213> ORGANISM: Artificial Sequence
<220> FEATURE:
<223> OTHER INFORMATION: Synthetic Construct

<400> SEQUENCE: 764

Phe Tyr Cys His Thr Ile Ser Glu
1               5

<210> SEQ ID NO 765
<211> LENGTH: 8
<212> TYPE: PRT
<213> ORGANISM: Artificial Sequence
<220> FEATURE:
<223> OTHER INFORMATION: Synthetic Construct

<400> SEQUENCE: 765

Phe Tyr Cys His Thr Ile Gln Glu
1               5

<210> SEQ ID NO 766
<211> LENGTH: 8
<212> TYPE: PRT
<213> ORGANISM: Artificial Sequence
<220> FEATURE:
<223> OTHER INFORMATION: Synthetic Construct

<400> SEQUENCE: 766

Phe Tyr Cys His Thr Ile Glu Glu
1               5

<210> SEQ ID NO 767
<211> LENGTH: 8
<212> TYPE: PRT
<213> ORGANISM: Artificial Sequence
<220> FEATURE:
<223> OTHER INFORMATION: Synthetic Construct

<400> SEQUENCE: 767

Phe Tyr Cys His Thr Ile Leu Glu
1               5

<210> SEQ ID NO 768
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 768

Phe Tyr Cys His Thr Ile Lys Glu
1               5

<210> SEQ ID NO 769
<211> LENGTH: 8
<212> TYPE: PRT
<213> ORGANISM: Artificial Sequence
<220> FEATURE:
<223> OTHER INFORMATION: Synthetic Construct

<400> SEQUENCE: 769

Phe Tyr Cys His Thr Leu Gln Glu
1               5

<210> SEQ ID NO 770
<211> LENGTH: 8
<212> TYPE: PRT
<213> ORGANISM: Artificial Sequence
<220> FEATURE:
<223> OTHER INFORMATION: Synthetic Construct

<400> SEQUENCE: 770

Phe Tyr Cys His Thr Leu Glu Glu
1               5

<210> SEQ ID NO 771
<211> LENGTH: 8
<212> TYPE: PRT
<213> ORGANISM: Artificial Sequence
<220> FEATURE:
<223> OTHER INFORMATION: Synthetic Construct

<400> SEQUENCE: 771

Phe Tyr Cys His Thr Leu Leu Glu
1               5

<210> SEQ ID NO 772
<211> LENGTH: 8
<212> TYPE: PRT
<213> ORGANISM: Artificial Sequence
<220> FEATURE:
<223> OTHER INFORMATION: Synthetic Construct

<400> SEQUENCE: 772

Phe Tyr Cys His Thr Ile Thr Glu
1               5

<210> SEQ ID NO 773
<211> LENGTH: 8
<212> TYPE: PRT
<213> ORGANISM: Artificial Sequence
<220> FEATURE:
<223> OTHER INFORMATION: Synthetic Construct

<400> SEQUENCE: 773

Phe Tyr Cys His Thr Leu Ala Glu
1               5

<210> SEQ ID NO 774
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 774

Phe Tyr Cys His Thr Leu Arg Glu
1               5

<210> SEQ ID NO 775
<211> LENGTH: 8
<212> TYPE: PRT
<213> ORGANISM: Artificial Sequence
<220> FEATURE:
<223> OTHER INFORMATION: Synthetic Construct

<400> SEQUENCE: 775

Phe Tyr Cys His Thr Leu Asp Glu
1               5

<210> SEQ ID NO 776
<211> LENGTH: 8
<212> TYPE: PRT
<213> ORGANISM: Artificial Sequence
<220> FEATURE:
<223> OTHER INFORMATION: Synthetic Construct

<400> SEQUENCE: 776

Phe Tyr Cys His Thr Leu Thr Glu
1               5

<210> SEQ ID NO 777
<211> LENGTH: 8
<212> TYPE: PRT
<213> ORGANISM: Artificial Sequence
<220> FEATURE:
<223> OTHER INFORMATION: Synthetic Construct

<400> SEQUENCE: 777

Phe Tyr Cys His Thr Lys Ala Glu
1               5

<210> SEQ ID NO 778
<211> LENGTH: 8
<212> TYPE: PRT
<213> ORGANISM: Artificial Sequence
<220> FEATURE:
<223> OTHER INFORMATION: Synthetic Construct

<400> SEQUENCE: 778

Phe Tyr Cys His Thr Lys Gln Glu
1               5

<210> SEQ ID NO 779
<211> LENGTH: 8
<212> TYPE: PRT
<213> ORGANISM: Artificial Sequence
<220> FEATURE:
<223> OTHER INFORMATION: Synthetic Construct

<400> SEQUENCE: 779

Phe Tyr Cys His Thr Leu Lys Glu
1               5

<210> SEQ ID NO 780
<211> LENGTH: 8
<212> TYPE: PRT
<213> ORGANISM: Artificial Sequence
<220> FEATURE:
<223> OTHER INFORMATION: Synthetic Construct

<400> SEQUENCE: 780

Phe Tyr Cys His Thr Leu Met Glu
1               5

<210> SEQ ID NO 781
<211> LENGTH: 8
<212> TYPE: PRT
<213> ORGANISM: Artificial Sequence
<220> FEATURE:
<223> OTHER INFORMATION: Synthetic Construct

<400> SEQUENCE: 781

Phe Tyr Cys His Thr Leu Pro Glu
1               5

<210> SEQ ID NO 782
<211> LENGTH: 8
<212> TYPE: PRT
<213> ORGANISM: Artificial Sequence
<220> FEATURE:
<223> OTHER INFORMATION: Synthetic Construct

<400> SEQUENCE: 782

Phe Tyr Cys His Thr Leu Ser Glu
1               5

<210> SEQ ID NO 783
<211> LENGTH: 8
<212> TYPE: PRT
<213> ORGANISM: Artificial Sequence
<220> FEATURE:
<223> OTHER INFORMATION: Synthetic Construct

<400> SEQUENCE: 783

Phe Tyr Cys His Thr Lys Ser Glu
1               5

<210> SEQ ID NO 784
<211> LENGTH: 8
<212> TYPE: PRT
<213> ORGANISM: Artificial Sequence
<220> FEATURE:
<223> OTHER INFORMATION: Synthetic Construct

<400> SEQUENCE: 784

Phe Tyr Cys His Thr Lys Arg Glu
1               5

<210> SEQ ID NO 785
<211> LENGTH: 8
<212> TYPE: PRT
<213> ORGANISM: Artificial Sequence
<220> FEATURE:
<223> OTHER INFORMATION: Synthetic Construct

<400> SEQUENCE: 785

Phe Tyr Cys His Thr Ala Glu Glu
1               5

<210> SEQ ID NO 786
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 786

Phe Tyr Cys His Thr Lys Glu Glu
1               5

<210> SEQ ID NO 787
<211> LENGTH: 8
<212> TYPE: PRT
<213> ORGANISM: Artificial Sequence
<220> FEATURE:
<223> OTHER INFORMATION: Synthetic Construct

<400> SEQUENCE: 787

Phe Tyr Cys His Thr Lys Leu Glu
1               5

<210> SEQ ID NO 788
<211> LENGTH: 8
<212> TYPE: PRT
<213> ORGANISM: Artificial Sequence
<220> FEATURE:
<223> OTHER INFORMATION: Synthetic Construct

<400> SEQUENCE: 788

Phe Tyr Cys His Thr Lys Lys Glu
1               5

<210> SEQ ID NO 789
<211> LENGTH: 8
<212> TYPE: PRT
<213> ORGANISM: Artificial Sequence
<220> FEATURE:
<223> OTHER INFORMATION: Synthetic Construct

<400> SEQUENCE: 789

Phe Tyr Cys His Thr Lys Met Glu
1               5

<210> SEQ ID NO 790
<211> LENGTH: 8
<212> TYPE: PRT
<213> ORGANISM: Artificial Sequence
<220> FEATURE:
<223> OTHER INFORMATION: Synthetic Construct

<400> SEQUENCE: 790

Phe Tyr Cys His Trp Lys Pro Glu
1               5

<210> SEQ ID NO 791
<211> LENGTH: 8
<212> TYPE: PRT
<213> ORGANISM: Artificial Sequence
<220> FEATURE:
<223> OTHER INFORMATION: Synthetic Construct

<400> SEQUENCE: 791

Phe Tyr Cys His Trp Lys Asp Glu
1               5

<210> SEQ ID NO 792
<211> LENGTH: 8
<212> TYPE: PRT
<213> ORGANISM: Artificial Sequence
<220> FEATURE:
<223> OTHER INFORMATION: Synthetic Construct

<400> SEQUENCE: 792
```

```
Phe Tyr Cys His Trp Ala Met Glu
1               5

<210> SEQ ID NO 793
<211> LENGTH: 8
<212> TYPE: PRT
<213> ORGANISM: Artificial Sequence
<220> FEATURE:
<223> OTHER INFORMATION: Synthetic Construct

<400> SEQUENCE: 793

Phe Tyr Cys His Thr Ala Leu Glu
1               5

<210> SEQ ID NO 794
<211> LENGTH: 8
<212> TYPE: PRT
<213> ORGANISM: Artificial Sequence
<220> FEATURE:
<223> OTHER INFORMATION: Synthetic Construct

<400> SEQUENCE: 794

Phe Tyr Cys His Thr Ala Lys Glu
1               5

<210> SEQ ID NO 795
<211> LENGTH: 8
<212> TYPE: PRT
<213> ORGANISM: Artificial Sequence
<220> FEATURE:
<223> OTHER INFORMATION: Synthetic Construct

<400> SEQUENCE: 795

Phe Tyr Cys His Thr Ala Thr Glu
1               5

<210> SEQ ID NO 796
<211> LENGTH: 8
<212> TYPE: PRT
<213> ORGANISM: Artificial Sequence
<220> FEATURE:
<223> OTHER INFORMATION: Synthetic Construct

<400> SEQUENCE: 796

Phe Tyr Cys His Trp Ala Ala Glu
1               5

<210> SEQ ID NO 797
<211> LENGTH: 8
<212> TYPE: PRT
<213> ORGANISM: Artificial Sequence
<220> FEATURE:
<223> OTHER INFORMATION: Synthetic Construct

<400> SEQUENCE: 797

Phe Tyr Cys His Trp Gln Arg Glu
1               5

<210> SEQ ID NO 798
<211> LENGTH: 8
<212> TYPE: PRT
<213> ORGANISM: Artificial Sequence
<220> FEATURE:
<223> OTHER INFORMATION: Synthetic Construct

<400> SEQUENCE: 798
```

Phe Tyr Cys His Trp Gln Asp Glu
1               5

<210> SEQ ID NO 799
<211> LENGTH: 8
<212> TYPE: PRT
<213> ORGANISM: Artificial Sequence
<220> FEATURE:
<223> OTHER INFORMATION: Synthetic Construct

<400> SEQUENCE: 799

Phe Tyr Cys His Trp Gln Gln Glu
1               5

<210> SEQ ID NO 800
<211> LENGTH: 8
<212> TYPE: PRT
<213> ORGANISM: Artificial Sequence
<220> FEATURE:
<223> OTHER INFORMATION: Synthetic Construct

<400> SEQUENCE: 800

Phe Tyr Cys His Trp Ala Pro Glu
1               5

<210> SEQ ID NO 801
<211> LENGTH: 8
<212> TYPE: PRT
<213> ORGANISM: Artificial Sequence
<220> FEATURE:
<223> OTHER INFORMATION: Synthetic Construct

<400> SEQUENCE: 801

Phe Tyr Cys His Trp Ala Ser Glu
1               5

<210> SEQ ID NO 802
<211> LENGTH: 8
<212> TYPE: PRT
<213> ORGANISM: Artificial Sequence
<220> FEATURE:
<223> OTHER INFORMATION: Synthetic Construct

<400> SEQUENCE: 802

Phe Tyr Cys His Trp Ala Thr Glu
1               5

<210> SEQ ID NO 803
<211> LENGTH: 8
<212> TYPE: PRT
<213> ORGANISM: Artificial Sequence
<220> FEATURE:
<223> OTHER INFORMATION: Synthetic Construct

<400> SEQUENCE: 803

Phe Tyr Cys His Trp Gln Ala Glu
1               5

<210> SEQ ID NO 804
<211> LENGTH: 8
<212> TYPE: PRT
<213> ORGANISM: Artificial Sequence
<220> FEATURE:
<223> OTHER INFORMATION: Synthetic Construct

<400> SEQUENCE: 804

Phe Tyr Cys His Trp Gln Pro Glu 1               5

<210> SEQ ID NO 805
<211> LENGTH: 8
<212> TYPE: PRT
<213> ORGANISM: Artificial Sequence
<220> FEATURE:
<223> OTHER INFORMATION: Synthetic Construct

<400> SEQUENCE: 805

Phe Tyr Cys His Trp Gln Ser Glu
1               5

<210> SEQ ID NO 806
<211> LENGTH: 8
<212> TYPE: PRT
<213> ORGANISM: Artificial Sequence
<220> FEATURE:
<223> OTHER INFORMATION: Synthetic Construct

<400> SEQUENCE: 806

Phe Tyr Cys His Trp Gln Thr Glu
1               5

<210> SEQ ID NO 807
<211> LENGTH: 8
<212> TYPE: PRT
<213> ORGANISM: Artificial Sequence
<220> FEATURE:
<223> OTHER INFORMATION: Synthetic Construct

<400> SEQUENCE: 807

Phe Tyr Cys His Trp Gln Glu Glu
1               5

<210> SEQ ID NO 808
<211> LENGTH: 8
<212> TYPE: PRT
<213> ORGANISM: Artificial Sequence
<220> FEATURE:
<223> OTHER INFORMATION: Synthetic Construct

<400> SEQUENCE: 808

Phe Tyr Cys His Trp Gln Leu Glu
1               5

<210> SEQ ID NO 809
<211> LENGTH: 8
<212> TYPE: PRT
<213> ORGANISM: Artificial Sequence
<220> FEATURE:
<223> OTHER INFORMATION: Synthetic Construct

<400> SEQUENCE: 809

Phe Tyr Cys His Trp Gln Lys Glu
1               5

<210> SEQ ID NO 810
<211> LENGTH: 8
<212> TYPE: PRT
<213> ORGANISM: Artificial Sequence
<220> FEATURE:
<223> OTHER INFORMATION: Synthetic Construct

<400> SEQUENCE: 810

Phe Tyr Cys His Trp Gln Met Glu
1               5

```
<210> SEQ ID NO 811
<211> LENGTH: 8
<212> TYPE: PRT
<213> ORGANISM: Artificial Sequence
<220> FEATURE:
<223> OTHER INFORMATION: Synthetic Construct

<400> SEQUENCE: 811

Phe Tyr Cys His Trp Glu Glu Glu
1               5

<210> SEQ ID NO 812
<211> LENGTH: 8
<212> TYPE: PRT
<213> ORGANISM: Artificial Sequence
<220> FEATURE:
<223> OTHER INFORMATION: Synthetic Construct

<400> SEQUENCE: 812

Phe Tyr Cys His Trp Glu Leu Glu
1               5

<210> SEQ ID NO 813
<211> LENGTH: 8
<212> TYPE: PRT
<213> ORGANISM: Artificial Sequence
<220> FEATURE:
<223> OTHER INFORMATION: Synthetic Construct

<400> SEQUENCE: 813

Phe Tyr Cys His Trp Glu Lys Glu
1               5

<210> SEQ ID NO 814
<211> LENGTH: 8
<212> TYPE: PRT
<213> ORGANISM: Artificial Sequence
<220> FEATURE:
<223> OTHER INFORMATION: Synthetic Construct

<400> SEQUENCE: 814

Phe Tyr Cys His Trp Glu Ala Glu
1               5

<210> SEQ ID NO 815
<211> LENGTH: 8
<212> TYPE: PRT
<213> ORGANISM: Artificial Sequence
<220> FEATURE:
<223> OTHER INFORMATION: Synthetic Construct

<400> SEQUENCE: 815

Phe Tyr Cys His Trp Glu Arg Glu
1               5

<210> SEQ ID NO 816
<211> LENGTH: 8
<212> TYPE: PRT
<213> ORGANISM: Artificial Sequence
<220> FEATURE:
<223> OTHER INFORMATION: Synthetic Construct

<400> SEQUENCE: 816

Phe Tyr Cys His Trp Glu Asp Glu
1               5
```

```
<210> SEQ ID NO 817
<211> LENGTH: 8
<212> TYPE: PRT
<213> ORGANISM: Artificial Sequence
<220> FEATURE:
<223> OTHER INFORMATION: Synthetic Construct

<400> SEQUENCE: 817

Phe Tyr Cys His Trp Glu Gln Glu
1               5

<210> SEQ ID NO 818
<211> LENGTH: 8
<212> TYPE: PRT
<213> ORGANISM: Artificial Sequence
<220> FEATURE:
<223> OTHER INFORMATION: Synthetic Construct

<400> SEQUENCE: 818

Phe Tyr Cys His Trp Ile Ala Glu
1               5

<210> SEQ ID NO 819
<211> LENGTH: 8
<212> TYPE: PRT
<213> ORGANISM: Artificial Sequence
<220> FEATURE:
<223> OTHER INFORMATION: Synthetic Construct

<400> SEQUENCE: 819

Phe Tyr Cys His Trp Ile Arg Glu
1               5

<210> SEQ ID NO 820
<211> LENGTH: 8
<212> TYPE: PRT
<213> ORGANISM: Artificial Sequence
<220> FEATURE:
<223> OTHER INFORMATION: Synthetic Construct

<400> SEQUENCE: 820

Phe Tyr Cys His Trp Ile Asp Glu
1               5

<210> SEQ ID NO 821
<211> LENGTH: 8
<212> TYPE: PRT
<213> ORGANISM: Artificial Sequence
<220> FEATURE:
<223> OTHER INFORMATION: Synthetic Construct

<400> SEQUENCE: 821

Phe Tyr Cys His Trp Glu Met Glu
1               5

<210> SEQ ID NO 822
<211> LENGTH: 8
<212> TYPE: PRT
<213> ORGANISM: Artificial Sequence
<220> FEATURE:
<223> OTHER INFORMATION: Synthetic Construct

<400> SEQUENCE: 822

Phe Tyr Cys His Trp Glu Pro Glu
1               5
```

```
<210> SEQ ID NO 823
<211> LENGTH: 8
<212> TYPE: PRT
<213> ORGANISM: Artificial Sequence
<220> FEATURE:
<223> OTHER INFORMATION: Synthetic Construct

<400> SEQUENCE: 823

Phe Tyr Cys His Trp Glu Ser Glu
1               5

<210> SEQ ID NO 824
<211> LENGTH: 8
<212> TYPE: PRT
<213> ORGANISM: Artificial Sequence
<220> FEATURE:
<223> OTHER INFORMATION: Synthetic Construct

<400> SEQUENCE: 824

Phe Tyr Cys His Trp Glu Thr Glu
1               5

<210> SEQ ID NO 825
<211> LENGTH: 8
<212> TYPE: PRT
<213> ORGANISM: Artificial Sequence
<220> FEATURE:
<223> OTHER INFORMATION: Synthetic Construct

<400> SEQUENCE: 825

Phe Tyr Cys His Trp Ile Met Glu
1               5

<210> SEQ ID NO 826
<211> LENGTH: 8
<212> TYPE: PRT
<213> ORGANISM: Artificial Sequence
<220> FEATURE:
<223> OTHER INFORMATION: Synthetic Construct

<400> SEQUENCE: 826

Phe Tyr Cys His Trp Ile Pro Glu
1               5

<210> SEQ ID NO 827
<211> LENGTH: 8
<212> TYPE: PRT
<213> ORGANISM: Artificial Sequence
<220> FEATURE:
<223> OTHER INFORMATION: Synthetic Construct

<400> SEQUENCE: 827

Phe Tyr Cys His Trp Ile Ser Glu
1               5

<210> SEQ ID NO 828
<211> LENGTH: 8
<212> TYPE: PRT
<213> ORGANISM: Artificial Sequence
<220> FEATURE:
<223> OTHER INFORMATION: Synthetic Construct

<400> SEQUENCE: 828

Phe Tyr Cys His Trp Ile Gln Glu
1               5

<210> SEQ ID NO 829
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 829

Phe Tyr Cys His Trp Ile Glu Glu
1               5

<210> SEQ ID NO 830
<211> LENGTH: 8
<212> TYPE: PRT
<213> ORGANISM: Artificial Sequence
<220> FEATURE:
<223> OTHER INFORMATION: Synthetic Construct

<400> SEQUENCE: 830

Phe Tyr Cys His Trp Ile Leu Glu
1               5

<210> SEQ ID NO 831
<211> LENGTH: 8
<212> TYPE: PRT
<213> ORGANISM: Artificial Sequence
<220> FEATURE:
<223> OTHER INFORMATION: Synthetic Construct

<400> SEQUENCE: 831

Phe Tyr Cys His Trp Ile Lys Glu
1               5

<210> SEQ ID NO 832
<211> LENGTH: 8
<212> TYPE: PRT
<213> ORGANISM: Artificial Sequence
<220> FEATURE:
<223> OTHER INFORMATION: Synthetic Construct

<400> SEQUENCE: 832

Phe Tyr Cys His Trp Leu Gln Glu
1               5

<210> SEQ ID NO 833
<211> LENGTH: 8
<212> TYPE: PRT
<213> ORGANISM: Artificial Sequence
<220> FEATURE:
<223> OTHER INFORMATION: Synthetic Construct

<400> SEQUENCE: 833

Phe Tyr Cys His Trp Leu Glu Glu
1               5

<210> SEQ ID NO 834
<211> LENGTH: 8
<212> TYPE: PRT
<213> ORGANISM: Artificial Sequence
<220> FEATURE:
<223> OTHER INFORMATION: Synthetic Construct

<400> SEQUENCE: 834

Phe Tyr Cys His Trp Leu Leu Glu
1               5

<210> SEQ ID NO 835
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 835

Phe Tyr Cys His Trp Ile Thr Glu
1               5

<210> SEQ ID NO 836
<211> LENGTH: 8
<212> TYPE: PRT
<213> ORGANISM: Artificial Sequence
<220> FEATURE:
<223> OTHER INFORMATION: Synthetic Construct

<400> SEQUENCE: 836

Phe Tyr Cys His Trp Leu Ala Glu
1               5

<210> SEQ ID NO 837
<211> LENGTH: 8
<212> TYPE: PRT
<213> ORGANISM: Artificial Sequence
<220> FEATURE:
<223> OTHER INFORMATION: Synthetic Construct

<400> SEQUENCE: 837

Phe Tyr Cys His Trp Leu Arg Glu
1               5

<210> SEQ ID NO 838
<211> LENGTH: 8
<212> TYPE: PRT
<213> ORGANISM: Artificial Sequence
<220> FEATURE:
<223> OTHER INFORMATION: Synthetic Construct

<400> SEQUENCE: 838

Phe Tyr Cys His Trp Leu Asp Glu
1               5

<210> SEQ ID NO 839
<211> LENGTH: 8
<212> TYPE: PRT
<213> ORGANISM: Artificial Sequence
<220> FEATURE:
<223> OTHER INFORMATION: Synthetic Construct

<400> SEQUENCE: 839

Phe Tyr Cys His Trp Leu Thr Glu
1               5

<210> SEQ ID NO 840
<211> LENGTH: 8
<212> TYPE: PRT
<213> ORGANISM: Artificial Sequence
<220> FEATURE:
<223> OTHER INFORMATION: Synthetic Construct

<400> SEQUENCE: 840

Phe Tyr Cys His Trp Lys Ala Glu
1               5

<210> SEQ ID NO 841
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 841

Phe Tyr Cys His Trp Lys Gln Glu
1               5

<210> SEQ ID NO 842
<211> LENGTH: 8
<212> TYPE: PRT
<213> ORGANISM: Artificial Sequence
<220> FEATURE:
<223> OTHER INFORMATION: Synthetic Construct

<400> SEQUENCE: 842

Phe Tyr Cys His Trp Leu Lys Glu
1               5

<210> SEQ ID NO 843
<211> LENGTH: 8
<212> TYPE: PRT
<213> ORGANISM: Artificial Sequence
<220> FEATURE:
<223> OTHER INFORMATION: Synthetic Construct

<400> SEQUENCE: 843

Phe Tyr Cys His Trp Leu Met Glu
1               5

<210> SEQ ID NO 844
<211> LENGTH: 8
<212> TYPE: PRT
<213> ORGANISM: Artificial Sequence
<220> FEATURE:
<223> OTHER INFORMATION: Synthetic Construct

<400> SEQUENCE: 844

Phe Tyr Cys His Trp Leu Pro Glu
1               5

<210> SEQ ID NO 845
<211> LENGTH: 8
<212> TYPE: PRT
<213> ORGANISM: Artificial Sequence
<220> FEATURE:
<223> OTHER INFORMATION: Synthetic Construct

<400> SEQUENCE: 845

Phe Tyr Cys His Trp Leu Ser Glu
1               5

<210> SEQ ID NO 846
<211> LENGTH: 8
<212> TYPE: PRT
<213> ORGANISM: Artificial Sequence
<220> FEATURE:
<223> OTHER INFORMATION: Synthetic Construct

<400> SEQUENCE: 846

Phe Tyr Cys His Trp Lys Ser Glu
1               5

<210> SEQ ID NO 847
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 847

Phe Tyr Cys His Trp Lys Arg Glu
1               5

<210> SEQ ID NO 848
<211> LENGTH: 8
<212> TYPE: PRT
<213> ORGANISM: Artificial Sequence
<220> FEATURE:
<223> OTHER INFORMATION: Synthetic Construct

<400> SEQUENCE: 848

Phe Tyr Cys His Trp Ala Arg Glu
1               5

<210> SEQ ID NO 849
<211> LENGTH: 8
<212> TYPE: PRT
<213> ORGANISM: Artificial Sequence
<220> FEATURE:
<223> OTHER INFORMATION: Synthetic Construct

<400> SEQUENCE: 849

Phe Tyr Cys His Trp Lys Glu Glu
1               5

<210> SEQ ID NO 850
<211> LENGTH: 8
<212> TYPE: PRT
<213> ORGANISM: Artificial Sequence
<220> FEATURE:
<223> OTHER INFORMATION: Synthetic Construct

<400> SEQUENCE: 850

Phe Tyr Cys His Trp Lys Leu Glu
1               5

<210> SEQ ID NO 851
<211> LENGTH: 8
<212> TYPE: PRT
<213> ORGANISM: Artificial Sequence
<220> FEATURE:
<223> OTHER INFORMATION: Synthetic Construct

<400> SEQUENCE: 851

Phe Tyr Cys His Trp Lys Lys Glu
1               5

<210> SEQ ID NO 852
<211> LENGTH: 8
<212> TYPE: PRT
<213> ORGANISM: Artificial Sequence
<220> FEATURE:
<223> OTHER INFORMATION: Synthetic Construct

<400> SEQUENCE: 852

Phe Tyr Cys His Trp Lys Met Glu
1               5

<210> SEQ ID NO 853
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 853

Phe Tyr Cys His Trp Ala Lys Glu
1               5

<210> SEQ ID NO 854
<211> LENGTH: 8
<212> TYPE: PRT
<213> ORGANISM: Artificial Sequence
<220> FEATURE:
<223> OTHER INFORMATION: Synthetic Construct

<400> SEQUENCE: 854

Phe Tyr Cys His Trp Lys Thr Glu
1               5

<210> SEQ ID NO 855
<211> LENGTH: 8
<212> TYPE: PRT
<213> ORGANISM: Artificial Sequence
<220> FEATURE:
<223> OTHER INFORMATION: Synthetic Construct

<400> SEQUENCE: 855

Phe Tyr Cys His Tyr Ala Met Glu
1               5

<210> SEQ ID NO 856
<211> LENGTH: 8
<212> TYPE: PRT
<213> ORGANISM: Artificial Sequence
<220> FEATURE:
<223> OTHER INFORMATION: Synthetic Construct

<400> SEQUENCE: 856

Phe Tyr Cys His Trp Ala Asp Glu
1               5

<210> SEQ ID NO 857
<211> LENGTH: 8
<212> TYPE: PRT
<213> ORGANISM: Artificial Sequence
<220> FEATURE:
<223> OTHER INFORMATION: Synthetic Construct

<400> SEQUENCE: 857

Phe Tyr Cys His Trp Ala Gln Glu
1               5

<210> SEQ ID NO 858
<211> LENGTH: 8
<212> TYPE: PRT
<213> ORGANISM: Artificial Sequence
<220> FEATURE:
<223> OTHER INFORMATION: Synthetic Construct

<400> SEQUENCE: 858

Phe Tyr Cys His Trp Ala Glu Glu
1               5

<210> SEQ ID NO 859
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 859

Phe Tyr Cys His Trp Ala Leu Glu
1               5

<210> SEQ ID NO 860
<211> LENGTH: 8
<212> TYPE: PRT
<213> ORGANISM: Artificial Sequence
<220> FEATURE:
<223> OTHER INFORMATION: Synthetic Construct

<400> SEQUENCE: 860

Phe Tyr Cys His Tyr Gln Arg Glu
1               5

<210> SEQ ID NO 861
<211> LENGTH: 8
<212> TYPE: PRT
<213> ORGANISM: Artificial Sequence
<220> FEATURE:
<223> OTHER INFORMATION: Synthetic Construct

<400> SEQUENCE: 861

Phe Tyr Cys His Tyr Gln Asp Glu
1               5

<210> SEQ ID NO 862
<211> LENGTH: 8
<212> TYPE: PRT
<213> ORGANISM: Artificial Sequence
<220> FEATURE:
<223> OTHER INFORMATION: Synthetic Construct

<400> SEQUENCE: 862

Phe Tyr Cys His Tyr Gln Gln Glu
1               5

<210> SEQ ID NO 863
<211> LENGTH: 8
<212> TYPE: PRT
<213> ORGANISM: Artificial Sequence
<220> FEATURE:
<223> OTHER INFORMATION: Synthetic Construct

<400> SEQUENCE: 863

Phe Tyr Cys His Tyr Ala Pro Glu
1               5

<210> SEQ ID NO 864
<211> LENGTH: 8
<212> TYPE: PRT
<213> ORGANISM: Artificial Sequence
<220> FEATURE:
<223> OTHER INFORMATION: Synthetic Construct

<400> SEQUENCE: 864

Phe Tyr Cys His Tyr Ala Ser Glu
1               5

<210> SEQ ID NO 865
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 865

Phe Tyr Cys His Tyr Ala Thr Glu
1               5

<210> SEQ ID NO 866
<211> LENGTH: 8
<212> TYPE: PRT
<213> ORGANISM: Artificial Sequence
<220> FEATURE:
<223> OTHER INFORMATION: Synthetic Construct

<400> SEQUENCE: 866

Phe Tyr Cys His Tyr Gln Ala Glu
1               5

<210> SEQ ID NO 867
<211> LENGTH: 8
<212> TYPE: PRT
<213> ORGANISM: Artificial Sequence
<220> FEATURE:
<223> OTHER INFORMATION: Synthetic Construct

<400> SEQUENCE: 867

Phe Tyr Cys His Tyr Gln Pro Glu
1               5

<210> SEQ ID NO 868
<211> LENGTH: 8
<212> TYPE: PRT
<213> ORGANISM: Artificial Sequence
<220> FEATURE:
<223> OTHER INFORMATION: Synthetic Construct

<400> SEQUENCE: 868

Phe Tyr Cys His Tyr Gln Ser Glu
1               5

<210> SEQ ID NO 869
<211> LENGTH: 8
<212> TYPE: PRT
<213> ORGANISM: Artificial Sequence
<220> FEATURE:
<223> OTHER INFORMATION: Synthetic Construct

<400> SEQUENCE: 869

Phe Tyr Cys His Trp Gln Thr Glu
1               5

<210> SEQ ID NO 870
<211> LENGTH: 8
<212> TYPE: PRT
<213> ORGANISM: Artificial Sequence
<220> FEATURE:
<223> OTHER INFORMATION: Synthetic Construct

<400> SEQUENCE: 870

Phe Tyr Cys His Tyr Gln Glu Glu
1               5

<210> SEQ ID NO 871
<211> LENGTH: 8
<212> TYPE: PRT
<213> ORGANISM: Artificial Sequence
<220> FEATURE:
<223> OTHER INFORMATION: Synthetic Construct

<400> SEQUENCE: 871
```

Phe Tyr Cys His Tyr Gln Leu Glu
1               5

<210> SEQ ID NO 872
<211> LENGTH: 8
<212> TYPE: PRT
<213> ORGANISM: Artificial Sequence
<220> FEATURE:
<223> OTHER INFORMATION: Synthetic Construct

<400> SEQUENCE: 872

Phe Tyr Cys His Tyr Gln Lys Glu
1               5

<210> SEQ ID NO 873
<211> LENGTH: 8
<212> TYPE: PRT
<213> ORGANISM: Artificial Sequence
<220> FEATURE:
<223> OTHER INFORMATION: Synthetic Construct

<400> SEQUENCE: 873

Phe Tyr Cys His Tyr Gln Met Glu
1               5

<210> SEQ ID NO 874
<211> LENGTH: 8
<212> TYPE: PRT
<213> ORGANISM: Artificial Sequence
<220> FEATURE:
<223> OTHER INFORMATION: Synthetic Construct

<400> SEQUENCE: 874

Phe Tyr Cys His Trp Glu Glu Glu
1               5

<210> SEQ ID NO 875
<211> LENGTH: 8
<212> TYPE: PRT
<213> ORGANISM: Artificial Sequence
<220> FEATURE:
<223> OTHER INFORMATION: Synthetic Construct

<400> SEQUENCE: 875

Phe Tyr Cys His Trp Glu Leu Glu
1               5

<210> SEQ ID NO 876
<211> LENGTH: 8
<212> TYPE: PRT
<213> ORGANISM: Artificial Sequence
<220> FEATURE:
<223> OTHER INFORMATION: Synthetic Construct

<400> SEQUENCE: 876

Phe Tyr Cys His Trp Glu Lys Glu
1               5

<210> SEQ ID NO 877
<211> LENGTH: 8
<212> TYPE: PRT
<213> ORGANISM: Artificial Sequence
<220> FEATURE:
<223> OTHER INFORMATION: Synthetic Construct

<400> SEQUENCE: 877

Phe Tyr Cys His Trp Glu Ala Glu
1               5

<210> SEQ ID NO 878
<211> LENGTH: 8
<212> TYPE: PRT
<213> ORGANISM: Artificial Sequence
<220> FEATURE:
<223> OTHER INFORMATION: Synthetic Construct

<400> SEQUENCE: 878

Phe Tyr Cys His Trp Glu Arg Glu
1               5

<210> SEQ ID NO 879
<211> LENGTH: 8
<212> TYPE: PRT
<213> ORGANISM: Artificial Sequence
<220> FEATURE:
<223> OTHER INFORMATION: Synthetic Construct

<400> SEQUENCE: 879

Phe Tyr Cys His Trp Glu Asp Glu
1               5

<210> SEQ ID NO 880
<211> LENGTH: 8
<212> TYPE: PRT
<213> ORGANISM: Artificial Sequence
<220> FEATURE:
<223> OTHER INFORMATION: Synthetic Construct

<400> SEQUENCE: 880

Phe Tyr Cys His Trp Glu Gln Glu
1               5

<210> SEQ ID NO 881
<211> LENGTH: 8
<212> TYPE: PRT
<213> ORGANISM: Artificial Sequence
<220> FEATURE:
<223> OTHER INFORMATION: Synthetic Construct

<400> SEQUENCE: 881

Phe Tyr Cys His Trp Ile Ala Glu
1               5

<210> SEQ ID NO 882
<211> LENGTH: 8
<212> TYPE: PRT
<213> ORGANISM: Artificial Sequence
<220> FEATURE:
<223> OTHER INFORMATION: Synthetic Construct

<400> SEQUENCE: 882

Phe Tyr Cys His Trp Ile Arg Glu
1               5

<210> SEQ ID NO 883
<211> LENGTH: 8
<212> TYPE: PRT
<213> ORGANISM: Artificial Sequence
<220> FEATURE:
<223> OTHER INFORMATION: Synthetic Construct

<400> SEQUENCE: 883

Phe Tyr Cys His Tyr Ile Asp Glu

```
<210> SEQ ID NO 884
<211> LENGTH: 8
<212> TYPE: PRT
<213> ORGANISM: Artificial Sequence
<220> FEATURE:
<223> OTHER INFORMATION: Synthetic Construct

<400> SEQUENCE: 884

Phe Tyr Cys His Trp Glu Met Glu
1               5

<210> SEQ ID NO 885
<211> LENGTH: 8
<212> TYPE: PRT
<213> ORGANISM: Artificial Sequence
<220> FEATURE:
<223> OTHER INFORMATION: Synthetic Construct

<400> SEQUENCE: 885

Phe Tyr Cys His Trp Glu Pro Glu
1               5

<210> SEQ ID NO 886
<211> LENGTH: 8
<212> TYPE: PRT
<213> ORGANISM: Artificial Sequence
<220> FEATURE:
<223> OTHER INFORMATION: Synthetic Construct

<400> SEQUENCE: 886

Phe Tyr Cys His Trp Glu Ser Glu
1               5

<210> SEQ ID NO 887
<211> LENGTH: 8
<212> TYPE: PRT
<213> ORGANISM: Artificial Sequence
<220> FEATURE:
<223> OTHER INFORMATION: Synthetic Construct

<400> SEQUENCE: 887

Phe Tyr Cys His Trp Glu Thr Glu
1               5

<210> SEQ ID NO 888
<211> LENGTH: 8
<212> TYPE: PRT
<213> ORGANISM: Artificial Sequence
<220> FEATURE:
<223> OTHER INFORMATION: Synthetic Construct

<400> SEQUENCE: 888

Phe Tyr Cys His Tyr Ile Met Glu
1               5

<210> SEQ ID NO 889
<211> LENGTH: 8
<212> TYPE: PRT
<213> ORGANISM: Artificial Sequence
<220> FEATURE:
<223> OTHER INFORMATION: Synthetic Construct

<400> SEQUENCE: 889

Phe Tyr Cys His Tyr Ile Pro Glu
1               5
```

```
<210> SEQ ID NO 890
<211> LENGTH: 8
<212> TYPE: PRT
<213> ORGANISM: Artificial Sequence
<220> FEATURE:
<223> OTHER INFORMATION: Synthetic Construct

<400> SEQUENCE: 890

Phe Tyr Cys His Tyr Ile Ser Glu
1               5

<210> SEQ ID NO 891
<211> LENGTH: 8
<212> TYPE: PRT
<213> ORGANISM: Artificial Sequence
<220> FEATURE:
<223> OTHER INFORMATION: Synthetic Construct

<400> SEQUENCE: 891

Phe Tyr Cys His Tyr Ile Gln Glu
1               5

<210> SEQ ID NO 892
<211> LENGTH: 8
<212> TYPE: PRT
<213> ORGANISM: Artificial Sequence
<220> FEATURE:
<223> OTHER INFORMATION: Synthetic Construct

<400> SEQUENCE: 892

Phe Tyr Cys His Tyr Ile Glu Glu
1               5

<210> SEQ ID NO 893
<211> LENGTH: 8
<212> TYPE: PRT
<213> ORGANISM: Artificial Sequence
<220> FEATURE:
<223> OTHER INFORMATION: Synthetic Construct

<400> SEQUENCE: 893

Phe Tyr Cys His Tyr Ile Leu Glu
1               5

<210> SEQ ID NO 894
<211> LENGTH: 8
<212> TYPE: PRT
<213> ORGANISM: Artificial Sequence
<220> FEATURE:
<223> OTHER INFORMATION: Synthetic Construct

<400> SEQUENCE: 894

Phe Tyr Cys His Tyr Ile Lys Glu
1               5

<210> SEQ ID NO 895
<211> LENGTH: 8
<212> TYPE: PRT
<213> ORGANISM: Artificial Sequence
<220> FEATURE:
<223> OTHER INFORMATION: Synthetic Construct

<400> SEQUENCE: 895

Phe Tyr Cys His Tyr Leu Gln Glu
1               5
```

```
<210> SEQ ID NO 896
<211> LENGTH: 8
<212> TYPE: PRT
<213> ORGANISM: Artificial Sequence
<220> FEATURE:
<223> OTHER INFORMATION: Synthetic Construct

<400> SEQUENCE: 896

Phe Tyr Cys His Tyr Leu Glu Glu
1               5

<210> SEQ ID NO 897
<211> LENGTH: 8
<212> TYPE: PRT
<213> ORGANISM: Artificial Sequence
<220> FEATURE:
<223> OTHER INFORMATION: Synthetic Construct

<400> SEQUENCE: 897

Phe Tyr Cys His Tyr Leu Leu Glu
1               5

<210> SEQ ID NO 898
<211> LENGTH: 8
<212> TYPE: PRT
<213> ORGANISM: Artificial Sequence
<220> FEATURE:
<223> OTHER INFORMATION: Synthetic Construct

<400> SEQUENCE: 898

Phe Tyr Cys His Tyr Ile Thr Glu
1               5

<210> SEQ ID NO 899
<211> LENGTH: 8
<212> TYPE: PRT
<213> ORGANISM: Artificial Sequence
<220> FEATURE:
<223> OTHER INFORMATION: Synthetic Construct

<400> SEQUENCE: 899

Phe Tyr Cys His Tyr Leu Ala Glu
1               5

<210> SEQ ID NO 900
<211> LENGTH: 8
<212> TYPE: PRT
<213> ORGANISM: Artificial Sequence
<220> FEATURE:
<223> OTHER INFORMATION: Synthetic Construct

<400> SEQUENCE: 900

Phe Tyr Cys His Tyr Leu Arg Glu
1               5

<210> SEQ ID NO 901
<211> LENGTH: 8
<212> TYPE: PRT
<213> ORGANISM: Artificial Sequence
<220> FEATURE:
<223> OTHER INFORMATION: Synthetic Construct

<400> SEQUENCE: 901

Phe Tyr Cys His Tyr Leu Asp Glu
1               5
```

```
<210> SEQ ID NO 902
<211> LENGTH: 8
<212> TYPE: PRT
<213> ORGANISM: Artificial Sequence
<220> FEATURE:
<223> OTHER INFORMATION: Synthetic Construct

<400> SEQUENCE: 902

Phe Tyr Cys His Tyr Leu Thr Glu
1               5

<210> SEQ ID NO 903
<211> LENGTH: 8
<212> TYPE: PRT
<213> ORGANISM: Artificial Sequence
<220> FEATURE:
<223> OTHER INFORMATION: Synthetic Construct

<400> SEQUENCE: 903

Phe Tyr Cys His Tyr Lys Ala Glu
1               5

<210> SEQ ID NO 904
<211> LENGTH: 8
<212> TYPE: PRT
<213> ORGANISM: Artificial Sequence
<220> FEATURE:
<223> OTHER INFORMATION: Synthetic Construct

<400> SEQUENCE: 904

Phe Tyr Cys His Tyr Lys Gln Glu
1               5

<210> SEQ ID NO 905
<211> LENGTH: 8
<212> TYPE: PRT
<213> ORGANISM: Artificial Sequence
<220> FEATURE:
<223> OTHER INFORMATION: Synthetic Construct

<400> SEQUENCE: 905

Phe Tyr Cys His Tyr Leu Lys Glu
1               5

<210> SEQ ID NO 906
<211> LENGTH: 8
<212> TYPE: PRT
<213> ORGANISM: Artificial Sequence
<220> FEATURE:
<223> OTHER INFORMATION: Synthetic Construct

<400> SEQUENCE: 906

Phe Tyr Cys His Tyr Leu Met Glu
1               5

<210> SEQ ID NO 907
<211> LENGTH: 8
<212> TYPE: PRT
<213> ORGANISM: Artificial Sequence
<220> FEATURE:
<223> OTHER INFORMATION: Synthetic Construct

<400> SEQUENCE: 907

Phe Tyr Cys His Tyr Leu Pro Glu
1               5

<210> SEQ ID NO 908
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 908

Phe Tyr Cys His Tyr Leu Ser Glu
1               5

<210> SEQ ID NO 909
<211> LENGTH: 8
<212> TYPE: PRT
<213> ORGANISM: Artificial Sequence
<220> FEATURE:
<223> OTHER INFORMATION: Synthetic Construct

<400> SEQUENCE: 909

Phe Tyr Cys His Tyr Lys Ser Glu
1               5

<210> SEQ ID NO 910
<211> LENGTH: 8
<212> TYPE: PRT
<213> ORGANISM: Artificial Sequence
<220> FEATURE:
<223> OTHER INFORMATION: Synthetic Construct

<400> SEQUENCE: 910

Phe Tyr Cys His Tyr Lys Arg Glu
1               5

<210> SEQ ID NO 911
<211> LENGTH: 8
<212> TYPE: PRT
<213> ORGANISM: Artificial Sequence
<220> FEATURE:
<223> OTHER INFORMATION: Synthetic Construct

<400> SEQUENCE: 911

Phe Tyr Cys His Tyr Ala Arg Glu
1               5

<210> SEQ ID NO 912
<211> LENGTH: 8
<212> TYPE: PRT
<213> ORGANISM: Artificial Sequence
<220> FEATURE:
<223> OTHER INFORMATION: Synthetic Construct

<400> SEQUENCE: 912

Phe Tyr Cys His Tyr Lys Glu Glu
1               5

<210> SEQ ID NO 913
<211> LENGTH: 8
<212> TYPE: PRT
<213> ORGANISM: Artificial Sequence
<220> FEATURE:
<223> OTHER INFORMATION: Synthetic Construct

<400> SEQUENCE: 913

Phe Tyr Cys His Tyr Lys Leu Glu
1               5

<210> SEQ ID NO 914
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 914

Phe Tyr Cys His Tyr Lys Lys Glu
1               5

<210> SEQ ID NO 915
<211> LENGTH: 8
<212> TYPE: PRT
<213> ORGANISM: Artificial Sequence
<220> FEATURE:
<223> OTHER INFORMATION: Synthetic Construct

<400> SEQUENCE: 915

Phe Tyr Cys His Tyr Lys Met Glu
1               5

<210> SEQ ID NO 916
<211> LENGTH: 8
<212> TYPE: PRT
<213> ORGANISM: Artificial Sequence
<220> FEATURE:
<223> OTHER INFORMATION: Synthetic Construct

<400> SEQUENCE: 916

Phe Tyr Cys His Tyr Ala Lys Glu
1               5

<210> SEQ ID NO 917
<211> LENGTH: 8
<212> TYPE: PRT
<213> ORGANISM: Artificial Sequence
<220> FEATURE:
<223> OTHER INFORMATION: Synthetic Construct

<400> SEQUENCE: 917

Phe Tyr Cys His Tyr Lys Thr Glu
1               5

<210> SEQ ID NO 918
<211> LENGTH: 8
<212> TYPE: PRT
<213> ORGANISM: Artificial Sequence
<220> FEATURE:
<223> OTHER INFORMATION: Synthetic Construct

<400> SEQUENCE: 918

Phe Tyr Cys His Tyr Ala Ala Glu
1               5

<210> SEQ ID NO 919
<211> LENGTH: 8
<212> TYPE: PRT
<213> ORGANISM: Artificial Sequence
<220> FEATURE:
<223> OTHER INFORMATION: Synthetic Construct

<400> SEQUENCE: 919

Phe Tyr Cys His Tyr Ala Asp Glu
1               5

<210> SEQ ID NO 920
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 920

Phe Tyr Cys His Tyr Ala Gln Glu
1               5

<210> SEQ ID NO 921
<211> LENGTH: 8
<212> TYPE: PRT
<213> ORGANISM: Artificial Sequence
<220> FEATURE:
<223> OTHER INFORMATION: Synthetic Construct

<400> SEQUENCE: 921

Phe Tyr Cys His Tyr Ala Glu Glu
1               5

<210> SEQ ID NO 922
<211> LENGTH: 8
<212> TYPE: PRT
<213> ORGANISM: Artificial Sequence
<220> FEATURE:
<223> OTHER INFORMATION: Synthetic Construct

<400> SEQUENCE: 922

Phe Tyr Cys His Tyr Ala Leu Glu
1               5

<210> SEQ ID NO 923
<211> LENGTH: 8
<212> TYPE: PRT
<213> ORGANISM: Artificial Sequence
<220> FEATURE:
<223> OTHER INFORMATION: Synthetic Construct

<400> SEQUENCE: 923

Phe Tyr Cys His Val Lys Asp Glu
1               5

<210> SEQ ID NO 924
<211> LENGTH: 8
<212> TYPE: PRT
<213> ORGANISM: Artificial Sequence
<220> FEATURE:
<223> OTHER INFORMATION: Synthetic Construct

<400> SEQUENCE: 924

Phe Tyr Cys His Val Gln Ser Glu
1               5

<210> SEQ ID NO 925
<211> LENGTH: 8
<212> TYPE: PRT
<213> ORGANISM: Artificial Sequence
<220> FEATURE:
<223> OTHER INFORMATION: Synthetic Construct

<400> SEQUENCE: 925

Phe Tyr Cys His Trp Gln Thr Glu
1               5

<210> SEQ ID NO 926
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 926

Phe Tyr Cys His Tyr Lys Pro Glu
1               5

<210> SEQ ID NO 927
<211> LENGTH: 8
<212> TYPE: PRT
<213> ORGANISM: Artificial Sequence
<220> FEATURE:
<223> OTHER INFORMATION: Synthetic Construct

<400> SEQUENCE: 927

Phe Tyr Cys His Tyr Lys Asp Glu
1               5

<210> SEQ ID NO 928
<211> LENGTH: 8
<212> TYPE: PRT
<213> ORGANISM: Artificial Sequence
<220> FEATURE:
<223> OTHER INFORMATION: Synthetic Construct

<400> SEQUENCE: 928

Phe Tyr Cys His Val Ala Ala Glu
1               5

<210> SEQ ID NO 929
<211> LENGTH: 8
<212> TYPE: PRT
<213> ORGANISM: Artificial Sequence
<220> FEATURE:
<223> OTHER INFORMATION: Synthetic Construct

<400> SEQUENCE: 929

Phe Tyr Cys His Val Lys Pro Glu
1               5

<210> SEQ ID NO 930
<211> LENGTH: 8
<212> TYPE: PRT
<213> ORGANISM: Artificial Sequence
<220> FEATURE:
<223> OTHER INFORMATION: Synthetic Construct

<400> SEQUENCE: 930

Phe Tyr Cys His Trp Glu Glu Glu
1               5

<210> SEQ ID NO 931
<211> LENGTH: 8
<212> TYPE: PRT
<213> ORGANISM: Artificial Sequence
<220> FEATURE:
<223> OTHER INFORMATION: Synthetic Construct

<400> SEQUENCE: 931

Phe Tyr Cys His Trp Glu Leu Glu
1               5

<210> SEQ ID NO 932
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 932

Phe Tyr Cys His Trp Glu Lys Glu
1               5

<210> SEQ ID NO 933
<211> LENGTH: 8
<212> TYPE: PRT
<213> ORGANISM: Artificial Sequence
<220> FEATURE:
<223> OTHER INFORMATION: Synthetic Construct

<400> SEQUENCE: 933

Phe Tyr Cys His Trp Glu Ala Glu
1               5

<210> SEQ ID NO 934
<211> LENGTH: 8
<212> TYPE: PRT
<213> ORGANISM: Artificial Sequence
<220> FEATURE:
<223> OTHER INFORMATION: Synthetic Construct

<400> SEQUENCE: 934

Phe Tyr Cys His Trp Glu Arg Glu
1               5

<210> SEQ ID NO 935
<211> LENGTH: 8
<212> TYPE: PRT
<213> ORGANISM: Artificial Sequence
<220> FEATURE:
<223> OTHER INFORMATION: Synthetic Construct

<400> SEQUENCE: 935

Phe Tyr Cys His Trp Glu Asp Glu
1               5

<210> SEQ ID NO 936
<211> LENGTH: 8
<212> TYPE: PRT
<213> ORGANISM: Artificial Sequence
<220> FEATURE:
<223> OTHER INFORMATION: Synthetic Construct

<400> SEQUENCE: 936

Phe Tyr Cys His Trp Glu Gln Glu
1               5

<210> SEQ ID NO 937
<211> LENGTH: 8
<212> TYPE: PRT
<213> ORGANISM: Artificial Sequence
<220> FEATURE:
<223> OTHER INFORMATION: Synthetic Construct

<400> SEQUENCE: 937

Phe Tyr Cys His Trp Ile Ala Glu
1               5

<210> SEQ ID NO 938
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 938

Phe Tyr Cys His Trp Ile Arg Glu
1               5

<210> SEQ ID NO 939
<211> LENGTH: 8
<212> TYPE: PRT
<213> ORGANISM: Artificial Sequence
<220> FEATURE:
<223> OTHER INFORMATION: Synthetic Construct

<400> SEQUENCE: 939

Phe Tyr Cys His Val Ile Asp Glu
1               5

<210> SEQ ID NO 940
<211> LENGTH: 8
<212> TYPE: PRT
<213> ORGANISM: Artificial Sequence
<220> FEATURE:
<223> OTHER INFORMATION: Synthetic Construct

<400> SEQUENCE: 940

Phe Tyr Cys His Trp Glu Met Glu
1               5

<210> SEQ ID NO 941
<211> LENGTH: 8
<212> TYPE: PRT
<213> ORGANISM: Artificial Sequence
<220> FEATURE:
<223> OTHER INFORMATION: Synthetic Construct

<400> SEQUENCE: 941

Phe Tyr Cys His Trp Glu Pro Glu
1               5

<210> SEQ ID NO 942
<211> LENGTH: 8
<212> TYPE: PRT
<213> ORGANISM: Artificial Sequence
<220> FEATURE:
<223> OTHER INFORMATION: Synthetic Construct

<400> SEQUENCE: 942

Phe Tyr Cys His Trp Glu Ser Glu
1               5

<210> SEQ ID NO 943
<211> LENGTH: 8
<212> TYPE: PRT
<213> ORGANISM: Artificial Sequence
<220> FEATURE:
<223> OTHER INFORMATION: Synthetic Construct

<400> SEQUENCE: 943

Phe Tyr Cys His Trp Glu Thr Glu
1               5

<210> SEQ ID NO 944
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 944

Phe Tyr Cys His Val Ile Met Glu
1               5

<210> SEQ ID NO 945
<211> LENGTH: 8
<212> TYPE: PRT
<213> ORGANISM: Artificial Sequence
<220> FEATURE:
<223> OTHER INFORMATION: Synthetic Construct

<400> SEQUENCE: 945

Phe Tyr Cys His Val Ile Pro Glu
1               5

<210> SEQ ID NO 946
<211> LENGTH: 8
<212> TYPE: PRT
<213> ORGANISM: Artificial Sequence
<220> FEATURE:
<223> OTHER INFORMATION: Synthetic Construct

<400> SEQUENCE: 946

Phe Tyr Cys His Val Ile Ser Glu
1               5

<210> SEQ ID NO 947
<211> LENGTH: 8
<212> TYPE: PRT
<213> ORGANISM: Artificial Sequence
<220> FEATURE:
<223> OTHER INFORMATION: Synthetic Construct

<400> SEQUENCE: 947

Phe Tyr Cys His Val Ile Gln Glu
1               5

<210> SEQ ID NO 948
<211> LENGTH: 8
<212> TYPE: PRT
<213> ORGANISM: Artificial Sequence
<220> FEATURE:
<223> OTHER INFORMATION: Synthetic Construct

<400> SEQUENCE: 948

Phe Tyr Cys His Val Ile Glu Glu
1               5

<210> SEQ ID NO 949
<211> LENGTH: 8
<212> TYPE: PRT
<213> ORGANISM: Artificial Sequence
<220> FEATURE:
<223> OTHER INFORMATION: Synthetic Construct

<400> SEQUENCE: 949

Phe Tyr Cys His Val Ile Leu Glu
1               5

<210> SEQ ID NO 950
<211> LENGTH: 8
<212> TYPE: PRT
<213> ORGANISM: Artificial Sequence
<220> FEATURE:
<223> OTHER INFORMATION: Synthetic Construct

<400> SEQUENCE: 950
```

```
Phe Tyr Cys His Val Ile Lys Glu
1               5

<210> SEQ ID NO 951
<211> LENGTH: 8
<212> TYPE: PRT
<213> ORGANISM: Artificial Sequence
<220> FEATURE:
<223> OTHER INFORMATION: Synthetic Construct

<400> SEQUENCE: 951

Phe Tyr Cys His Val Leu Gln Glu
1               5

<210> SEQ ID NO 952
<211> LENGTH: 8
<212> TYPE: PRT
<213> ORGANISM: Artificial Sequence
<220> FEATURE:
<223> OTHER INFORMATION: Synthetic Construct

<400> SEQUENCE: 952

Phe Tyr Cys His Val Leu Glu Glu
1               5

<210> SEQ ID NO 953
<211> LENGTH: 8
<212> TYPE: PRT
<213> ORGANISM: Artificial Sequence
<220> FEATURE:
<223> OTHER INFORMATION: Synthetic Construct

<400> SEQUENCE: 953

Phe Tyr Cys His Val Leu Leu Glu
1               5

<210> SEQ ID NO 954
<211> LENGTH: 8
<212> TYPE: PRT
<213> ORGANISM: Artificial Sequence
<220> FEATURE:
<223> OTHER INFORMATION: Synthetic Construct

<400> SEQUENCE: 954

Phe Tyr Cys His Val Ile Thr Glu
1               5

<210> SEQ ID NO 955
<211> LENGTH: 8
<212> TYPE: PRT
<213> ORGANISM: Artificial Sequence
<220> FEATURE:
<223> OTHER INFORMATION: Synthetic Construct

<400> SEQUENCE: 955

Phe Tyr Cys His Val Leu Ala Glu
1               5

<210> SEQ ID NO 956
<211> LENGTH: 8
<212> TYPE: PRT
<213> ORGANISM: Artificial Sequence
<220> FEATURE:
<223> OTHER INFORMATION: Synthetic Construct

<400> SEQUENCE: 956
```

-continued

Phe Tyr Cys His Val Leu Arg Glu
1               5

<210> SEQ ID NO 957
<211> LENGTH: 8
<212> TYPE: PRT
<213> ORGANISM: Artificial Sequence
<220> FEATURE:
<223> OTHER INFORMATION: Synthetic Construct

<400> SEQUENCE: 957

Phe Tyr Cys His Val Leu Asp Glu
1               5

<210> SEQ ID NO 958
<211> LENGTH: 8
<212> TYPE: PRT
<213> ORGANISM: Artificial Sequence
<220> FEATURE:
<223> OTHER INFORMATION: Synthetic Construct

<400> SEQUENCE: 958

Phe Tyr Cys His Val Leu Thr Glu
1               5

<210> SEQ ID NO 959
<211> LENGTH: 8
<212> TYPE: PRT
<213> ORGANISM: Artificial Sequence
<220> FEATURE:
<223> OTHER INFORMATION: Synthetic Construct

<400> SEQUENCE: 959

Phe Tyr Cys His Val Lys Ala Glu
1               5

<210> SEQ ID NO 960
<211> LENGTH: 8
<212> TYPE: PRT
<213> ORGANISM: Artificial Sequence
<220> FEATURE:
<223> OTHER INFORMATION: Synthetic Construct

<400> SEQUENCE: 960

Phe Tyr Cys His Val Lys Gln Glu
1               5

<210> SEQ ID NO 961
<211> LENGTH: 8
<212> TYPE: PRT
<213> ORGANISM: Artificial Sequence
<220> FEATURE:
<223> OTHER INFORMATION: Synthetic Construct

<400> SEQUENCE: 961

Phe Tyr Cys His Val Leu Lys Glu
1               5

<210> SEQ ID NO 962
<211> LENGTH: 8
<212> TYPE: PRT
<213> ORGANISM: Artificial Sequence
<220> FEATURE:
<223> OTHER INFORMATION: Synthetic Construct

<400> SEQUENCE: 962

Phe Tyr Cys His Val Leu Met Glu

```
<210> SEQ ID NO 963
<211> LENGTH: 8
<212> TYPE: PRT
<213> ORGANISM: Artificial Sequence
<220> FEATURE:
<223> OTHER INFORMATION: Synthetic Construct

<400> SEQUENCE: 963

Phe Tyr Cys His Val Leu Pro Glu
1               5

<210> SEQ ID NO 964
<211> LENGTH: 8
<212> TYPE: PRT
<213> ORGANISM: Artificial Sequence
<220> FEATURE:
<223> OTHER INFORMATION: Synthetic Construct

<400> SEQUENCE: 964

Phe Tyr Cys His Val Leu Ser Glu
1               5

<210> SEQ ID NO 965
<211> LENGTH: 8
<212> TYPE: PRT
<213> ORGANISM: Artificial Sequence
<220> FEATURE:
<223> OTHER INFORMATION: Synthetic Construct

<400> SEQUENCE: 965

Phe Tyr Cys His Val Lys Ser Glu
1               5

<210> SEQ ID NO 966
<211> LENGTH: 8
<212> TYPE: PRT
<213> ORGANISM: Artificial Sequence
<220> FEATURE:
<223> OTHER INFORMATION: Synthetic Construct

<400> SEQUENCE: 966

Phe Tyr Cys His Val Lys Arg Glu
1               5

<210> SEQ ID NO 967
<211> LENGTH: 8
<212> TYPE: PRT
<213> ORGANISM: Artificial Sequence
<220> FEATURE:
<223> OTHER INFORMATION: Synthetic Construct

<400> SEQUENCE: 967

Phe Tyr Cys His Val Ala Arg Glu
1               5

<210> SEQ ID NO 968
<211> LENGTH: 8
<212> TYPE: PRT
<213> ORGANISM: Artificial Sequence
<220> FEATURE:
<223> OTHER INFORMATION: Synthetic Construct

<400> SEQUENCE: 968

Phe Tyr Cys His Val Lys Glu Glu
1               5
```

```
<210> SEQ ID NO 969
<211> LENGTH: 8
<212> TYPE: PRT
<213> ORGANISM: Artificial Sequence
<220> FEATURE:
<223> OTHER INFORMATION: Synthetic Construct

<400> SEQUENCE: 969

Phe Tyr Cys His Val Lys Leu Glu
1               5

<210> SEQ ID NO 970
<211> LENGTH: 8
<212> TYPE: PRT
<213> ORGANISM: Artificial Sequence
<220> FEATURE:
<223> OTHER INFORMATION: Synthetic Construct

<400> SEQUENCE: 970

Phe Tyr Cys His Val Lys Lys Glu
1               5

<210> SEQ ID NO 971
<211> LENGTH: 8
<212> TYPE: PRT
<213> ORGANISM: Artificial Sequence
<220> FEATURE:
<223> OTHER INFORMATION: Synthetic Construct

<400> SEQUENCE: 971

Phe Tyr Cys His Val Lys Met Glu
1               5

<210> SEQ ID NO 972
<211> LENGTH: 8
<212> TYPE: PRT
<213> ORGANISM: Artificial Sequence
<220> FEATURE:
<223> OTHER INFORMATION: Synthetic Construct

<400> SEQUENCE: 972

Phe Tyr Cys His Val Ala Lys Glu
1               5

<210> SEQ ID NO 973
<211> LENGTH: 8
<212> TYPE: PRT
<213> ORGANISM: Artificial Sequence
<220> FEATURE:
<223> OTHER INFORMATION: Synthetic Construct

<400> SEQUENCE: 973

Phe Tyr Cys His Val Lys Thr Glu
1               5

<210> SEQ ID NO 974
<211> LENGTH: 8
<212> TYPE: PRT
<213> ORGANISM: Artificial Sequence
<220> FEATURE:
<223> OTHER INFORMATION: Synthetic Construct

<400> SEQUENCE: 974

Phe Tyr Cys His Val Ala Met Glu
1               5
```

<210> SEQ ID NO 975
<211> LENGTH: 8
<212> TYPE: PRT
<213> ORGANISM: Artificial Sequence
<220> FEATURE:
<223> OTHER INFORMATION: Synthetic Construct

<400> SEQUENCE: 975

Phe Tyr Cys His Val Ala Asp Glu
1               5

<210> SEQ ID NO 976
<211> LENGTH: 8
<212> TYPE: PRT
<213> ORGANISM: Artificial Sequence
<220> FEATURE:
<223> OTHER INFORMATION: Synthetic Construct

<400> SEQUENCE: 976

Phe Tyr Cys His Val Ala Gln Glu
1               5

<210> SEQ ID NO 977
<211> LENGTH: 8
<212> TYPE: PRT
<213> ORGANISM: Artificial Sequence
<220> FEATURE:
<223> OTHER INFORMATION: Synthetic Construct

<400> SEQUENCE: 977

Phe Tyr Cys His Val Ala Glu Glu
1               5

<210> SEQ ID NO 978
<211> LENGTH: 8
<212> TYPE: PRT
<213> ORGANISM: Artificial Sequence
<220> FEATURE:
<223> OTHER INFORMATION: Synthetic Construct

<400> SEQUENCE: 978

Phe Tyr Cys His Val Ala Leu Glu
1               5

<210> SEQ ID NO 979
<211> LENGTH: 8
<212> TYPE: PRT
<213> ORGANISM: Artificial Sequence
<220> FEATURE:
<223> OTHER INFORMATION: Synthetic Construct

<400> SEQUENCE: 979

Phe Tyr Cys His Val Gln Arg Glu
1               5

<210> SEQ ID NO 980
<211> LENGTH: 8
<212> TYPE: PRT
<213> ORGANISM: Artificial Sequence
<220> FEATURE:
<223> OTHER INFORMATION: Synthetic Construct

<400> SEQUENCE: 980

Phe Tyr Cys His Val Gln Asp Glu
1               5

```
<210> SEQ ID NO 981
<211> LENGTH: 8
<212> TYPE: PRT
<213> ORGANISM: Artificial Sequence
<220> FEATURE:
<223> OTHER INFORMATION: Synthetic Construct

<400> SEQUENCE: 981

Phe Tyr Cys His Val Gln Gln Glu
1               5

<210> SEQ ID NO 982
<211> LENGTH: 8
<212> TYPE: PRT
<213> ORGANISM: Artificial Sequence
<220> FEATURE:
<223> OTHER INFORMATION: Synthetic Construct

<400> SEQUENCE: 982

Phe Tyr Cys His Val Ala Pro Glu
1               5

<210> SEQ ID NO 983
<211> LENGTH: 8
<212> TYPE: PRT
<213> ORGANISM: Artificial Sequence
<220> FEATURE:
<223> OTHER INFORMATION: Synthetic Construct

<400> SEQUENCE: 983

Phe Tyr Cys His Val Ala Ser Glu
1               5

<210> SEQ ID NO 984
<211> LENGTH: 8
<212> TYPE: PRT
<213> ORGANISM: Artificial Sequence
<220> FEATURE:
<223> OTHER INFORMATION: Synthetic Construct

<400> SEQUENCE: 984

Phe Tyr Cys His Val Ala Thr Glu
1               5

<210> SEQ ID NO 985
<211> LENGTH: 8
<212> TYPE: PRT
<213> ORGANISM: Artificial Sequence
<220> FEATURE:
<223> OTHER INFORMATION: Synthetic Construct

<400> SEQUENCE: 985

Phe Tyr Cys His Val Gln Ala Glu
1               5

<210> SEQ ID NO 986
<211> LENGTH: 8
<212> TYPE: PRT
<213> ORGANISM: Artificial Sequence
<220> FEATURE:
<223> OTHER INFORMATION: Synthetic Construct

<400> SEQUENCE: 986

Phe Tyr Cys His Val Gln Pro Glu
1               5

<210> SEQ ID NO 987
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 987

Phe Tyr Cys His Val Gln Glu Glu
1               5

<210> SEQ ID NO 988
<211> LENGTH: 8
<212> TYPE: PRT
<213> ORGANISM: Artificial Sequence
<220> FEATURE:
<223> OTHER INFORMATION: Synthetic Construct

<400> SEQUENCE: 988

Phe Tyr Cys His Val Gln Leu Glu
1               5

<210> SEQ ID NO 989
<211> LENGTH: 8
<212> TYPE: PRT
<213> ORGANISM: Artificial Sequence
<220> FEATURE:
<223> OTHER INFORMATION: Synthetic Construct

<400> SEQUENCE: 989

Phe Tyr Cys His Val Gln Lys Glu
1               5

<210> SEQ ID NO 990
<211> LENGTH: 8
<212> TYPE: PRT
<213> ORGANISM: Artificial Sequence
<220> FEATURE:
<223> OTHER INFORMATION: Synthetic Construct

<400> SEQUENCE: 990

Phe Tyr Cys His Val Gln Met Glu
1               5

<210> SEQ ID NO 991
<211> LENGTH: 8
<212> TYPE: PRT
<213> ORGANISM: Artificial Sequence
<220> FEATURE:
<223> OTHER INFORMATION: Synthetic Construct

<400> SEQUENCE: 991

Phe Tyr Ala His Cys Ala Ala Glu
1               5

<210> SEQ ID NO 992
<211> LENGTH: 8
<212> TYPE: PRT
<213> ORGANISM: Artificial Sequence
<220> FEATURE:
<223> OTHER INFORMATION: Synthetic Construct

<400> SEQUENCE: 992

Phe Tyr Ala His Cys Ala Arg Glu
1               5

<210> SEQ ID NO 993
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 993

Phe Tyr Ala His Cys Ala Asp Glu
1               5

<210> SEQ ID NO 994
<211> LENGTH: 8
<212> TYPE: PRT
<213> ORGANISM: Artificial Sequence
<220> FEATURE:
<223> OTHER INFORMATION: Synthetic Construct

<400> SEQUENCE: 994

Phe Tyr Ala His Cys Ala Gln Glu
1               5

<210> SEQ ID NO 995
<211> LENGTH: 8
<212> TYPE: PRT
<213> ORGANISM: Artificial Sequence
<220> FEATURE:
<223> OTHER INFORMATION: Synthetic Construct

<400> SEQUENCE: 995

Phe Tyr Ala His Cys Ala Glu Glu
1               5

<210> SEQ ID NO 996
<211> LENGTH: 8
<212> TYPE: PRT
<213> ORGANISM: Artificial Sequence
<220> FEATURE:
<223> OTHER INFORMATION: Synthetic Construct

<400> SEQUENCE: 996

Phe Tyr Ala His Cys Ala Leu Glu
1               5

<210> SEQ ID NO 997
<211> LENGTH: 8
<212> TYPE: PRT
<213> ORGANISM: Artificial Sequence
<220> FEATURE:
<223> OTHER INFORMATION: Synthetic Construct

<400> SEQUENCE: 997

Phe Tyr Ala His Cys Ala Lys Glu
1               5

<210> SEQ ID NO 998
<211> LENGTH: 8
<212> TYPE: PRT
<213> ORGANISM: Artificial Sequence
<220> FEATURE:
<223> OTHER INFORMATION: Synthetic Construct

<400> SEQUENCE: 998

Phe Tyr Ala His Cys Ala Met Glu
1               5

<210> SEQ ID NO 999
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 999

Phe Tyr Ala His Cys Ala Pro Glu
1               5

<210> SEQ ID NO 1000
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1000

Phe Tyr Ala His Cys Ala Ser Glu
1               5

<210> SEQ ID NO 1001
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1001

Phe Tyr Ala His Cys Ala Thr Glu
1               5

<210> SEQ ID NO 1002
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1002

Phe Tyr Ala His Cys Gln Glu Glu
1               5

<210> SEQ ID NO 1003
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1003

Phe Tyr Ala His Cys Gln Leu Glu
1               5

<210> SEQ ID NO 1004
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1004

Phe Tyr Ala His Cys Gln Lys Glu
1               5

<210> SEQ ID NO 1005
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 1005

Phe Tyr Ala His Cys Gln Met Glu
1               5

<210> SEQ ID NO 1006
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1006

Phe Tyr Ala His Cys Gln Pro Glu
1               5

<210> SEQ ID NO 1007
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1007

Phe Tyr Ala His Cys Gln Ser Glu
1               5

<210> SEQ ID NO 1008
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1008

Phe Tyr Ala His Cys Gln Thr Glu
1               5

<210> SEQ ID NO 1009
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1009

Phe Tyr Ala His Cys Gln Ala Glu
1               5

<210> SEQ ID NO 1010
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1010

Phe Tyr Ala His Cys Gln Arg Glu
1               5

<210> SEQ ID NO 1011
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 1011

Phe Tyr Ala His Cys Gln Asp Glu
1               5

<210> SEQ ID NO 1012
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1012

Phe Tyr Ala His Cys Gln Gln Glu
1               5

<210> SEQ ID NO 1013
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1013

Phe Tyr Ala His Cys Glu Ala Glu
1               5

<210> SEQ ID NO 1014
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1014

Phe Tyr Ala His Cys Glu Arg Glu
1               5

<210> SEQ ID NO 1015
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1015

Phe Tyr Ala His Cys Glu Asp Glu
1               5

<210> SEQ ID NO 1016
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1016

Phe Tyr Ala His Cys Glu Glu Glu
1               5

<210> SEQ ID NO 1017
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1017

Phe Tyr Ala His Cys Glu Leu Glu
1               5

<210> SEQ ID NO 1018
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1018

Phe Tyr Ala His Cys Glu Lys Glu
1               5

<210> SEQ ID NO 1019
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1019

Phe Tyr Ala His Cys Glu Met Glu
1               5

<210> SEQ ID NO 1020
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1020

Phe Tyr Ala His Cys Glu Pro Glu
1               5

<210> SEQ ID NO 1021
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1021

Phe Tyr Ala His Cys Glu Ser Glu
1               5

<210> SEQ ID NO 1022
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1022

Phe Tyr Ala His Cys Glu Thr Glu
1               5

<210> SEQ ID NO 1023
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1023

Phe Tyr Ala His Cys Glu Gln Glu
1               5

<210> SEQ ID NO 1024
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1024

Phe Tyr Ala His Cys Ile Ala Glu
1               5

<210> SEQ ID NO 1025
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1025

Phe Tyr Ala His Cys Ile Arg Glu
1               5

<210> SEQ ID NO 1026
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1026

Phe Tyr Ala His Cys Ile Asp Glu
1               5

<210> SEQ ID NO 1027
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1027

Phe Tyr Ala His Cys Ile Gln Glu
1               5

<210> SEQ ID NO 1028
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1028

Phe Tyr Ala His Cys Ile Glu Glu
1               5

<210> SEQ ID NO 1029
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1029

```
Phe Tyr Ala His Cys Ile Leu Glu
1               5

<210> SEQ ID NO 1030
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1030

Phe Tyr Ala His Cys Ile Lys Glu
1               5

<210> SEQ ID NO 1031
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1031

Phe Tyr Ala His Cys Ile Met Glu
1               5

<210> SEQ ID NO 1032
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1032

Phe Tyr Ala His Cys Ile Pro Glu
1               5

<210> SEQ ID NO 1033
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1033

Phe Tyr Ala His Cys Ile Ser Glu
1               5

<210> SEQ ID NO 1034
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1034

Phe Tyr Ala His Cys Ile Thr Glu
1               5

<210> SEQ ID NO 1035
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1035
```

Phe Tyr Ala His Cys Leu Ala Glu
1               5

<210> SEQ ID NO 1036
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1036

Phe Tyr Ala His Cys Leu Arg Glu
1               5

<210> SEQ ID NO 1037
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1037

Phe Tyr Ala His Cys Leu Asp Glu
1               5

<210> SEQ ID NO 1038
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1038

Phe Tyr Ala His Cys Leu Gln Glu
1               5

<210> SEQ ID NO 1039
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1039

Phe Tyr Ala His Cys Leu Glu Glu
1               5

<210> SEQ ID NO 1040
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1040

Phe Tyr Ala His Cys Leu Leu Glu
1               5

<210> SEQ ID NO 1041
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1041

Phe Tyr Ala His Cys Leu Lys Glu 1               5

<210> SEQ ID NO 1042
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1042

Phe Tyr Ala His Cys Leu Met Glu
1               5

<210> SEQ ID NO 1043
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1043

Phe Tyr Ala His Cys Leu Pro Glu
1               5

<210> SEQ ID NO 1044
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1044

Phe Tyr Ala His Cys Leu Ser Glu
1               5

<210> SEQ ID NO 1045
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1045

Phe Tyr Ala His Cys Leu Thr Glu
1               5

<210> SEQ ID NO 1046
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1046

Phe Tyr Ala His Cys Lys Ala Glu
1               5

<210> SEQ ID NO 1047
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1047

Phe Tyr Ala His Cys Lys Arg Glu
1               5

<210> SEQ ID NO 1048
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1048

Phe Tyr Ala His Cys Lys Ser Glu
1               5

<210> SEQ ID NO 1049
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1049

Phe Tyr Ala His Cys Lys Thr Glu
1               5

<210> SEQ ID NO 1050
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1050

Phe Tyr Ala His Cys Lys Pro Glu
1               5

<210> SEQ ID NO 1051
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1051

Phe Tyr Ala His Cys Lys Asp Glu
1               5

<210> SEQ ID NO 1052
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1052

Phe Tyr Ala His Cys Lys Gln Glu
1               5

<210> SEQ ID NO 1053
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1053

Phe Tyr Ala His Cys Lys Glu Glu
1               5

<210> SEQ ID NO 1054
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1054

Phe Tyr Ala His Cys Lys Leu Glu
1               5

<210> SEQ ID NO 1055
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1055

Phe Tyr Ala His Cys Lys Lys Glu
1               5

<210> SEQ ID NO 1056
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1056

Phe Tyr Ala His Cys Lys Met Glu
1               5

<210> SEQ ID NO 1057
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1057

Phe Tyr Arg His Cys Ala Ala Glu
1               5

<210> SEQ ID NO 1058
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1058

Phe Tyr Arg His Cys Ala Glu Glu
1               5

<210> SEQ ID NO 1059
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1059

Phe Tyr Arg His Cys Ala Leu Glu
1               5

```
<210> SEQ ID NO 1060
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1060

Phe Tyr Arg His Cys Ala Lys Glu
1               5

<210> SEQ ID NO 1061
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1061

Phe Tyr Arg His Cys Ala Met Glu
1               5

<210> SEQ ID NO 1062
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1062

Phe Tyr Arg His Cys Ala Pro Glu
1               5

<210> SEQ ID NO 1063
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1063

Phe Tyr Arg His Cys Ala Ser Glu
1               5

<210> SEQ ID NO 1064
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1064

Phe Tyr Arg His Cys Ala Thr Glu
1               5

<210> SEQ ID NO 1065
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1065

Phe Tyr Arg His Cys Gln Glu Glu
1               5

<210> SEQ ID NO 1066
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1066

Phe Tyr Arg His Cys Gln Leu Glu
1               5

<210> SEQ ID NO 1067
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1067

Phe Tyr Arg His Cys Gln Lys Glu
1               5

<210> SEQ ID NO 1068
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1068

Phe Tyr Arg His Cys Gln Met Glu
1               5

<210> SEQ ID NO 1069
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1069

Phe Tyr Arg His Cys Gln Pro Glu
1               5

<210> SEQ ID NO 1070
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1070

Phe Tyr Arg His Cys Gln Ser Glu
1               5

<210> SEQ ID NO 1071
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1071

Phe Tyr Arg His Cys Gln Thr Glu
1               5

<210> SEQ ID NO 1072
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1072

Phe Tyr Arg His Cys Gln Ala Glu
1               5

<210> SEQ ID NO 1073
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1073

Phe Tyr Arg His Cys Gln Arg Glu
1               5

<210> SEQ ID NO 1074
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1074

Phe Tyr Arg His Cys Gln Asp Glu
1               5

<210> SEQ ID NO 1075
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1075

Phe Tyr Arg His Cys Gln Gln Glu
1               5

<210> SEQ ID NO 1076
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1076

Phe Tyr Arg His Cys Glu Ala Glu
1               5

<210> SEQ ID NO 1077
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1077

Phe Tyr Arg His Cys Glu Arg Glu
1               5

<210> SEQ ID NO 1078
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 1078

Phe Tyr Arg His Cys Glu Asp Glu
1               5

<210> SEQ ID NO 1079
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1079

Phe Tyr Arg His Cys Glu Glu Glu
1               5

<210> SEQ ID NO 1080
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1080

Phe Tyr Arg His Cys Glu Leu Glu
1               5

<210> SEQ ID NO 1081
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1081

Phe Tyr Arg His Cys Glu Lys Glu
1               5

<210> SEQ ID NO 1082
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1082

Phe Tyr Arg His Cys Glu Met Glu
1               5

<210> SEQ ID NO 1083
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1083

Phe Tyr Arg His Cys Glu Pro Glu
1               5

<210> SEQ ID NO 1084
<211> LENGTH: 8
<212> TYPE: PRT
<213> ORGANISM: Artificial Sequence
```

<220> FEATURE:
<223> OTHER INFORMATION: Synthetic Construct

<400> SEQUENCE: 1084

Phe Tyr Arg His Cys Glu Ser Glu
1               5

<210> SEQ ID NO 1085
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1085

Phe Tyr Arg His Cys Glu Thr Glu
1               5

<210> SEQ ID NO 1086
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1086

Phe Tyr Arg His Cys Glu Gln Glu
1               5

<210> SEQ ID NO 1087
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1087

Phe Tyr Arg His Cys Ile Ala Glu
1               5

<210> SEQ ID NO 1088
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1088

Phe Tyr Arg His Cys Ile Arg Glu
1               5

<210> SEQ ID NO 1089
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1089

Phe Tyr Arg His Cys Ile Asp Glu
1               5

<210> SEQ ID NO 1090
<211> LENGTH: 8
<212> TYPE: PRT
<213> ORGANISM: Artificial Sequence
<220> FEATURE:

<223> OTHER INFORMATION: Synthetic Construct

<400> SEQUENCE: 1090

Phe Tyr Arg His Cys Ile Gln Glu
1               5

<210> SEQ ID NO 1091
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1091

Phe Tyr Arg His Cys Ile Glu Glu
1               5

<210> SEQ ID NO 1092
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1092

Phe Tyr Arg His Cys Ile Leu Glu
1               5

<210> SEQ ID NO 1093
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1093

Phe Tyr Arg His Cys Ile Lys Glu
1               5

<210> SEQ ID NO 1094
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1094

Phe Tyr Arg His Cys Ile Met Glu
1               5

<210> SEQ ID NO 1095
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1095

Phe Tyr Arg His Cys Ile Pro Glu
1               5

<210> SEQ ID NO 1096
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1096

Phe Tyr Arg His Cys Ile Ser Glu
1               5

<210> SEQ ID NO 1097
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1097

Phe Tyr Arg His Cys Ile Thr Glu
1               5

<210> SEQ ID NO 1098
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1098

Phe Tyr Arg His Cys Leu Ala Glu
1               5

<210> SEQ ID NO 1099
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1099

Phe Tyr Arg His Cys Leu Arg Glu
1               5

<210> SEQ ID NO 1100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1100

Phe Tyr Arg His Cys Leu Asp Glu
1               5

<210> SEQ ID NO 1101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1101

Phe Tyr Arg His Cys Leu Gln Glu
1               5

<210> SEQ ID NO 1102
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 1102

Phe Tyr Arg His Cys Leu Glu Glu
1               5

<210> SEQ ID NO 1103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1103

Phe Tyr Arg His Cys Leu Leu Glu
1               5

<210> SEQ ID NO 1104
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1104

Phe Tyr Arg His Cys Leu Lys Glu
1               5

<210> SEQ ID NO 1105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1105

Phe Tyr Arg His Cys Leu Met Glu
1               5

<210> SEQ ID NO 1106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1106

Phe Tyr Arg His Cys Leu Pro Glu
1               5

<210> SEQ ID NO 1107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1107

Phe Tyr Arg His Cys Leu Ser Glu
1               5

<210> SEQ ID NO 1108
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1108
```

```
Phe Tyr Arg His Cys Leu Thr Glu
1               5

<210> SEQ ID NO 1109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1109

Phe Tyr Arg His Cys Lys Ala Glu
1               5

<210> SEQ ID NO 1110
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1110

Phe Tyr Arg His Cys Lys Arg Glu
1               5

<210> SEQ ID NO 1111
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1111

Phe Tyr Arg His Cys Lys Asp Glu
1               5

<210> SEQ ID NO 1112
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1112

Phe Tyr Arg His Cys Lys Thr Glu
1               5

<210> SEQ ID NO 1113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1113

Phe Tyr Arg His Cys Lys Pro Glu
1               5

<210> SEQ ID NO 1114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1114
```

Phe Tyr Arg His Cys Ala Arg Glu
1               5

<210> SEQ ID NO 1115
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1115

Phe Tyr Arg His Cys Ala Asp Glu
1               5

<210> SEQ ID NO 1116
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1116

Phe Tyr Arg His Cys Ala Gln Glu
1               5

<210> SEQ ID NO 1117
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1117

Phe Tyr Arg His Cys Lys Asp Glu
1               5

<210> SEQ ID NO 1118
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1118

Phe Tyr Arg His Cys Lys Gln Glu
1               5

<210> SEQ ID NO 1119
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1119

Phe Tyr Arg His Cys Lys Glu Glu
1               5

<210> SEQ ID NO 1120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1120

Phe Tyr Arg His Cys Lys Leu Glu

```
<210> SEQ ID NO 1121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1121

Phe Tyr Arg His Cys Lys Lys Glu
1               5

<210> SEQ ID NO 1122
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1122

Phe Tyr Arg His Cys Lys Met Glu
1               5

<210> SEQ ID NO 1123
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1123

Phe Tyr Asn His Cys Ala Ala Glu
1               5

<210> SEQ ID NO 1124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1124

Phe Tyr Asn His Cys Lys Lys Glu
1               5

<210> SEQ ID NO 1125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1125

Phe Tyr Asn His Cys Lys Met Glu
1               5

<210> SEQ ID NO 1126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1126

Phe Tyr Asn His Cys Ala Arg Glu
1               5
```

```
<210> SEQ ID NO 1127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1127

Phe Tyr Asn His Cys Ala Asp Glu
1               5

<210> SEQ ID NO 1128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1128

Phe Tyr Asn His Cys Ala Glu Glu
1               5

<210> SEQ ID NO 1129
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1129

Phe Tyr Asn His Cys Ala Leu Glu
1               5

<210> SEQ ID NO 1130
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1130

Phe Tyr Asn His Cys Ala Lys Glu
1               5

<210> SEQ ID NO 1131
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1131

Phe Tyr Asn His Cys Ala Met Glu
1               5

<210> SEQ ID NO 1132
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1132

Phe Tyr Asn His Cys Ala Pro Glu
1               5
```

<210> SEQ ID NO 1133
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1133

Phe Tyr Asn His Cys Ala Ser Glu
1               5

<210> SEQ ID NO 1134
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1134

Phe Tyr Asn His Cys Ala Thr Glu
1               5

<210> SEQ ID NO 1135
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1135

Phe Tyr Asn His Cys Gln Glu Glu
1               5

<210> SEQ ID NO 1136
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1136

Phe Tyr Asn His Cys Gln Leu Glu
1               5

<210> SEQ ID NO 1137
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1137

Phe Tyr Asn His Cys Gln Lys Glu
1               5

<210> SEQ ID NO 1138
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1138

Phe Tyr Asn His Cys Gln Met Glu
1               5

```
<210> SEQ ID NO 1139
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1139

Phe Tyr Asn His Cys Gln Pro Glu
1               5

<210> SEQ ID NO 1140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1140

Phe Tyr Asn His Cys Gln Ser Glu
1               5

<210> SEQ ID NO 1141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1141

Phe Tyr Asn His Cys Gln Thr Glu
1               5

<210> SEQ ID NO 1142
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1142

Phe Tyr Asn His Cys Gln Ala Glu
1               5

<210> SEQ ID NO 1143
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1143

Phe Tyr Asn His Cys Gln Arg Glu
1               5

<210> SEQ ID NO 1144
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1144

Phe Tyr Asn His Cys Gln Asp Glu
1               5

<210> SEQ ID NO 1145
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1145

Phe Tyr Asn His Cys Gln Gln Glu
1               5

<210> SEQ ID NO 1146
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1146

Phe Tyr Asn His Cys Glu Ala Glu
1               5

<210> SEQ ID NO 1147
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1147

Phe Tyr Asn His Cys Glu Arg Glu
1               5

<210> SEQ ID NO 1148
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1148

Phe Tyr Asn His Cys Glu Asp Glu
1               5

<210> SEQ ID NO 1149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1149

Phe Tyr Asn His Cys Glu Glu Glu
1               5

<210> SEQ ID NO 1150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1150

Phe Tyr Asn His Cys Glu Leu Glu
1               5

<210> SEQ ID NO 1151
<211> LENGTH: 8
```

<212> TYPE: PRT
<213> ORGANISM: Artificial Sequence
<220> FEATURE:
<223> OTHER INFORMATION: Synthetic Construct

<400> SEQUENCE: 1151

Phe Tyr Asn His Cys Glu Lys Glu
1               5

<210> SEQ ID NO 1152
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1152

Phe Tyr Asn His Cys Glu Met Glu
1               5

<210> SEQ ID NO 1153
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1153

Phe Tyr Asn His Cys Glu Pro Glu
1               5

<210> SEQ ID NO 1154
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1154

Phe Tyr Asn His Cys Glu Ser Glu
1               5

<210> SEQ ID NO 1155
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1155

Phe Tyr Asn His Cys Glu Thr Glu
1               5

<210> SEQ ID NO 1156
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1156

Phe Tyr Asn His Cys Glu Gln Glu
1               5

<210> SEQ ID NO 1157
<211> LENGTH: 8
<212> TYPE: PRT

<213> ORGANISM: Artificial Sequence
<220> FEATURE:
<223> OTHER INFORMATION: Synthetic Construct

<400> SEQUENCE: 1157

Phe Tyr Asn His Cys Ile Ala Glu
1               5

<210> SEQ ID NO 1158
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1158

Phe Tyr Asn His Cys Ile Arg Glu
1               5

<210> SEQ ID NO 1159
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1159

Phe Tyr Asn His Cys Ile Asp Glu
1               5

<210> SEQ ID NO 1160
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1160

Phe Tyr Asn His Cys Ile Gln Glu
1               5

<210> SEQ ID NO 1161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1161

Phe Tyr Asn His Cys Ile Glu Glu
1               5

<210> SEQ ID NO 1162
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1162

Phe Tyr Asn His Cys Ile Leu Glu
1               5

<210> SEQ ID NO 1163
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 1163

Phe Tyr Asn His Cys Ile Lys Glu
1               5

<210> SEQ ID NO 1164
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1164

Phe Tyr Asn His Cys Ile Met Glu
1               5

<210> SEQ ID NO 1165
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1165

Phe Tyr Asn His Cys Ile Pro Glu
1               5

<210> SEQ ID NO 1166
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1166

Phe Tyr Asn His Cys Ile Ser Glu
1               5

<210> SEQ ID NO 1167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1167

Phe Tyr Asn His Cys Ile Thr Glu
1               5

<210> SEQ ID NO 1168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1168

Phe Tyr Asn His Cys Leu Ala Glu
1               5

<210> SEQ ID NO 1169
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 1169

Phe Tyr Asn His Cys Leu Arg Glu
1               5

<210> SEQ ID NO 1170
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1170

Phe Tyr Asn His Cys Leu Asp Glu
1               5

<210> SEQ ID NO 1171
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1171

Phe Tyr Asn His Cys Leu Gln Glu
1               5

<210> SEQ ID NO 1172
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1172

Phe Tyr Asn His Cys Leu Glu Glu
1               5

<210> SEQ ID NO 1173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1173

Phe Tyr Asn His Cys Leu Leu Glu
1               5

<210> SEQ ID NO 1174
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1174

Phe Tyr Asn His Cys Leu Lys Glu
1               5

<210> SEQ ID NO 1175
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1175

Phe Tyr Asn His Cys Leu Met Glu
1               5

<210> SEQ ID NO 1176
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1176

Phe Tyr Asn His Cys Leu Pro Glu
1               5

<210> SEQ ID NO 1177
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1177

Phe Tyr Asn His Cys Leu Ser Glu
1               5

<210> SEQ ID NO 1178
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1178

Phe Tyr Asn His Cys Leu Thr Glu
1               5

<210> SEQ ID NO 1179
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1179

Phe Tyr Asn His Cys Lys Ala Glu
1               5

<210> SEQ ID NO 1180
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1180

Phe Tyr Asn His Cys Lys Arg Glu
1               5

<210> SEQ ID NO 1181
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 1181

Phe Tyr Asn His Cys Lys Ser Glu
1               5

<210> SEQ ID NO 1182
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1182

Phe Tyr Asn His Cys Lys Thr Glu
1               5

<210> SEQ ID NO 1183
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1183

Phe Tyr Asn His Cys Lys Pro Glu
1               5

<210> SEQ ID NO 1184
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1184

Phe Tyr Asn His Cys Ala Gln Glu
1               5

<210> SEQ ID NO 1185
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1185

Phe Tyr Asn His Cys Lys Asp Glu
1               5

<210> SEQ ID NO 1186
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1186

Phe Tyr Asn His Cys Lys Gln Glu
1               5

<210> SEQ ID NO 1187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1187
```

Phe Tyr Asn His Cys Lys Glu Glu
1               5

<210> SEQ ID NO 1188
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1188

Phe Tyr Asn His Cys Lys Leu Glu
1               5

<210> SEQ ID NO 1189
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1189

Phe Tyr Asp His Cys Ala Ala Glu
1               5

<210> SEQ ID NO 1190
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1190

Phe Tyr Asp His Cys Lys Lys Glu
1               5

<210> SEQ ID NO 1191
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1191

Phe Tyr Asp His Cys Ala Glu Glu
1               5

<210> SEQ ID NO 1192
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1192

Phe Tyr Asp His Cys Ala Leu Glu
1               5

<210> SEQ ID NO 1193
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1193

Phe Tyr Asp His Cys Ala Lys Glu
1               5

<210> SEQ ID NO 1194
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1194

Phe Tyr Asp His Cys Ala Met Glu
1               5

<210> SEQ ID NO 1195
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1195

Phe Tyr Asp His Cys Ala Pro Glu
1               5

<210> SEQ ID NO 1196
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1196

Phe Tyr Asp His Cys Ala Ser Glu
1               5

<210> SEQ ID NO 1197
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1197

Phe Tyr Asp His Cys Ala Thr Glu
1               5

<210> SEQ ID NO 1198
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1198

Phe Tyr Asp His Cys Gln Glu Glu
1               5

<210> SEQ ID NO 1199
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1199

Phe Tyr Asp His Cys Gln Leu Glu

```
1               5

<210> SEQ ID NO 1200
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1200

Phe Tyr Asp His Cys Gln Lys Glu
1               5

<210> SEQ ID NO 1201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1201

Phe Tyr Asp His Cys Gln Met Glu
1               5

<210> SEQ ID NO 1202
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1202

Phe Tyr Asp His Cys Gln Pro Glu
1               5

<210> SEQ ID NO 1203
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1203

Phe Tyr Asp His Cys Gln Ser Glu
1               5

<210> SEQ ID NO 1204
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1204

Phe Tyr Asp His Cys Gln Thr Glu
1               5

<210> SEQ ID NO 1205
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1205

Phe Tyr Asp His Cys Gln Ala Glu
1               5
```

<210> SEQ ID NO 1206
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1206

Phe Tyr Asp His Cys Gln Arg Glu
1               5

<210> SEQ ID NO 1207
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1207

Phe Tyr Asp His Cys Gln Asp Glu
1               5

<210> SEQ ID NO 1208
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1208

Phe Tyr Asp His Cys Gln Gln Glu
1               5

<210> SEQ ID NO 1209
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1209

Phe Tyr Asp His Cys Glu Ala Glu
1               5

<210> SEQ ID NO 1210
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1210

Phe Tyr Asp His Cys Glu Arg Glu
1               5

<210> SEQ ID NO 1211
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1211

Phe Tyr Asp His Cys Glu Asp Glu
1               5

```
<210> SEQ ID NO 1212
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1212

Phe Tyr Asp His Cys Glu Glu Glu
1               5

<210> SEQ ID NO 1213
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1213

Phe Tyr Asp His Cys Glu Leu Glu
1               5

<210> SEQ ID NO 1214
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1214

Phe Tyr Asp His Cys Glu Lys Glu
1               5

<210> SEQ ID NO 1215
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1215

Phe Tyr Asp His Cys Glu Met Glu
1               5

<210> SEQ ID NO 1216
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1216

Phe Tyr Asp His Cys Glu Pro Glu
1               5

<210> SEQ ID NO 1217
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1217

Phe Tyr Asp His Cys Glu Ser Glu
1               5
```

```
<210> SEQ ID NO 1218
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1218

Phe Tyr Asp His Cys Glu Thr Glu
1               5

<210> SEQ ID NO 1219
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1219

Phe Tyr Asp His Cys Glu Gln Glu
1               5

<210> SEQ ID NO 1220
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1220

Phe Tyr Asp His Cys Ile Ala Glu
1               5

<210> SEQ ID NO 1221
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1221

Phe Tyr Asp His Cys Ile Arg Glu
1               5

<210> SEQ ID NO 1222
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1222

Phe Tyr Asp His Cys Ile Asp Glu
1               5

<210> SEQ ID NO 1223
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1223

Phe Tyr Asp His Cys Ile Gln Glu
1               5

<210> SEQ ID NO 1224
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1224

Phe Tyr Asp His Cys Ile Glu Glu
1               5

<210> SEQ ID NO 1225
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1225

Phe Tyr Asp His Cys Ile Leu Glu
1               5

<210> SEQ ID NO 1226
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1226

Phe Tyr Asp His Cys Ile Lys Glu
1               5

<210> SEQ ID NO 1227
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1227

Phe Tyr Asp His Cys Ile Met Glu
1               5

<210> SEQ ID NO 1228
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1228

Phe Tyr Asp His Cys Ile Pro Glu
1               5

<210> SEQ ID NO 1229
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1229

Phe Tyr Asp His Cys Ile Ser Glu
1               5

<210> SEQ ID NO 1230
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1230

Phe Tyr Asp His Cys Ile Thr Glu
1               5

<210> SEQ ID NO 1231
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1231

Phe Tyr Asp His Cys Leu Ala Glu
1               5

<210> SEQ ID NO 1232
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1232

Phe Tyr Asp His Cys Leu Arg Glu
1               5

<210> SEQ ID NO 1233
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1233

Phe Tyr Asp His Cys Leu Asp Glu
1               5

<210> SEQ ID NO 1234
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1234

Phe Tyr Asp His Cys Leu Gln Glu
1               5

<210> SEQ ID NO 1235
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1235

Phe Tyr Asp His Cys Leu Glu Glu
1               5

<210> SEQ ID NO 1236
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 1236

Phe Tyr Asp His Cys Leu Leu Glu
1               5

<210> SEQ ID NO 1237
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1237

Phe Tyr Asp His Cys Leu Lys Glu
1               5

<210> SEQ ID NO 1238
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1238

Phe Tyr Asp His Cys Leu Met Glu
1               5

<210> SEQ ID NO 1239
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1239

Phe Tyr Asp His Cys Leu Pro Glu
1               5

<210> SEQ ID NO 1240
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1240

Phe Tyr Asp His Cys Leu Ser Glu
1               5

<210> SEQ ID NO 1241
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1241

Phe Tyr Asp His Cys Leu Thr Glu
1               5

<210> SEQ ID NO 1242
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 1242

Phe Tyr Asp His Cys Lys Ala Glu
1               5

<210> SEQ ID NO 1243
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1243

Phe Tyr Asp His Cys Lys Arg Glu
1               5

<210> SEQ ID NO 1244
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1244

Phe Tyr Asp His Cys Lys Ser Glu
1               5

<210> SEQ ID NO 1245
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1245

Phe Tyr Asp His Cys Lys Thr Glu
1               5

<210> SEQ ID NO 1246
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1246

Phe Tyr Asp His Cys Lys Pro Glu
1               5

<210> SEQ ID NO 1247
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1247

Phe Tyr Asp His Cys Lys Met Glu
1               5

<210> SEQ ID NO 1248
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 1248

Phe Tyr Asp His Cys Ala Arg Glu
1               5

<210> SEQ ID NO 1249
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1249

Phe Tyr Asp His Cys Ala Asp Glu
1               5

<210> SEQ ID NO 1250
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1250

Phe Tyr Asp His Cys Ala Gln Glu
1               5

<210> SEQ ID NO 1251
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1251

Phe Tyr Asp His Cys Lys Asp Glu
1               5

<210> SEQ ID NO 1252
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1252

Phe Tyr Asp His Cys Lys Gln Glu
1               5

<210> SEQ ID NO 1253
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1253

Phe Tyr Asp His Cys Lys Glu Glu
1               5

<210> SEQ ID NO 1254
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1254

Phe Tyr Asp His Cys Lys Leu Glu
1               5

<210> SEQ ID NO 1255
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1255

Phe Tyr Ile His Cys Ala Ala Glu
1               5

<210> SEQ ID NO 1256
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1256

Phe Tyr Ile His Cys Lys Lys Glu
1               5

<210> SEQ ID NO 1257
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1257

Phe Tyr Ile His Cys Lys Met Glu
1               5

<210> SEQ ID NO 1258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1258

Phe Tyr Ile His Cys Ala Arg Glu
1               5

<210> SEQ ID NO 1259
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1259

Phe Tyr Ile His Cys Ala Asp Glu
1               5

<210> SEQ ID NO 1260
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1260

Phe Tyr Ile His Cys Ala Gln Glu
1               5

<210> SEQ ID NO 1261
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1261

Phe Tyr Ile His Cys Ala Glu Glu
1               5

<210> SEQ ID NO 1262
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1262

Phe Tyr Ile His Cys Ala Leu Glu
1               5

<210> SEQ ID NO 1263
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1263

Phe Tyr Ile His Cys Ala Lys Glu
1               5

<210> SEQ ID NO 1264
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1264

Phe Tyr Ile His Cys Ala Met Glu
1               5

<210> SEQ ID NO 1265
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1265

Phe Tyr Ile His Cys Ala Pro Glu
1               5

<210> SEQ ID NO 1266
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1266
```

Phe Tyr Ile His Cys Ala Ser Glu
1               5

<210> SEQ ID NO 1267
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1267

Phe Tyr Ile His Cys Ala Thr Glu
1               5

<210> SEQ ID NO 1268
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1268

Phe Tyr Ile His Cys Gln Glu Glu
1               5

<210> SEQ ID NO 1269
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1269

Phe Tyr Ile His Cys Gln Leu Glu
1               5

<210> SEQ ID NO 1270
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1270

Phe Tyr Ile His Cys Gln Lys Glu
1               5

<210> SEQ ID NO 1271
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1271

Phe Tyr Ile His Cys Gln Met Glu
1               5

<210> SEQ ID NO 1272
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1272

Phe Tyr Ile His Cys Gln Pro Glu
1               5

<210> SEQ ID NO 1273
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1273

Phe Tyr Ile His Cys Gln Ser Glu
1               5

<210> SEQ ID NO 1274
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1274

Phe Tyr Ile His Cys Gln Thr Glu
1               5

<210> SEQ ID NO 1275
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1275

Phe Tyr Ile His Cys Gln Ala Glu
1               5

<210> SEQ ID NO 1276
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1276

Phe Tyr Ile His Cys Gln Arg Glu
1               5

<210> SEQ ID NO 1277
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1277

Phe Tyr Ile His Cys Gln Asp Glu
1               5

<210> SEQ ID NO 1278
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1278

Phe Tyr Ile His Cys Gln Gln Glu

```
1               5

<210> SEQ ID NO 1279
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1279

Phe Tyr Ile His Cys Glu Ala Glu
1               5

<210> SEQ ID NO 1280
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1280

Phe Tyr Ile His Cys Glu Arg Glu
1               5

<210> SEQ ID NO 1281
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1281

Phe Tyr Ile His Cys Glu Asp Glu
1               5

<210> SEQ ID NO 1282
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1282

Phe Tyr Ile His Cys Glu Glu Glu
1               5

<210> SEQ ID NO 1283
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1283

Phe Tyr Ile His Cys Glu Leu Glu
1               5

<210> SEQ ID NO 1284
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1284

Phe Tyr Ile His Cys Glu Lys Glu
1               5
```

<210> SEQ ID NO 1285
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1285

Phe Tyr Ile His Cys Glu Met Glu
1               5

<210> SEQ ID NO 1286
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1286

Phe Tyr Ile His Cys Glu Pro Glu
1               5

<210> SEQ ID NO 1287
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1287

Phe Tyr Ile His Cys Glu Ser Glu
1               5

<210> SEQ ID NO 1288
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1288

Phe Tyr Ile His Cys Glu Thr Glu
1               5

<210> SEQ ID NO 1289
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1289

Phe Tyr Ile His Cys Glu Gln Glu
1               5

<210> SEQ ID NO 1290
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1290

Phe Tyr Ile His Cys Ile Ala Glu
1               5

<210> SEQ ID NO 1291
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1291

Phe Tyr Ile His Cys Ile Arg Glu
1               5

<210> SEQ ID NO 1292
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1292

Phe Tyr Ile His Cys Ile Asp Glu
1               5

<210> SEQ ID NO 1293
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1293

Phe Tyr Ile His Cys Ile Gln Glu
1               5

<210> SEQ ID NO 1294
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1294

Phe Tyr Ile His Cys Ile Glu Glu
1               5

<210> SEQ ID NO 1295
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1295

Phe Tyr Ile His Cys Ile Leu Glu
1               5

<210> SEQ ID NO 1296
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1296

Phe Tyr Ile His Cys Ile Lys Glu
1               5

<210> SEQ ID NO 1297
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1297

Phe Tyr Ile His Cys Ile Met Glu
1               5

<210> SEQ ID NO 1298
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1298

Phe Tyr Ile His Cys Ile Pro Glu
1               5

<210> SEQ ID NO 1299
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1299

Phe Tyr Ile His Cys Ile Ser Glu
1               5

<210> SEQ ID NO 1300
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1300

Phe Tyr Ile His Cys Ile Thr Glu
1               5

<210> SEQ ID NO 1301
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1301

Phe Tyr Ile His Cys Leu Ala Glu
1               5

<210> SEQ ID NO 1302
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1302

Phe Tyr Ile His Cys Leu Arg Glu
1               5

<210> SEQ ID NO 1303

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1303

Phe Tyr Ile His Cys Leu Asp Glu
1               5

<210> SEQ ID NO 1304
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1304

Phe Tyr Ile His Cys Leu Gln Glu
1               5

<210> SEQ ID NO 1305
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1305

Phe Tyr Ile His Cys Leu Glu Glu
1               5

<210> SEQ ID NO 1306
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1306

Phe Tyr Ile His Cys Leu Leu Glu
1               5

<210> SEQ ID NO 1307
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1307

Phe Tyr Ile His Cys Leu Lys Glu
1               5

<210> SEQ ID NO 1308
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1308

Phe Tyr Ile His Cys Leu Met Glu
1               5

<210> SEQ ID NO 1309
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1309

Phe Tyr Ile His Cys Leu Pro Glu
1               5

<210> SEQ ID NO 1310
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1310

Phe Tyr Ile His Cys Leu Ser Glu
1               5

<210> SEQ ID NO 1311
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1311

Phe Tyr Ile His Cys Leu Thr Glu
1               5

<210> SEQ ID NO 1312
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1312

Phe Tyr Ile His Cys Lys Ala Glu
1               5

<210> SEQ ID NO 1313
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1313

Phe Tyr Ile His Cys Lys Arg Glu
1               5

<210> SEQ ID NO 1314
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1314

Phe Tyr Ile His Cys Lys Ser Glu
1               5

<210> SEQ ID NO 1315
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 1315

Phe Tyr Ile His Cys Lys Thr Glu
1               5

<210> SEQ ID NO 1316
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1316

Phe Tyr Ile His Cys Lys Pro Glu
1               5

<210> SEQ ID NO 1317
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1317

Phe Tyr Ile His Cys Lys Asp Glu
1               5

<210> SEQ ID NO 1318
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1318

Phe Tyr Ile His Cys Lys Gln Glu
1               5

<210> SEQ ID NO 1319
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1319

Phe Tyr Ile His Cys Lys Glu Glu
1               5

<210> SEQ ID NO 1320
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1320

Phe Tyr Ile His Cys Lys Leu Glu
1               5

<210> SEQ ID NO 1321
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 1321

Phe Tyr Pro His Cys Ala Ala Glu
1               5

<210> SEQ ID NO 1322
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1322

Phe Tyr Pro His Cys Lys Lys Glu
1               5

<210> SEQ ID NO 1323
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1323

Phe Tyr Pro His Cys Lys Met Glu
1               5

<210> SEQ ID NO 1324
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1324

Phe Tyr Pro His Cys Ala Glu Glu
1               5

<210> SEQ ID NO 1325
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1325

Phe Tyr Pro His Cys Ala Leu Glu
1               5

<210> SEQ ID NO 1326
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1326

Phe Tyr Pro His Cys Ala Lys Glu
1               5

<210> SEQ ID NO 1327
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 1327

Phe Tyr Pro His Cys Ala Met Glu
1               5

<210> SEQ ID NO 1328
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1328

Phe Tyr Pro His Cys Ala Pro Glu
1               5

<210> SEQ ID NO 1329
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1329

Phe Tyr Pro His Cys Ala Ser Glu
1               5

<210> SEQ ID NO 1330
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1330

Phe Tyr Pro His Cys Ala Thr Glu
1               5

<210> SEQ ID NO 1331
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1331

Phe Tyr Pro His Cys Gln Glu Glu
1               5

<210> SEQ ID NO 1332
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1332

Phe Tyr Pro His Cys Gln Leu Glu
1               5

<210> SEQ ID NO 1333
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 1333

Phe Tyr Pro His Cys Gln Lys Glu
1               5

<210> SEQ ID NO 1334
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1334

Phe Tyr Pro His Cys Gln Met Glu
1               5

<210> SEQ ID NO 1335
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1335

Phe Tyr Pro His Cys Gln Pro Glu
1               5

<210> SEQ ID NO 1336
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1336

Phe Tyr Pro His Cys Gln Ser Glu
1               5

<210> SEQ ID NO 1337
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1337

Phe Tyr Pro His Cys Gln Thr Glu
1               5

<210> SEQ ID NO 1338
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1338

Phe Tyr Pro His Cys Gln Ala Glu
1               5

<210> SEQ ID NO 1339
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1339

Phe Tyr Pro His Cys Gln Arg Glu
1               5

<210> SEQ ID NO 1340
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1340

Phe Tyr Pro His Cys Gln Asp Glu
1               5

<210> SEQ ID NO 1341
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1341

Phe Tyr Pro His Cys Gln Gln Glu
1               5

<210> SEQ ID NO 1342
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1342

Phe Tyr Pro His Cys Glu Ala Glu
1               5

<210> SEQ ID NO 1343
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1343

Phe Tyr Pro His Cys Glu Arg Glu
1               5

<210> SEQ ID NO 1344
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1344

Phe Tyr Pro His Cys Glu Asp Glu
1               5

<210> SEQ ID NO 1345
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1345
```

Phe Tyr Pro His Cys Glu Glu Glu
1               5

<210> SEQ ID NO 1346
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1346

Phe Tyr Pro His Cys Glu Leu Glu
1               5

<210> SEQ ID NO 1347
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1347

Phe Tyr Pro His Cys Glu Lys Glu
1               5

<210> SEQ ID NO 1348
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1348

Phe Tyr Pro His Cys Glu Met Glu
1               5

<210> SEQ ID NO 1349
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1349

Phe Tyr Pro His Cys Glu Pro Glu
1               5

<210> SEQ ID NO 1350
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1350

Phe Tyr Pro His Cys Glu Ser Glu
1               5

<210> SEQ ID NO 1351
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1351

Phe Tyr Pro His Cys Glu Thr Glu
1               5

<210> SEQ ID NO 1352
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1352

Phe Tyr Pro His Cys Glu Gln Glu
1               5

<210> SEQ ID NO 1353
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1353

Phe Tyr Pro His Cys Ile Ala Glu
1               5

<210> SEQ ID NO 1354
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1354

Phe Tyr Pro His Cys Ile Arg Glu
1               5

<210> SEQ ID NO 1355
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1355

Phe Tyr Pro His Cys Ile Asp Glu
1               5

<210> SEQ ID NO 1356
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1356

Phe Tyr Pro His Cys Ile Gln Glu
1               5

<210> SEQ ID NO 1357
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1357

Phe Tyr Pro His Cys Ile Glu Glu

```
1               5
```

<210> SEQ ID NO 1358
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1358

```
Phe Tyr Pro His Cys Ile Leu Glu
1               5
```

<210> SEQ ID NO 1359
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1359

```
Phe Tyr Pro His Cys Ile Lys Glu
1               5
```

<210> SEQ ID NO 1360
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1360

```
Phe Tyr Pro His Cys Ile Met Glu
1               5
```

<210> SEQ ID NO 1361
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1361

```
Phe Tyr Pro His Cys Ile Pro Glu
1               5
```

<210> SEQ ID NO 1362
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1362

```
Phe Tyr Pro His Cys Ile Ser Glu
1               5
```

<210> SEQ ID NO 1363
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1363

```
Phe Tyr Pro His Cys Ile Thr Glu
1               5
```

```
<210> SEQ ID NO 1364
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1364

Phe Tyr Pro His Cys Leu Ala Glu
1               5

<210> SEQ ID NO 1365
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1365

Phe Tyr Pro His Cys Leu Arg Glu
1               5

<210> SEQ ID NO 1366
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1366

Phe Tyr Pro His Cys Leu Asp Glu
1               5

<210> SEQ ID NO 1367
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1367

Phe Tyr Pro His Cys Leu Gln Glu
1               5

<210> SEQ ID NO 1368
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1368

Phe Tyr Pro His Cys Leu Glu Glu
1               5

<210> SEQ ID NO 1369
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1369

Phe Tyr Pro His Cys Leu Leu Glu
1               5
```

<210> SEQ ID NO 1370
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1370

Phe Tyr Pro His Cys Leu Lys Glu
1               5

<210> SEQ ID NO 1371
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1371

Phe Tyr Pro His Cys Leu Met Glu
1               5

<210> SEQ ID NO 1372
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1372

Phe Tyr Pro His Cys Leu Pro Glu
1               5

<210> SEQ ID NO 1373
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1373

Phe Tyr Pro His Cys Leu Ser Glu
1               5

<210> SEQ ID NO 1374
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1374

Phe Tyr Pro His Cys Leu Thr Glu
1               5

<210> SEQ ID NO 1375
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1375

Phe Tyr Pro His Cys Lys Ala Glu
1               5

<210> SEQ ID NO 1376
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1376

Phe Tyr Pro His Cys Lys Arg Glu
1               5

<210> SEQ ID NO 1377
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1377

Phe Tyr Pro His Cys Lys Ser Glu
1               5

<210> SEQ ID NO 1378
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1378

Phe Tyr Pro His Cys Lys Thr Glu
1               5

<210> SEQ ID NO 1379
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1379

Phe Tyr Pro His Cys Lys Pro Glu
1               5

<210> SEQ ID NO 1380
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1380

Phe Tyr Pro His Cys Lys Asp Glu
1               5

<210> SEQ ID NO 1381
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1381

Phe Tyr Pro His Cys Lys Gln Glu
1               5

<210> SEQ ID NO 1382

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1382

Phe Tyr Pro His Cys Lys Glu Glu
1               5

<210> SEQ ID NO 1383
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1383

Phe Tyr Pro His Cys Lys Leu Glu
1               5

<210> SEQ ID NO 1384
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1384

Phe Tyr Pro His Cys Ala Arg Glu
1               5

<210> SEQ ID NO 1385
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1385

Phe Tyr Pro His Cys Ala Asp Glu
1               5

<210> SEQ ID NO 1386
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1386

Phe Tyr Pro His Cys Ala Gln Glu
1               5

<210> SEQ ID NO 1387
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1387

Phe Tyr Thr His Cys Ala Ala Glu
1               5

<210> SEQ ID NO 1388
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1388

Phe Tyr Thr His Cys Lys Lys Glu
1               5

<210> SEQ ID NO 1389
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1389

Phe Tyr Thr His Cys Lys Met Glu
1               5

<210> SEQ ID NO 1390
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1390

Phe Tyr Thr His Cys Lys Asp Glu
1               5

<210> SEQ ID NO 1391
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1391

Phe Tyr Thr His Cys Lys Gln Glu
1               5

<210> SEQ ID NO 1392
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1392

Phe Tyr Thr His Cys Lys Glu Glu
1               5

<210> SEQ ID NO 1393
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1393

Phe Tyr Thr His Cys Lys Leu Glu
1               5

<210> SEQ ID NO 1394
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 1394

Phe Tyr Thr His Cys Ala Glu Glu
1               5

<210> SEQ ID NO 1395
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1395

Phe Tyr Thr His Cys Ala Leu Glu
1               5

<210> SEQ ID NO 1396
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1396

Phe Tyr Thr His Cys Ala Lys Glu
1               5

<210> SEQ ID NO 1397
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1397

Phe Tyr Thr His Cys Ala Met Glu
1               5

<210> SEQ ID NO 1398
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1398

Phe Tyr Thr His Cys Ala Pro Glu
1               5

<210> SEQ ID NO 1399
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1399

Phe Tyr Thr His Cys Ala Ser Glu
1               5

<210> SEQ ID NO 1400
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 1400

Phe Tyr Thr His Cys Ala Thr Glu
1               5

<210> SEQ ID NO 1401
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1401

Phe Tyr Thr His Cys Gln Glu Glu
1               5

<210> SEQ ID NO 1402
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1402

Phe Tyr Thr His Cys Gln Leu Glu
1               5

<210> SEQ ID NO 1403
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1403

Phe Tyr Thr His Cys Gln Lys Glu
1               5

<210> SEQ ID NO 1404
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1404

Phe Tyr Thr His Cys Gln Met Glu
1               5

<210> SEQ ID NO 1405
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1405

Phe Tyr Thr His Cys Gln Pro Glu
1               5

<210> SEQ ID NO 1406
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 1406

Phe Tyr Thr His Cys Gln Ser Glu
1               5

<210> SEQ ID NO 1407
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1407

Phe Tyr Thr His Cys Gln Thr Glu
1               5

<210> SEQ ID NO 1408
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1408

Phe Tyr Thr His Cys Gln Ala Glu
1               5

<210> SEQ ID NO 1409
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1409

Phe Tyr Thr His Cys Gln Arg Glu
1               5

<210> SEQ ID NO 1410
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1410

Phe Tyr Thr His Cys Gln Asp Glu
1               5

<210> SEQ ID NO 1411
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1411

Phe Tyr Thr His Cys Gln Gln Glu
1               5

<210> SEQ ID NO 1412
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 1412

Phe Tyr Thr His Cys Glu Ala Glu
1               5

<210> SEQ ID NO 1413
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1413

Phe Tyr Thr His Cys Glu Arg Glu
1               5

<210> SEQ ID NO 1414
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1414

Phe Tyr Thr His Cys Glu Asp Glu
1               5

<210> SEQ ID NO 1415
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1415

Phe Tyr Thr His Cys Glu Glu Glu
1               5

<210> SEQ ID NO 1416
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1416

Phe Tyr Thr His Cys Glu Leu Glu
1               5

<210> SEQ ID NO 1417
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1417

Phe Tyr Thr His Cys Glu Lys Glu
1               5

<210> SEQ ID NO 1418
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1418

Phe Tyr Thr His Cys Glu Met Glu
1               5

<210> SEQ ID NO 1419
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1419

Phe Tyr Thr His Cys Glu Pro Glu
1               5

<210> SEQ ID NO 1420
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1420

Phe Tyr Thr His Cys Glu Ser Glu
1               5

<210> SEQ ID NO 1421
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1421

Phe Tyr Thr His Cys Glu Thr Glu
1               5

<210> SEQ ID NO 1422
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1422

Phe Tyr Thr His Cys Glu Gln Glu
1               5

<210> SEQ ID NO 1423
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1423

Phe Tyr Thr His Cys Ile Ala Glu
1               5

<210> SEQ ID NO 1424
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1424
```

```
Phe Tyr Thr His Cys Ile Arg Glu
1               5

<210> SEQ ID NO 1425
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1425

Phe Tyr Thr His Cys Ile Asp Glu
1               5

<210> SEQ ID NO 1426
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1426

Phe Tyr Thr His Cys Ile Gln Glu
1               5

<210> SEQ ID NO 1427
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1427

Phe Tyr Thr His Cys Ile Glu Glu
1               5

<210> SEQ ID NO 1428
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1428

Phe Tyr Thr His Cys Ile Leu Glu
1               5

<210> SEQ ID NO 1429
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1429

Phe Tyr Thr His Cys Ile Lys Glu
1               5

<210> SEQ ID NO 1430
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1430
```

Phe Tyr Thr His Cys Ile Met Glu
1               5

<210> SEQ ID NO 1431
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1431

Phe Tyr Thr His Cys Ile Pro Glu
1               5

<210> SEQ ID NO 1432
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1432

Phe Tyr Thr His Cys Ile Ser Glu
1               5

<210> SEQ ID NO 1433
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1433

Phe Tyr Thr His Cys Ile Thr Glu
1               5

<210> SEQ ID NO 1434
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1434

Phe Tyr Thr His Cys Leu Ala Glu
1               5

<210> SEQ ID NO 1435
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1435

Phe Tyr Thr His Cys Leu Arg Glu
1               5

<210> SEQ ID NO 1436
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1436

Phe Tyr Thr His Cys Leu Asp Glu

```
1               5
```

<210> SEQ ID NO 1437
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1437

```
Phe Tyr Thr His Cys Leu Gln Glu
1               5
```

<210> SEQ ID NO 1438
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1438

```
Phe Tyr Thr His Cys Leu Glu Glu
1               5
```

<210> SEQ ID NO 1439
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1439

```
Phe Tyr Thr His Cys Leu Leu Glu
1               5
```

<210> SEQ ID NO 1440
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1440

```
Phe Tyr Thr His Cys Leu Lys Glu
1               5
```

<210> SEQ ID NO 1441
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1441

```
Phe Tyr Thr His Cys Leu Met Glu
1               5
```

<210> SEQ ID NO 1442
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1442

```
Phe Tyr Thr His Cys Leu Pro Glu
1               5
```

<210> SEQ ID NO 1443
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1443

Phe Tyr Thr His Cys Leu Ser Glu
1               5

<210> SEQ ID NO 1444
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1444

Phe Tyr Thr His Cys Leu Thr Glu
1               5

<210> SEQ ID NO 1445
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1445

Phe Tyr Thr His Cys Lys Ala Glu
1               5

<210> SEQ ID NO 1446
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1446

Phe Tyr Thr His Cys Lys Arg Glu
1               5

<210> SEQ ID NO 1447
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1447

Phe Tyr Thr His Cys Lys Ser Glu
1               5

<210> SEQ ID NO 1448
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1448

Phe Tyr Thr His Cys Lys Thr Glu
1               5

<210> SEQ ID NO 1449
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1449

Phe Tyr Thr His Cys Lys Pro Glu
1               5

<210> SEQ ID NO 1450
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1450

Phe Tyr Thr His Cys Ala Arg Glu
1               5

<210> SEQ ID NO 1451
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1451

Phe Tyr Thr His Cys Ala Asp Glu
1               5

<210> SEQ ID NO 1452
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1452

Phe Tyr Thr His Cys Ala Gln Glu
1               5

<210> SEQ ID NO 1453
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1453

Phe Tyr Trp His Cys Ala Ala Glu
1               5

<210> SEQ ID NO 1454
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1454

Phe Tyr Trp His Cys Lys Lys Glu
1               5

```
<210> SEQ ID NO 1455
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1455

Phe Tyr Trp His Cys Lys Met Glu
1               5

<210> SEQ ID NO 1456
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1456

Phe Tyr Trp His Cys Lys Asp Glu
1               5

<210> SEQ ID NO 1457
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1457

Phe Tyr Trp His Cys Ala Glu Glu
1               5

<210> SEQ ID NO 1458
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1458

Phe Tyr Trp His Cys Ala Leu Glu
1               5

<210> SEQ ID NO 1459
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1459

Phe Tyr Trp His Cys Ala Lys Glu
1               5

<210> SEQ ID NO 1460
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1460

Phe Tyr Trp His Cys Ala Met Glu
1               5

<210> SEQ ID NO 1461
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1461

Phe Tyr Trp His Cys Ala Pro Glu
1               5

<210> SEQ ID NO 1462
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1462

Phe Tyr Trp His Cys Ala Ser Glu
1               5

<210> SEQ ID NO 1463
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1463

Phe Tyr Trp His Cys Ala Thr Glu
1               5

<210> SEQ ID NO 1464
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1464

Phe Tyr Trp His Cys Gln Glu Glu
1               5

<210> SEQ ID NO 1465
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1465

Phe Tyr Trp His Cys Gln Leu Glu
1               5

<210> SEQ ID NO 1466
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1466

Phe Tyr Trp His Cys Gln Lys Glu
1               5

<210> SEQ ID NO 1467
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1467

Phe Tyr Trp His Cys Gln Met Glu
1               5

<210> SEQ ID NO 1468
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1468

Phe Tyr Trp His Cys Gln Pro Glu
1               5

<210> SEQ ID NO 1469
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1469

Phe Tyr Trp His Cys Gln Ser Glu
1               5

<210> SEQ ID NO 1470
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1470

Phe Tyr Trp His Cys Gln Thr Glu
1               5

<210> SEQ ID NO 1471
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1471

Phe Tyr Trp His Cys Gln Ala Glu
1               5

<210> SEQ ID NO 1472
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1472

Phe Tyr Trp His Cys Gln Arg Glu
1               5

<210> SEQ ID NO 1473
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 1473

Phe Tyr Trp His Cys Gln Asp Glu
1               5

<210> SEQ ID NO 1474
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1474

Phe Tyr Trp His Cys Gln Gln Glu
1               5

<210> SEQ ID NO 1475
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1475

Phe Tyr Trp His Cys Glu Ala Glu
1               5

<210> SEQ ID NO 1476
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1476

Phe Tyr Trp His Cys Glu Arg Glu
1               5

<210> SEQ ID NO 1477
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1477

Phe Tyr Trp His Cys Glu Asp Glu
1               5

<210> SEQ ID NO 1478
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1478

Phe Tyr Trp His Cys Glu Glu Glu
1               5

<210> SEQ ID NO 1479
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 1479

Phe Tyr Trp His Cys Glu Leu Glu
1               5

<210> SEQ ID NO 1480
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1480

Phe Tyr Trp His Cys Glu Lys Glu
1               5

<210> SEQ ID NO 1481
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1481

Phe Tyr Trp His Cys Glu Met Glu
1               5

<210> SEQ ID NO 1482
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1482

Phe Tyr Trp His Cys Glu Pro Glu
1               5

<210> SEQ ID NO 1483
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1483

Phe Tyr Trp His Cys Glu Ser Glu
1               5

<210> SEQ ID NO 1484
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1484

Phe Tyr Trp His Cys Glu Thr Glu
1               5

<210> SEQ ID NO 1485
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 1485

Phe Tyr Trp His Cys Glu Gln Glu
1               5

<210> SEQ ID NO 1486
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1486

Phe Tyr Trp His Cys Ile Ala Glu
1               5

<210> SEQ ID NO 1487
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1487

Phe Tyr Trp His Cys Ile Arg Glu
1               5

<210> SEQ ID NO 1488
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1488

Phe Tyr Trp His Cys Ile Asp Glu
1               5

<210> SEQ ID NO 1489
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1489

Phe Tyr Trp His Cys Ile Gln Glu
1               5

<210> SEQ ID NO 1490
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1490

Phe Tyr Trp His Cys Ile Glu Glu
1               5

<210> SEQ ID NO 1491
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1491

Phe Tyr Trp His Cys Ile Leu Glu
1               5

<210> SEQ ID NO 1492
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1492

Phe Tyr Trp His Cys Ile Lys Glu
1               5

<210> SEQ ID NO 1493
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1493

Phe Tyr Trp His Cys Ile Met Glu
1               5

<210> SEQ ID NO 1494
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1494

Phe Tyr Trp His Cys Ile Pro Glu
1               5

<210> SEQ ID NO 1495
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1495

Phe Tyr Trp His Cys Ile Ser Glu
1               5

<210> SEQ ID NO 1496
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1496

Phe Tyr Trp His Cys Ile Thr Glu
1               5

<210> SEQ ID NO 1497
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 1497

Phe Tyr Trp His Cys Leu Ala Glu
1               5

<210> SEQ ID NO 1498
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1498

Phe Tyr Trp His Cys Leu Arg Glu
1               5

<210> SEQ ID NO 1499
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1499

Phe Tyr Trp His Cys Leu Asp Glu
1               5

<210> SEQ ID NO 1500
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1500

Phe Tyr Trp His Cys Leu Gln Glu
1               5

<210> SEQ ID NO 1501
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1501

Phe Tyr Trp His Cys Leu Glu Glu
1               5

<210> SEQ ID NO 1502
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1502

Phe Tyr Trp His Cys Leu Leu Glu
1               5

<210> SEQ ID NO 1503
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1503
```

Phe Tyr Trp His Cys Leu Lys Glu
1               5

<210> SEQ ID NO 1504
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1504

Phe Tyr Trp His Cys Leu Met Glu
1               5

<210> SEQ ID NO 1505
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1505

Phe Tyr Trp His Cys Leu Pro Glu
1               5

<210> SEQ ID NO 1506
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1506

Phe Tyr Trp His Cys Leu Ser Glu
1               5

<210> SEQ ID NO 1507
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1507

Phe Tyr Trp His Cys Leu Thr Glu
1               5

<210> SEQ ID NO 1508
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1508

Phe Tyr Trp His Cys Lys Ala Glu
1               5

<210> SEQ ID NO 1509
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1509

Phe Tyr Trp His Cys Lys Arg Glu
1               5

<210> SEQ ID NO 1510
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1510

Phe Tyr Trp His Cys Lys Ser Glu
1               5

<210> SEQ ID NO 1511
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1511

Phe Tyr Trp His Cys Lys Thr Glu
1               5

<210> SEQ ID NO 1512
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1512

Phe Tyr Trp His Cys Lys Pro Glu
1               5

<210> SEQ ID NO 1513
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1513

Phe Tyr Trp His Cys Lys Gln Glu
1               5

<210> SEQ ID NO 1514
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1514

Phe Tyr Trp His Cys Lys Glu Glu
1               5

<210> SEQ ID NO 1515
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1515

Phe Tyr Trp His Cys Lys Leu Glu

```
1               5

<210> SEQ ID NO 1516
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1516

Phe Tyr Trp His Cys Ala Arg Glu
1               5

<210> SEQ ID NO 1517
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1517

Phe Tyr Trp His Cys Ala Asp Glu
1               5

<210> SEQ ID NO 1518
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1518

Phe Tyr Trp His Cys Ala Gln Glu
1               5

<210> SEQ ID NO 1519
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1519

Phe Tyr Tyr His Cys Ala Ala Glu
1               5

<210> SEQ ID NO 1520
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1520

Phe Tyr Tyr His Cys Ala Glu Glu
1               5

<210> SEQ ID NO 1521
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1521

Phe Tyr Tyr His Cys Ala Leu Glu
1               5
```

```
<210> SEQ ID NO 1522
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1522

Phe Tyr Tyr His Cys Ala Lys Glu
1               5

<210> SEQ ID NO 1523
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1523

Phe Tyr Tyr His Cys Ala Met Glu
1               5

<210> SEQ ID NO 1524
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1524

Phe Tyr Tyr His Cys Ala Pro Glu
1               5

<210> SEQ ID NO 1525
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1525

Phe Tyr Tyr His Cys Ala Ser Glu
1               5

<210> SEQ ID NO 1526
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1526

Phe Tyr Tyr His Cys Ala Thr Glu
1               5

<210> SEQ ID NO 1527
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1527

Phe Tyr Tyr His Cys Gln Glu Glu
1               5
```

```
<210> SEQ ID NO 1528
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1528

Phe Tyr Tyr His Cys Gln Leu Glu
1               5

<210> SEQ ID NO 1529
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1529

Phe Tyr Tyr His Cys Gln Lys Glu
1               5

<210> SEQ ID NO 1530
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1530

Phe Tyr Tyr His Cys Gln Met Glu
1               5

<210> SEQ ID NO 1531
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1531

Phe Tyr Tyr His Cys Gln Pro Glu
1               5

<210> SEQ ID NO 1532
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1532

Phe Tyr Tyr His Cys Gln Ser Glu
1               5

<210> SEQ ID NO 1533
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1533

Phe Tyr Tyr His Cys Gln Thr Glu
1               5
```

```
<210> SEQ ID NO 1534
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1534

Phe Tyr Tyr His Cys Gln Ala Glu
1               5

<210> SEQ ID NO 1535
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1535

Phe Tyr Tyr His Cys Gln Arg Glu
1               5

<210> SEQ ID NO 1536
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1536

Phe Tyr Tyr His Cys Gln Asp Glu
1               5

<210> SEQ ID NO 1537
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1537

Phe Tyr Tyr His Cys Gln Gln Glu
1               5

<210> SEQ ID NO 1538
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1538

Phe Tyr Tyr His Cys Glu Ala Glu
1               5

<210> SEQ ID NO 1539
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1539

Phe Tyr Tyr His Cys Glu Arg Glu
1               5

<210> SEQ ID NO 1540
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1540

Phe Tyr Tyr His Cys Glu Asp Glu
1               5

<210> SEQ ID NO 1541
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1541

Phe Tyr Tyr His Cys Glu Glu Glu
1               5

<210> SEQ ID NO 1542
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1542

Phe Tyr Tyr His Cys Glu Leu Glu
1               5

<210> SEQ ID NO 1543
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1543

Phe Tyr Tyr His Cys Glu Lys Glu
1               5

<210> SEQ ID NO 1544
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1544

Phe Tyr Tyr His Cys Glu Met Glu
1               5

<210> SEQ ID NO 1545
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1545

Phe Tyr Tyr His Cys Glu Pro Glu
1               5

<210> SEQ ID NO 1546
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 1546

Phe Tyr Tyr His Cys Glu Ser Glu
1               5

<210> SEQ ID NO 1547
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1547

Phe Tyr Tyr His Cys Glu Thr Glu
1               5

<210> SEQ ID NO 1548
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1548

Phe Tyr Tyr His Cys Glu Gln Glu
1               5

<210> SEQ ID NO 1549
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1549

Phe Tyr Tyr His Cys Ile Ala Glu
1               5

<210> SEQ ID NO 1550
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1550

Phe Tyr Tyr His Cys Ile Arg Glu
1               5

<210> SEQ ID NO 1551
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1551

Phe Tyr Tyr His Cys Ile Asp Glu
1               5

<210> SEQ ID NO 1552
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 1552

Phe Tyr Tyr His Cys Ile Gln Glu
1               5

<210> SEQ ID NO 1553
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1553

Phe Tyr Tyr His Cys Ile Glu Glu
1               5

<210> SEQ ID NO 1554
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1554

Phe Tyr Tyr His Cys Ile Leu Glu
1               5

<210> SEQ ID NO 1555
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1555

Phe Tyr Tyr His Cys Ile Lys Glu
1               5

<210> SEQ ID NO 1556
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1556

Phe Tyr Tyr His Cys Ile Met Glu
1               5

<210> SEQ ID NO 1557
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1557

Phe Tyr Tyr His Cys Ile Pro Glu
1               5

<210> SEQ ID NO 1558
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 1558

Phe Tyr Tyr His Cys Ile Ser Glu
1               5

<210> SEQ ID NO 1559
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1559

Phe Tyr Tyr His Cys Ile Thr Glu
1               5

<210> SEQ ID NO 1560
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1560

Phe Tyr Tyr His Cys Leu Ala Glu
1               5

<210> SEQ ID NO 1561
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1561

Phe Tyr Tyr His Cys Leu Arg Glu
1               5

<210> SEQ ID NO 1562
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1562

Phe Tyr Tyr His Cys Leu Asp Glu
1               5

<210> SEQ ID NO 1563
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1563

Phe Tyr Tyr His Cys Leu Gln Glu
1               5

<210> SEQ ID NO 1564
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 1564

Phe Tyr Tyr His Cys Leu Glu Glu
1               5

<210> SEQ ID NO 1565
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1565

Phe Tyr Tyr His Cys Leu Leu Glu
1               5

<210> SEQ ID NO 1566
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1566

Phe Tyr Tyr His Cys Leu Lys Glu
1               5

<210> SEQ ID NO 1567
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1567

Phe Tyr Tyr His Cys Leu Met Glu
1               5

<210> SEQ ID NO 1568
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1568

Phe Tyr Tyr His Cys Leu Pro Glu
1               5

<210> SEQ ID NO 1569
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1569

Phe Tyr Tyr His Cys Leu Ser Glu
1               5

<210> SEQ ID NO 1570
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1570

Phe Tyr Tyr His Cys Leu Thr Glu
1               5

<210> SEQ ID NO 1571
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1571

Phe Tyr Tyr His Cys Lys Ala Glu
1               5

<210> SEQ ID NO 1572
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1572

Phe Tyr Tyr His Cys Lys Arg Glu
1               5

<210> SEQ ID NO 1573
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1573

Phe Tyr Tyr His Cys Lys Ser Glu
1               5

<210> SEQ ID NO 1574
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1574

Phe Tyr Tyr His Cys Lys Thr Glu
1               5

<210> SEQ ID NO 1575
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1575

Phe Tyr Tyr His Cys Lys Pro Glu
1               5

<210> SEQ ID NO 1576
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 1576

Phe Tyr Tyr His Cys Lys Lys Glu
1               5

<210> SEQ ID NO 1577
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1577

Phe Tyr Tyr His Cys Lys Met Glu
1               5

<210> SEQ ID NO 1578
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1578

Phe Tyr Tyr His Cys Lys Asp Glu
1               5

<210> SEQ ID NO 1579
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1579

Phe Tyr Tyr His Cys Lys Gln Glu
1               5

<210> SEQ ID NO 1580
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1580

Phe Tyr Tyr His Cys Lys Glu Glu
1               5

<210> SEQ ID NO 1581
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1581

Phe Tyr Tyr His Cys Lys Leu Glu
1               5

<210> SEQ ID NO 1582
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1582
```

```
Phe Tyr Tyr His Cys Ala Arg Glu
1               5

<210> SEQ ID NO 1583
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1583

Phe Tyr Tyr His Cys Ala Asp Glu
1               5

<210> SEQ ID NO 1584
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1584

Phe Tyr Tyr His Cys Ala Gln Glu
1               5

<210> SEQ ID NO 1585
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1585

Phe Tyr Cys His Asn Gln Arg
1               5

<210> SEQ ID NO 1586
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1586

Phe Tyr Cys His Asn Glu Arg
1               5

<210> SEQ ID NO 1587
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1587

Phe Tyr Cys His Asn His Arg
1               5

<210> SEQ ID NO 1588
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1588
```

Phe Tyr Cys His Asn Ile Arg
1               5

<210> SEQ ID NO 1589
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1589

Phe Tyr Cys His Asn Lys Arg
1               5

<210> SEQ ID NO 1590
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1590

Phe Tyr Cys His Asn Met Arg
1               5

<210> SEQ ID NO 1591
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1591

Phe Tyr Cys His Asn Phe Arg
1               5

<210> SEQ ID NO 1592
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1592

Phe Tyr Cys His Asn Phe Trp Arg
1               5

<210> SEQ ID NO 1593
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1593

Phe Tyr Cys His Asp Gln Arg
1               5

<210> SEQ ID NO 1594
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1594

Phe Tyr Cys His Asp Glu Arg

```
1               5

<210> SEQ ID NO 1595
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1595

Phe Tyr Cys His Asp His Arg
1               5

<210> SEQ ID NO 1596
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1596

Phe Tyr Cys His Asp Ile Arg
1               5

<210> SEQ ID NO 1597
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1597

Phe Tyr Cys His Asp Lys Arg
1               5

<210> SEQ ID NO 1598
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1598

Phe Tyr Cys His Asp Met Arg
1               5

<210> SEQ ID NO 1599
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1599

Phe Tyr Cys His Asp Phe Arg
1               5

<210> SEQ ID NO 1600
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1600

Phe Tyr Cys His Asp Phe Trp Arg
1               5
```

```
<210> SEQ ID NO 1601
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1601

Phe Tyr Cys His Gln Gln Arg
1               5

<210> SEQ ID NO 1602
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1602

Phe Tyr Cys His Gln Glu Arg
1               5

<210> SEQ ID NO 1603
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1603

Phe Tyr Cys His Gln His Arg
1               5

<210> SEQ ID NO 1604
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1604

Phe Tyr Cys His Gln Lys Arg
1               5

<210> SEQ ID NO 1605
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1605

Phe Tyr Cys His Gln Met Arg
1               5

<210> SEQ ID NO 1606
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1606

Phe Tyr Cys His Gln Phe Arg
1               5
```

```
<210> SEQ ID NO 1607
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1607

Phe Tyr Cys His Gln Phe Trp Arg
1               5

<210> SEQ ID NO 1608
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1608

Phe Tyr Cys His Gln Ile Arg
1               5

<210> SEQ ID NO 1609
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1609

Phe Tyr Cys His Glu Gln Arg
1               5

<210> SEQ ID NO 1610
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1610

Phe Tyr Cys His Glu Glu Arg
1               5

<210> SEQ ID NO 1611
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1611

Phe Tyr Cys His Glu Lys Arg
1               5

<210> SEQ ID NO 1612
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1612

Phe Tyr Cys His Glu Met Arg
1               5
```

```
<210> SEQ ID NO 1613
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1613

Phe Tyr Cys His Glu Phe Arg
1               5

<210> SEQ ID NO 1614
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1614

Phe Tyr Cys His Glu Phe Trp Arg
1               5

<210> SEQ ID NO 1615
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1615

Phe Tyr Cys His Glu Ile Arg
1               5

<210> SEQ ID NO 1616
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1616

Phe Tyr Cys His Glu His Arg
1               5

<210> SEQ ID NO 1617
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1617

Phe Tyr Cys His His Gln Arg
1               5

<210> SEQ ID NO 1618
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1618

Phe Tyr Cys His His Glu Arg
1               5

<210> SEQ ID NO 1619
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1619

Phe Tyr Cys His His Lys Arg
1               5

<210> SEQ ID NO 1620
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1620

Phe Tyr Cys His His Met Arg
1               5

<210> SEQ ID NO 1621
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1621

Phe Tyr Cys His His Phe Arg
1               5

<210> SEQ ID NO 1622
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1622

Phe Tyr Cys His His Phe Trp Arg
1               5

<210> SEQ ID NO 1623
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1623

Phe Tyr Cys His His Ile Arg
1               5

<210> SEQ ID NO 1624
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1624

Phe Tyr Cys His His His Arg
1               5

<210> SEQ ID NO 1625
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 1625

Phe Tyr Cys His Ile Gln Arg
1               5

<210> SEQ ID NO 1626
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1626

Phe Tyr Cys His Ile Glu Arg
1               5

<210> SEQ ID NO 1627
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1627

Phe Tyr Cys His Ile Lys Arg
1               5

<210> SEQ ID NO 1628
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1628

Phe Tyr Cys His Ile Met Arg
1               5

<210> SEQ ID NO 1629
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1629

Phe Tyr Cys His Ile Phe Arg
1               5

<210> SEQ ID NO 1630
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1630

Phe Tyr Cys His Ile Phe Trp Arg
1               5

<210> SEQ ID NO 1631
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 1631

Phe Tyr Cys His Ile Ile Arg
1               5

<210> SEQ ID NO 1632
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1632

Phe Tyr Cys His Ile His Arg
1               5

<210> SEQ ID NO 1633
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1633

Phe Tyr Cys His Lys Gln Arg
1               5

<210> SEQ ID NO 1634
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1634

Phe Tyr Cys His Lys Glu Arg
1               5

<210> SEQ ID NO 1635
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1635

Phe Tyr Cys His Lys Lys Arg
1               5

<210> SEQ ID NO 1636
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1636

Phe Tyr Cys His Lys Met Arg
1               5

<210> SEQ ID NO 1637
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 1637

Phe Tyr Cys His Lys Phe Arg
1               5

<210> SEQ ID NO 1638
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1638

Phe Tyr Cys His Lys Phe Trp Arg
1               5

<210> SEQ ID NO 1639
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1639

Phe Tyr Cys His Lys Ile Arg
1               5

<210> SEQ ID NO 1640
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1640

Phe Tyr Cys His Lys His Arg
1               5

<210> SEQ ID NO 1641
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1641

Phe Tyr Cys His Met Gln Arg
1               5

<210> SEQ ID NO 1642
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1642

Phe Tyr Cys His Met Glu Arg
1               5

<210> SEQ ID NO 1643
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 1643

Phe Tyr Cys His Met Lys Arg
1               5

<210> SEQ ID NO 1644
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1644

Phe Tyr Cys His Met Met Arg
1               5

<210> SEQ ID NO 1645
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1645

Phe Tyr Cys His Met Phe Arg
1               5

<210> SEQ ID NO 1646
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1646

Phe Tyr Cys His Met Phe Trp Arg
1               5

<210> SEQ ID NO 1647
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1647

Phe Tyr Cys His Met Ile Arg
1               5

<210> SEQ ID NO 1648
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1648

Phe Tyr Cys His Met His Arg
1               5

<210> SEQ ID NO 1649
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 1649

Phe Tyr Cys His Phe Gln Arg
1               5

<210> SEQ ID NO 1650
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1650

Phe Tyr Cys His Phe Glu Arg
1               5

<210> SEQ ID NO 1651
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1651

Phe Tyr Cys His Phe Lys Arg
1               5

<210> SEQ ID NO 1652
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1652

Phe Tyr Cys His Phe Met Arg
1               5

<210> SEQ ID NO 1653
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1653

Phe Tyr Cys His Phe Phe Arg
1               5

<210> SEQ ID NO 1654
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1654

Phe Tyr Cys His Phe Phe Trp Arg
1               5

<210> SEQ ID NO 1655
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 1655

Phe Tyr Cys His Phe Ile Arg
1               5

<210> SEQ ID NO 1656
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1656

Phe Tyr Cys His Phe His Arg
1               5

<210> SEQ ID NO 1657
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1657

Phe Tyr Cys His Pro Gln Arg
1               5

<210> SEQ ID NO 1658
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1658

Phe Tyr Cys His Pro Glu Arg
1               5

<210> SEQ ID NO 1659
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1659

Phe Tyr Cys His Pro Lys Arg
1               5

<210> SEQ ID NO 1660
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1660

Phe Tyr Cys His Pro Met Arg
1               5

<210> SEQ ID NO 1661
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1661
```

Phe Tyr Cys His Pro Phe Arg
1               5

<210> SEQ ID NO 1662
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1662

Phe Tyr Cys His Pro Phe Trp Arg
1               5

<210> SEQ ID NO 1663
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1663

Phe Tyr Cys His Pro Ile Arg
1               5

<210> SEQ ID NO 1664
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1664

Phe Tyr Cys His Pro His Arg
1               5

<210> SEQ ID NO 1665
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1665

Phe Tyr Cys His Thr Gln Arg
1               5

<210> SEQ ID NO 1666
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1666

Phe Tyr Cys His Thr Glu Arg
1               5

<210> SEQ ID NO 1667
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1667

Phe Tyr Cys His Thr Lys Arg
1               5

<210> SEQ ID NO 1668
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1668

Phe Tyr Cys His Thr Met Arg
1               5

<210> SEQ ID NO 1669
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1669

Phe Tyr Cys His Thr Phe Arg
1               5

<210> SEQ ID NO 1670
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1670

Phe Tyr Cys His Thr Phe Trp Arg
1               5

<210> SEQ ID NO 1671
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1671

Phe Tyr Cys His Thr Ile Arg
1               5

<210> SEQ ID NO 1672
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1672

Phe Tyr Cys His Thr His Arg
1               5

<210> SEQ ID NO 1673
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1673

Phe Tyr Cys His Trp Gln Arg

```
1               5
```

<210> SEQ ID NO 1674
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1674

```
Phe Tyr Cys His Trp Glu Arg
1               5
```

<210> SEQ ID NO 1675
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1675

```
Phe Tyr Cys His Trp Lys Arg
1               5
```

<210> SEQ ID NO 1676
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1676

```
Phe Tyr Cys His Trp Met Arg
1               5
```

<210> SEQ ID NO 1677
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1677

```
Phe Tyr Cys His Trp Phe Arg
1               5
```

<210> SEQ ID NO 1678
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1678

```
Phe Tyr Cys His Trp Phe Trp Arg
1               5
```

<210> SEQ ID NO 1679
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1679

```
Phe Tyr Cys His Trp Ile Arg
1               5
```

```
<210> SEQ ID NO 1680
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1680

Phe Tyr Cys His Trp His Arg
1               5

<210> SEQ ID NO 1681
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1681

Phe Tyr Cys His Tyr Gln Arg
1               5

<210> SEQ ID NO 1682
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1682

Phe Tyr Cys His Tyr Glu Arg
1               5

<210> SEQ ID NO 1683
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1683

Phe Tyr Cys His Tyr Lys Arg
1               5

<210> SEQ ID NO 1684
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1684

Phe Tyr Cys His Tyr Met Arg
1               5

<210> SEQ ID NO 1685
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1685

Phe Tyr Cys His Tyr Phe Arg
1               5
```

<210> SEQ ID NO 1686
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1686

Phe Tyr Cys His Tyr Phe Trp Arg
1               5

<210> SEQ ID NO 1687
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1687

Phe Tyr Cys His Tyr Ile Arg
1               5

<210> SEQ ID NO 1688
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1688

Phe Tyr Cys His Tyr His Arg
1               5

<210> SEQ ID NO 1689
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1689

Phe Tyr Cys His Val Gln Arg
1               5

<210> SEQ ID NO 1690
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1690

Phe Tyr Cys His Val Glu Arg
1               5

<210> SEQ ID NO 1691
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1691

Phe Tyr Cys His Val Lys Arg
1               5

```
<210> SEQ ID NO 1692
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1692

Phe Tyr Cys His Val Met Arg
1               5

<210> SEQ ID NO 1693
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1693

Phe Tyr Cys His Val Phe Arg
1               5

<210> SEQ ID NO 1694
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1694

Phe Tyr Cys His Val Phe Trp Arg
1               5

<210> SEQ ID NO 1695
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1695

Phe Tyr Cys His Val Ile Arg
1               5

<210> SEQ ID NO 1696
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1696

Phe Tyr Cys His Val His Arg
1               5

<210> SEQ ID NO 1697
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1697

Phe Tyr Ala His Cys Gln Arg
1               5

<210> SEQ ID NO 1698
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1698

Phe Tyr Ala His Cys Glu Arg
1               5

<210> SEQ ID NO 1699
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1699

Phe Tyr Ala His Cys His Arg
1               5

<210> SEQ ID NO 1700
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1700

Phe Tyr Ala His Cys Ile Arg
1               5

<210> SEQ ID NO 1701
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1701

Phe Tyr Ala His Cys Lys Arg
1               5

<210> SEQ ID NO 1702
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1702

Phe Tyr Ala His Cys Met Arg
1               5

<210> SEQ ID NO 1703
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1703

Phe Tyr Ala His Cys Phe Arg
1               5

<210> SEQ ID NO 1704
<211> LENGTH: 7
```

-continued

```
<212> TYPE: PRT
<213> ORGANISM: Artificial Sequence
<220> FEATURE:
<223> OTHER INFORMATION: Synthetic Construct

<400> SEQUENCE: 1704

Phe Tyr Ala His Cys Trp Arg
1               5

<210> SEQ ID NO 1705
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1705

Phe Tyr Arg His Cys Gln Arg
1               5

<210> SEQ ID NO 1706
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1706

Phe Tyr Arg His Cys Glu Arg
1               5

<210> SEQ ID NO 1707
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1707

Phe Tyr Arg His Cys His Arg
1               5

<210> SEQ ID NO 1708
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1708

Phe Tyr Arg His Cys Ile Arg
1               5

<210> SEQ ID NO 1709
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1709

Phe Tyr Arg His Cys Lys Arg
1               5

<210> SEQ ID NO 1710
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 1710

Phe Tyr Arg His Cys Met Arg
1               5

<210> SEQ ID NO 1711
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1711

Phe Tyr Arg His Cys Phe Arg
1               5

<210> SEQ ID NO 1712
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1712

Phe Tyr Arg His Cys Trp Arg
1               5

<210> SEQ ID NO 1713
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1713

Phe Tyr Asn His Cys Gln Arg
1               5

<210> SEQ ID NO 1714
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1714

Phe Tyr Asn His Cys Glu Arg
1               5

<210> SEQ ID NO 1715
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1715

Phe Tyr Asn His Cys His Arg
1               5

<210> SEQ ID NO 1716
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 1716

Phe Tyr Asn His Cys Ile Arg
1               5

<210> SEQ ID NO 1717
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1717

Phe Tyr Asn His Cys Lys Arg
1               5

<210> SEQ ID NO 1718
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1718

Phe Tyr Asn His Cys Met Arg
1               5

<210> SEQ ID NO 1719
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1719

Phe Tyr Asn His Cys Phe Arg
1               5

<210> SEQ ID NO 1720
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1720

Phe Tyr Asn His Cys Trp Arg
1               5

<210> SEQ ID NO 1721
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1721

Phe Tyr Asp His Cys Gln Arg
1               5

<210> SEQ ID NO 1722
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 1722

Phe Tyr Asp His Cys Glu Arg
1               5

<210> SEQ ID NO 1723
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1723

Phe Tyr Asp His Cys His Arg
1               5

<210> SEQ ID NO 1724
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1724

Phe Tyr Asp His Cys Ile Arg
1               5

<210> SEQ ID NO 1725
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1725

Phe Tyr Asp His Cys Lys Arg
1               5

<210> SEQ ID NO 1726
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1726

Phe Tyr Asp His Cys Met Arg
1               5

<210> SEQ ID NO 1727
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1727

Phe Tyr Asp His Cys Phe Arg
1               5

<210> SEQ ID NO 1728
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 1728

Phe Tyr Asp His Cys Trp Arg
1               5

<210> SEQ ID NO 1729
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1729

Phe Tyr Ile His Cys Gln Arg
1               5

<210> SEQ ID NO 1730
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1730

Phe Tyr Ile His Cys Glu Arg
1               5

<210> SEQ ID NO 1731
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1731

Phe Tyr Ile His Cys His Arg
1               5

<210> SEQ ID NO 1732
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1732

Phe Tyr Ile His Cys Ile Arg
1               5

<210> SEQ ID NO 1733
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1733

Phe Tyr Ile His Cys Lys Arg
1               5

<210> SEQ ID NO 1734
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 1734

Phe Tyr Ile His Cys Met Arg
1               5

<210> SEQ ID NO 1735
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1735

Phe Tyr Ile His Cys Phe Arg
1               5

<210> SEQ ID NO 1736
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1736

Phe Tyr Ile His Cys Trp Arg
1               5

<210> SEQ ID NO 1737
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1737

Phe Tyr Pro His Cys Glu Arg
1               5

<210> SEQ ID NO 1738
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1738

Phe Tyr Pro His Cys His Arg
1               5

<210> SEQ ID NO 1739
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1739

Phe Tyr Pro His Cys Ile Arg
1               5

<210> SEQ ID NO 1740
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1740
```

Phe Tyr Pro His Cys Lys Arg
1               5

<210> SEQ ID NO 1741
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1741

Phe Tyr Pro His Cys Met Arg
1               5

<210> SEQ ID NO 1742
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1742

Phe Tyr Pro His Cys Phe Arg
1               5

<210> SEQ ID NO 1743
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1743

Phe Tyr Pro His Cys Trp Arg
1               5

<210> SEQ ID NO 1744
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1744

Phe Tyr Pro His Cys Gln Arg
1               5

<210> SEQ ID NO 1745
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1745

Phe Tyr Thr His Cys Gln Arg
1               5

<210> SEQ ID NO 1746
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1746

Phe Tyr Thr His Cys Glu Arg
1               5

<210> SEQ ID NO 1747
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1747

Phe Tyr Thr His Cys His Arg
1               5

<210> SEQ ID NO 1748
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1748

Phe Tyr Thr His Cys Ile Arg
1               5

<210> SEQ ID NO 1749
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1749

Phe Tyr Thr His Cys Lys Arg
1               5

<210> SEQ ID NO 1750
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1750

Phe Tyr Thr His Cys Met Arg
1               5

<210> SEQ ID NO 1751
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1751

Phe Tyr Thr His Cys Phe Arg
1               5

<210> SEQ ID NO 1752
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1752

Phe Tyr Thr His Cys Trp Arg

```
1               5

<210> SEQ ID NO 1753
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1753

Phe Tyr Trp His Cys Gln Arg
1               5

<210> SEQ ID NO 1754
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1754

Phe Tyr Trp His Cys Glu Arg
1               5

<210> SEQ ID NO 1755
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1755

Phe Tyr Trp His Cys His Arg
1               5

<210> SEQ ID NO 1756
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1756

Phe Tyr Trp His Cys Ile Arg
1               5

<210> SEQ ID NO 1757
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1757

Phe Tyr Trp His Cys Lys Arg
1               5

<210> SEQ ID NO 1758
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1758

Phe Tyr Trp His Cys Met Arg
1               5
```

```
<210> SEQ ID NO 1759
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1759

Phe Tyr Trp His Cys Phe Arg
1               5

<210> SEQ ID NO 1760
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1760

Phe Tyr Trp His Cys Trp Arg
1               5

<210> SEQ ID NO 1761
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1761

Phe Tyr Tyr His Cys Gln Arg
1               5

<210> SEQ ID NO 1762
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1762

Phe Tyr Tyr His Cys Glu Arg
1               5

<210> SEQ ID NO 1763
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1763

Phe Tyr Tyr His Cys His Arg
1               5

<210> SEQ ID NO 1764
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1764

Phe Tyr Tyr His Cys Ile Arg
1               5
```

<210> SEQ ID NO 1765
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1765

Phe Tyr Tyr His Cys Lys Arg
1               5

<210> SEQ ID NO 1766
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1766

Phe Tyr Tyr His Cys Met Arg
1               5

<210> SEQ ID NO 1767
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1767

Phe Tyr Tyr His Cys Phe Arg
1               5

<210> SEQ ID NO 1768
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1768

Phe Tyr Tyr His Cys Trp Arg
1               5

<210> SEQ ID NO 1769
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1769

Phe Tyr Ala Cys Arg Asn Glu
1               5

<210> SEQ ID NO 1770
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1770

Phe Tyr Ala Cys Arg Asp Glu
1               5

```
<210> SEQ ID NO 1771
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1771

Phe Tyr Ala Cys Arg Gln Glu
1               5

<210> SEQ ID NO 1772
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1772

Phe Tyr Ala Cys Arg Glu Glu
1               5

<210> SEQ ID NO 1773
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1773

Phe Tyr Ala Cys Arg Leu Glu
1               5

<210> SEQ ID NO 1774
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1774

Phe Tyr Ala Cys Arg Met Glu
1               5

<210> SEQ ID NO 1775
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1775

Phe Tyr Ala Cys Arg Ser Glu
1               5

<210> SEQ ID NO 1776
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1776

Phe Tyr Ala Cys Arg Thr Glu
1               5

<210> SEQ ID NO 1777
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1777

Phe Tyr Ala Cys Arg Trp Glu
1               5

<210> SEQ ID NO 1778
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1778

Phe Tyr Arg Cys Arg Asn Glu
1               5

<210> SEQ ID NO 1779
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1779

Phe Tyr Arg Cys Arg Asp Glu
1               5

<210> SEQ ID NO 1780
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1780

Phe Tyr Arg Cys Arg Gln Glu
1               5

<210> SEQ ID NO 1781
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1781

Phe Tyr Arg Cys Arg Glu Glu
1               5

<210> SEQ ID NO 1782
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1782

Phe Tyr Arg Cys Arg Leu Glu
1               5

<210> SEQ ID NO 1783
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 1783

Phe Tyr Arg Cys Arg Met Glu
1               5

<210> SEQ ID NO 1784
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1784

Phe Tyr Arg Cys Arg Ser Glu
1               5

<210> SEQ ID NO 1785
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1785

Phe Tyr Arg Cys Arg Thr Glu
1               5

<210> SEQ ID NO 1786
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1786

Phe Tyr Arg Cys Arg Trp Glu
1               5

<210> SEQ ID NO 1787
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1787

Phe Tyr Asn Cys Arg Asn Glu
1               5

<210> SEQ ID NO 1788
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1788

Phe Tyr Asn Cys Arg Asp Glu
1               5

<210> SEQ ID NO 1789
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 1789

Phe Tyr Asn Cys Arg Gln Glu
1               5

<210> SEQ ID NO 1790
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1790

Phe Tyr Asn Cys Arg Glu Glu
1               5

<210> SEQ ID NO 1791
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1791

Phe Tyr Asn Cys Arg Leu Glu
1               5

<210> SEQ ID NO 1792
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1792

Phe Tyr Asn Cys Arg Met Glu
1               5

<210> SEQ ID NO 1793
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1793

Phe Tyr Asn Cys Arg Ser Glu
1               5

<210> SEQ ID NO 1794
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1794

Phe Tyr Asn Cys Arg Thr Glu
1               5

<210> SEQ ID NO 1795
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 1795

Phe Tyr Asn Cys Arg Trp Glu
1               5

<210> SEQ ID NO 1796
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1796

Phe Tyr Asp Cys Arg Asn Glu
1               5

<210> SEQ ID NO 1797
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1797

Phe Tyr Asp Cys Arg Asp Glu
1               5

<210> SEQ ID NO 1798
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1798

Phe Tyr Asp Cys Arg Gln Glu
1               5

<210> SEQ ID NO 1799
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1799

Phe Tyr Asp Cys Arg Glu Glu
1               5

<210> SEQ ID NO 1800
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1800

Phe Tyr Asp Cys Arg Leu Glu
1               5

<210> SEQ ID NO 1801
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 1801

Phe Tyr Asp Cys Arg Met Glu
1               5

<210> SEQ ID NO 1802
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1802

Phe Tyr Asp Cys Arg Ser Glu
1               5

<210> SEQ ID NO 1803
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1803

Phe Tyr Asp Cys Arg Thr Glu
1               5

<210> SEQ ID NO 1804
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1804

Phe Tyr Asp Cys Arg Trp Glu
1               5

<210> SEQ ID NO 1805
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1805

Phe Tyr Gln Cys Arg Asn Glu
1               5

<210> SEQ ID NO 1806
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1806

Phe Tyr Gln Cys Arg Asp Glu
1               5

<210> SEQ ID NO 1807
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1807

Phe Tyr Gln Cys Arg Gln Glu
1               5

<210> SEQ ID NO 1808
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1808

Phe Tyr Gln Cys Arg Glu Glu
1               5

<210> SEQ ID NO 1809
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1809

Phe Tyr Gln Cys Arg Leu Glu
1               5

<210> SEQ ID NO 1810
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1810

Phe Tyr Gln Cys Arg Met Glu
1               5

<210> SEQ ID NO 1811
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1811

Phe Tyr Gln Cys Arg Ser Glu
1               5

<210> SEQ ID NO 1812
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1812

Phe Tyr Gln Cys Arg Thr Glu
1               5

<210> SEQ ID NO 1813
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 1813

Phe Tyr Gln Cys Arg Trp Glu
1               5

<210> SEQ ID NO 1814
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1814

Phe Tyr Glu Cys Arg Gln Glu
1               5

<210> SEQ ID NO 1815
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1815

Phe Tyr Glu Cys Arg Glu Glu
1               5

<210> SEQ ID NO 1816
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1816

Phe Tyr Glu Cys Arg Leu Glu
1               5

<210> SEQ ID NO 1817
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1817

Phe Tyr Glu Cys Arg Met Glu
1               5

<210> SEQ ID NO 1818
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1818

Phe Tyr Glu Cys Arg Ser Glu
1               5

<210> SEQ ID NO 1819
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1819
```

Phe Tyr Glu Cys Arg Thr Glu
1               5

<210> SEQ ID NO 1820
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1820

Phe Tyr Glu Cys Arg Trp Glu
1               5

<210> SEQ ID NO 1821
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1821

Phe Tyr Glu Cys Arg Asn Glu
1               5

<210> SEQ ID NO 1822
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1822

Phe Tyr Glu Cys Arg Asp Glu
1               5

<210> SEQ ID NO 1823
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1823

Phe Tyr Gly Cys Arg Asn Glu
1               5

<210> SEQ ID NO 1824
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1824

Phe Tyr Gly Cys Arg Asp Glu
1               5

<210> SEQ ID NO 1825
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1825

Phe Tyr Gly Cys Arg Gln Glu
1               5

<210> SEQ ID NO 1826
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1826

Phe Tyr Gly Cys Arg Glu Glu
1               5

<210> SEQ ID NO 1827
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1827

Phe Tyr Gly Cys Arg Leu Glu
1               5

<210> SEQ ID NO 1828
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1828

Phe Tyr Gly Cys Arg Met Glu
1               5

<210> SEQ ID NO 1829
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1829

Phe Tyr Gly Cys Arg Ser Glu
1               5

<210> SEQ ID NO 1830
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1830

Phe Tyr Gly Cys Arg Thr Glu
1               5

<210> SEQ ID NO 1831
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1831

Phe Tyr Gly Cys Arg Trp Glu

<210> SEQ ID NO 1832
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1832

Phe Tyr His Cys Arg Asn Glu
1               5

<210> SEQ ID NO 1833
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1833

Phe Tyr His Cys Arg Asp Glu
1               5

<210> SEQ ID NO 1834
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1834

Phe Tyr His Cys Arg Gln Glu
1               5

<210> SEQ ID NO 1835
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1835

Phe Tyr His Cys Arg Glu Glu
1               5

<210> SEQ ID NO 1836
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1836

Phe Tyr His Cys Arg Leu Glu
1               5

<210> SEQ ID NO 1837
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1837

Phe Tyr His Cys Arg Met Glu
1               5

```
<210> SEQ ID NO 1838
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1838

Phe Tyr His Cys Arg Ser Glu
1               5

<210> SEQ ID NO 1839
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1839

Phe Tyr His Cys Arg Thr Glu
1               5

<210> SEQ ID NO 1840
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1840

Phe Tyr His Cys Arg Trp Glu
1               5

<210> SEQ ID NO 1841
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1841

Phe Tyr Ile Cys Arg Asn Glu
1               5

<210> SEQ ID NO 1842
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1842

Phe Tyr Ile Cys Arg Asp Glu
1               5

<210> SEQ ID NO 1843
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1843

Phe Tyr Ile Cys Arg Asn Glu
1               5
```

<210> SEQ ID NO 1844
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1844

Phe Tyr Ile Cys Arg Glu Glu
1               5

<210> SEQ ID NO 1845
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1845

Phe Tyr Ile Cys Arg Leu Glu
1               5

<210> SEQ ID NO 1846
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1846

Phe Tyr Ile Cys Arg Met Glu
1               5

<210> SEQ ID NO 1847
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1847

Phe Tyr Ile Cys Arg Ser Glu
1               5

<210> SEQ ID NO 1848
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1848

Phe Tyr Ile Cys Arg Thr Glu
1               5

<210> SEQ ID NO 1849
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1849

Phe Tyr Ile Cys Arg Trp Glu
1               5

```
<210> SEQ ID NO 1850
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1850

Phe Tyr Leu Cys Arg Asn Glu
1               5

<210> SEQ ID NO 1851
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1851

Phe Tyr Leu Cys Arg Asp Glu
1               5

<210> SEQ ID NO 1852
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1852

Phe Tyr Leu Cys Arg Gln Glu
1               5

<210> SEQ ID NO 1853
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1853

Phe Tyr Leu Cys Arg Glu Glu
1               5

<210> SEQ ID NO 1854
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1854

Phe Tyr Leu Cys Arg Leu Glu
1               5

<210> SEQ ID NO 1855
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1855

Phe Tyr Leu Cys Arg Met Glu
1               5

<210> SEQ ID NO 1856
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1856

Phe Tyr Leu Cys Arg Ser Glu
1               5

<210> SEQ ID NO 1857
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1857

Phe Tyr Leu Cys Arg Thr Glu
1               5

<210> SEQ ID NO 1858
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1858

Phe Tyr Leu Cys Arg Trp Glu
1               5

<210> SEQ ID NO 1859
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1859

Phe Tyr Lys Cys Arg Asn Glu
1               5

<210> SEQ ID NO 1860
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1860

Phe Tyr Lys Cys Arg Asp Glu
1               5

<210> SEQ ID NO 1861
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1861

Phe Tyr Lys Cys Arg Gln Glu
1               5

<210> SEQ ID NO 1862
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 1862

Phe Tyr Lys Cys Arg Glu Glu
1               5

<210> SEQ ID NO 1863
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1863

Phe Tyr Lys Cys Arg Leu Glu
1               5

<210> SEQ ID NO 1864
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1864

Phe Tyr Lys Cys Arg Met Glu
1               5

<210> SEQ ID NO 1865
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1865

Phe Tyr Lys Cys Arg Ser Glu
1               5

<210> SEQ ID NO 1866
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1866

Phe Tyr Lys Cys Arg Thr Glu
1               5

<210> SEQ ID NO 1867
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1867

Phe Tyr Lys Cys Arg Trp Glu
1               5

<210> SEQ ID NO 1868
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 1868

Phe Tyr Met Cys Arg Asn Glu
1               5

<210> SEQ ID NO 1869
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1869

Phe Tyr Met Cys Arg Asp Glu
1               5

<210> SEQ ID NO 1870
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1870

Phe Tyr Met Cys Arg Gln Glu
1               5

<210> SEQ ID NO 1871
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1871

Phe Tyr Met Cys Arg Glu Glu
1               5

<210> SEQ ID NO 1872
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1872

Phe Tyr Met Cys Arg Leu Glu
1               5

<210> SEQ ID NO 1873
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1873

Phe Tyr Met Cys Arg Met Glu
1               5

<210> SEQ ID NO 1874
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 1874

Phe Tyr Met Cys Arg Ser Glu
1               5

<210> SEQ ID NO 1875
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1875

Phe Tyr Met Cys Arg Thr Glu
1               5

<210> SEQ ID NO 1876
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1876

Phe Tyr Met Cys Arg Trp Glu
1               5

<210> SEQ ID NO 1877
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1877

Phe Tyr Phe Cys Arg Gln Glu
1               5

<210> SEQ ID NO 1878
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1878

Phe Tyr Phe Cys Arg Glu Glu
1               5

<210> SEQ ID NO 1879
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1879

Phe Tyr Phe Cys Arg Leu Glu
1               5

<210> SEQ ID NO 1880
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 1880

Phe Tyr Phe Cys Arg Met Glu
1               5

<210> SEQ ID NO 1881
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1881

Phe Tyr Phe Cys Arg Ser Glu
1               5

<210> SEQ ID NO 1882
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1882

Phe Tyr Phe Cys Arg Thr Glu
1               5

<210> SEQ ID NO 1883
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1883

Phe Tyr Phe Cys Arg Trp Glu
1               5

<210> SEQ ID NO 1884
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1884

Phe Tyr Phe Cys Arg Asn Glu
1               5

<210> SEQ ID NO 1885
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1885

Phe Tyr Phe Cys Arg Asp Glu
1               5

<210> SEQ ID NO 1886
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 1886

Phe Tyr Pro Cys Arg Asn Glu
1               5

<210> SEQ ID NO 1887
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1887

Phe Tyr Pro Cys Arg Asp Glu
1               5

<210> SEQ ID NO 1888
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1888

Phe Tyr Pro Cys Arg Gln Glu
1               5

<210> SEQ ID NO 1889
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1889

Phe Tyr Pro Cys Arg Glu Glu
1               5

<210> SEQ ID NO 1890
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1890

Phe Tyr Pro Cys Arg Leu Glu
1               5

<210> SEQ ID NO 1891
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1891

Phe Tyr Pro Cys Arg Met Glu
1               5

<210> SEQ ID NO 1892
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 1892

Phe Tyr Pro Cys Arg Ser Glu
1               5

<210> SEQ ID NO 1893
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1893

Phe Tyr Pro Cys Arg Thr Glu
1               5

<210> SEQ ID NO 1894
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1894

Phe Tyr Pro Cys Arg Trp Glu
1               5

<210> SEQ ID NO 1895
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1895

Phe Tyr Trp Cys Arg Asn Glu
1               5

<210> SEQ ID NO 1896
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1896

Phe Tyr Trp Cys Arg Asp Glu
1               5

<210> SEQ ID NO 1897
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1897

Phe Tyr Trp Cys Arg Gln Glu
1               5

<210> SEQ ID NO 1898
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1898
```

Phe Tyr Trp Cys Arg Glu Glu
1               5

<210> SEQ ID NO 1899
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1899

Phe Tyr Trp Cys Arg Leu Glu
1               5

<210> SEQ ID NO 1900
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1900

Phe Tyr Trp Cys Arg Met Glu
1               5

<210> SEQ ID NO 1901
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1901

Phe Tyr Trp Cys Arg Ser Glu
1               5

<210> SEQ ID NO 1902
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1902

Phe Tyr Trp Cys Arg Thr Glu
1               5

<210> SEQ ID NO 1903
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1903

Phe Tyr Trp Cys Arg Trp Glu
1               5

<210> SEQ ID NO 1904
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1904

Phe Tyr Tyr Cys Arg Asn Glu
1               5

<210> SEQ ID NO 1905
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1905

Phe Tyr Tyr Cys Arg Asp Glu
1               5

<210> SEQ ID NO 1906
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1906

Phe Tyr Tyr Cys Arg Gln Glu
1               5

<210> SEQ ID NO 1907
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1907

Phe Tyr Tyr Cys Arg Glu Glu
1               5

<210> SEQ ID NO 1908
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1908

Phe Tyr Tyr Cys Arg Leu Glu
1               5

<210> SEQ ID NO 1909
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1909

Phe Tyr Tyr Cys Arg Met Glu
1               5

<210> SEQ ID NO 1910
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1910

Phe Tyr Tyr Cys Arg Ser Glu

```
1               5

<210> SEQ ID NO 1911
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1911

Phe Tyr Tyr Cys Arg Thr Glu
1               5

<210> SEQ ID NO 1912
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1912

Phe Tyr Tyr Cys Arg Trp Glu
1               5

<210> SEQ ID NO 1913
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1913

Phe Tyr Val Cys Arg Asn Glu
1               5

<210> SEQ ID NO 1914
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1914

Phe Tyr Val Cys Arg Asp Glu
1               5

<210> SEQ ID NO 1915
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1915

Phe Tyr Val Cys Arg Gln Glu
1               5

<210> SEQ ID NO 1916
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1916

Phe Tyr Val Cys Arg Glu Glu
1               5
```

```
<210> SEQ ID NO 1917
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1917

Phe Tyr Val Cys Arg Leu Glu
1               5

<210> SEQ ID NO 1918
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1918

Phe Tyr Val Cys Arg Met Glu
1               5

<210> SEQ ID NO 1919
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1919

Phe Tyr Val Cys Arg Ser Glu
1               5

<210> SEQ ID NO 1920
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1920

Phe Tyr Val Cys Arg Thr Glu
1               5

<210> SEQ ID NO 1921
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1921

Phe Tyr Val Cys Arg Trp Glu
1               5

<210> SEQ ID NO 1922
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1922

Tyr Phe Asn Cys Arg Asn Glu
1               5
```

<210> SEQ ID NO 1923
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1923

Tyr Phe Asn Cys Arg Asp Glu
1               5

<210> SEQ ID NO 1924
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1924

Tyr Phe Asn Cys Arg Gln Glu
1               5

<210> SEQ ID NO 1925
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1925

Tyr Phe Asn Cys Arg Glu Glu
1               5

<210> SEQ ID NO 1926
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1926

Tyr Phe Asn Cys Arg Leu Glu
1               5

<210> SEQ ID NO 1927
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1927

Tyr Phe Asn Cys Arg Met Glu
1               5

<210> SEQ ID NO 1928
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1928

Tyr Phe Asn Cys Arg Ser Glu
1               5

```
<210> SEQ ID NO 1929
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1929

Tyr Phe Asn Cys Arg Thr Glu
1               5

<210> SEQ ID NO 1930
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1930

Tyr Phe Asn Cys Arg Trp Glu
1               5

<210> SEQ ID NO 1931
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1931

Tyr Phe Asp Cys Arg Asn Glu
1               5

<210> SEQ ID NO 1932
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1932

Tyr Phe Asp Cys Arg Asp Glu
1               5

<210> SEQ ID NO 1933
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1933

Tyr Phe Asp Cys Arg Gln Glu
1               5

<210> SEQ ID NO 1934
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1934

Tyr Phe Asp Cys Arg Glu Glu
1               5

<210> SEQ ID NO 1935
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1935

Tyr Phe Asp Cys Arg Leu Glu
1               5

<210> SEQ ID NO 1936
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1936

Tyr Phe Asp Cys Arg Met Glu
1               5

<210> SEQ ID NO 1937
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1937

Tyr Phe Asp Cys Arg Ser Glu
1               5

<210> SEQ ID NO 1938
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1938

Tyr Phe Asp Cys Arg Thr Glu
1               5

<210> SEQ ID NO 1939
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1939

Tyr Phe Asp Cys Arg Trp Glu
1               5

<210> SEQ ID NO 1940
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1940

Tyr Phe Glu Cys Arg Gln Glu
1               5

<210> SEQ ID NO 1941
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 1941

Tyr Phe Glu Cys Arg Glu Glu
1               5

<210> SEQ ID NO 1942
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1942

Tyr Phe Glu Cys Arg Leu Glu
1               5

<210> SEQ ID NO 1943
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1943

Tyr Phe Glu Cys Arg Met Glu
1               5

<210> SEQ ID NO 1944
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1944

Tyr Phe Glu Cys Arg Ser Glu
1               5

<210> SEQ ID NO 1945
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1945

Tyr Phe Glu Cys Arg Thr Glu
1               5

<210> SEQ ID NO 1946
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1946

Tyr Phe Glu Cys Arg Trp Glu
1               5

<210> SEQ ID NO 1947
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 1947

Tyr Phe Glu Cys Arg Asn Glu
1               5

<210> SEQ ID NO 1948
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1948

Tyr Phe Glu Cys Arg Asp Glu
1               5

<210> SEQ ID NO 1949
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1949

Tyr Phe His Cys Arg Asn Glu
1               5

<210> SEQ ID NO 1950
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1950

Tyr Phe His Cys Arg Asp Glu
1               5

<210> SEQ ID NO 1951
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1951

Tyr Phe His Cys Arg Gln Glu
1               5

<210> SEQ ID NO 1952
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1952

Tyr Phe His Cys Arg Glu Glu
1               5

<210> SEQ ID NO 1953
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 1953

Tyr Phe His Cys Arg Leu Glu
1               5

<210> SEQ ID NO 1954
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1954

Tyr Phe His Cys Arg Met Glu
1               5

<210> SEQ ID NO 1955
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1955

Tyr Phe His Cys Arg Ser Glu
1               5

<210> SEQ ID NO 1956
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1956

Tyr Phe His Cys Arg Thr Glu
1               5

<210> SEQ ID NO 1957
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1957

Tyr Phe His Cys Arg Trp Glu
1               5

<210> SEQ ID NO 1958
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1958

Tyr Phe Ile Cys Arg Asn Glu
1               5

<210> SEQ ID NO 1959
<211> LENGTH: 7
<212> TYPE: PRT
<213> ORGANISM: Artificial Sequence
<220> FEATURE:

<223> OTHER INFORMATION: Synthetic Construct

<400> SEQUENCE: 1959

Tyr Phe Ile Cys Arg Asp Glu
1               5

<210> SEQ ID NO 1960
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1960

Tyr Phe Ile Cys Arg Gln Glu
1               5

<210> SEQ ID NO 1961
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1961

Tyr Phe Ile Cys Arg Glu Glu
1               5

<210> SEQ ID NO 1962
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1962

Tyr Phe Ile Cys Arg Leu Glu
1               5

<210> SEQ ID NO 1963
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1963

Tyr Phe Ile Cys Arg Met Glu
1               5

<210> SEQ ID NO 1964
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1964

Tyr Phe Ile Cys Arg Ser Glu
1               5

<210> SEQ ID NO 1965
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 1965

Tyr Phe Ile Cys Arg Thr Glu
1               5

<210> SEQ ID NO 1966
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1966

Tyr Phe Ile Cys Arg Trp Glu
1               5

<210> SEQ ID NO 1967
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1967

Tyr Phe Leu Cys Arg Asn Glu
1               5

<210> SEQ ID NO 1968
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1968

Tyr Phe Leu Cys Arg Asp Glu
1               5

<210> SEQ ID NO 1969
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1969

Tyr Phe Leu Cys Arg Gln Glu
1               5

<210> SEQ ID NO 1970
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1970

Tyr Phe Leu Cys Arg Glu Glu
1               5

<210> SEQ ID NO 1971
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 1971

Tyr Phe Leu Cys Arg Leu Glu
1               5

<210> SEQ ID NO 1972
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1972

Tyr Phe Leu Cys Arg Met Glu
1               5

<210> SEQ ID NO 1973
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1973

Tyr Phe Leu Cys Arg Ser Glu
1               5

<210> SEQ ID NO 1974
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1974

Tyr Phe Leu Cys Arg Thr Glu
1               5

<210> SEQ ID NO 1975
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1975

Tyr Phe Leu Cys Arg Trp Glu
1               5

<210> SEQ ID NO 1976
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1976

Tyr Phe Lys Cys Arg Asn Glu
1               5

<210> SEQ ID NO 1977
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1977

Tyr Phe Lys Cys Arg Asp Glu
1               5

<210> SEQ ID NO 1978
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1978

Tyr Phe Lys Cys Arg Gln Glu
1               5

<210> SEQ ID NO 1979
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1979

Tyr Phe Lys Cys Arg Glu Glu
1               5

<210> SEQ ID NO 1980
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1980

Tyr Phe Lys Cys Arg Leu Glu
1               5

<210> SEQ ID NO 1981
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1981

Tyr Phe Lys Cys Arg Met Glu
1               5

<210> SEQ ID NO 1982
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1982

Tyr Phe Lys Cys Arg Ser Glu
1               5

<210> SEQ ID NO 1983
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1983

```
Tyr Phe Lys Cys Arg Thr Glu
1               5

<210> SEQ ID NO 1984
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1984

Tyr Phe Lys Cys Arg Trp Glu
1               5

<210> SEQ ID NO 1985
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1985

Tyr Phe Met Cys Arg Asn Glu
1               5

<210> SEQ ID NO 1986
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1986

Tyr Phe Met Cys Arg Asp Glu
1               5

<210> SEQ ID NO 1987
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1987

Tyr Phe Met Cys Arg Gln Glu
1               5

<210> SEQ ID NO 1988
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1988

Tyr Phe Met Cys Arg Glu Glu
1               5

<210> SEQ ID NO 1989
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1989

Tyr Phe Met Cys Arg Leu Glu
```

1               5

<210> SEQ ID NO 1990
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1990

Tyr Phe Met Cys Arg Met Glu
1               5

<210> SEQ ID NO 1991
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1991

Tyr Phe Met Cys Arg Ser Glu
1               5

<210> SEQ ID NO 1992
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1992

Tyr Phe Met Cys Arg Thr Glu
1               5

<210> SEQ ID NO 1993
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1993

Tyr Phe Met Cys Arg Trp Glu
1               5

<210> SEQ ID NO 1994
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1994

Tyr Phe Pro Cys Arg Asn Glu
1               5

<210> SEQ ID NO 1995
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1995

Tyr Phe Pro Cys Arg Asp Glu
1               5

```
<210> SEQ ID NO 1996
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1996

Tyr Phe Pro Cys Arg Gln Glu
1               5

<210> SEQ ID NO 1997
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1997

Tyr Phe Pro Cys Arg Glu Glu
1               5

<210> SEQ ID NO 1998
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1998

Tyr Phe Pro Cys Arg Leu Glu
1               5

<210> SEQ ID NO 1999
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1999

Tyr Phe Pro Cys Arg Met Glu
1               5

<210> SEQ ID NO 2000
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2000

Tyr Phe Pro Cys Arg Ser Glu
1               5

<210> SEQ ID NO 2001
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2001

Tyr Phe Pro Cys Arg Thr Glu
1               5
```

```
<210> SEQ ID NO 2002
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2002

Tyr Phe Pro Cys Arg Trp Glu
1               5

<210> SEQ ID NO 2003
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2003

Tyr Phe Ser Cys Arg Gln Glu
1               5

<210> SEQ ID NO 2004
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2004

Tyr Phe Ser Cys Arg Glu Glu
1               5

<210> SEQ ID NO 2005
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2005

Tyr Phe Ser Cys Arg Leu Glu
1               5

<210> SEQ ID NO 2006
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2006

Tyr Phe Ser Cys Arg Met Glu
1               5

<210> SEQ ID NO 2007
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2007

Tyr Phe Ser Cys Arg Ser Glu
1               5
```

```
<210> SEQ ID NO 2008
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2008

Tyr Phe Ser Cys Arg Thr Glu
1               5

<210> SEQ ID NO 2009
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2009

Tyr Phe Ser Cys Arg Trp Glu
1               5

<210> SEQ ID NO 2010
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2010

Tyr Phe Ser Cys Arg Asn Glu
1               5

<210> SEQ ID NO 2011
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2011

Tyr Phe Ser Cys Arg Asp Glu
1               5

<210> SEQ ID NO 2012
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2012

Tyr Phe Thr Cys Arg Asn Glu
1               5

<210> SEQ ID NO 2013
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2013

Tyr Phe Thr Cys Arg Asp Glu
1               5

<210> SEQ ID NO 2014
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2014

Tyr Phe Thr Cys Arg Gln Glu
1               5

<210> SEQ ID NO 2015
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2015

Tyr Phe Thr Cys Arg Glu Glu
1               5

<210> SEQ ID NO 2016
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2016

Tyr Phe Thr Cys Arg Leu Glu
1               5

<210> SEQ ID NO 2017
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2017

Tyr Phe Thr Cys Arg Met Glu
1               5

<210> SEQ ID NO 2018
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2018

Tyr Phe Thr Cys Arg Ser Glu
1               5

<210> SEQ ID NO 2019
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2019

Tyr Phe Thr Cys Arg Thr Glu
1               5

<210> SEQ ID NO 2020
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 2020

Tyr Phe Thr Cys Arg Trp Glu
1               5

<210> SEQ ID NO 2021
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2021

Tyr Phe Tyr Cys Arg Asn Glu
1               5

<210> SEQ ID NO 2022
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2022

Tyr Phe Tyr Cys Arg Asp Glu
1               5

<210> SEQ ID NO 2023
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2023

Tyr Phe Tyr Cys Arg Gln Glu
1               5

<210> SEQ ID NO 2024
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2024

Tyr Phe Tyr Cys Arg Glu Glu
1               5

<210> SEQ ID NO 2025
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2025

Tyr Phe Tyr Cys Arg Leu Glu
1               5

<210> SEQ ID NO 2026
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 2026

Tyr Phe Tyr Cys Arg Met Glu
1               5

<210> SEQ ID NO 2027
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2027

Tyr Phe Tyr Cys Arg Ser Glu
1               5

<210> SEQ ID NO 2028
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2028

Tyr Phe Tyr Cys Arg Thr Glu
1               5

<210> SEQ ID NO 2029
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2029

Tyr Phe Tyr Cys Arg Trp Glu
1               5

<210> SEQ ID NO 2030
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2030

Tyr Phe Val Cys Arg Asn Glu
1               5

<210> SEQ ID NO 2031
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2031

Tyr Phe Val Cys Arg Asp Glu
1               5

<210> SEQ ID NO 2032
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 2032

Tyr Phe Val Cys Arg Gln Glu
1               5

<210> SEQ ID NO 2033
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2033

Tyr Phe Val Cys Arg Glu Glu
1               5

<210> SEQ ID NO 2034
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2034

Tyr Phe Val Cys Arg Leu Glu
1               5

<210> SEQ ID NO 2035
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2035

Tyr Phe Val Cys Arg Met Glu
1               5

<210> SEQ ID NO 2036
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2036

Tyr Phe Val Cys Arg Ser Glu
1               5

<210> SEQ ID NO 2037
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2037

Tyr Phe Val Cys Arg Thr Glu
1               5

<210> SEQ ID NO 2038
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 2038

Tyr Phe Val Cys Arg Trp Glu
1               5

<210> SEQ ID NO 2039
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2039

His Ala Tyr Phe Cys Gln Arg
1               5

<210> SEQ ID NO 2040
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2040

His Ala Tyr Phe Cys His Arg
1               5

<210> SEQ ID NO 2041
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2041

His Ala Tyr Phe Cys Lys Arg
1               5

<210> SEQ ID NO 2042
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2042

His Ala Tyr Phe Cys Ser Arg
1               5

<210> SEQ ID NO 2043
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2043

His Ala Tyr Phe Cys Trp Arg
1               5

<210> SEQ ID NO 2044
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 2044

His Ala Tyr Phe Cys Tyr Arg
1               5

<210> SEQ ID NO 2045
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2045

His Arg Tyr Phe Cys Gln Arg
1               5

<210> SEQ ID NO 2046
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2046

His Arg Tyr Phe Cys His Arg
1               5

<210> SEQ ID NO 2047
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2047

His Arg Tyr Phe Cys Lys Arg
1               5

<210> SEQ ID NO 2048
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2048

His Arg Tyr Phe Cys Ser Arg
1               5

<210> SEQ ID NO 2049
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2049

His Arg Tyr Phe Cys Trp Arg
1               5

<210> SEQ ID NO 2050
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 2050

His Arg Tyr Phe Cys Tyr Arg
1               5

<210> SEQ ID NO 2051
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2051

His Asn Tyr Phe Cys Gln Arg
1               5

<210> SEQ ID NO 2052
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2052

His Asn Tyr Phe Cys His Arg
1               5

<210> SEQ ID NO 2053
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2053

His Asn Tyr Phe Cys Lys Arg
1               5

<210> SEQ ID NO 2054
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2054

His Asn Tyr Phe Cys Ser Arg
1               5

<210> SEQ ID NO 2055
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2055

His Asn Tyr Phe Cys Trp Arg
1               5

<210> SEQ ID NO 2056
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2056
```

His Asn Tyr Phe Cys Tyr Arg
1               5

<210> SEQ ID NO 2057
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2057

His Asp Tyr Phe Cys Gln Arg
1               5

<210> SEQ ID NO 2058
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2058

His Asp Tyr Phe Cys His Arg
1               5

<210> SEQ ID NO 2059
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2059

His Asp Tyr Phe Cys Lys Arg
1               5

<210> SEQ ID NO 2060
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2060

His Asp Tyr Phe Cys Ser Arg
1               5

<210> SEQ ID NO 2061
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2061

His Asp Tyr Phe Cys Trp Arg
1               5

<210> SEQ ID NO 2062
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2062

His Asp Tyr Phe Cys Tyr Arg
1               5

<210> SEQ ID NO 2063
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2063

His Ile Tyr Phe Cys Gln Arg
1               5

<210> SEQ ID NO 2064
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2064

His Ile Tyr Phe Cys His Arg
1               5

<210> SEQ ID NO 2065
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2065

His Ile Tyr Phe Cys Lys Arg
1               5

<210> SEQ ID NO 2066
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2066

His Ile Tyr Phe Cys Ser Arg
1               5

<210> SEQ ID NO 2067
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2067

His Ile Tyr Phe Cys Trp Arg
1               5

<210> SEQ ID NO 2068
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2068

His Ile Tyr Phe Cys Tyr Arg

```
1               5

<210> SEQ ID NO 2069
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2069

His Pro Tyr Phe Cys Gln Arg
1               5

<210> SEQ ID NO 2070
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2070

His Pro Tyr Phe Cys His Arg
1               5

<210> SEQ ID NO 2071
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2071

His Pro Tyr Phe Cys Lys Arg
1               5

<210> SEQ ID NO 2072
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2072

His Pro Tyr Phe Cys Ser Arg
1               5

<210> SEQ ID NO 2073
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2073

His Pro Tyr Phe Cys Trp Arg
1               5

<210> SEQ ID NO 2074
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2074

His Pro Tyr Phe Cys Tyr Arg
1               5
```

```
<210> SEQ ID NO 2075
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2075

His Thr Tyr Phe Cys Gln Arg
1               5

<210> SEQ ID NO 2076
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2076

His Thr Tyr Phe Cys His Arg
1               5

<210> SEQ ID NO 2077
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2077

His Thr Tyr Phe Cys Lys Arg
1               5

<210> SEQ ID NO 2078
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2078

His Thr Tyr Phe Cys Ser Arg
1               5

<210> SEQ ID NO 2079
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2079

His Thr Tyr Phe Cys Trp Arg
1               5

<210> SEQ ID NO 2080
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2080

His Thr Tyr Phe Cys Tyr Arg
1               5
```

```
<210> SEQ ID NO 2081
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2081

His Trp Tyr Phe Cys Gln Arg
1               5

<210> SEQ ID NO 2082
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2082

His Trp Tyr Phe Cys His Arg
1               5

<210> SEQ ID NO 2083
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2083

His Trp Tyr Phe Cys Lys Arg
1               5

<210> SEQ ID NO 2084
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2084

His Trp Tyr Phe Cys Ser Arg
1               5

<210> SEQ ID NO 2085
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2085

His Trp Tyr Phe Cys Trp Arg
1               5

<210> SEQ ID NO 2086
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2086

His Trp Tyr Phe Cys Tyr Arg
1               5
```

```
<210> SEQ ID NO 2087
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2087

His Tyr Tyr Phe Cys Gln Arg
1               5

<210> SEQ ID NO 2088
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2088

His Tyr Tyr Phe Cys His Arg
1               5

<210> SEQ ID NO 2089
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2089

His Tyr Tyr Phe Cys Lys Arg
1               5

<210> SEQ ID NO 2090
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2090

His Tyr Tyr Phe Cys Ser Arg
1               5

<210> SEQ ID NO 2091
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2091

His Tyr Tyr Phe Cys Trp Arg
1               5

<210> SEQ ID NO 2092
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2092

His Tyr Tyr Phe Cys Tyr Arg
1               5

<210> SEQ ID NO 2093
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2093

His Ala Tyr Phe Cys Ala Lys
1               5

<210> SEQ ID NO 2094
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2094

His Ala Tyr Phe Cys Arg Lys
1               5

<210> SEQ ID NO 2095
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2095

His Ala Tyr Phe Cys Gln Lys
1               5

<210> SEQ ID NO 2096
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2096

His Ala Tyr Phe Cys His Lys
1               5

<210> SEQ ID NO 2097
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2097

His Ala Tyr Phe Cys Lys Lys
1               5

<210> SEQ ID NO 2098
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2098

His Ala Tyr Phe Cys Phe Lys
1               5

<210> SEQ ID NO 2099
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 2099

His Ala Tyr Phe Cys Trp Lys
 1               5

<210> SEQ ID NO 2100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2100

His Ala Tyr Phe Cys Tyr Lys
 1               5

<210> SEQ ID NO 2101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2101

His Ala Tyr Phe Cys Val Lys
 1               5

<210> SEQ ID NO 2102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2102

His Arg Tyr Phe Cys Ala Lys
 1               5

<210> SEQ ID NO 2103
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2103

His Arg Tyr Phe Cys Arg Lys
 1               5

<210> SEQ ID NO 2104
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2104

His Arg Tyr Phe Cys Gln Lys
 1               5

<210> SEQ ID NO 2105
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 2105

His Arg Tyr Phe Cys His Lys
1               5

<210> SEQ ID NO 2106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2106

His Arg Tyr Phe Cys Lys Lys
1               5

<210> SEQ ID NO 2107
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2107

His Arg Tyr Phe Cys Phe Lys
1               5

<210> SEQ ID NO 2108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2108

His Arg Tyr Phe Cys Trp Lys
1               5

<210> SEQ ID NO 2109
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2109

His Arg Tyr Phe Cys Tyr Lys
1               5

<210> SEQ ID NO 2110
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2110

His Arg Tyr Phe Cys Val Lys
1               5

<210> SEQ ID NO 2111
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 2111

His Asn Tyr Phe Cys Ala Lys
1               5

<210> SEQ ID NO 2112
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2112

His Asn Tyr Phe Cys Arg Lys
1               5

<210> SEQ ID NO 2113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2113

His Asn Tyr Phe Cys Gln Lys
1               5

<210> SEQ ID NO 2114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2114

His Asn Tyr Phe Cys His Lys
1               5

<210> SEQ ID NO 2115
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2115

His Asn Tyr Phe Cys Lys Lys
1               5

<210> SEQ ID NO 2116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2116

His Asn Tyr Phe Cys Phe Lys
1               5

<210> SEQ ID NO 2117
<211> LENGTH: 7
<212> TYPE: PRT
<213> ORGANISM: Artificial Sequence
<220> FEATURE:

<223> OTHER INFORMATION: Synthetic Construct

<400> SEQUENCE: 2117

His Asn Tyr Phe Cys Trp Lys
1               5

<210> SEQ ID NO 2118
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2118

His Asn Tyr Phe Cys Tyr Lys
1               5

<210> SEQ ID NO 2119
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2119

His Asn Tyr Phe Cys Val Lys
1               5

<210> SEQ ID NO 2120
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2120

His Asp Tyr Phe Cys Ala Lys
1               5

<210> SEQ ID NO 2121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2121

His Asp Tyr Phe Cys Arg Lys
1               5

<210> SEQ ID NO 2122
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2122

His Asp Tyr Phe Cys Gln Lys
1               5

<210> SEQ ID NO 2123
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 2123

His Asp Tyr Phe Cys His Lys
1               5

<210> SEQ ID NO 2124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2124

His Asp Tyr Phe Cys Lys Lys
1               5

<210> SEQ ID NO 2125
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2125

His Asp Tyr Phe Cys Phe Lys
1               5

<210> SEQ ID NO 2126
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2126

His Asp Tyr Phe Cys Trp Lys
1               5

<210> SEQ ID NO 2127
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2127

His Asp Tyr Phe Cys Tyr Lys
1               5

<210> SEQ ID NO 2128
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2128

His Asp Tyr Phe Cys Val Lys
1               5

<210> SEQ ID NO 2129
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 2129

His Ile Tyr Phe Cys Gln Lys
1               5

<210> SEQ ID NO 2130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2130

His Ile Tyr Phe Cys His Lys
1               5

<210> SEQ ID NO 2131
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2131

His Ile Tyr Phe Cys Lys Lys
1               5

<210> SEQ ID NO 2132
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2132

His Ile Tyr Phe Cys Phe Lys
1               5

<210> SEQ ID NO 2133
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2133

His Ile Tyr Phe Cys Trp Lys
1               5

<210> SEQ ID NO 2134
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2134

His Ile Tyr Phe Cys Tyr Lys
1               5

<210> SEQ ID NO 2135
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2135
```

```
His Ile Tyr Phe Cys Val Lys
1               5

<210> SEQ ID NO 2136
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2136

His Ile Tyr Phe Cys Ala Lys
1               5

<210> SEQ ID NO 2137
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2137

His Ile Tyr Phe Cys Arg Lys
1               5

<210> SEQ ID NO 2138
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2138

His Pro Tyr Phe Cys Ala Lys
1               5

<210> SEQ ID NO 2139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2139

His Pro Tyr Phe Cys Arg Lys
1               5

<210> SEQ ID NO 2140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2140

His Pro Tyr Phe Cys Gln Lys
1               5

<210> SEQ ID NO 2141
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2141
```

His Pro Tyr Phe Cys His Lys
1               5

<210> SEQ ID NO 2142
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2142

His Pro Tyr Phe Cys Lys Lys
1               5

<210> SEQ ID NO 2143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2143

His Pro Tyr Phe Cys Phe Lys
1               5

<210> SEQ ID NO 2144
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2144

His Pro Tyr Phe Cys Trp Lys
1               5

<210> SEQ ID NO 2145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2145

His Pro Tyr Phe Cys Tyr Lys
1               5

<210> SEQ ID NO 2146
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2146

His Pro Tyr Phe Cys Val Lys
1               5

<210> SEQ ID NO 2147
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2147

His Thr Tyr Phe Cys Ala Lys 1               5

<210> SEQ ID NO 2148
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2148

His Thr Tyr Phe Cys Arg Lys
1               5

<210> SEQ ID NO 2149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2149

His Thr Tyr Phe Cys Gln Lys
1               5

<210> SEQ ID NO 2150
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2150

His Thr Tyr Phe Cys His Lys
1               5

<210> SEQ ID NO 2151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2151

His Thr Tyr Phe Cys Lys Lys
1               5

<210> SEQ ID NO 2152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2152

His Thr Tyr Phe Cys Phe Lys
1               5

<210> SEQ ID NO 2153
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2153

His Thr Tyr Phe Cys Trp Lys
1               5

```
<210> SEQ ID NO 2154
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2154

His Thr Tyr Phe Cys Tyr Lys
1               5

<210> SEQ ID NO 2155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2155

His Thr Tyr Phe Cys Val Lys
1               5

<210> SEQ ID NO 2156
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2156

His Trp Tyr Phe Cys Ala Lys
1               5

<210> SEQ ID NO 2157
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2157

His Trp Tyr Phe Cys Arg Lys
1               5

<210> SEQ ID NO 2158
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2158

His Trp Tyr Phe Cys Gln Lys
1               5

<210> SEQ ID NO 2159
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2159

His Trp Tyr Phe Cys His Lys
1               5
```

<210> SEQ ID NO 2160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2160

His Trp Tyr Phe Cys Lys Lys
1               5

<210> SEQ ID NO 2161
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2161

His Trp Tyr Phe Cys Phe Lys
1               5

<210> SEQ ID NO 2162
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2162

His Trp Thr Phe Cys Trp Lys
1               5

<210> SEQ ID NO 2163
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2163

His Trp Tyr Phe Cys Tyr Lys
1               5

<210> SEQ ID NO 2164
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2164

His Trp Tyr Phe Cys Val Lys
1               5

<210> SEQ ID NO 2165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2165

His Tyr Tyr Phe Cys Ala Lys
1               5

<210> SEQ ID NO 2166
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2166

His Tyr Tyr Phe Cys Arg Lys
1               5

<210> SEQ ID NO 2167
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2167

His Tyr Tyr Phe Cys Gln Lys
1               5

<210> SEQ ID NO 2168
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2168

His Tyr Tyr Phe Cys His Lys
1               5

<210> SEQ ID NO 2169
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2169

His Tyr Tyr Phe Cys Lys Lys
1               5

<210> SEQ ID NO 2170
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2170

His Tyr Tyr Phe Cys Phe Lys
1               5

<210> SEQ ID NO 2171
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2171

His Tyr Thr Phe Cys Trp Lys
1               5

<210> SEQ ID NO 2172

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2172

His Tyr Tyr Phe Cys Tyr Lys
1               5

<210> SEQ ID NO 2173
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2173

His Tyr Tyr Phe Cys Val Lys
1               5
```

METHOD FOR CONSTRUCTING A NOVEL AFFINITY PEPTIDE LIBRARY FOR BINDING IMMUNOGLOBULIN G BASED ON A PROTEIN AFFINITY MODEL OF PROTEIN A

TECHNICAL FIELD OF THE INVENTION

The present invention relates to biomimetic design of affinity peptide ligands for target protein using molecular simulation methods, and the purification of target protein by affinity chromatography. The invention belongs to the field of in silico modeling and protein purification of biotechnology.

BACKGROUND OF THE INVENTION

Antibodies (immunoglobulin, Ig) exist in blood and interstitial fluid of animals, which belong to a kind of glycoprotein produced by B lymphocytes in immune response to antigens, Antibodies are widely used in biological studies and clinic treatment on account of their high affinity for antigens. Especially under gradual maturity of genetic technology and clone technology, monoclonal antibodies (mAbs) have become effective therapeutics for inflammation, tumor, and infectious diseases. Up to now, there're approximately 20 mAbs that have been approved by FDA and at least 300 are under research and development. The output value of mAb-based drugs had reached 20.6 billion dollars in 2006. The increasing significance of antibodies in medical treatment calls for an urgent need of an efficient, stable, and low-cost manufacturing technique. Due to the complexity of antibody expression and high-quality standard required for pharmaceutical antibodies, antibody purification has become a critical step in the whole production process. IgG is the main component of Igs in blood serum, accounting for 75% of the total Igs, and also has the highest market demand among all Igs.

Antibody purification is often conducted by multi-steps including salting-out, gel-filtration chromatography, hydrophobic interaction chromatography, and ion-exchange chromatography and affinity chromatography. The feature of efficient and specific purification of target protein has made affinity chromatography into one of the most commonly used chromatographic methods in later period of antibody purification. Affinity chromatography makes use of the affinity ligand that specifically and reversibly binds the target molecule thus to separate it from complicated biological samples. It has the advantage of high selectivity and high purification efficiency. The purification performance of affinity chromatography depends on the affinity between the ligand and the target molecule. Therefore, the exploitation of suitable affinity ligand targeting specific molecule is the priority of building an affinity chromatographic system.

*Staphylococal* Protein A (SpA), protein G, and protein L have been widely used as affinity ligands for producing high-purity antibodies. Such ligands possess high selectivity, nonetheless need harsh elution condition, which tends to denature target proteins and causes ligands to fall off, leading to a low adsorption capacity. Moreover, protein ligands are difficult to prepare, costly, and are prone to lose some activity upon immobilization. These disadvantages have limited the application of the above protein ligands.

The research into affinity peptide ligands began with Geysen's study of synthetic peptide library in 1986, who proposed that the short peptide containing key residues could simulate the protein determinant. And in most cases, the non-covalent interactions between a few of key residues and the target molecule constitute the main interaction force for the complex binding. The two viewpoints have laid the theoretical basis for affinity peptide ligands. Firstly, peptide ligands are usually comprised of a few amino acids and therefore have little chance of causing immunogenic responses in use. Secondly, peptide ligands have a small molecular size. So even if they fall off from the stationary phase and mix with the products, it is easy to remove them from the end-products. Finally, the peptide ligands interact with target protein in mild conditions, which can make it easier to control the separation conditions and avoid the denaturation of target proteins. Compared with the high affinity ligands such as protein ligands, peptide ligands also exhibit sufficient affinity for binding target proteins. Besides, the conformation and physicochemical properties of peptide ligands are more stable than those of protein ligands, and thus the ligands can sustain harsh acid or base elution and regeneration conditions during the separation process, realizing the large-scale aseptic manufacturing that meets GMP requirements. In recent years, some peptide ligands with great purification performance for antibodies have sprung up, such as TG19318, Peptide H, Mabsorbent A1P and A2P, 8/7, and linear peptide ligand (HWRGWV etc.).

Although affinity peptide ligands have such many advantages, there are only a limited number of peptides that have affinity for specific target proteins in nature. In addition, although the above-mentioned micromolecule ligands have a huge superiority in antibody purification, they have some deficiencies compared with SpA affinity resin, like weak specificity and affinity, etc. Therefore, research in screening and designing ligands for affinity chromatography is vital. The question about how to choose proper peptides as affinity ligands and how to improve the affinity and selectivity of the peptide ligands is crucial in the application of affinity chromatography. The present screening and designing methods are mainly divided into two kinds of approaches, namely experimental screening and rational design. Experimental screening is based on the combinatorial library technology to conduct high-throughput screening. According to the different ways of constructing peptide library, the screening methods for affinity ligands are mainly divided into combinatorial chemistry synthetic peptide library technology, such as TG19318/D-TG19318, Peptide H, Mabsorbent A1P and A2P, and 8/7 mentioned above; phage display peptide library technology, such as HWRGWV, HYFKFD, and HFRRHL; and ribosome display peptide library technology. Rational design is mainly based on the structure and properties of the target protein or the known ligands to design new ligands. As the computer technique, computational chemistry, and medicinal chemistry develop, the design of affinity ligands has entered the rational design phase dominated by computer aided design. The various virtual screening and rational design methods of computer aided ligand design include molecular docking, 3D-QSAR, pharmacophore model, molecular dynamics (MD) simulation, and de novo design, etc.

Molecular docking involves two molecules recognizing each other through geometric matching and energy matching. Molecular docking is a calculation process in which the ligand is put on the binding site of the target protein, and the binding strength is evaluated via the criteria of geometric complementarity, energy complementarity, and chemical environment complementarity. Meanwhile, the best binding conformation can be found. Since molecular docking has considered the interaction between the target protein and the ligand, so in principle, molecular docking is a direct design method on the basis of the receptor. In recent years, as the protein crystal structure data grows rapidly and the small molecule databases updates constantly, molecular docking has become the most important structure-based design method. The common softwares include DOCK, Autodock, and FlexX, etc.

Molecular dynamics (MD) simulation is a kind of molecular simulation method on the basis of Newtonian mechanics. It has been used for studying the particle movement in many-particle system. The basic procedure in MD simulation can be divided into four steps: (1) initialization; (2) calculation of atomic force; (3) updating the atom coordinates and speed; (4) analysis of trajectory. According to the atom coordinates, speed, and force of the last step, the coordinates and speed of next step can be obtained. Steps (2) and (3) are repeated to obtain the change of physicochemical properties in the system with simulation time. The softwares commonly used in MD simulation include GROMACS, NAMD, AMBER, and CHARMM, etc. Based on the analysis of MD simulation trajectories, we can study the physicochemical properties of the simulation system, such as conformation, energy, kinetic property, and the interaction force between the ligand and the target protein, etc.

Combination of a few of rational design methods and proper combination strategy can reduce the cost and realize higher-accuracy ligand design. In early phase, some methods of rapid speed but limited accuracy can be used to enrich potential candidates, like molecular docking. Then, some methods with more calculation but also more accuracy can be adopted to further select the best ligand molecules, like MD simulation. In the final phase, experiments which are time-consuming and costly are used to conduct the last verification.

SUMMARY OF THE INVENTION

The purpose of the invention is to provide a method of constructing a novel affinity ligand peptide library of IgG on the basis of Protein A affinity model, and the application of the design method. In this invention, this simulation design method is firstly adopted to identify affinity peptide ligands for antibodies, and is verified to be feasible.

In the invention, the novel affinity ligand peptide library of IgG is constructed on the basis of Protein A affinity model, and the basis is six hot spots of SpA: F132, Y133, H137, E143, R146, and K154. In order to immobilize the ligands, cysteine is added to the middle region of the peptides. Thus eight models for the peptide library are obtained:

```
FYCHXXXE, FYXHCXXE, FYCHXXR, FYXHCXR, FYXCRXE,
YFXCRXE, HXYFCXR,
and
HXYFCXK;
```

The 'X' denotes the common 19 kinds of amino acids except Cys.

The application of the design method is using amino acid location method to determine the kinds of amino acids ('X') in the peptide models on the basis of above peptide library, which are summarized in the following table:

| Peptide models & Number | Amino acids 'X' |
|---|---|
| FYCHXXXE (990) | X_1: A, R, N, D, Q, E, H, I, L, K, M, T, W, Y, V (15)<br>X_2: A, Q, E, I, L, K (6)<br>X_3: A, R, D, Q, E, L, K, M, P, S, T (11) |
| FYXHCXXE (594) | X_1: A, R, N, D, I, P, T, W, Y (9)<br>X_2: A, Q, E, I, L, K (6)<br>X_3: A, R, D, Q, E, L, K, M, P, S, T (11) |
| FYCHXXR (112) | X_1: N, D, Q, E, H, I, K, M, F, P, T, W, Y, V (14)<br>X_2: Q, E, H, I, K, M, F, W (8) |
| FYXHCXR (72) | X_1: A, R, N, D, I, P, T, W, Y (9)<br>X_2: Q, E, H, I, K, M, F, W (8) |
| FYXCRXE (153) | X_1: A, R, N, D, Q, E, G, H, I, L, K, M, F, P, W, Y, V (17)<br>X_2: N, D, Q, E, L, M, S, T, W (9) |
| YFXCRXE (117) | X_1: N, D, E, H, I, L, K, M, P, S, T, Y, V (13)<br>X_2: N, D, Q, E, L, M, S, T, W (9) |
| HXYFCXR (54) | X_1: A, R, N, D, I, P, T, W, Y (9)<br>X_2: Q, H, K, S, W, Y (6) |
| HXYFCXK (81) | X_1: A, R, N, D, I, P, T, W, Y (9)<br>X_2: A, R, Q, H, K, F, W, Y, V (9) |

The detailed peptide sequences are listed in Table 5.

The peptide library is then screened by molecular docking, root-mean-square deviation (RMSD) comparison and rescreened by MD simulations to identify the peptide ligands of high affinity for the target protein. The peptide ligands that are predicted to have high affinity for human IgG (hIgG) are: FYWHCLDE, FYFCRWE, FYIHCLPE, FYYHCKKE, FYCHWALE, FYCHWQDE, FYCHTIDE, FYRHCQRE, FYCHHKTE, FYCHLQKE, FYCHRKAE, FYCHNQDE, FYCHRQEE, and FYNHCASE.

What needs to be stressed is that the overall 2173 peptides contained in the above peptide library are all likely to be affinity ligands of hIgG theoretically; the purpose of carrying out molecular docking screening and MD simulation rescreening is to enrich the peptides that have high affinity for hIgG, and effectively reduce the number of peptide candidates so as to feasibly validate their affinity using later experimental methods. The finally obtained 14 peptides bear the maximum probability of high affinity for hIgG. Although in silico modeling has constantly developed towards maturity so far, the prediction of the intermolecular interaction has not yet been completely in line with the actual situation, resulting in some deficiencies that molecular simulation softwares have revealed unavoidably (e.g., the different softwares or parameters adopted may lead to different results). And therefore the prediction could just approach the actual situation as far as possible. There may exist two cases when molecular simulation is utilized for screening peptides: first, the hit rate of peptides that have high affinity for hIgG is increasing with screening times; second, the chance of missing and excluding affinity peptide ligands for hIgG is also increasing with screening times. As a result, it can't be ruled out that the other 2159 peptides are also likely affinity peptide ligands of hIgG.

The method of this invention obtains affinity peptide ligands of hIgG utilizing molecular simulation and experimental measures, and the method is listed as the 1-5 steps below:

1. Through free energy calculation and decomposition method on the basis of Molecular Mechanics—Poisson-Boltzmann surface area (MM/PBSA) method, the hot spots of the SpA-hIgG1 complex (FIG. 1) as well as SpA simplified affinity binding model (FIG. 2) are identified. First, MM/PBSA analysis is used to calculate the absolute binding free energies between SpA and hIgG1, and then free energy decomposition method coupled with MM/PBSA is adopted to study the molecular mechanism of high affinity between SpA and hIgG1, and the contribution of the residues in the complex binding surface to the binding free energy. According to the free energy contribution of each residue and pair residues interaction analysis, the hot spots of the SpA-hIgG1 complex are identified.

2. According to the conformations and the relative positions of the six discrete hot spots of SpA affinity model, the lengths of designed peptide sequences are calculated and the inserted amino acids are identified through Autodock Vina (Vina for short) molecular docking software; a cysteine is added to the middle region of the peptide so as to conveniently and directionally immobilize the peptide onto the chromatography resin-Thiopropyl Sepharose 6B, thus sufficient freedom could be provided to the hot spots at two ends of the peptide, which could play the critical role of having affinity interaction with hIgG freely. And the affinity could not be weakened after peptide immobilization. At last, a peptide library comprising a series of heptapeptides and octapeptides is acquired.

Detailed operations are depicted as follows: first, the 3D coordinate files of Fc fragment and SpA B domain are derived form the crystal structure of hIgG1-SpA complex (PDB ID: 1FC2); second, the coordinate structures of the six hot spots (F132, Y133, H137, E143, R146, and K154) are obtained from the coordinate files of SpA B domain, and the distance between the C and N terminal of two hot spots are calculated. Thereafter, according to the principle of amino acid insertion, the number of residues that should be inserted into between the hot spots is calculated and the peptide models are identified (Table 1); then one of the middle residues is determined to be Cys (Table 2); after that, the corresponding Fc region located between every two hot spots is chosen and covered in the grid box in Vina docking. Then each of the 19 common amino acids except Cys is docked to the Fc region contained in the grid box sequentially, and the top 20 conformations with highest docking scores are selected for each amino acid. The screening criteria for amino acid selection is listed as below: first, the conformation should be proper, namely the C/N terminal of the amino acid conformation should be located end to end with the N/C terminal of the nearby hot spots, thus they could be linked up to form peptide bonds. Second, the affinity binding energy should be less than −2.0 kcal/mol. At last, we identify all the unknown amino acide 'X's in the peptide models (Table 3). A perl script invoking CHARMM is used to build the peptide library, which comprises 2173 peptides (Table 5). Every peptide contains four hot spots.

3. After the peptide library is constructed, Vina and Rosetta FlexPepDock (FlexPepDock) are chosen for docking each peptide of the entire peptide library to the Fc fragment of hIgG1 successively, and the peptides of high binding affinity for Fc are identified according to the score rankings. It should be noted that, first, the score criterion is artificially defined according to the score distribution, which is a value that is selected by empirical experiences and most likely to enrich effective candidates; second, the purpose of using molecular docking software for library screening is to enrich the peptides that have affinity for hIgG and remove the molecules that have less possibility, which could save the operating costs of the follow-up confirmatory experiments, rather than to regard the peptides that do not pass the criteria as non-affinity ligand of hIgG and therefore get rid of them. These peptides just do not meet the criteria set in this invention. Researchers can raise or lower the score criterion appropriately on the basis of practical needs. Although the number of candidates obtained from screening will change (raising or lowering the score criterion would correspondingly reduce or increase the number of candidates that would enter next round of screening; the latter would reduce the possibility of missing true affinity ligands, but on the other side, it would add complexity to the whole researching process. The best case is to find a balance point which will neither miss too many potential candidates nor fill the candidate library with too many ineffective molecules or those of weak effect), it is in line with the aim of this invention and also accords with the spirit. The Vina docking box covered exactly the binding region (consensus-binding site located between CH2 and CH3 domains) of Fc-SpA complex. After the box was fixed, the peptides from the library were docked to the Fc motif contained in the box sequentially. 754 peptides with binding free energy (i.e. rating score) less than −6.5 kcal/mol are selected. Herein it should be noted that the score criterion of less than −6.5 kcal/mol is set for the ligand selection, and the reason for choosing this criterion will be explained in detail in the following section. The root-mean-square deviation (RMSD) values between the hot spots in SpA and those corresponding in the 754 peptides obtained by docking are calculated sequentially by the auxiliary program g_rms provided by the GROMACS 4.5.3 simulation package. And herein the conformations of the hot spots in SpA and those corresponding in the peptides are compared. Encad all-atom force field is chosen, and the RMSD values of the hot spots excluding hydrogen atoms are calculated. The smaller the RMSD value, the more alike the two conformations of the corresponding hot spots are. The results show that the RMSD values are in the range of 0.2 to 0.6 nm, and 150 peptides with RMSD values less than 0.4 nm are selected for further study. What needs to be noted is that the RMSD criterion for screening peptide ligands can also be made appropriate changes according to practical conditions. In similar researching background or conditions, related researchers can refer to this invention and set a proper RMSD criterion, to keep a moderate number of candidates obtained from screening and meanwhile not miss too many potential molecules. The conformation of peptide-Fc complex derived from Vina docking is deemed as the initial conformation, and then the 150 peptides from previous docking and RMSD comparison are docked to Fc sequentially by FlexPepDock protocol. The docking parameters (FlexPepDock.flags) are:
pep_refine
use_input_sc
ex1
ex2aro
ignore_unrecognized_res
nstruct 1
out:suffix pepdock
lowres_preoptimize
scorefile flexpepdock.sc The FlexPepDock docking is performed twice to reduce the randomness of just one docking process. It is found that only a few peptides could not bind to Fc and the other majority could. The docking scores (interface energy score, I_sc) of the majority of peptides are in the range of −4 to −22 and most I_sc values are in the range of −14 to −16. The I_sc value of no more than −16 is selected as the screening criterion, thus it could be possible to avoid the waste of computing resource (considering that the next round of MD simulation rescreening could consume too much computing resource and the speed would be slow), and avoid missing too many potential candidates. Certainly related researchers can set a more proper I_sc value as screening criterion according to their own research conditions. There are 15 peptides with both I_sc values from two parallel dockings less than −16 and they are selected for further MD simulations.

4. MD simulations are performed for the 15 peptides selected from step three with Fc of hIgG1 to rescreen the peptide ligands. The aim is to obtain the peptides that can bind Fc stably during the simulation time scale, namely the putative ligands that may have high affinity for hIgG. The conformations of the peptide-hIgG1 complexes obtained from FlexPepDock docking are set as the initial conformations for MD simulation. MD simulations are performed using the GROMACS 4.5.3 package with GROMOS96 53a6 force field. The pdb coordinate structures of the 15 candidate peptides are transformed into gro structures which are specially used in GROMACS by pdb2gmx command; the peptide-protein complexes are put at the center of a rectangular water box by editconf command, of which the distance from the edge of the box is 0.9 nm at least; then genbox command is used to add water molecules to the simulation box and SPC216 water model is used; thereafter the grompp command is utilized to integrate the parameters marked in mdp files into structure and topology files, thus tpr files are produced. Meanwhile the genion command was used to add the corresponding kind and number of ions to balance the net charge of the system; after that, energy minimization is conducted to remove atom clashes and incorrect geometrical conformations in the system; next the mdrun command is used to carry out 100 ps of constrained kinetic equilibrium under NVT and NPT ensembles, successively, and at last, the 20 ns unconstrained MD simulation still utilizes mdrum command. Related technicians can change the parameters according to the practical conditions of their own researches to make the MD simulation suit specific and different researching conditions.

5. Selected peptides are synthesized and immobilized onto Thiopropyl Sepharose 6B chromatography gel to form the affinity gel, and then the prepared affinity gel is loaded into a column to perform affinity chromatography verification. Pulse injection of hIgG solution is investigated as well as the hIgG separation and electrophoretic conditions in human serum.

In this invention, free energy calculation and free energy decomposition method coupled with MM/PBSA are utilized to obtain the hot spots of Protein A that has high affinity for human IgG, and a SpA affinity binding model of hIgG is constructed on the basis of the hot spots. Then, amino acid location, insertion of a Cys into the middle region of the peptide, and molecular docking are conducted for building the peptide library; thereafter, molecular docking is used to screen and MD simulation is used to rescreen the peptide library, and a pool of peptide ligands of high affinity for IgG is obtained. We have identified two peptides that could effectively purify hIgG—FYWHCLDE and FYCHWALE. A series of experimental methods including affinity chromatography, SDS-PAGE, and UV-Vis spectrometer are conducted to investigate the IgG purification and related characterizations.

It should be noted that, all the 2173 peptides of the library may be affinity ligands of hIgG in theory. But due to the limitations of molecular simulations, it cannot fully simulate the actual situation and can just approach it as far as possible. Therefore experimental methods are needed to verify the results. Since time and resources were limited, the invention could not verify all the peptides through experimental methods. Only two peptides were randomly selected from the finally obtained 14 peptides to perform experimental characterizations. The main purpose is to explain how to use experimental methods to verify the effectiveness of the peptides as affinity ligands of hIgG rather than to indicate just the two peptides mentioned in the invention are effective. Researchers can verify other peptides of the library by the experimental methods used in this invention.

EMBODIMENTS OF THE INVENTION

Combined with the attached figures, the followings are the further description of the invention in detail. The implementation cases are to elucidate rather than confine the invention in any way.

EXAMPLE 1

Obtainment of the SpA Simplified Affinity Binding Model

First, MM/PBSA was used to calculate the absolute binding free energy of SpA-hIgG1 complex. Then, free energy decomposition method based on MM/PBSA was utilized to analyze the molecular mechanism of high affinity between SpA and hIgG1 as well as the contribution of residues on the binding surface of SpA-hIgG1 complex to the binding free energy. According to the free energy contribution of each residue and pair residues interaction analysis, the hot spots of the SpA-hIgG1 complex were identified. At last, SpA affinity binding model was constructed on the basis of the molecular mechanism and hot spots obtained from the above analyses.

Figure 1:
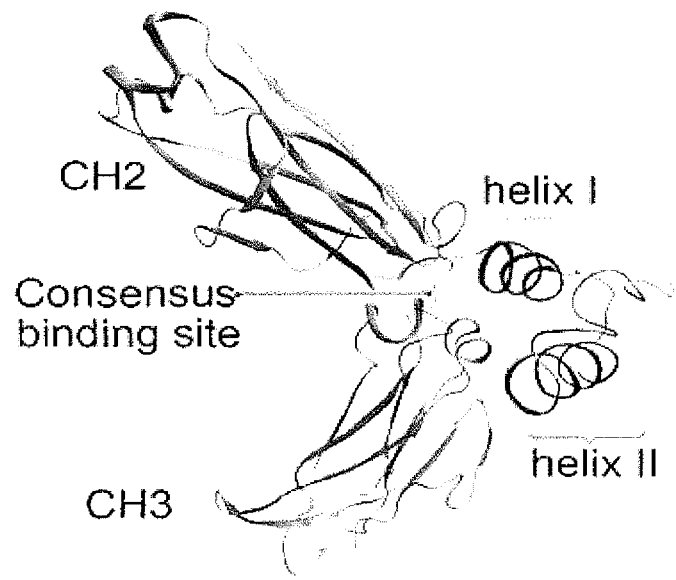
FIG. 1 illustrates the three-dimensional structure of Protein A-hIgG complex; two helices I and II are consisted in the B domain, and bind the hinge region located between CH2 and CH3 domains of Fc which is called "consensus-binding site (CBC)".

SpA-hIgG1 molecular system was investigated in MD simulations. The complex model contained a single heavy chain of the Fc fragment and the B domain of SpA. The structure of the SpA-hIgG1 complex was obtained from Protein Data Bank (PDB ID: 1FC2) (FIG. 1). All MD simulations were performed using CHARMM with the all-atom CHARMM27 force field. The SpA-hIgG1 complex was first solvated in a cuboid box (100×80×60 Å) using TIP3P water molecule model. The system was neutralized by adding Na$^+$ or Cl$^-$ as counterions. After energy minimization, the system was equilibrated for 200 ps using the NPT ensemble. Then, the production phase of the simulation was carried out for 15 ns using the NVT ensemble. The temperature of the system was set to 298K, using the Nose-Hoover method for keeping a constant temperature during the simulation process. Periodic boundary condition was used for all MD simulations. A 12 Å cutoff for nonbonded interactions was used, and the Particle Mesh Ewald method (PME) was used to handle long-range electrostatic interactions. The SHAKE method was applied to restrain covalent bonds involving all hydrogen atoms, which allowed use of a time step of 2 fs. A distance restraint was imposed on the two terminal residues of the Fc fragment to avoid the relative bending of the CH2 and CH3 domains, since the system only contained a single chain of the Fc fragment. Finally, uniform sampling was made with an interval of 40 ps from the last 3 ns of the equilibrium phase, and a total of 75 frames of conformations were acquired for later analysis.

The binding free energy ($\Delta G_{bind}$) for SpA-hIgG1 complex was calculated using the MM/PBSA method. It was estimated as the sum of the gas-phase energy ($\Delta G_{gas}$), the solvation energy ($\Delta G_{sol}$), and the entropic energy ($-TS$), according to $$\Delta G_{bind} = <\Delta G_{gas}> + <\Delta G_{sol}> - <T_\Delta S>$$

The brackets, <...>, indicate an average of an energy term along the MD simulation trajectory. T is the absolute temperature, and S is the solute entropy.

$G_{gas}$ contains an intermolecular electrostatic term ($G_{elec}$), a van derWaals (vdW) term ($G_{vdW}$), and an internal energy term ($G_{inter}$).

In this study, "the same trajectory method" was used in all analyses. So, the internal energy term ($\Delta G_{inter}$) is zero. Thus, for the contribution to the bind free energy, $\Delta G_{gas}$ is the sum of $\Delta G_{elec}$ and $\Delta G_{vdW}$:

$$\Delta G_{gas} = \Delta G_{elec} + \Delta G_{vdW}$$

The solvation energy is divided into the electrostatic salvation energy ($G_{PB}$) and the nonpolar solvation energy ($G_{np}$):

$$G_{sol} = G_{PB} + G_{np}$$

$G_{PB}$ was calculated by solving the linear Poisson-Boltzmann (PB) equation using the PBEQ module of the CHARMM program. The solute and solvent dielectric constants were set to 1 and 80 in all BP calculations, respectively. The ionic strength was set to zero. The solvent molecule radius was set to 1.4 Å. $G_{np}$, which could be considered as the sum of a solvent-solvent cavity term and a solute-solvent vdW term, was calculated according to $$G_{np} = \gamma \times SASA + b$$

The constants $\gamma$ and b were set to 0.00542 kcal/(mol·Å2) and 0.92 kcal/mol, respectively. SASA represents the solvent accessible surface area.

The entropy (S) can be decomposed into translational ($S_{trans}$), rotational ($S_{rot.}$), and vibrational ($S_{vib}$) entropies. These terms were calculated according to the statistical mechanics. $S_{trans}$ and $S_{rot.}$ were functions of the mass and moments of inertia of the molecule, respectively. The vibrational entropy ($S_{vib}$) was estimated by normal-mode analysis (NMA) using the VIBRAN module of the CHARMM program.

The free energy contribution of each residue can be divided into polar ($G_{polar}$) and nonpolar interactions ($G_{nonpolar}$).

Herein each part is the sum of two energy terms. In the following analysis, $G_{polar}$ is considered as the electrostatic interaction and $G_{nonpolar}$ as hydrophobic interaction. It is important to note that $G_{residue}$ only provides a decomposition of $G_{polar}$ and $G_{nonpolar}$ (i.e., it does not contain the contribution of the entropy). $G_{residue} = G_{polar} + G_{nonpolar}$, $G_{polar} = G_{elec} + G_{PB}$, $G_{nonpolar} = G_{vdW} G_{np}$. The electrostatic energy of each residue ($G_{polar}$) is the sum of the intermolecular electrostatic energy ($G_{elec}$) and the electrostatic solvation energy ($G_{PB}$). The linear PB equation allowed the decomposition of electrostatic solvation energy as contributions of each atom. The $G_{vdW}$ contribution of each residue in SpA is half the $G_{vdW}$ between the residue and Fc fragment and vice versa for the $G_{vdW}$ contribution of residues in Fc. $G_{nonpolar}$ of each residue is proportional to the loss of SASA in the residue. From the above analyses we obtained $\Delta G_{bind}$ of the SpA-hIgG1 complex, the free energy contribution of each residue, and thereby the hot spots interacted between SpA and hIgG1.

In the SpA-hIgG1 complex, the SpA residues in contact with Fc fragment are discretely located on helix I (K126 to H137), helix II (E144 to D155), and irregular curl (L138 to E143). In this invention, the hot spots are identified as the residues that have large contribution to the binding free energy and that are involved in the important intermolecular interaction formation to compensate the unfavorable salvation. The residues contributing a lot to the free energy are identified on the basis of the criterion of ±2.5 kcal/mol. In order to recognize the significant residues in the complex for guiding the rational design of affinity ligands, a higher criterion than that often used in other literatures was adopted in this invention. For SpA, the residues F132, Y133, H137, R146, and K154 are found to have large contributions to the binding. Though the residue E143 of SpA has only little energy contribution (−1.2 kcal/mol), its free energy deviation is as high as −6.7 kcal/mol. Moreover, the side chain of E143 in SpA has a negatively charged [COO−] group, mainly offering electrostatic force. Therefore, the free energy contribution of E143 is highly sensitive to the conformation of residues. E143 of SpA has strong electrostatic attraction with the residue K317 of hIgG1. On the contrary, it has weak electrostatic repulsion with both D280 and D315 of hIgG1. So, though E143 does not contribute a lot of binding free energy directly, it creates a favorable local binding environment for K317 of hIgG1. Thus E143 is considered as one of the hot spots of SpA.

Figure 2:
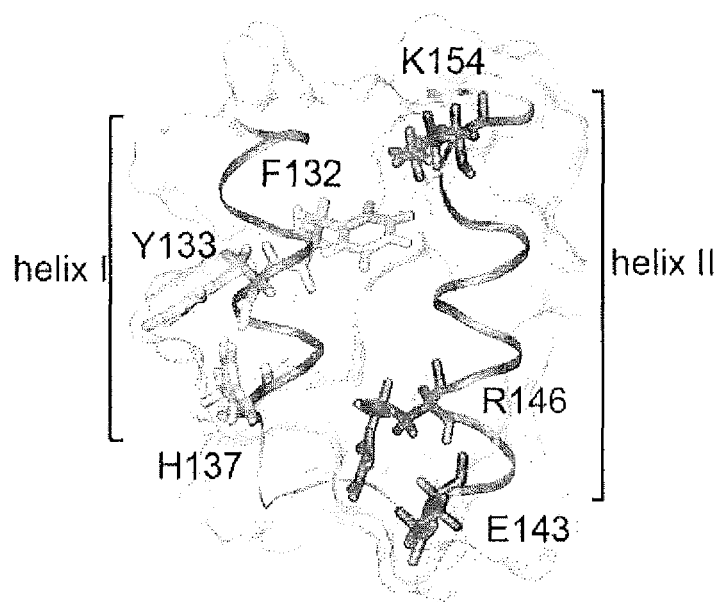
FIG. 2 shows the SpA simplified affinity binding model; helix I contains three hot spots: F132, Y133, and H137; helix II contains three other hot spots: E143, R146, and K154.

Helix I of SpA binds the Fc fragment mainly by hydrophobic interaction. Particularly, hot spots F132 and Y133 in helix I offer the majority of hydrophobic inteactions. MD simulation results indicate that the aromatic side chains of F132 and Y133 bind tightly at the shallow slot of the hydrophobic pocket on Fc fragment. In contrast, helix II of SpA binds the Fc fragment mainly by electrostatic interaction. Helix II contains three polar hot spots (E143, R146, and K154), which have strong electrostatic attraction with the polar residues (H310, Q311, D315, K317, and K338) located around the hydrophobic area at the binding site. Hence, hydrophobic interactions and special electrostatic interactions should be both considered in the rational design process to develop novel SpA-mimetic affinity ligands. According to the affinity mechanism of SpA in interaction with hIgG and the hot spots distribution of SpA, a simplified SpA binding motif has been constructed, wherein six hot spots are F132, Y133, H137, E143, R1461, and K154 (FIG. 2), and this motif may be used as the starting point for the rational design of SpA-mimetic ligands of IgG

EXAMPLE 2

Construction of Peptide Library

1. Identification of the Length of Peptide Sequences

It is known that the length of a peptide bond and an amino acid backbone is about 1.33 and 2.78 Å, respectively. The length needed to insert an amino acid residue is about the length of two peptide bonds plus one amino acid backbone length (2×1.33+2.78=5.44 Å); the length needed to insert two amino acid residues is about the length of three peptide bonds plus the length of two amino acid backbones (3×1.33+ 2×2.78=9.55 Å).

Figure 3:
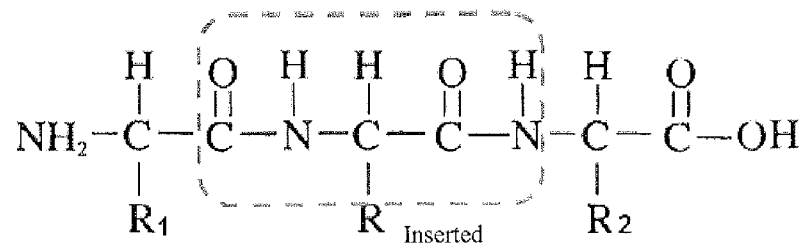
FIG. 3 shows the graphic expression of amino acid insertion; the dotted box covers the inserted amino acid residue.
Figure 4:
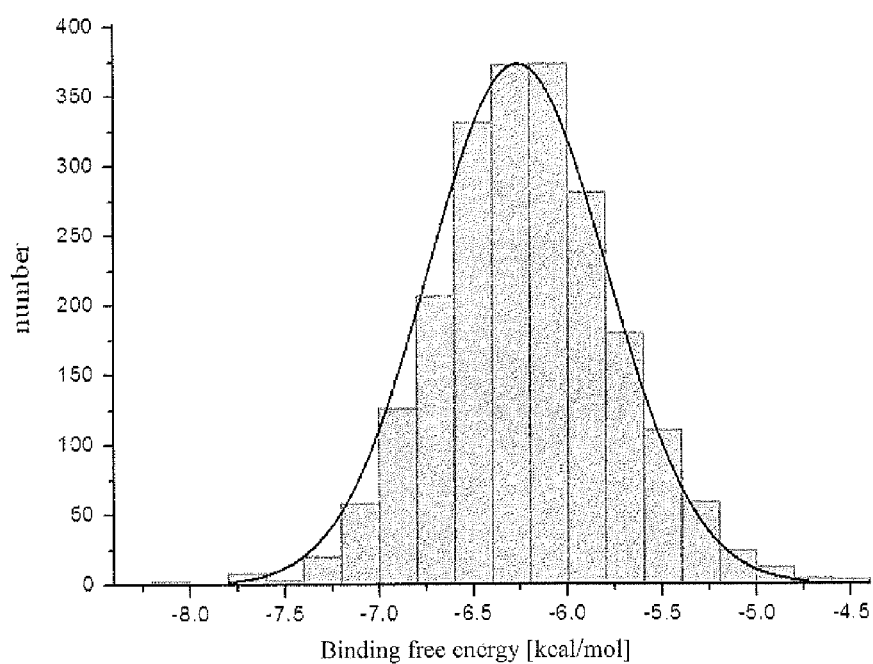
FIG. 4 demonstrates the score distribution of peptides docked to Fc by Vina; the less the binding free energy is, the higher the affinity between the ligand and Fc is.
Figure 5:
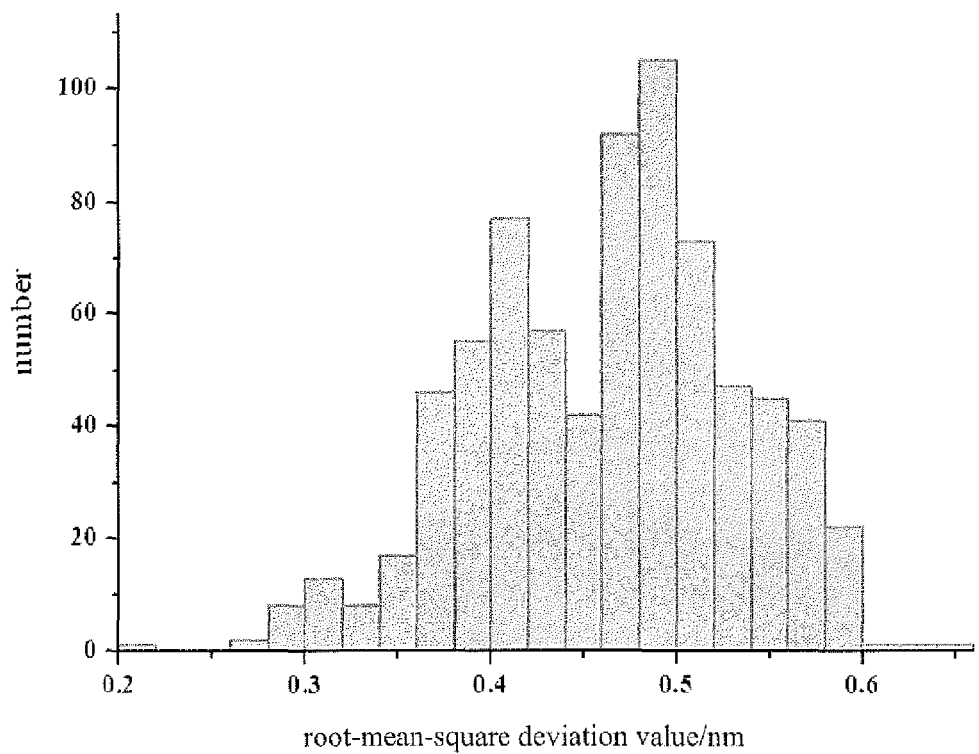
FIG. 5 shows the root-mean-square deviation value distribution of the hot spots of SpA compared with the corresponding residues of the peptides. The smaller the value is, the more alike the two conformations are.

FIG. 3 shows an instance of an amino acid residue insertion (the lines contained in the dotted box represent the added bonds of an amino acid residue). If the distance between the C/N terminal of one hot spot and N/C terminal of another (i.e. insertion distance) is less than 5.44 Å, then one amino acid residue can be inserted; if the insertion distance is in the range of 5.44 to 9.55 Å (9.55 Å is excluded), then adding two amino acid residues could be considered; if the insertion distance is more than 9.55 Å, then it is possible to insert three or more amino acid residues.

On the basis of the distance between the corresponding C and N terminal of two hot spots of SpA (which is calculated through Visual Molecular Dynamics software VMD), the number of amino acid residues inserted between the hot spots was worked out and the peptide construction models were identified as shown in Table 1.

TABLE 1

| No. | Peptide construction models |
|---|---|
| 1 | FYXHXXXE |
| 2 | FYXHXXR |
| 3 | FYXXRXE |
| 4 | YFXXRXE |
| 5 | HXYFXXR |
| 6 | HXYFXXK |

Among them, the No. 1 was an octapeptide mode, and the others were the heptapeptide modes. Considering that the C/N terminal residues of these peptide ligands are consisted of hot spots, which have high affinity for IgG, in order to maintain the high affinity between the ligand and antibodies after its immobilization, Cys was considered to insert into the middle region of the ligand, and thus the peptide could be immobilized onto Thiopropyl Sepharose 6B via disulfide bond. Thus, a residue Cys was inserted in the middle region of the peptide sequence to facilitate the peptide immobilization. This can make sure that sufficient flexibility could be offered to the terminal key residues upon peptide immobilization onto the resin, and then the key residues at two terminals could fully play the role of affinity so as to keep its affinity with Fc fragment of IgG. According to the hot spots of SpA and the number of residues inserted between them, finally eight peptide models were obtained (Table 2).

TABLE 2

| No. | Peptide models |
|---|---|
| 1 | FYCHXXXE |
| 2 | FYXHCXXE |
| 3 | FYCHXXR |
| 4 | FYXHCXR |
| 5 | FYXCRXE |
| 6 | YFXCRXE |
| 7 | HXYFCXR |
| 8 | HXYFCXK |

2. Identification of the Kinds of Amino Acid Residues Inserted Between Hot Spots Fragment location method was used to identify the amino acids inserted between hot spots. Fragment location method is a kind of simulation methods which uses molecular simulation method to identify the best orientation of a specific atom or fragment in the binding cavity. First, the different interaction regions of the binding cavity should be identified, such as electrostatic area, hydrophobic area, hydrogen bonding donor area, and hydrogen bonding acceptor area. Then, based on the principle of chemical environment matching, the ligand molecule that matches the chemical property of the binding cavity is placed there. That is, the ligand molecule fragment placed in the vicinity of the hydrophobic area of the receptor is also a hydrophobic group, like benzene ring and aliphatic hydrophobic chain, etc; the positively/negatively charged area of the receptor should match the negatively/positively charged area of the ligand. First, the Fc fragment region corresponding to the vacant small area between the six hot spots of SpA was selected, and then all the 19 amino acids (except cysteine, in order for later peptide ligand immobilization) were docked to the Fc fragment region successively using molecular docking software Vina. After the amino acids that had high affinity for the vacant area were all determined, their residues were linked with the hot spots to form candidate peptide ligands.

The identification of the kinds of the inserted amino acids was conducted using amino acid location method, and the peptide library was built accordingly.

The criteria for selecting amino acids are listed as follows: firstly, the candidate amino acid should have a proper binding conformation. Namely, the C/N terminal of its docked conformation is located end to end with the NIC terminal of other residues; secondly, the binding free energy is less than −2.0 kcal/mol. The kinds of unknown 'X' residues in the peptides were detected as summarized in Table 3.

TABLE 3

| Peptide models | Inserted amino acids |
|---|---|
| FYCHXXXE (990) | X_1: A, R, N, D, Q, E, H, I, L, K, M, T, W, Y, V (15)<br>X_2: A, Q, E, I, L, K (6)<br>X_3: A, R, D, Q, E, L, K, M, P, S, T (11) |
| FYXHCXXE (594) | X_1: A, R, N, D, I, P, T, W, Y (9)<br>X2: A, Q, E, I, L, K (6)<br>X_3: A, R, D, Q, E, L, K, M, P, S, T (11) |
| FYCHXXR (112) | X_1: N, D, Q, E, H, I, K, M, F, P, T, W, Y, V (14)<br>X_2: Q, E, H, I, K, M, F, W (8) |
| FYXHCXR (72) | X1: A, R, N, D, I, P, T, W, Y (9)<br>X_2: Q, E, H, I, K, M, F, W (8) |
| FYXCRXE (153) | X1: A, R, N, D, Q, E, G, H, I, L, K, M, F, P, W, Y, V (17)<br>X_2: N, D, Q, E, L, M, S, T, W (9) |
| YFXCRXE (117) | X_1: N, D, E, H, I, L, K, M, P, S, T, Y, V (13)<br>X_2: N, D, Q, E, L, M, S, T, W (9) |
| HXYFCXR (54) | X_1: A, R, N, D, I, P, T, W, Y (9)<br>X2: Q, H, K, S, W, Y (9) |
| HXYFCXK (81) | X_1: A, R, N, D, I, P, T, W, Y<br>X_2: A, R, Q, H, K, F, W, Y, V |

Perl scripts invoking CHRAMM software are utilized to acquire the peptide library, which includes 2173 peptide sequences, and every peptide sequence contains four hot spots.

EXAMPLE 3

Docking of Peptide Molecules to Fc Fragment

1. Docking of Peptides to Fc Fragment Using Vina

That individual residue having strong affinity for Fc dose not necessarily means that the peptide comprised by these residues must have strong interaction with Fc, so Vina was used to dock all the peptides in the library to the "consensus binding site" of Fc fragment sequentially. It is found that all the peptides of the library could bind Fc, and the predicted binding energies of the docked peptides were in the range of −4.5 to −8.2 kcal/mol. This range is in line with the requirement that affinity ligands should have medium affinity (the binding constant is in the range of $10^4$-$10^8$ $M^{-1}$). Among them, the peptides with binding free energy around −6.5 kcal/mol were accounting for the most. In order to avoid missing the promising ligands, 754 peptides with binding free energy less than −6.5 kcal/mol were selected. The docking scores distribution is presented in FIG. 4.

It is expected that the hot spots could fully exhibit their affinity for IgG, so it is necessary to seek out the peptide sequences of which the conformations of the hot spots were similar to those of corresponding hot spots in SpA, and therefore the peptide sequences may simulate effective affinity binding formed between SpA and Fc fragment.

Herein, for analyzing the differences between the conformations of the hot spots in peptide ligands and those in SpA, the auxiliary program g_rms provided by the GROMACS molecular simulation package was used to calculate the RMSD values between the hot spots in 754 peptide sequences obtained through vina docking and those corresponding in SpA. Encad all-atom force field was chosen, and RMSD values for key hot spots excluding hydrogen atoms were calculated. The smaller the RMSD value is, the more alike the two conformations of the corresponding hot spots are. The RMSD values are found in the range of 0.2 to 0.6 run (FIG. 5), and 150 peptide sequences with RMSD values less than 0.4 nm were selected for further study.

2. Rescreening Peptides Using FlexPepDock

Common molecular docking softwares like Autodock, DOCK, PatchDock, and MEDdock are only suitable for the docking of small molecules with a few of rotatable bonds. Since peptides have more side chains and more freedom than small organic molecules, therefore the virtual screening using the above softwares will have some limitations. FlexPepDock is a novel software aimed at docking peptides to target proteins using the Monte-Carlo minimization approach, and fully incorporates the flexibility of backbones and side chains of peptides as well as side chain flexibility for the receptor protein. If the binding site and the approximate binding model of the peptide-protein complex are available, FlexPepDock could realize the high-resolution prediction of the binding conformation between the peptide and target protein. The scoring function of FlexPepDock is a kind of generic full-atom energy function, including Lennard-Jones all-atom attractive and repulsive energy, lazaridis-jarplus solvation energy, and hydrogen bonding, etc. Many reports have indicated that the binding surface energy score (I_sc) can mainly evaluate the binding strength of peptide with proteins.

Figure 6:
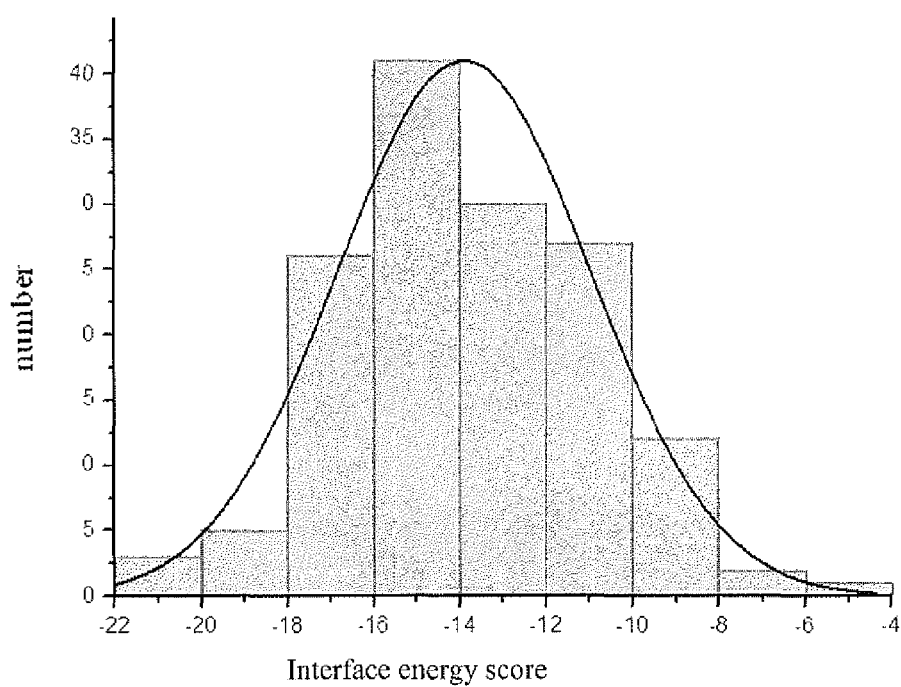
FIG. 6 demonstrates the first FlexPepDock docking score distribution of peptides docked to Fc; the less the interface energy score, the stronger the binding is.

All the 150 peptides obtained from the last round were docked to Fc using FlexPepDock successively. It is found only a few peptides couldn't bind to Fc and the other majority could. The I_sc values of the other majority of peptides were in the range of −5 to −22, and the less the value of I_sc is, the stronger the binding is. Among them, the peptide sequences with I_sc values less than −16 were selected. Two parallel dockings were conducted, and there were 34 peptide sequences whose I_sc values were less than −16 from the first docking result (FIG. 6). In the second docking, there were 38 peptides whose I_sc values were less than −16. And it was found that there were 15 peptides with both I_sc values less than −16 in the two FlexPepDock docking processes. In Table 4, Vina_score means the Vina docking score, I_sc-1 means the score from the first FlexPepDock docking, and I_sc-2 means the docking score from the second parallel docking.

TABLE 4

| Peptide | Vina_score | I_sc-1 | I_sc-2 |
| --- | --- | --- | --- |
| FYWHCLDE | −7.3 | −21.3 | −22.0 |
| FYFCRWE | −7.0 | −16.9 | −19.3 |
| FYIHCLPE | −6.9 | −18.2 | −18.8 |
| FYYHCKKE | −6.5 | −16.7 | −18,8 |
| FYCHWALE | −7.6 | −17.1 | −18.1 |
| FYCHWQDE | −7.7 | −20.1 | −17.8 |
| FYCHTIDE | −6.8 | −17.8 | −17.4 |
| FYRHCQRE | −6.5 | −19.7 | −16.9 |
| FYCHHKTE | −6.6 | −17.0 | −16.9 |
| FYCHLQKE | −6.7 | −17.2 | −16.8 |
| FYCHRKAE | −6.9 | −17.6 | −16.8 |
| FYCHNQDE | −6.6 | −19.9 | −16.7 |
| FYCHRQEE | −6.7 | −17.6 | −16.6 |

TABLE 4-continued

| Peptide | Vina_score | I_sc-1 | I_sc-2 |
| --- | --- | --- | --- |
| FYNHCASE | −7.1 | −16.8 | −16.1 |
| FYTHCAKE | −7.0 | −17.1 | −16.1 |

So, herein we chose the 15 peptides for further MD simulations to analyze the affinity for IgG.

EXAMPLE 4

Molecular Dynamics Simulations

MD simulation is an effective tool for studying protein dynamic behaviors. Fast inner movement, slower conformational changes, and folding process in protein can all be investigated using MD simulations. In order to further assess the affinity in the IgG-peptide complexes, not only their static structures (using molecular docking) but their dynamic behaviors should be considered. Next, the binding dynamics of the selected 15 peptides with Fc fragment of IgG were studied by MD simulations.

All MD simulations were performed using the GROMACS 4.5.3 package with GROMOS96 53a6 force field. The peptide-protein complexes were put at the center of a rectangular water box, of which the distance from the edge of the box was at least 0.9 nm. A cutoff value of 0.9 nm was used for Coulomb as well as Lennard-Jones interactions. Particle Mesh Ewald (PME) method was used to calculate the long-range electrostatic interactions with a grid-spacing of 0.12 nm and an interpolation order of 4. Temperature (300 K) and pressure (1 bar) were controlled by the v-rescale thermostat and Parrinello-Rahman pressostat, respectively. An integration time step of 2 fs was used together with the LINCS constraint solver for all covalent bonds. First, 50,000 steps of steepest descent method were used to conduct energy minimization for the system. Then the system went through 100 ps of restrained kinetic equilibrium under NVT and NPT ensemble, sequentially. At last, 20 nm of unrestrained dynamic simulation was performed. Structures were saved every 500 ps for analysis, resulting in 40 conformations for total 20-ns simulation. All MD simulations were run on a 64-CPU Dawning A620r-F server.

First, VMD was used to calculate the changes of interaction and relative locations between peptides and Fc fragments, and it was found only FYTHCAKE in the 15 peptides was detached from Fc fragment and got apart from it gradually along the MD simulation. The change of $C_\alpha$ RMSD values over simulation time was found during the study of FYTHCAKE in interaction with Fc, and it was observed that in the whole 20 ns simulation, the $C_\alpha$ RMSD values of both FYTHCAKE and Fc were severely fluctuating and could not achieve stability. Compared with its initial conformation (Flexpepdock docking conformation), the $C_\alpha$ RMSD value of the final conformation reached 0.45 nm. The contact number and minimum distance between atoms of FYTHCAKE and Fc over simulation time were also analyzed. It was found that at around 15 ns, the peptide began to separate from Fc, and meanwhile the contact number abruptly declined from 600 and correspondingly the minimum distance rapidly increased. The two molecules were completely separate from each other at around 18 ns, indicating weak affinity between FYTHCAKE and IgG. In contrast, the other 14 peptides could all bind Fc in the overall MD simulation process, suggesting they could be able to be effective affinity ligands of IgG, which were FYWHCLDE, FYFCRWE, FYIHCLPE, FYYHCKKE, FYCHWALE, FYCHWQDE, FYCHTIDE, FYRHCQRE, FYCHHKTE, FYCHLQKE, FYCHRKAE, FYCHNQDE, FYCHRQEE, and FYNHCASE.

EXAMPLE 5

Affinity Chromatography Verification

1. Peptide Ligand Immobilization and Preparation of Affinity Column

Peptide powders purchased from GL Biochem Ltd. (Shanghai, China) had been purified by high performance liquid chromatography (HPLC) with a purity of 96.36%. 1 g of resin (Thiopropyl Sepharose 6B, purchased from GE Healthcare) was weighed and washed for 15 min with 200 mL of deionized water in a buchner funnel. After being filtered and getting rid of water, two aliquots of 1.0 g of drained gel were transferred into two 25-mL Erlenmeyer flasks, respectively. Then 6 mL and 10.7 mL of linking buffer (0.1 M Tris-HCl, pH 7.5, 0.5 M NaCl and 1 mM EDTA) were added to the two flasks respectively, to fully pre-equilibrate the gels. Two peptides (FYWHCLDE and FYCHWALE) were randomly selected from the 14 peptides obtained by MD simulations, weighed and dissolved in 500 µL of 50% (v/v) ethylene glycol solution. The peptides were fully mixed with the gels in corresponding flasks and initial peptide concentrations of 1.0 mg/mL were obtained. The mixtures were reacting in a shaking bath at a rate of 180 rpm, at 25° C. for 2 h. 500 µL of supernatant was acquired each hour for analyzing the residue peptide content in the reaction solution with reversed-phase high pressure liquid chromatography (RP-HPLC). When the peptide content did not change any more, 8 mg cysteine was added and then the reaction was going on for 30 min to block the unreacted groups on the gel so as not to disturb the affinity interaction between proteins and the ligands. After the reaction was finished, the reaction system was centrifuged and the supernatant was removed, then the gel was washed repeatedly with washing buffer (10 mM PBS, pH 7.2, 150 mM NaCl) in a buchner funnel to get rid of the free peptides. Finally, equilibriation buffer (20 mmol/L citrate buffers, pH 5.0-5.5; or 20 mmol/L PBS buffers, pH 5.5-6.0) was used to suspend the gel to 1 mL, and after being degassed, the gel was slowly loaded into the glass column (Tricorn chromatogram column, Tricorn 5×5, GE healthcare). The column was first washed with equilibration buffer at 0.1 mL/min, and then the speed of the buffer was increased to 0.2 mL/min when the column pressure was stable, and the speed of the buffer was increased according to above operation till it reached 1.0 mL/min. Till the height of the gel did not drop any longer, the height adjuster should be screwed to the upper surface of the gel column.

2. Determination of Peptide Content in the Supernatant

The residue peptide content in the supernatant was determined with RP-HPLC, and the detailed assay parameters were shown below: mobile phase A, aqueous solution containing 0.1% trifluoroacetic acid (TFA); mobile phase B, acetonitrile solution containing 0.1% TFA; loading amount: 10 µL; flow rate: 0.5 mL/min; detection wavelength: 220 nm. The results showed that almost all FYWHCLDE molecules could be immobilized onto the gel, and the immobilization ratio of FYCHWALE was 93.7%.

3. Affinity Chromatography (1) Equilibration: the affinity column was washed with equilibration buffer until a stable baseline was reached. The flow rate of buffer was 0.5 mL/min, keep washing another five column volumes (CVs) before sample injection.

(2) Sample injection: unless specifically stated, all protein samples were prepared by equilibration buffer. After sample injection, the column was equilibrated with 5-10 CVs of equilibration buffer (20 mmol/L citrate buffer, pH≤5.5; or 20 mmol/L PBS buffer, pH≥5.5). The sample loading amount was 100 µL, protein sample concentration was 1.0 mg/mL, and the flow rate was 0.5 mL/min.

(3) Elution: the column was washed with 5-10 CVs of elution buffer, and the flow rate was 0.8 mL/min.

(4) Storage: first 10 CVs of deionized water was used to wash the column, followed by another 10 CVs of 20% ethanol solution. Then the affinity gel was stored in this solution. All buffers should be filtered through a filter and degassed before use.

At pH 5.0-6.0, FYWHCLDE peptide ligand had a strong binding of hIgG. On the contrary, as for BSA, the ligand only had a large binding at pH 5.5. The affinity interaction between FYWHCLDE and hIgG mainly involved specific electrostatic interaction. At pH 5.5-7.0, FYCHWALE ligand could bind a lot of hIgGs. However at pH 6.0, it could bind almost all hIgGs. So the best binding buffer for FYCHWALE was 20 mM PBS at pH 6.0. Again, the affinity between FYCHWALE and hIgG mainly involved electrostatic interactions, and therefore the ionic strength of the binding system should be proper and could not be too high, avoiding a decreased binding of antibodies. FYCHWALE ligand could bind about half of bovine serum albumin (BSA) at pH 5.5, ⅓ of BSA at pH 6.0, and trace BSA at pH 6.5. The above results suggested that both the two peptide ligands had specific binding for hIgG at pH 6.0.

4. Protein Content Determination

The total protein concentration in mixed protein solution was determined by Bradford method, and the operation was as follows: a series of 1 mL of BSA solutions with concentrations of 15, 30, 45, 60, 75, and 90 µg/mL were prepared, and the blank control was 1 mL of distilled water. When the data points were determined, 3 mL of coomassie blue G-250 was added to the protein solutions and the control solution, respectively. After fully mixed, their absorbance was determined at 595 nm within 1-2 min. The protein concentrations were plotted against the absorbance values to obtain the protein content standard curve. The IgG concentration standard curve was produced by preparing hIgG solutions of concentrations ranged from 0 to 2.0 mg/mL, and the standard curve was plotted on the basis of the hIgG solution absorbance values at 280 nm using spectrophotometry method. The IgG concentration standard curve was only used to determine the pure protein solution only containing IgG. The absorbance values of collected fractions from protein chromatography were determined at 280 nm and 595 nm, and then the protein contents were identified according to the standard curve.

5. Chromatographic Purification of IgG from Serum Sample

Figure 7:
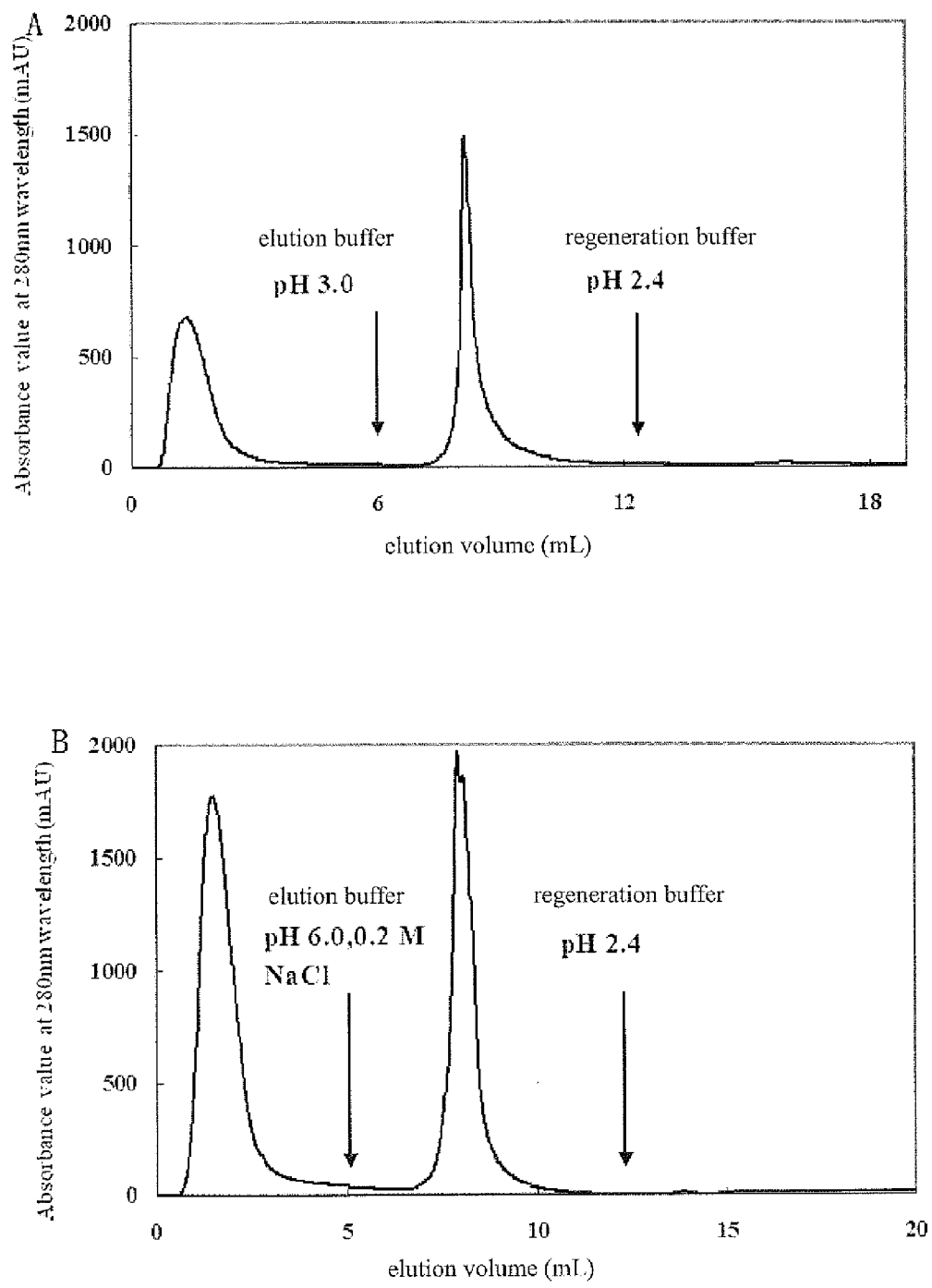
FIG. 7 shows the purification of IgG from human serum sample using affinity peptide column. Equilibrium buffer: 20 mM PBS, pH 6.0; regeneration buffer: 100 mM Gly-HCl buffer, pH 2.4. (A) Affinity column coupled with peptide ligand FYWHCLDE, elution buffer: 50 mM sodium citrate buffer, pH 3.0; (B) affinity column coupled with peptide ligand FYCHWALE, elution buffer: Equilibrium buffer containing 0.2 mol/L NaCl, pH 6.0.

After the affinity gel was fully equilibrated with equilibration buffers (20 mM PBS at pH 6.0 or 6.5), namely all parameters had reached the baseline, 500 µL of serum sample, which was prepared by diluting human serum with 9 time volumes of binding buffer, was loaded. Another 5 CVs of equilibration buffer were loaded to wash the column, and then 0.5 or 0.2 M NaCl in equilibration buffer was used for elution; or 50 mM citrate buffer (pH 3.0) was used as elution buffer. When the elution peak was completely separate, 0.1 M Gly-HCl buffer (pH 2.4) was used to regenerate the affinity gel. The separation results were shown in FIG. 7.

6. Sodium Dodecyl Sulfate Polyacrylamide Gel Electrophoresis (SDS-PAGE)

The main solutions:

(1). 10% separation gel, 4 mL: 1330 µL of 30% gel (acrylamide:methylene diacrylamide=29:1); 1670 µL of deionized water; 1000 µL of 1.5 M Low Tris buffer; 40 µL of 10% ammonium persulfate (APS); 10 µL of TEMED.

(2). Low Tris buffer: 18.17 g of Tris, 2.5 mL of dense HCl, and 0.4 g of SDS were weighed and dissolved in water to 100 mL with pH value adjusted to 8.8.

(3). 10% APS: 0.1 g of APS was weighed and dissolved in water to 1 mL.

(4). Upp Tris buffer: 3.03 g of Tris, 2 mL of concentrated HCl, and 0.2 g of SDS were weighed and dissolved in water to 50 mL with pH value adjusted to 6.8.

(5). 5% stacking gel, 4 mL: 665 µL of 30% gel; 2335 µL of deionized water; 1000 µL of 1.0 M Upp Tris; 40µL of 10% APS; 16 µL of TEMED.

(6). Non-reducing electrophoresis sample buffer: 5.5 mL of Upp Tris, 8.8 mL of glycerin, 2g of SDS and 5-8 mg of bromophenol blue were weighed and dissolved in water to 50 mL.

(7). PAGE electrophoresis staining solution: 0.625 g of coomassie blue (R-250), 250 mL of methanol, and 50 mL of acetic acid were weighed and dissolved in water to 500 mL.

(8). PAGE electrophoresis decoloring solution: 150 mL of methanol and 50 mL of acetic acid were mixed with water to a volume of 500 mL.

(9). PAGE buffer: 7.5 g of Tris, 1.0 g of SDS, and 36 g of glycine were dissolved in water to a volume of 500 µL with pH value adjusted to 8.3. Usage: 100 mL was taken and diluted 5 times with water; the PAGE buffer should submerge the platform and be recycled after the electrophoresis was finished.

Sample preparation: 25 µL of raw sample solution was mixed with 25 µL of sample buffer thoroughly. 5 µL of marker and 10 µL of sample were injected. The separation gel was loaded into the electrophoresis groove of SE/250 vertical plate until a distance of 1.5 cm from the glass plate was reached. Then gently cover the separation gel with a sheet of water. When the separation gel was solidified, the water was poured out, the stacking gel was loaded and a comb was inserted. When the stacking gel was solidified, the comb was pulled out. And the samples to be tested were added to the comb holes using a microsyringe. The protein amount of the sample is proper to be 10 µg. The electrophoresis was conducted at 10 mA until the indicator strip was reaching the bottom of the stacking gel, then the electric current was increased to 25 mA until the indicator strip was reaching the bottom of the separation gel, thus electrophoresis was completed. After that, coomassie blue (R-250) staining method was used. This method had high sensitivity, and the minimum detection limit was 0.3~10 µg. The gel was drenched in the staining solution for 4 h at room temperature to be fixed and stained. Thereafter, the gel was decolored using destaining solution until the background of the gel was close to colorless. Then pictures were taken for the destained gel by Bio-RAP and the results were analyzed with Gel-Pro software.

Figure 8:
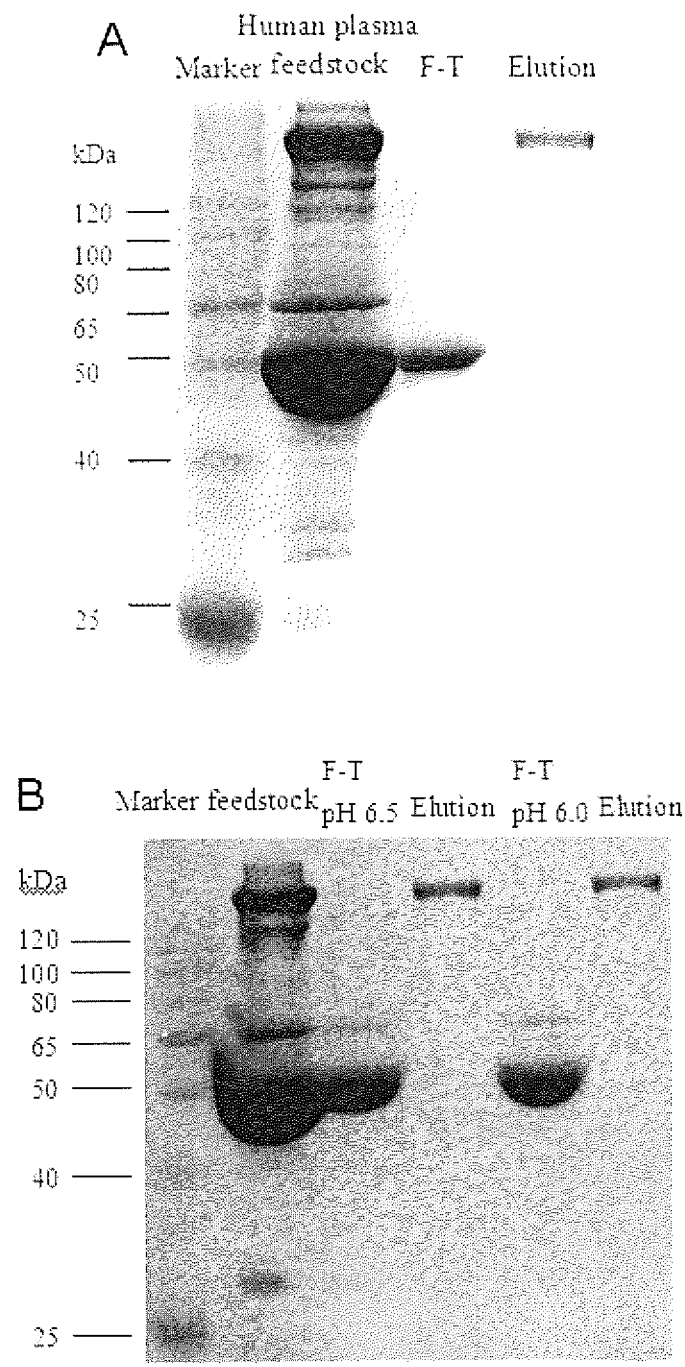
FIG. 8 shows the SDS-PAGE analyses of collected fractions from chromatography. From left to right are the bands which represent the standard protein maker (30-120 kDa), human serum sample (feedstock), flow-through fraction (F-T), and elution fraction (Elution). (A) electrophoretogram of FYWHCLDE affinity column, (B) electrophoretogram of FYCHWALE affinity column.

The flow-through peak fractions and elution peak fractions collected from the human serum separation were analyzed by SDS-PAGE, and the electrophoretograms were shown in FIG. 8. The purity of IgG was obtained by Gel-Pro analysis, and the recovery yield was calculated by Bradford method. The IgG content of human serum was 18.07%, and the purified IgG of the elution peak fraction by FYWH-CLDE accounted for 88.86% with a recovery yield of 65.5%. The IgG content of the elution peak fraction by FYCHWALE was 89.6% (binding system with pH 6.5) and 88.5% (binding system with pH 6.0), and the recovery yield of IgG was 71% (binding system with pH 6.0). Compared with the purification performances of other affinity ligands for hIgG mentioned in other reports, the peptide ligands designed in this invention could purify hIgG with a high purity and a high recovery yield. Therefore both of them were effective affinity ligands of hIgG.

Compared with other methods of designing novel peptide ligands, such as combinatorial chemistry synthetic peptide library screening, phage display peptide library screening, and ribosome display peptide library screening, the biomimetic method for designing peptide ligands of human IgG using molecular simulation introduced in this invention has the following advantages: first, there is no need for complex and costly raw materials. It is easier to handle than experimental operations and less costly; second, it is possible to construct a library including a huge number of candidates, realizing the large-scale high-throughput screening in a real sense. The peptides obtained from screening are not only the affinity ligands of human IgG, but also applicable to other receptor molecules. That is, they also could efficiently purify IgG of pigs and sheep. The molecular docking screening, molecular dynamics simulation rescreening, and experimental verification introduced in this invention can apply to all the peptides in the peptide library. Due to the various limited factors, we could not verify all the peptides in the library by experimental methods, and could only enrich effective candidate peptides with various screening methods, But one thing is for sure that besides the 14 finally obtained peptides, other peptides distributed in the library are also possible to be affinity peptide ligands of IgG. Related researchers can select some of them to conduct experimental verifications if needed. According to the available experimental data, the peptides in the library are predicated to be effective potential affinity peptide ligands of human IgG. It is hoped that the peptide ligands with good performance can be commercialized and therefore benefit humankind,

TABLE 5

| | | | | | | |
|---|---|---|---|---|---|---|
| FYCHAAAE | FYCHAARE | FYCHAADE | FYCHAAQE | FYCHAAEE | FYCHAALE | FYCHAAKE |
| FYCHAAME | FYCHAAPE | FYCHAASE | FYCHAATE | FYCHAQAE | FYCHAQRE | FYCHAQDE |
| FYCHAQQE | FYCHAQEE | FYCHAQLE | FYCHAQKE | FYCHAQME | FYCHAQPE | FYCHAQSE |
| FYCHAQTE | FYCHAEAE | FYCHAERE | FYCHAEDE | FYCHAEQE | FYCHAEEE | FYCHAELE |
| FYCHAEKE | FYCHAEME | FYCHAEPE | FYCHAESE | FYCHAETE | FYCHAIAE | FYCHAIRE |
| FYCHAIDE | FYCHAIQE | FYCHAIEE | FYCHAILE | FYCHAIKE | FYCHAIME | FYCHAIPE |

TABLE 5-continued

```
FYCHAISE FYCHAITE FYCHALAE FYCHALRE FYCHALDE FYCHALQE FYCHALEE
FYCHALLE FYCHALKE FYCHALME FYCHALPE FYCHALSE FYCHALTE FYCHAKAE
FYCHAKRE FYCHAKDE FYCHAKQE FYCHAKEE FYCHAKLE FYCHAKKE FYCHAKME
FYCHAKPE FYCHAKSE FYCHAKTE FYCHRAAE FYCHRARE FYCHRADE FYCHRAQE
FYCHRAEE FYCHRALE FYCHRAKE FYCHRAME FYCHRAPE FYCHRASE FYCHRATE
FYCHRQAE FYCHRQRE FYCHRQDE FYCHRQQE FYCHRQEE FYCHRQLE FYCHRQKE
FYCHRQME FYCHRQPE FYCHRQSE FYCHRQTE FYCHREAE FYCHRERE FYCHREDE
FYCHREQE FYCHREEE FYCHAELE FYCHREKE FYCHREME FYCHREPE FYCHRESE
FYCHRETE FYCHRIAE FYCHRIRE FYCHRIDE FYCHRIQE FYCHRIEE FYCHRILE
FYCHRIKE FYCHRIME FYCHRIPE FYCHRISE FYCHRITE FYCHRLAE FYCHRLRE
FYCHRLDE FYCHALQE FYCHRLEE FYCHRLLE FYCHRLKE FYCHRLME FYCHRLPE
FYCHRLSE FYCHRLTE FYCHRKAE FYCHRKRE FYCHRKDE FYCHRKQE FYCHRKEE
FYCHRKLE FYCHRKKE FYCHRKME FYCHRKPE FYCHRKSE FYCHAKTE FYCHNKTE
FYCHNAAE FYCHNARE FYCHNADE FYCHNAQE FYCHAAEE FYCHNALE FYCHNAKE
FYCHNAME FYCHNAPE FYCHNASE FYCHNATE FYCHNQAE FYCHNQRE FYCHNQDE
FYCHNQQE FYCHNQEE FYCHNQLE FYCHNQKE FYCHNQME FYCHNQPE FYCHNQSE
FYCHNQTE FYCHNEAE FYCHNERE FYCHNEDE FYCHNEQE FYCHNEEE FYCHNELE
FYCHNEKE FYCHNEME FYCHNEPE FYCHNESE FYCHNETE FYCHAIAE FYCHNIRE
FYCHNIDE FYCHNIQE FYCHNIEE FYCHNILE FYCHNIKE FYCHNIME FYCHNIPE
FYCHNISE FYCHNITE FYCHNLAE FYCHNLRE FYCHNLDE FYCHNLQE FYCHNLEE
FYCHNLLE FYCHNLKE FYCHNLME FYCHNLPE FYCHNLSE FYCHNLTE FYCHNKAE
FYCHNKRE FYCHNKDE FYCHNKQE FYCHNKEE FYCHNKLE FYCHNKKE FYCHNKME
FYCHNKKE FYCHNKSE FYCHDKTE FYCHDKPE FYCHDKSE FYCHDKRE FYCHDKDE
FYCHDAAE FYCHDARE FYCHDADE FYCHDAQE FYCHDAEE FYCHDALE FYCHDAKE
FYCHDAME FYCHDAPE FYCHDASE FYCHDATE FYCHDQAE FYCHDQRE FYCHDQDE
FYCHDQQE FYCHDQEE FYCHDQLE FYCHDQKE FYCHDQME FYCHDQPE FYCHDQSE
FYCHDQTE FYCHDEAE FYCHDERE FYCHDEDE FYCHDEQE FYCHDEEE FYCHDELE
FYCHDEKE FYCHDEME FYCHDEPE FYCHDESE FYCHDETE FYCHDIAE FYCHDIRE
FYCHDIDE FYCHDIQE FYCHDIEE FYCHDILE FYCHDIKE FYCHDIME FYCHDIPE
FYCHDISE FYCHDITE FYCHDLAE FYCHDLRE FYCHDLDE FYCHDLQE FYCHDLEE
FYCHDLLE FYCHDLKE FYCHDLME FYCHDLPE FYCHDLSE FYCHDLTE FYCHDKAE
FYCHDKQE FYCHDKEE FYCHDKLE FYCHDKKE FYCHDKME FYCHQKTE FYCHQKPE
FYCHQAAE FYCHQARE FYCHQADE FYCHQAQE FYCHQAEE FYCHQALE FYCHQAKE
FYCHQAME FYCHQAPE FYCHQASE FYCHQATE FYCHQQAE FYCHQQRE FYCHQQDE
FYCHQQQE FYCHQQEE FYCHQQLE FYCHQQKE FYCHQQME FYCHQQPE FYCHQQSE
FYCHQQTE FYCHQEAE FYCHQERE FYCHQEDE FYCHQEQE FYCHQEEE FYCHQELE
FYCHQEKE FYCHQEME FYCHQEPE FYCHQESE FYCHQETE FYCHQIAE FYCHQIRE
FYCHQIDE FYCHQIQE FYCHQIEE FYCHQILE FYCHQIKE FYCHQIME FYCHQIPE
FYCHQISE FYCHQITE FYCHQLAE FYCHQLRE FYCHQLDE FYCHQLQE FYCHQLEE
FYCHQLLE FYCHQLKE FYCHQLME FYCHQLPE FYCHQLSE FYCHQLTE FYCHQKAE
```

TABLE 5-continued

```
FYCHQKQE FYCHQKEE FYCHQKLE FYCHQKKE FYCHQKME FYCHQKSE FYCHQKRE
FYCHQKDE FYCHEKTE FYCHEKPE FYCHEKDE FYCHEKME FYCHEKSE FYCHEKRE
FYCHEAAE FYCHEARE FYCHEADE FYCHEAQE FYCHEAEE FYCHEALE FYCHEAKE
FYCHEAME FYCHEAPE FYCHEASE FYCHEATE FYCHEQAE FYCHEQRE FYCHEQDE
FYCHEQQE FYCHEQEE FYCHEQLE FYCHEQKE FYCHEQME FYCHEQPE FYCHEQSE
FYCHEQTE FYCHEEAE FYCHEERE FYCHEEDE FYCHEEQE FYCHEEEE FYCHEELE
FYCHEEKE FYCHEEME FYCHEEPE FYCHEESE FYCHEETE FYCHEIAE FYCHEIRE
FYCHEIDE FYCHEIQE FYCHDIEE FYCHEILE FYCHEIKE FYCHEIME FYCHEIPE
FYCHEISE FYCHEITE FYCHELAE FYCHELRE FYCHELDE FYCHELQE FYCHELEE
FYCHELLE FYCHELKE FYCHELME FYCHELPE FYCHELSE FYCHELTE FYCHEKAE
FYCHEKQE FYCHEKEE FYCHEKLE FYCHEKKE FYCHHKTE FYCHHKPE FYCHHKDE
FYCHHAAE FYCHHARE FYCHHADE FYCHHAQE FYCHDAEE FYCHHALE FYCHHAKE
FYCHHAME FYCHHAPE FYCHHASE FYCHHATE FYCHHQAE FYCHHQRE FYCHHQDE
FYCHHQQE FYCHDQEE FYCHHQLE FYCHHQKE FYCHHQME FYCHHQPE FYCHHQSE
FYCHHQTE FYCHHEAE FYCHHERE FYCHHEDE FYCHHEQE FYCHHEEE FYCHHELE
FYCHHEKE FYCHHEME FYCHHEPE FYCHHESE FYCHHETE FYCHHIAE FYCHHIRE
FYCHHIDE FYCHHIQE FYCHHIEE FYCHHILE FYCHHIKE FYCHHIME FYCHHIPE
FYCHHISE FYCHHITE FYCHHLAE FYCHHLRE FYCHHLDE FYCHHLQE FYCHHLEE
FYCHHLLE FYCHHLKE FYCHHLME FYCHHLPE FYCHHLSE FYCHHLTE FYCHHKAE
FYCHHKQE FYCHHKEE FYCHHKLE FYCHHKKE FYCHHKME FYCHHKSE FYCHHKRE
FYCHIAAE FYCHIARE FYCHIADE FYCHIAQE FYCHIAEE FYCHIALE FYCHIAKE
FYCHIAME FYCHIAPE FYCHIASE FYCHIATE FYCHIQAE FYCHIQRE FYCHIQDE
FYCHIQQE FYCHIQEE FYCHIQLE FYCHIQKE FYCHIQME FYCHIQPE FYCHIQSE
FYCHIQTE FYCHIEAE FYCHIERE FYCHIEDE FYCHIEQE FYCHIEEE FYCHIELE
FYCHIEKE FYCHIEME FYCHHEPE FYCHIESE FYCHIETE FYCHIIAE FYCHIIRE
FYCHIIDE FYCHIIQE FYCHIIEE FYCHIILE FYCHIIKE FYCHIIME FYCHIIPE
FYCHIISE FYCHIITE FYCHILAE FYCHILRE FYCHILDE FYCHILQE FYCHILEE
FYCHILLE FYCHILKE FYCHILME FYCHILPE FYCHILSE FYCHILTE FYCHIKAE
FYCHIKQE FYCHIKEE FYCHIKLE FYCHIKKE FYCHIKME FYCHIKSE FYCHIKRE
FYCHIKTE FYCHIKPE FYCHIKDE FYCHLAAE FYCHLARE FYCHLADE FYCHLAQE
FYCHLAME FYCHLAPE FYCHLASE FYCHLATE FYCHLQAE FYCHLQRE FYCHLQDE
FYCHLQQE FYCHLQEE FYCHLQLE FYCHLQKE FYCHLQME FYCHLQPE FYCHLQSE
FYCHLQTE FYCHLEAE FYCHLERE FYCHLEDE FYCHLEQE FYCHLEEE FYCHLELE
FYCHLEKE FYCHLEME FYCHLEPE FYCHLESE FYCHLETE FYCHLIAE FYCHLIRE
FYCHLIDE FYCHLIQE FYCHLIEE FYCHLILE FYCHLIKE FYCHLIME FYCHLIPE
FYCHLISE FYCHLITE FYCHLLAE FYCHLLRE FYCHLLDE FYCHLLQE FYCHLLEE
FYCHLLLE FYCHLLKE FYCHLLME FYCHLLPE FYCHLLSE FYCHLLTE FYCHLKAE
FYCHLKQE FYCHLKEE FYCHLKLE FYCHLKKE FYCHLKME FYCHLKSE FYCHLKRE
FYCHLAEE FYCHLALE FYCHLAKE FYCHLKTE FYCHLKPE FYCHLKDE FYCHKAAE
FYCHKKME FYCHKAPE FYCHKASE FYCHKATE FYCHKQAE FYCHKQRE FYCHKQDE
```

TABLE 5-continued

```
FYCHKQQE FYCHKQEE FYCHKQLE FYCHKQKE FYCHKQME FYCHKQPE FYCHKQSE
FYCHKQTE FYCHKEAE FYCHKERE FYCHKEDE FYCHKEQE FYCHKEEE FYCHKELE
FYCHKEKE FYCHKEME FYCHKEPE FYCHKESE FYCHKETE FYCHKIAE FYCHKIRE
FYCHKIDE FYCHKIQE FYCHKIEE FYCHKILE FYCHKIKE FYCHKIME FYCHKIPE
FYCHKISE FYCHKITE FYCHKLAE FYCHKLRE FYCHKLDE FYCHKLQE FYCHKLEE
FYCHKLLE FYCHKLKE FYCHKLME FYCHKLPE FYCHKLSE FYCHKLTE FYCHKKAE
FYCHKKQE FYCHKKEE FYCHKKLE FYCHKKKE FYCHKKME FYCHKKSE FYCHKKRE
FYCHKARE FYCHKADE FYCHKAQE FYCHKAEE FYCHKALE FYCHKAKE FYCHKKTE
FYCHKKPE FYCHKKDE FYCHMAAE FYCHMKPE FYCHMKDE FYCHMARE FYCHMADE
FYCHMAME FYCHMAPE FYCHMASE FYCHMATE FYCHMQAE FYCHMQRE FYCHMQDE
FYCHMQQE FYCHMQEE FYCHMQLE FYCHMQKE FYCHMQME FYCHMQPE FYCHMQSE
FYCHMQTE FYCHMEAE FYCHMERE FYCHMEDE FYCHMEQE FYCHMEEE FYCHMELE
FYCHMEKE FYCHMEME FYCHMEPE FYCHMESE FYCHMETE FYCHMIAE FYCHMIRE
FYCHMIDE FYCHMQQE FYCHMQEE FYCHMILE FYCHMIKE FYCHMIME FYCHMIPE
FYCHMISE FYCHMQTE FYCHMLAE FYCHMLRE FYCHMLDE FYCHMLQE FYCHMLEE
FYCHMLLE FYCHMLKE FYCHMLME FYCHMLPE FYCHMLSE FYCHMLTE FYCHMKAE
FYCHMQQE FYCHMKEE FYCHMKLE FYCHMKKE FYCHMKME FYCHMKSE FYCHMKRE
FYCHMAQE FYCHMAEE FYCHMALE FYCHMAKE FYCHMKTE FYCHTADE FYCHTAQE
FYCHTAME FYCHTAAE FYCHTKPE FYCHTKDE FYCHTARE FYCHTQRE FYCHTQDE
FYCHTQQE FYCHTAPE FYCHTADE FYCHTATE FYCHTQAE FYCHTQPE FYCHTQSE
FYCHTQTE FYCHTQEE FYCHTQLE FYCHTQKE FYCHTQME FYCHTEEE FYCHTELE
FYCHTEKE FYCHTEAE FYCHTERE FYCHTEDE FYCHTEQE FYCHMIAE FYCHTIRE
FYCHTIDE FYCHTEME FYCHTEPE FYCHTESE FYCHTETE FYCHTIME FYCHTIPE
FYCHTISE FYCHTAQE FYCHTIEE FYCHTILE FYCHTIKE FYCHTLQE FYCHTLEE
FYCHTLLE FYCHTITE FYCHTLAE FYCHTLRE FYCHTLDE FYCHTLTE FYCHTKAE
FYCHTKQE FYCHTLKE FYCHTLME FYCHTLPE FYCHTLSE FYCHTKSE FYCHTKRE
FYCHTAEE FYCHTKEE FYCHTKLE FYCHTKKE FYCHTKME FYCHWKPE FYCHWKDE
FYCHWAME FYCHTALE FYCHTAKE FYCHTKTE FYCHWAAE FYCHWQRE FYCHWQDE
FYCHWQQE FYCHWAPE FYCHWASE FYCHWATE FYCHWQAE FYCHWQPE FYCHWQSE
FYCHWQTE FYCHWQEE FYCHWQLE FYCHWQKE FYCHWQME FYCHWEEE FYCHWELE
FYCHWEKE FYCHWEAE FYCHWERE FYCHWEDE FYCHWEQE FYCHWIAE FYCHWIRE
FYCHWIDE FYCHWEME FYCHWEPE FYCHWESE FYCHWETE FYCHWIME FYCHWIPE
FYCHWISE FYCHWQQE FYCHWIEE FYCHWILE FYCHWIKE FYCHWLQE FYCHWLEE
FYCHWLLE FYCHWITE FYCHWLAE FYCHWLRE FYCHWLDE FYCHWLTE FYCHWKAE
FYCHWKQE FYCHWLKE FYCHWLME FYCHWLPE FYCHWLSE FYCHWKSE FYCHWKRE
FYCHWARE FYCHWKEE FYCHWKLE FYCHWKKE FYCHWKME FYCHWAKE FYCHWKTE
FYCHYAME FYCHWADE FYCHWAQE FYCHWAEE FYCHWALE FYCHYQRE FYCHYQDE
FYCHYQQE FYCHYAPE FYCHYASE FYCHYATE FYCHYQAE FYCHYQPE FYCHYQSE
FYCHWQTE FYCHYQEE FYCHYQLE FYCHYQKE FYCHYQME FYCHWEEE FYCHWELE
FYCHWEKE FYCHWEAE FYCHWERE FYCHWEDE FYCHWEQE FYCHWIAE FYCHWIRE
```

TABLE 5-continued

```
FYCHYIDE FYCHWEME FYCHWEPE FYCHWESE FYCHWETE FYCHYIME FYCHYIPE
FYCHYISE FYCHYIQE FYCHYIEE FYCHYILE FYCHYIKE FYCHYLQE FYCHYLEE
FYCHYLLE FYCHYITE FYCHYLAE FYCHYLRE FYCHYLDE FYCHYLTE FYCHYKAE
FYCHYKQE FYCHYLKE FYCHYLME FYCHYLPE FYCHYLSE FYCHYKSE FYCHYKRE
FYCHYARE FYCHYKEE FYCHYKLE FYCHYKKE FYCHYKME FYCHYAKE FYCHYKTE
FYCHYAAE FYCHYADE FYCHYAQE FYCHYAEE FYCHYALE FYCHVKDE FYCHVQSE
FYCHWQTE FYCHYKPE FYCHYKDE FYCHVAAE FYCHVKPE FYCHWEEE FYCHWELE
FYCHWEKE FYCHWEAE FYCHWERE FYCHWEDE FYCHWEQE FYCHWEAE FYCHWIRE
FYCHVIDE FYCHWEME FYCHWEPE FYCHWESE FYCHWETE FYCHVIME FYCHVIPE
FYCHVISE FYCHVIQE FYCHVIEE FYCHVILE FYCHVIKE FYCHVLQE FYCHVLEE
FYCHVLLE FYCHVITE FYCHVLAE FYCHVLRE FYCHVLDE FYCHVLTE FYCHVKAE
FYCHVKQE FYCHVLKE FYCHVLME FYCHVLPE FYCHVLSE FYCHVKSE FYCHVKRE
FYCHVARE FYCHVKEE FYCHVKLE FYCHVKKE FYCHVKME FYCHVAKE FYCHVKTE
FYCHVAME FYCHVADE FYCHVAQE FYCHVAEE FYCHVALE FYCHVQRE FYCHVQDE
FYCHVQQE FYCHVAPE FYCHVASE FYCHVATE FYCHVQAE FYCHVQPE FYCHVQEE
FYCHVQLE FYCHVQKE FYCHVQME FYAHCAAE FYAHCARE FYAHCADE FYAHCAQE
FYAHCAEE FYAHCALE FYAHCAKE FYAHCAME FYAHCAPE FYAHCASE FYAHCATE
FYAHCQEE FYAHCQLE FYAHCQKE FYAHCQME FYAHCQPE FYAHCQSE FYAHCQTE
FYAHCQAE FYAHCQRE FYAHCQDE FYAHCQQE FYAHCEAE FYAHCERE FYAHCEDE
FYAHCEEE FYAHCELE FYAHCEKE FYAHCEME FYAHCEPE FYAHCESE FYAHCETE
FYAHCEQE FYAHCIAE FYAHCIRE FYAHCIDE FYAHCIQE FYAHCIEE FYAHCILE
FYAHCIKE FYAHCIME FYAHCIPE FYAHCISE FYAHCITE FYAHCLAE FYAHCLRE
FYAHCLDE FYAHCLQE FYAHCLEE FYAHCLLE FYAHCLKE FYAHCLME FYAHCLPE
FYAHCLSE FYAHCLTE FYAHCKAE FYAHCKKE FYAHCKSE FYAHCKTE FYAHCKPE
FYAHCKDE FYAHCKQE FYAHCKEE FYAHCKLE FYAHCKLE FYAHCKME FYRHCAAE
FYRHCAEE FYRHCALE FYRHCAKE FYRHCAME FYRHCAPE FYRHCASE FYRHCATE
FYRHCQEE FYRHCQLE FYRHCQKE FYRHCQME FYRHCQPE FYRHCQSE FYRHCQTE
FYRHCQAE FYAHCQRE FYRHCQDE FYRHCQQE FYRHCEAE FYRHCERE FYRHCEDE
FYAHCEEE FYRHCELE FYRHCEKE FYRHCEME FYRHCEPE FYRHCESE FYRHCETE
FYRHCEQE FYRHCIAE FYRHCIRE FYRHCIDE FYAHCIQE FYRHCIEE FYRHCILE
FYRHCIKE FYRHCIME FYRHCIPE FYRHCISE FYRHCITE FYRHCLAE FYRHCLRE
FYRHCLDE FYRHCLQE FYRHCLEE FYRHCLLE FYRHCLKE FYRHCLME FYRHCLPE
FYRHCLSE FYRHCLTE FYRHCKAE FYRHCKRE FYRHCKSE FYRHCKTE FYRHCKPE
FYRHCARE FYRHCADE FYRHCAQE FYRHCKDE FYRHCKQE FYRHCKEE FYRHCKLE
FYRHCKKE FYRHCKME FYNHCAAE FYNHCKKE FYNHCKME FYNHCARE FYNHCADE
FYNHCAEE FYNHCALE FYNHCAKE FYNHCAME FYNHCAPE FYNHCASE FYNHCATE
FYNHCQEE FYNHCQLE FYNHCQKE FYNHCQME FYNHCQPE FYNHCQSE FYNHCQTE
FYNHCQAE FYNHCQRE FYNHCQDE FYNHCQQE FYNHCEAE FYNHCERE FYNHCEDE
FYNHCEEE FYNHCELE FYNHCEKE FYNHCEME FYNHCEPE FYNHCESE FYNHCETE
FYNHCEQE FYNHCIAE FYNHCIRE FYNHCIDE FYNHCIQE FYNHCIEE FYNHCILE
```

TABLE 5-continued

```
FYNHCIKE FYNHCIME FYNHCIPE FYNHCISE FYNHCITE FYNHCLAE FYNHCLRE
FYNHCLDE FYNHCLQE FYNHCLEE FYNHCLLE FYNHCLKE FYNHCLME FYNHCLPE
FYNHCLSE FYNHCLTE FYNHCKAE FYNHCKRE FYNHCKSE FYNHCKTE FYNHCKPE
FYNHCAQE FYNHCKDE FYNHCKQE FYNHCKEE FYNHCKLE FYDHCAAE FYDHCKKE
FYDHCAEE FYDHCALE FYDHCAKE FYDHCAME FYDHCAPE FYDHCASE FYDHCATE
FYDHCQEE FYDHCQLE FYDHCQKE FYDHCQME FYDHCQPE FYDHCQSE FYDHCQTE
FYDHCQAE FYDHCQRE FYDHCQDE FYDHCQQE FYDHCEAE FYDHCERE FYDHCEDE
FYDHCEEE FYDHCELE FYDHCEKE FYDHCEME FYDHCEPE FYDHCESE FYDHCETE
FYDHCEQE FYDHCIAE FYDHCIRE FYDHCIDE FYDHCIQE FYDHCIEE FYDHCILE
FYDHCIKE FYDHCIME FYDHCIPE FYDHCISE FYDHCITE FYDHCLAE FYDHCLRE
FYDHCLDE FYDHCLQE FYDHCLEE FYDHCLLE FYDHCLKE FYDHCLME FYDHCLPE
FYDHCLSE FYDHCLTE FYDHCKAE FYDHCKRE FYDHCKSE FYDHCKTE FYDHCKPE
FYDHCKME FYDHCARE FYDHCADE FYDHCAQE FYDHCKDE FYDHCKQE FYDHCKEE
FYDHCKLE FYIHCAAE FYIHCKKE FYIHCKME FYIHCARE FYIHCADE FYIHCAQE
FYIHCAEE FYIHCALE FYIHCAKE FYIHCAME FYIHCAPE FYIHCASE FYIHCATE
FYIHCQEE FYIHCQLE FYIHCQKE FYIHCQME FYIHCQPE FYIHCQSE FYIHCQTE
FYIHCQAE FYIHCQRE FYIHCQDE FYIHCQQE FYIHCEAE FYIHCERE FYIHCEDE
FYIHCEEE FYIHCELE FYIHCEKE FYIHCEME FYIHCEPE FYIHCESE FYIHCETE
FYIHCEQE FYIHCIAE FYIHCIRE FYIHCIDE FYIHCIQE FYIHCIEE FYIHCILE
FYIHCIKE FYIHCIME FYIHCIPE FYIHCISE FYIHCITE FYIHCLAE FYIHCLRE
FYIHCLDE FYIHCLQE FYIHCLEE FYIHCLLE FYIHCLKE FYIHCLME FYIHCLPE
FYIHCLSE FYIHCLTE FYIHCKAE FYIHCKRE FYIHCKSE FYIHCKTE FYIHCKPE
FYIHCKDE FYIHCKQE FYIHCKEE FYIHCKLE FYPHCAAE FYPHCKKE FYPHCKME
FYPHCAEE FYPHCALE FYPHCAKE FYPHCAME FYPHCAPE FYPHCASE FYPHCATE
FYPHCQEE FYPHCQLE FYPHCQKE FYPHCQME FYPHCQPE FYPHCQSE FYPHCQTE
FYPHCQAE FYPHCQRE FYPHCQDE FYPHCQQE FYPHCEAE FYPHCERE FYPHCEDE
FYPHCEEE FYPHCELE FYPHCEKE FYPHCEME FYPHCEPE FYPHCESE FYPHCETE
FYPHCEQE FYPHCIAE FYPHCIRE FYPHCIDE FYPHCIQE FYPHCIEE FYPHCILE
FYPHCIKE FYPHCIME FYPHCIPE FYPHCISE FYPHCITE FYPHCLAE FYPHCLRE
FYPHCLDE FYPHCLQE FYPHCLEE FYPHCLLE FYPHCLKE FYPHCLME FYPHCLPE
FYPHCLSE FYPHCLTE FYPHCKAE FYPHCKRE FYPHCKSE FYPHCKTE FYPHCKPE
FYPHCKDE FYPHCKQE FYPHCKEE FYPHCKLE FYPHCARE FYPHCADE FYPHCAQE
FYTHCAAE FYTHCKKE FYTHCKME FYTHCKDE FYTHCKQE FYTHCKEE FYTHCKLE
FYTHCAEE FYTHCALE FYTHCAKE FYTHCAME FYTHCAPE FYTHCASE FYTHCATE
FYTHCQEE FYTHCQLE FYTHCQKE FYTHCQME FYTHCQPE FYTHCQSE FYTHCQTE
FYTHCQAE FYTHCQRE FYTHCQDE FYTHCQQE FYTHCEAE FYTHCERE FYTHCEDE
FYTHCEEE FYTHCELE FYTHCEKE FYTHCEME FYTHCEPE FYTHCESE FYTHCETE
FYTHCEQE FYTHCIAE FYTHCIRE FYTHCIDE FYTHCIQE FYTHCIEE FYTHCILE
FYTHCIKE FYTHCIME FYTHCIPE FYTHCISE FYTHCITE FYTHCLAE FYTHCLRE
FYTHCLDE FYTHCLQE FYTHCLEE FYTHCLLE FYTHCLKE FYTHCLME FYTHCLPE
```

TABLE 5-continued

```
FYTHCLSE FYTHCLTE FYTHCKAE FYTHCKRE FYTHCKSE FYTHCKTE FYTHCKPE
FYTHCARE FYTHCADE FYTHCAQE FYWHCAAE FYWHCKKE FYWHCKME FYWHCKDE
FYWHCAEE FYWHCALE FYWHCAKE FYWHCAME FYWHCAPE FYWHCASE FYWHCATE
FYWHCQEE FYWHCQLE FYWHCQKE FYWHCQME FYWHCQPE FYWHCQSE FYWHCQTE
FYWHCQAE FYWHCQRE FYWHCQDE FYWHCQQE FYWHCEAE FYWHCERE FYWHCEDE
FYWHCEEE FYWHCELE FYWHCEKE FYWHCEME FYWHCEPE FYWHCESE FYWHCETE
FYWHCEQE FYWHCIAE FYWHCIRE FYWHCIDE FYWHCIQE FYWHCIEE FYWHCILE
FYWHCIKE FYWHCIME FYWHCIPE FYWHCISE FYWHCITE FYWHCLAE FYWHCLRE
FYWHCLDE FYWHCLQE FYWHCLEE FYWHCLLE FYWHCLKE FYWHCLME FYWHCLPE
FYWHCLSE FYWHCLTE FYWHCKAE FYWHCKRE FYWHCKSE FYWHCKTE FYWHCKPE
FYWHCKQE FYWHCKEE FYWHCKLE FYWHCARE FYWHCADE FYWHCAQE FYYHCAAE
FYYHCAEE FYYHCALE FYYHCAKE FYYHCAME FYYHCAPE FYYHCASE FYYHCATE
FYYHCQEE FYYHCQLE FYYHCQKE FYYHCQME FYYHCQPE FYYHCQSE FYYHCQTE
FYYHCQAE FYYHCQRE FYYHCQDE FYYHCQQE FYYHCEAE FYYHCERE FYYHCEDE
FYYHCEEE FYYHCELE FYYHCEKE FYYHCEME FYYHCEPE FYYHCESE FYYHCETE
FYYHCEQE FYYHCIAE FYYHCIRE FYYHCIDE FYYHCIQE FYYHCIEE FYYHCILE
FYYHCIKE FYYHCIME FYYHCIPE FYYHCISE FYYHCITE FYYHCLAE FYYHCLRE
FYYHCLDE FYYHCLQE FYYHCLEE FYYHCLLE FYYHCLKE FYYHCLME FYYHCLPE
FYYHCLSE FYYHCLTE FYYHCKAE FYYHCKRE FYYHCKSE FYYHCKTE FYYHCKPE
FYYHCKKE FYYHCKME FYYHCKDE FYYHCKQE FYYHCKEE FYYHCKLE FYYHCARE
FYYHCADE FYYHCAQE FYCHNQR  FYCHNER  FYCHNHR  FYCHNIR  FYCHNKR
FYCHNMR  FYCHNFR  FYCHNFWR FYCHDQR  FYCHDER  FYCHDHR  FYCHDIR
FYCHDKR  FYCHDMR  FYCHDFR  FYCHDFWR FYCHQQR  FYCHQER  FYCHQHR
FYCHQKR  FYCHQMR  FYCHQFR  FYCHQFWR FYCHQIR  FYCHEQR  FYCHEER
FYCHEKR  FYCHEMR  FYCHEFR  FYCHEFWR FYCHEIR  FYCHEHR  FYCHHQR
FYCHHER  FYCHHKR  FYCHHMR  FYCHHFR  FYCHHFWR FYCHHIR  FYCHHHR
FYCHIQR  FYCHIER  FYCHIKR  FYCHIMR  FYCHIFR  FYCHIFWR FYCHIIR
FYCHIHR  FYCHKQR  FYCHKER  FYCHKKR  FYCHKMR  FYCHKFR  FYCHKFWR
FYCHKIR  FYCHKHR  FYCHMQR  FYCHMER  FYCHMKR  FYCHMMR  FYCHMFR
FYCHMFWR FYCHMIR  FYCHMHR  FYCHFQR  FYCHFER  FYCHFKR  FYCHFMR
FYCHFFR  FYCHFFWR FYCHFIR  FYCHFHR  FYCHPQR  FYCHPER  FYCHPKR
FYCHPMR  FYCHPFR  FYCHPFWR FYCHPIR  FYCHPHR  FYCHTQR  FYCHTER
FYCHTKR  FYCHTMR  FYCHTFR  FYCHTFWR FYCHTIR  FYCHTHR  FYCHWQR
FYCHWER  FYCHWKR  FYCHWMR  FYCHWFR  FYCHWFWR FYCHWIR  FYCHWHR
FYCHYQR  FYCHYER  FYCHYKR  FYCHYMR  FYCHYFR  FYCHYFWR FYCHYIR
FYCHYHR  FYCHVQR  FYCHVER  FYCHVKR  FYCHVMR  FYCHVFR  FYCHVFWR
FYCHVIR  FYCHVHR  FYAHCQR  FYAHCER  FYAHCHR  FYAHCIR  FYAHCKR
FYAHCMR  FYAHCFR  FYAHCWR  FYRHCQR  FYRHCER  FYRHCHR  FYRHCIR
FYRHCKR  FYRHCMR  FYRHCFR  FYAHCWR  FYNHCQR  FYNHCER  FYNHCHR
FYNHCIR  FYNHCKR  FYNHCMR  FYNHCFR  FYNHCWR  FYDHCQR  FYDHCER
```

TABLE 5-continued

| | | | | | | |
|---|---|---|---|---|---|---|
| FYDHCHR | FYDHCIR | FYDHCKR | FYDHCMR | FYDHCFR | FYDHCWR | FYIHCQR |
| FYAHCER | FYIHCHR | FYIHCIR | FYIHCKR | FYIHCMR | FYIHCFR | FYIHCWR |
| FYPHCER | FYPHCHR | FYPHCIR | FYPHCKR | FYPHCMR | FYAHCFR | FYPHCWR |
| FYPHCQR | FYTHCQR | FYTHCER | FYTHCHR | FYTHCIR | FYTHCKR | FYTHCMR |
| FYTHCFR | FYTHCWR | FYWHCQR | FYWHCER | FYWHCHR | FYWHCIR | FYWHCKR |
| FYWHCMR | FYWHCFR | FYWHCWR | FYYHCQR | FYYHCER | FYYHCHR | FYYHCIR |
| FYYHCKR | FYYHCMR | FYYHCFR | FYYHCWR | FYACRNE | FYACRDE | FYACRQE |
| FYACREE | FYACRLE | FYACRME | FYACRSE | FYACRTE | FYACRWE | FYRCRNE |
| FYRCRDE | FYRCRQE | FYRCREE | FYRCRLE | FYRCRME | FYRCRSE | FYRCRTE |
| FYRCRWE | FYNCRNE | FYNCRDE | FYNCRQE | FYNCREE | FYNCRLE | FYNCRME |
| FYNCRSE | FYNCRTE | FYNCRWE | FYDCRNE | FYDCRDE | FYDCRQE | FYDCREE |
| FYDCRLE | FYDCRME | FYDCRSE | FYDCRTE | FYDCRWE | FYQCRNE | FYQCRDE |
| FYQCRQE | FYQCREE | FYQCRLE | FYQCRME | FYQCRSE | FYQCRTE | FYQCRWE |
| FYECRQE | FYECREE | FYECRLE | FYECRME | FYECRSE | FYECRTE | FYECRWE |
| FYECRNE | FYECRDE | FYGCRNE | FYGCRDE | FYGCRQE | FYGCREE | FYGCRLE |
| FYGCRME | FYGCRSE | FYGCRTE | FYGCRWE | FYHCRNE | FYHCRDE | FYHCRQE |
| FYHCREE | FYHCRLE | FYHCRME | FYHCRSE | FYHCRTE | FYHCRWE | FYACRNE |
| FYICRDE | FYICRQE | FYICREE | FYICRLE | FYICRME | FYICRSE | FYICRTE |
| FYICRWE | FYLCRNE | FYLCRDE | FYLCRQE | FYLCREE | FYLCRLE | FYLCRME |
| FYLCRSE | FYLCRTE | FYLCRWE | FYKCRNE | FYKCRDE | FYKCRQE | FYKCREE |
| FYKCRLE | FYKCRME | FYKCRSE | FYKCRTE | FYKCRWE | FYMCRNE | FYMCRDE |
| FYMCRQE | FYMCREE | FYMCRLE | FYMCRME | FYMCRSE | FYMCRTE | FYMCRWE |
| FYFCRQE | FYFCREE | FYFCRLE | FYFCRME | FYFCRSE | FYFCRTE | FYFCRWE |
| FYFCRNE | FYFCRDE | FYPCRNE | FYPCRDE | FYPCRQE | FYPCREE | FYPCRLE |
| FYPCRME | FYPCRSE | FYPCRTE | FYPCRWE | FYWCRNE | FYWCRDE | FYWCRQE |
| FYWCREE | FYWCRLE | FYWCRME | FYWCREE | FYWCRTE | FYWCRWE | FYYCRNE |
| FYYCRDE | FYYCRQE | FYYCREE | FYYCRLE | FYYCRME | FYYCRSE | FYYCRTE |
| FYYCRWE | FYVCRNE | FYVCRDE | FYVCRQE | FYVCREE | FYVCRLE | FYVCRME |
| FYVCRSE | FYVCRTE | FYVCRWE | YFNCRNE | YFNCRDE | YFNCRQE | YFNCREE |
| YFNCRLE | YFNCRME | YFNCRSE | YFNCRTE | YFNCRWE | YFDCRNE | YFDCRDE |
| YFDCRQE | YFDCREE | YFDCRLE | YFDCRME | YFDCRSE | YFDCRTE | YFDCRWE |
| YFECRQE | YFECREE | YFECRLE | YFECRME | YFECRSE | YFECRTE | YFECRWE |
| YFECRNE | YFECRDE | YFHCRNE | YFHCRDE | YFHCRQE | YFHCREE | YFHCRLE |
| YFHCRME | YFHCRSE | YFHCRTE | YFNCRWE | YFICRNE | YFNCRDE | YFICRQE |
| YFICREE | YFICRLE | YFICRME | YFICRSE | YFICRTE | YFICRWE | YFLCRNE |
| YFLCRDE | YFLCRQE | YFLCREE | YFLCRLE | YFLCRME | YFLCRSE | YFLCRTE |
| YFLCRWE | YFKCRNE | YFKCRDE | YFKCRQE | YFKCREE | YFKCRLE | YFKCRME |
| YFKCRSE | YFKCRTE | YFKCRWE | YFMCRNE | YFMCRDE | YFMCRQE | YFMCREE |
| YFMCRLE | YFMCRME | YFMCRSE | YFMCRTE | YFMCRWE | YFPCRNE | YFPCRDE |
| YFPCRQE | YFPCREE | YFPCRLE | YFPCRME | YFPCRSE | YFPCRTE | YFPCRWE |

TABLE 5-continued

| | | | | | | |
|---|---|---|---|---|---|---|
| YFSCRQE | YFSCREE | YFSCRLE | YFSCRME | YFSCRSE | YFSCRTE | YFSCRWE |
| YFNCRNE | YFSCRDE | YFTCRNE | YFTCRDE | YFTCRQE | YFTCREE | YFTCRLE |
| YFTCRME | YFTCRSE | YFTCRTE | YFTCRWE | YFYCRNE | YFYCRDE | YFYCRQE |
| YFYCREE | YFYCRLE | YFYCRME | YFYCRSE | YFYCRTE | YFYCRWE | YFVCRNE |
| YFVCRDE | YFVCRQE | YFVCREE | YFVCRLE | YFVCRME | YFVCRSE | YFVCRTE |
| YFVCRWE | HAYFCQR | HAYFCHR | HAYFCKR | HAYFCSR | HAYFCWR | HAYFCYR |
| HRYFCQR | HRYFCHR | HRYFCKR | HRYFCSR | HRYFCWR | HRYFCYR | HNYFCQR |
| HNYFCHR | HNYFCKR | HNYFCSR | HNYFCWR | HNYFCYR | HDYFCQR | HDYFCHR |
| HDYFCKR | HDYFCSR | HDYFCWR | HDYFCYR | HIYFCQR | HIYFCHR | HIYFCKR |
| HIYFCSR | HIYFCWR | HIYFCYR | HPYFCQR | HPYFCHR | HPYFCKR | HPYFCSR |
| HPYFCWR | HPYFCYR | HTYFCQR | HTYFCHR | HTYFCKR | HTYFCSR | HTYFCWR |
| HTYFCYR | HWYFCQR | HWYFCHR | HWYFCKR | HWYFCSR | HWYFCWR | HWYFCYR |
| HYYFCQR | HYYFCHR | HYYFCKR | HYYFCSR | HYYFCWR | HYYFCYR | HAYFCAK |
| HAYFCRK | HAYFCQK | HAYFCHK | HAYFCKK | HAYFCFK | HAYFCWK | HAYFCYK |
| HAYFCVK | HRYFCAK | HRYFCRK | HRYFCQK | HRYFCHK | HRYFCKK | HRYFCFK |
| HRYFCWK | HRYFCYK | HRYFCVK | HNYFCAK | HNYFCRK | HNYFCQK | HNYFCHK |
| HNYFCKK | HNYFCFK | HNYFCWK | HNYFCYK | HNYFCVK | HDYFCAK | HDYFCRK |
| HDYFCQK | HDYFCHK | HDYFCKK | HDYFCFK | HDYFCWK | HDYFCYK | HDYFCVK |
| HIYFCQK | HIYFCHK | HIYFCKK | HIYFCFK | HIYFCWK | HIYFCYK | HIYFCVK |
| HIYFCAK | HIYFCRK | HPYFCAK | HPYFCRK | HPYFCQK | HPYFCHK | HPYFCKK |
| HPYFCFK | HPYFCWK | HPYFCYK | HPYFCVK | HTYFCAK | HTYFCRK | HTYFCQK |
| HTYFCHK | HTYFCKK | HTYFCFK | HTYFCWK | HTYFCYK | HTYFCVK | HWYFCAK |
| HWYFCRK | HWYFCQK | HWYFCHK | HWYFCKK | HWYFCFK | HWYFCWK | HWYFCYK |
| HWYFCVK | HYYFCAK | HYYFCRK | HYYFCQK | HYYFCHK | HYYFCKK | HYYFCFK |
| HYYFCWK | HYYFCYK | HYYFCVK | | | | |

The invention claimed is:

1. A method for constructing a novel affinity ligand peptide library for binding immunoglobulin G on the basis of an affinity model of Protein A, comprising:

adding a cysteine to a middle region of a peptide to obtain the following peptides:

FYCHXXXE, FYXHCXXE, FYCHXXR, FYXHCXR, FYXCRXE,

YFXCRXE, HXYFCXR, and

HXYFCXK;

wherein 'X' represents the common 19 amino acids except cysteine; and synthesizing one or more of the peptides.

2. The method of claim 1, wherein, the constructing is on the basis of six *Staphylococal* Protein A hot spots: F132, Y133, H137, E143, R146, and K154.

3. The method of claim 1, further comprising determining the kinds of amino acids 'X' in the peptides that are within the scope of the peptide library using an amino acid location method.

4. The method of claim 3, wherein, a candidate peptide library is obtained and shown below:

| Peptide & Number of peptides | Amino acids 'X' represents |
|---|---|
| FYCHX$_1$X$_2$X$_3$E number: 990 | X$_1$: A, R, N, D, Q, E, H, I, L, K, M, T, W, Y, V |
| | X$_2$: A, Q, E, I, L, K |
| | X$_3$: A, R, D, Q, E, L, K, M, P, S, T |
| FYX$_1$HCX$_2$X$_3$E number: 594 | X$_1$: A, R, N, D, I, P, T, W, Y |
| | X$_2$: A, Q, E, I, L, K |
| | X$_3$: A, R, D, Q, E, L, K, M, P, S, T |
| FYCHX$_1$X$_2$R number: 112 | X$_1$: N, D, Q, E, H, I, K, M, F, P, T, W, Y, V |
| | X$_2$: Q, E, H, I, K, M, F, W |
| FYX$_1$HCX$_2$R number: 72 | X$_1$: A, R, N, D, I, P, T, W, Y |
| | X$_2$: Q, E, H, I, K, M, F, W |
| FYX$_1$CRX$_2$E number: 153 | X$_1$: A, R, N, D, Q, E, G, H, I, L, K, M, F, P, W, Y, V |
| | X$_2$: N, D, Q, E, L, M, S, T, W |
| YFX$_1$CRX$_2$E number: 117 | X$_1$: N, D, E, H, I, L, K, M, P, S, T, Y, V |
| | X$_2$: N, D, Q, E, L, M, S, T, W |
| HX$_1$YFCX$_2$R number: 54 | X$_1$: A, R, N, D, I, P, T, W, Y |
| | X$_2$: Q, H, K, S, W, Y |
| HX$_1$YFCX$_2$K number: 81 | X$_1$: A, R, N, D, I, P, T, W, Y |
| | X$_2$: A, R, Q, H, K, F, W, Y, V. |

5. The method of claim 4, wherein the peptides in the candidate peptide library are screened by molecular docking, RMSD comparison, and rescreened by molecular dynamics simulation, obtaining peptide ligands possessing high affinity for human immunoglobulin G, which are SEQ ID NO: 1499, FYWHCLDE;
SEQ ID NO: 1883, FYFCRWE;
SEQ ID NO: 1309, FYIHCLPE;
SEQ ID NO: 1576, FYYHCKKE;
SEQ ID NO: 859, FYCHWALE;
SEQ ID NO: 798, FYCHWQDE;
SEQ ID NO: 757, FYCHTIDE;
SEQ ID NO: 1073, FYRIICQRE;
SEQ ID NO: 397, FYCHHKTE;
SEQ ID NO: 606, FYCHLQKE;
SEQ ID NO: 122, FYCHRKAE;
SEQ ID NO: 147, FYCHNQDE;
SEQ ID NO: 82, FYCHRQEE; and
SEQ ID NO: 1133, FYNHCASE.

6. The method of claim 2, further comprising determining the kinds of amino acids 'X' in the peptides that are within the scope of the peptide library using an amino acid location method.

7. The method of claim 6, wherein, a candidate peptide library is obtained and shown below:

| Peptide & Number of peptides | Amino acids 'X' represents |
|---|---|
| FYCHX₁X₂X₃E number: 990 | X₁: A, R, N, D, Q, E, H, I, L, K, M, T, W, Y, V<br>X₂: A, Q, E, I, L, K<br>X₃: A, R, D, Q, E, L, K, M, P, S, T |
| FYX₁HCX₂X₃E number: 594 | X₁: A, R, N, D, I, P, T, W, Y<br>X₂: A, Q, E, I, L, K<br>X₃: A, R, D, Q, E, L, K, M, P, S, T |
| FYCHX₁X₂R number: 112 | X₁: N, D, Q, E, H, I, K, M, F, P, T, W, Y, V<br>X₂: Q, E, H, I, K, M, F, W |
| FYX₁HCX₂R number: 72 | X₁: A, R, N, D, I, P, T, W, Y<br>X₂: Q, E, H, I, K, M, F, W |
| FYX₁CRX₂E number: 153 | X₁: A, R, N, D, Q, E, G, H, I, L, K, M, F, P, W, Y, V<br>X₂: N, D, Q, E, L, M, S, T, W |
| YFX₁CRX₂E number: 117 | X₁: N, D, E, H, I, L, K, M, P, S, T, Y, V<br>X₂: N, D, Q, E, L, M, S, T, W |
| HX₁YFCX₂R number: 54 | X₁: A, R, N, D, I, P, T, W, Y<br>X₂: Q, H, K, S, W, Y |
| HX₁YFCX₂K number: 81 | X₁: A, R, N, D, I, P, T, W, Y<br>X₂: A, R, Q, H, K, F, W, Y, V. |

8. The method of claim 7, wherein, the peptides in the candidate peptide library are screened by molecular docking, RMSD comparison, and rescreened by molecular dynamics simulation, obtaining the top 14 peptide ligands possessing high affinity for human immunoglobulin G, which are SEQ ID NO: 1499, FYWHCLDE;
SEQ ID NO: 1883, FYFCRWE;
SEQ ID NO: 1309, FYIHCLPE;
SEQ ID NO: 1576, FYYHCKKE;
SEQ ID NO: 859, FYCHWALE;
SEQ ID NO: 798, FYCHWQDE;
SEQ ID NO: 757, FYCHTIDE;
SEQ ID NO: 1073, FYRHCQRE;
SEQ ID NO: 397, FYCHHKTE;
SEQ ID NO: 606, FYCHLQKE;
SEQ ID NO: 122, FYCHRKAE;
SEQ ID NO: 147, FYCHNQDE;
SEQ ID NO: 82, FYCHRQEE; and
SEQ ID NO: 1133, FYNHCASE.

* * * * *